United States Patent

Achard et al.

(10) Patent No.: US 6,858,603 B2
(45) Date of Patent: Feb. 22, 2005

(54) ACETINDINE DERIVATIVES, THEIR PREPARATION AND MEDICAMENTS CONTAINING THEM

(75) Inventors: Daniel Achard, Thiais (FR); Hervé Bouchard, Thiais (FR); Jean Bouquerel, Drancy (FR); Marc Capet, Viry-Chatillon (FR); Serg Grisoni, Choisy Le Roi (FR); Jean-Luc Malleron, Marcoussis (FR); Serge Mignani, Chatenay-Malabry (FR); Augustin Hittinger, Igny (FR)

(73) Assignee: Aventis Pharma S.A., Antony Cedex (FR)

( * ) Notice: Subject to any disclaimer, the term of this patent is extended or adjusted under 35 U.S.C. 154(b) by 75 days.

(21) Appl. No.: 10/320,344

(22) Filed: Dec. 16, 2002

(65) Prior Publication Data

US 2003/0162808 A1 Aug. 28, 2003

Related U.S. Application Data

(63) Continuation of application No. 09/803,723, filed on Mar. 9, 2001, now Pat. No. 6,518,264, which is a continuation of application No. PCT/FR99/02147, filed on Sep. 9, 1999.
(60) Provisional application No. 60/119,929, filed on Feb. 12, 1999.

(30) Foreign Application Priority Data

Sep. 11, 1998 (FR) .............................. 98 11342

(51) Int. Cl.$^7$ .................... C07D 205/04; C07D 205/06; C07D 403/06; A61P 3/04; A61P 25/30

(52) U.S. Cl. ............................ 514/210.01; 514/210.19; 514/210.2; 514/210.21
(58) Field of Search ....................... 514/210.01, 210.19, 514/210.2, 210.21

(56) References Cited

PUBLICATIONS

Tzavara ET, Davis RJ, Perry KW, Li X, Salhoff C, Bymaster FP, Witkin JM Nomikos GG, Br J Pharmacol. Feb 2003;138(4):544–53.*
Huestis, M.A. et al, Arch Gen Psychiatry. Apr. 2001;58(4):322–8 Medline abstract 11296091.*
Giuffrida, A. et al, J Pharmacol Exp Ther. Jul. 2001;298(1):7–14.*
Pertwee, R.G., Forsch Komplementarmed. Oct. 1999; 6 Suppl. 3:12–5, Medline abstract 10575283.*

* cited by examiner

*Primary Examiner*—Mukund J. Shah
*Assistant Examiner*—Thomas McKenzie
(74) *Attorney, Agent, or Firm*—Irving Newman

(57) ABSTRACT

Disclosed are azetidine derivatives of formula:

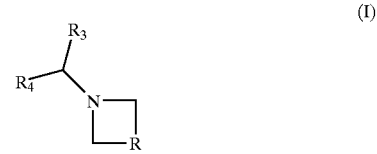

(I)

their optical isomers, their salts, their preparation and medicaments containing them.

20 Claims, No Drawings

ACETINDINE DERIVATIVES, THEIR PREPARATION AND MEDICAMENTS CONTAINING THEM

CROSS REFERENCE TO RELATED APPLICATIONS

This application is a continuation of U.S. application Ser. No. 09/803,723, filed Mar. 9, 2001, now U.S. Pat. No. 6,518,264, which is a continuation of International Application No. PCT/FR99/02147, filed Sep. 9, 1999, which, in turn, claims the benefit of U.S. Provisional Application No. 60/119,929, filed on Feb. 12, 1999, and of French Patent Application FR98/11342, filed on Sep. 11, 1998.

SUMMARY OF THE INVENTION

The present invention relates to azetidine derivatives of formula:

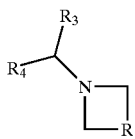
(I)

their optical isomers, their salts, their preparation and medicaments containing them, as well as to methods of using these derivatives to treat a variety of medical conditions and disorders.

DETAILED DESCRIPTION

In formula (I),
R represents a chain

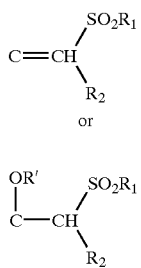

$R_1$ represents a methyl or ethyl radical, $R_2$ represents either an aromatic chosen from phenyl, naphthyl or indenyl, these aromatics being nonsubstituted or substituted with one or more halogens, alkyl, alkoxy, —CO-alk, hydroxyl, —COOR$_5$, formyl, trifluoromethyl, trifluoromethylsulfanyl, trifluoromethoxy, nitro, —NR$_6$R$_7$, —CO—NH— NR$_6$R$_7$, —N(alk)COOR, cyano, —CONHR$_9$, —CO— NR$_{16}$R$_{17}$, alkylsulfanyl, hydroxyalkyl, —O-alk- NR$_{12}$R$_{13}$ or alkylthioalkyl or a heteroaromatic chosen from the benzofuryl, benzothiazolyl, benzothienyl, benzoxazolyl, chromanyl, 2,3-dihydrobenzofuryl, 2,3-dihydrobenzothienyl, indolinyl, isochromanyl, isoquinolyl, pyridyl, quinolyl, 1,2,3,4-tetrahydroisoquinolyl, 1,2,3,4-tetrahydroquinolyl, thiazolyl, or thienyl rings, it being possible for these heteroaromatics to be nonsubstituted or substituted with a halogen, alkyl, alkoxy, —COOR$_5$, trifluoromethyl, trifluoromethylsulfanyl, trifluoromethoxy, nitro, —NR$_6$R$_7$, —CO—NH— NR$_6$R$_7$, cyano, —CONHR$_9$, alkylsulfanyl, hydroxyalkyl or alkylthioalkyl, $R_3$ and $R_4$, which are identical or different, represent either an aromatic chosen from phenyl, naphthyl or indenyl, these aromatics being nonsubstituted or substituted with one or more halogens, alkyl, alkoxy, formyl, hydroxyl, trifluoromethyl, trifluoromethoxy, —CO-alk, cyano, —COOR$_5$, —CONR$_{10}$R$_{11}$, —CO— NH—NR$_6$R$_7$, alkylsulfanyl, hydroxyalkyl, -alk-NR$_6$R$_7$ or alkylthioalkyl; or a heteroaromatic chosen from benzofuryl, benzothiazolyl, benzothienyl, benzoxazolyl, chromanyl, 2,3-dihydrobenzofuryl, 2,3-dihydrobenzothienyl, furyl, isochromanyl, isoquinolyl, pyrrolyl, quinolyl, 1,2,3,4-tetrahydroisoquinolyl, thiazolyl or thienyl rings, it being possible for these heteroaromatics to be nonsubstituted or substituted with a halogen, alkyl, alkoxy, hydroxyl, trifluoromethyl, trifluoromethoxy, cyano, —COOR$_5$, —CO—NH— NR$_6$R$_7$, —CONR$_{10}$R$_{11}$, -alk-NR$_6$R$_7$, alkylsulfanyl, hydroxyalkyl or alkylthioalkyl;

$R_5$ is an alkyl or phenyl radical which is optionally substituted with one or more halogen atoms, $R_6$ and $R_7$, which are identical or different, represent a hydrogen atom or an alkyl, —COOalk, cycloalkyl, alkylcycloalkyl, -alk-O-alk or hydroxyalkyl radical or alternatively $R_6$ and $R_7$ together form with the nitrogen atom to which they are attached a 3- to 10-membered saturated or unsaturated mono- or bicyclic heterocycle optionally containing another heteroatom chosen from oxygen, sulfur and nitrogen and being optionally substituted with one or more alkyl, —COalk, —COOalk, —CO—NHalk, —CS—NHalk, —CO-alk-NR$_{14}$R$_{15}$, oxo, hydroxyalkyl, -alk-O-alk or —CO—NH$_2$ radicals, $R_8$ represents an alkyl radical, $R_9$ represents a hydrogen atom or an alkyl radical or an alkyl radical substituted with a dialkylamino, phenyl, cycloalkyl (optionally substituted with —COOalk) or a 3- to 10-membered saturated or unsaturated mono- or bicyclic heterocycle optionally containing one or more heteroatoms chosen from oxygen, sulfur and nitrogen and being optionally substituted with one or more alkyl radicals, $R_{10}$ and $R_{11}$, which are identical or different, represent a hydrogen atom or an alkyl radical or alternatively $R_{10}$ and $R_{11}$ together form with the nitrogen atom to which they are attached a 3- to 10-membered saturated mono- or bicyclic heterocycle optionally containing another heteroatom chosen from oxygen, sulfur and nitrogen and being optionally substituted with an alkyl radical, $R_{12}$ and $R_{13}$, which are identical or different, represent a hydrogen atom or an alkyl or cycloalkyl radical or alternatively $R_{12}$ and $R_{13}$ together form with the nitrogen atom to which they are attached a 3- to 10-membered saturated mono- or bicyclic heterocycle optionally containing another heteroatom chosen from oxygen, sulfur and nitrogen and being optionally substituted with an alkyl, —COalk, —COOalk, —CO— NHalk, —CS—NHalk or —CO-alk-NR$_{14}$R$_{15}$ radical or a 3- to 10-membered saturated mono- or bicyclic heterocycle containing a heteroatom chosen from oxygen, sulfur and nitrogen, $R_{14}$ and $R_{15}$, which are identical or different, represent a hydrogen atom or an alkyl or —COOalk radical, $R_{16}$ and $R_{17}$ together form with the nitrogen atom to which they are attached a 3- to 10-membered saturated mono- or bicyclic heterocycle optionally containing another heteroatom chosen from oxygen, sulfur and nitrogen, R' represents a hydrogen atom or a —CO-alk radical, alk represents an alkyl or alkylene radical.

In the preceding definitions and in those which follow, unless otherwise stated, the alkyl and alkylene radicals and portions and the alkoxy radicals and portions are in the form of a straight or branched chain and contain 1 to 6 carbon atoms.

Among the alkyl radicals, there may be mentioned methyl, ethyl, n-propyl, isopropyl, n-butyl, sec-butyl, isobutyl, tert-butyl, pentyl and hexyl radicals. Among the alkoxy radicals, there may be mentioned methoxy, ethoxy, n-propoxy, iso-propoxy, n-butoxy, iso-butoxy, sec-butoxy, tert-butoxy and pentyloxy radicals.

The term halogen comprises chlorine, fluorine, bromine and iodine.

When $R_2$ and/or $R_3$ and/or $R_4$ represent independently a substituted phenyl, the latter is preferably mono-, di- or trisubstituted.

When $R_6$ and $R_7$ together form with the nitrogen atom to which they are attached a 3- to 10-membered saturated or unsaturated mono- or bicyclic heterocycle, the latter is preferably an azetidinyl, pyrrolidinyl, piperazinyl, piperidyl, morpholinyl, imidazolyl, thiomorpholinyl or furyl ring, these rings being optionally substituted with an alkyl, hydroxyalkyl, -alk-O-alk, —CONH$_2$, —COalk, —COOalk, oxo, —CSNHalk, —CONHalk or —CO-alk-NR$_{14}$R$_{15}$ radical and, in particular, with a methyl, ethyl, propyl, isobutyl, acetyl, N,N-dimethylaminomethylcarbonyl, methyloxycarbonyl, methylcarbamoyl, methylthiocarbamoyl, N-methylaminomethylcarbonyl, N-methyl-N-tertbutoxycarbonylaminomethylcarbonyl, oxo, —CSNHCH$_3$ or —CONHCH$_3$ radical.

When $R_{10}$ and $R_{11}$ together form with the nitrogen atom to which they are attached a 3- to 10-membered saturated mono- or bicyclic heterocycle, the latter is preferably an azetidinyl, pyrrolidinyl, piperazinyl, piperidyl, morpholinyl or thiomorpholinyl ring, these rings being optionally substituted with an alkyl.

When $R_{12}$ and $R_{13}$ form together with the nitrogen atom to which they are attached a 3- to 10-membered saturated mono- or bicyclic heterocycle, the latter is preferably an azetidinyl, pyrrolidinyl, piperazinyl, piperidyl, morpholinyl or thiomorpholinyl ring, these rings being optionally substituted with an alkyl, —COalk, —COOalk, —CO—NHalk, —CS—NHalk or —CO-alk-NR$_{14}$R$_{15}$ radical or a 3- to 10-membered saturated mono- or bicyclic heterocycle containing a heteroatom chosen from oxygen, sulfur and nitrogen, and, in particular, with a thiomorpholinyl radical.

When $R_{16}$ and $R_{17}$ together form with the nitrogen atom to which they are attached a 3- to 10-membered saturated mono- or bicyclic heterocycle, the latter is preferably a piperidyl ring.

When $R_9$ represents an alkyl radical substituted with a 3- to 10-membered saturated or unsaturated mono- or bicyclic heterocycle optionally containing one or more heteroatoms chosen from oxygen, sulfur and nitrogen, the latter is preferably a pyrrolidinyl, tetrahydrofuryl, morpholinyl or pyrrolyl ring, these rings being optionally substituted with one or more alkyl radicals.

The compounds of formula (I) may be provided in the form of enantiomers and diastereoisomers. These optical isomers and mixtures thereof form part of the invention.

The compounds of formula (I) for which R represents a chain of formula (A) may be prepared by dehydration of a corresponding compound of formula (Ia)

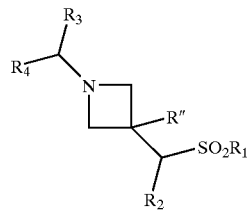

(Ia)

in which $R_1$, $R_2$, $R_3$ and $R_4$ have the same meanings as in formula (I) and R" represents a hydroxyl, methanesulfonyloxy or acetyloxy radical.

This dehydration is carried out by any method known to persons skilled in the art which makes it possible to dehydrate an alcohol or one of its derivatives in order to obtain the corresponding alkene. Preferably, derivatives are used for which R" is a methanesulfonyloxy or acetyloxy radical obtained from the corresponding derivative for which R" is a hydroxyl radical by the action of methanesulfonyl chloride or acetyl chloride, in an inert solvent such as pyridine, tetrahydrofuran, dioxane, a chlorinated solvent (dichloromethane or chloroform for example), at a temperature of between 5° C. and 20° C. and then the medium is treated with a base such as an alkali metal hydroxide (sodium hydroxide for example), an alkali metal carbonate (sodium or potassium carbonate for example), an amine such as a trialkylamine (triethylamine for example), 4-dimethylaminopyridine, diaza-1,8-bicyclo[5.4.0]undec-7-ene, at a temperature of between 0° C. and the boiling temperature of the reaction mixture. The methanesulfonyloxy and the acetyloxy may be isolated or otherwise.

The compounds of formula (I) for which R represents a chain (B) in which R' is a hydrogen atom may be prepared by reacting the derivative $R_1SO_2CH_2R_2$ (II) for which $R_1$ and $R_2$ have the same meanings as in formula (I) with an azetidinone of formula:

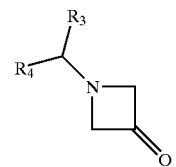

(III)

in which $R_3$ and $R_4$ have the same meanings as in formula (I).

The procedure is generally carried out in an inert solvent such as an ether (tetrahydrofuran for example), in the presence of a strong base such as lithium diisopropylamide, potassium tert-butoxide or n-butyllithium, at a temperature of between −70° C. and −15° C.

The derivatives of formula (II) may be obtained by application or adaptation of the methods described in the examples. In particular, the procedure is carried out according to the following reaction schemes:

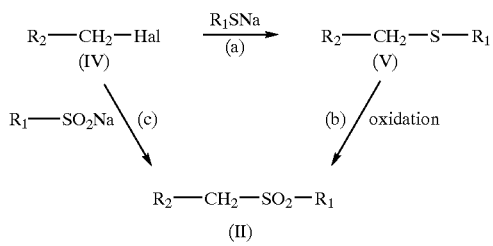

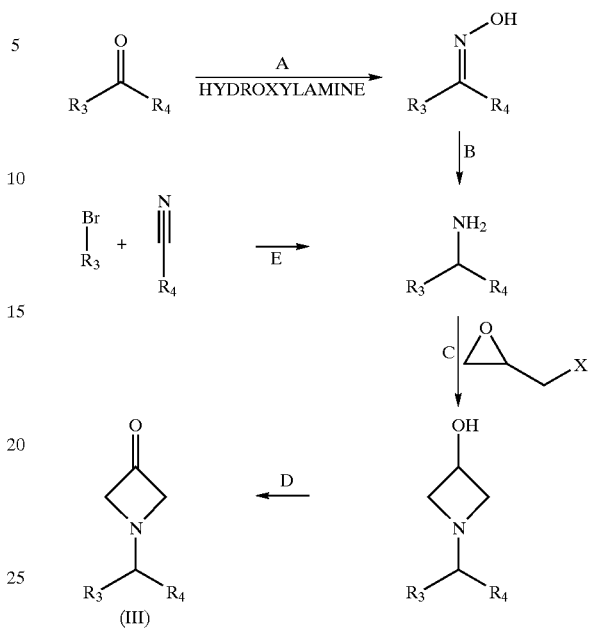

In these formulae Hal represents a halogen atom and, preferably, chlorine, bromine or iodine, $R_1$ and $R_2$ have the same meanings as in formula (I).

The reaction (a) is generally carried out in an inert solvent such as dimethylformamide or a 1-4C. aliphatic alcohol, at a temperature of between 20 and 30° C.

The reaction (b) is carried out by any known method which makes it possible to oxidize a sulfur-containing derivative without affecting the rest of the molecule such as the methods described by M. HUDLICKY, Oxidations in Organic Chemistry, ACS Monograph, 186, 252–263 (1990). For example, the procedure is carried out by the action of an organic peroxy acid or a salt of such a peroxy acid (peroxycarboxylic or peroxysulfonic acids, especially peroxybenzoic acid, 3-chloroperoxybenzoic acid, 4-nitroperoxybenzoic acid, peroxyacetic acid, trifluoroperoxyacetic acid, peroxyformic acid or monoperoxyphthalic acid) or in organic peracids or a salt of such an acid (for example periodic or persulfuric acid), in an inert solvent such as a chlorinated solvent (chloroform or dichloromethane for example), at a temperature of between 0 and 25° C. It is also possible to use hydrogen peroxide or a periodate (sodium periodate for example), in an inert solvent such as 1-4C aliphatic alcohol (methanol or ethanol for example), water or a mixture of these solvents, at a temperature of between 0 and 20° C. It is also possible to carry out the procedure using tertbutyl hydroperoxide in the presence of titanium tetraisopropoxide in a 1-4C aliphatic alcohol (methanol or ethanol for example) or a water-alcohol mixture, at a temperature close to 25° C. or using oxone$^R$ (potassium peroxymonosulfate), in a 1-4C aliphatic alcohol (methanol or ethanol for example), in the presence of water, acetic acid or sulfuric acid, at a temperature close to 20° C.

The reaction (c) is preferably carried out in an inert solvent such as a 1-4C aliphatic alcohol (methanol or ethanol for example), at a temperature of between 20° C. and the boiling temperature of the reaction medium.

The derivatives of formula (IV) are commercially available or may be obtained by application or adaptation of the methods described in the examples. In particular, the methylated derivative or the corresponding alcohol is halogenated using a halogenating agent such as hydrobromic acid, in acetic acid, at a temperature close to 20° C. or N-bromo- or chlorosuccinimide in the presence of benzoyl peroxide, in an inert solvent such as tetrachloromethane, at the boiling temperature of the reaction medium. The methylated derivatives or the corresponding alcohols are commercially available or may be obtained according to the methods described by BRINE G. A. et al., J. Heterocycl. Chem., 26, 677 (1989) and NAGARATHNAM D., Synthesis, 8, 743 (1992) and in the examples.

The azetidinones of formula (III) may be obtained by application or adaptation of the methods described by KATRITZKY A. R. et al., J. Heterocycl. Chem., 271 (1994) or DAVE P. R., J. Org. Chem., 61, 5453 (1996) and in the examples. The procedure is generally carried out according to the following reaction scheme:

In these formulae, $R_3$ and $R_4$ have the same meanings as in formula (I) and X represents a chlorine or bromine atom.

In step A, the procedure is preferably carried out in an inert solvent such as a 1-4C aliphatic alcohol (ethanol or methanol for example), optionally in the presence of an alkali metal hydroxide, at the boiling temperature of the reaction medium.

In step B, the reduction is generally carried out using lithium aluminum hydride, in tetrahydrofuran at the boiling temperature of the reaction medium.

In step C, the procedure is preferably carried out in an inert solvent such as a 1-4C aliphatic alcohol (ethanol or methanol for example) in the presence of sodium hydrogen carbonate, at a temperature of between 20° C. and the boiling temperature of the reaction medium.

In step D, the oxidation is preferably carried out in DMSO, using the sulfurtrioxide-pyridine complex, at a temperature close to 20° C. or using dimethyl sulfoxide, in the presence of oxalyl chloride and triethylamine, at a temperature of between −70 and −50° C.

In step E, the procedure is carried out according to the method described by GRISAR M. et al., in J. Med. Chem., 885 (1973). The magnesium compound of the brominated derivative is formed and then the nitrile is reacted, in an ether such as ethyl ether, at a temperature of between 0° C. and the boiling temperature of the reaction medium. After hydrolysis with an alcohol, the intermediate imine is reduced in situ with sodium borohydride at a temperature of between 0° C. and the boiling temperature of the reaction medium.

The $R_3$—CO—$R_4$ derivatives are commercially available or may be obtained by application or adaptation of the methods described by KUNDER N. G. et al. J. Chem. Soc. Perkin Trans 1, 2815 (1997); MORENO-MARRAS M., Eur. J. Med. Chem., 23 (5) 477 (1988); SKINNER et al., J. Med. Chem., 14 (6) 546 (1971); HURN N. K., Tet. Lett., 36 (52) 9453 (1995); MEDICI A. et al., Tet. Lett., 24 (28) 2901 (1983); RIECKE R. D. et al., J. Org. Chem., 62 (20) 6921 (1997); KNABE J. et al., Arch. Pharm., 306 (9) 648 (1973);

CONSONNI R. et al., J. Chem. Soc. Perkin Trans 1, 1809 (1996); FR-96-2481 and JP-94-261393.

The $R_3Br$ derivatives are commercially available or may be obtained by application or adaptation of the methods described by BRANDSMA L. et al., Synth. Comm., 20 (11) 1697 and 3153 (1990); LEMAIRE M. et al., Synth. Comm., 24 (1) 95 (1994); GODA H. et al., Synthesis, 9 849 (1992); BAEUERLE P. et al., J. Chem. Soc. Perkin Trans 2, 489 (1993).

The $R_4CN$ derivatives are commercially available or may be obtained by application or adaptation of the methods described by BOUYSSOU P. et al., J. Het. Chem., 29 (4) 895 (1992); SUZUKI N. et al., J. Chem. Soc. Chem. Comm., 1523 (1984); MARBURG S. et al., J. Het. Chem., 17 1333 (1980); PERCEC V. et al., J. Org. Chem. 60 (21) 6895 (1995).

The compounds of formula (I) for which R represents a chain (B) in which R' is a hydrogen atom may also be prepared by action of a derivative $R_3CH(Br)R_4$ (VI) for which $R_3$ and $R_4$ have the same meanings as in formula (I) with a derivative of formula:

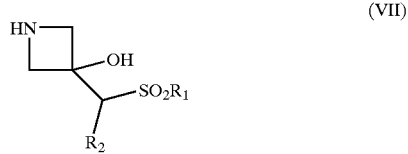

(VII)

in which $R_1$ and $R_2$ have the same meanings as in formula (I).

This reaction is generally carried out in the presence of a base such as an alkali metal carbonate (potassium carbonate for example), in an inert solvent such as acetonitrile, at the boiling temperature of the reaction medium.

The derivatives of formula (VI) are commercially available or may be obtained by application or adaptation of the method described by BACHMANN W. E., J. Am. Chem. Soc., 2135 (1933). Generally, the corresponding alcohol $R_3CHOHR_4$ is brominated using hydrobromic acid, in acetic acid, at a temperature of between 0° C. and the boiling temperature of the reaction medium.

The corresponding $R_3CHOHR_4$ alcohols are commercially available or may be obtained by application or adaptation of the methods described by PLASZ A. C. et al., J. Chem. Soc. Chem. Comm., 527 (1972).

The derivatives of formula (VII) may be obtained by hydrolysis of a derivative of formula:

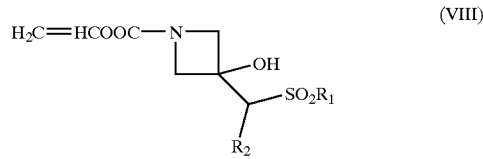

(VIII)

in which $R_1$ and $R_2$ have the same meanings as in formula (I).

This reaction is generally carried out using hydrochloric acid, in an inert solvent such as an ether (dioxane for example), at a temperature close to 20° C.

The derivatives of formula (VIII) are obtained by reacting vinyl chloroformate with a corresponding compound of formula (I) for [lacuna] R represents a chain of formula (B), R' represents a hydroxyl radical, $R_3$ and $R_4$ are phenyl radicals, in an inert solvent such as a chlorinated solvent (dichloromethane or chloroform for example), at a temperature of between 0° C. and the boiling temperature of the reaction mixture.

The compounds of formula (I) for which R is a chain (B) in which R' is a —CO-alk radical may be prepared by reacting a halide Hal-CO-alk in which Hal represents a halogen atom and, preferably, a chlorine atom and alk represents an alkyl radical with a corresponding compound of formula (I) for which R is a chain (B) in which R' is a hydrogen atom.

This reaction is generally carried out in an inert solvent such as tetrahydrofuran, dioxane, a chlorinated solvent (dichloromethane or chloroform for example), at a temperature of between −50° C. and 20° C., in the presence of n-butyllithium.

The compounds of formula (I) for which $R_2$ represents an aromatic or a heteroaromatic substituted with —$NR_6R_7$ in which $R_6$ and $R_7$ each represent a hydrogen atom may also be prepared by reducing a corresponding compound of formula (I) for which $R_2$ represents an aromatic or a heteroaromatic substituted with nitro.

This reaction is carried out by any known method which makes it possible to reduce a nitro to an amino without affecting the rest of the molecule. Preferably, iron is used in the presence of hydrochloric acid in a 1-4C aliphatic alcohol such as ethanol, at the boiling temperature of the reaction medium.

The compounds of formula (I) for which $R_2$ represents an aromatic or heteroaromatic substituted with —$COHNR_9$ and/or $R_3$ and/or $R_4$ represent an aromatic or a heteroaromatic substituted with —$CONR_{10}R_{11}$ may also be prepared by reacting a corresponding compound of formula (I) for which $R_2$ and/or $R_3$ and/or $R_4$ represent an aromatic or a heteroaromatic substituted with —$COOR_5$ for which $R_5$ is alkyl or phenyl optionally substituted with halogens with respectively an amine $H_2NR_9$ or $HNR_{10}R_{11}$ for which $R_9$, $R_{10}$ and $R_{11}$ have the same meanings as in formula (I).

This reaction is generally carried out in an inert solvent such as a chlorinated solvent (dichloromethane or chloroform for example) or a 1-4C aliphatic alcohol (methanol or ethanol for example), at a temperature of between 0° C. and the boiling temperature of the reaction mixture.

The compounds of formula (I) for which $R_2$ represents an aromatic substituted with hydroxyl and/or $R_3$ and/or $R_4$ represent an aromatic or a heteroaromatic substituted with hydroxyl may also be prepared by hydrolysis of a corresponding compound of formula (I) for which $R_2$ represents an aromatic substituted with alkoxy and/or $R_3$ and/or $R_4$ represent an aromatic or a heteroaromatic substituted with alkoxy.

This reaction is carried out by any method of hydrolyzing an alkoxy to a hydroxyl without affecting the rest of the molecule. Preferably, the hydrolysis is carried out using boron tribromide, in a chlorinated solvent such as dichloromethane, at a temperature close to 20° C.

The compounds of formula (I) for which $R_2$ represents an aromatic substituted with —$NR_6R_7$ for which $R_6$ represents an alkyl radical and $R_7$ represents a hydrogen atom may also be prepared by deprotecting a corresponding compound of formula (I) for which $R_2$ represents an aromatic substituted with an —$N(alk)COOR_8$ in which $R_8$ represents a tert-butyl radical.

This reaction is generally carried out using hydrochloric acid, in a solvent such as dioxane at a temperature close to 20° C.

The compounds of formula (I) for which $R_2$ and/or $R_3$ and/or $R_4$ represent an aromatic substituted with —$COOR_5$ may also be prepared by esterification of a derivative of formula:

(IX)

for which R represents a chain C=C(SO$_2$R$_1$)R'$_2$ or C(OR') CH(SO$_2$R$_1$)R'$_2$, R$_1$, R'$_2$, R'$_3$ and R'$_4$ have the same meanings as the substituents R$_1$, R$_2$, R$_3$ and R$_4$ of formula (I) with the proviso that at least one of the substituents R'$_2$, R'$_3$ and R'$_4$ represents an aromatic or a heteroaromatic substituted with carboxyl, using a derivative of formula R$_5$OH for which R$_5$ is alkyl or phenyl optionally substituted with one or more halogens.

When R$_5$ is alkyl, this reaction is generally carried out in the presence of an inorganic acid (sulfuric acid for example), at a temperature of between 20° C. and the boiling temperature of the reaction medium. When R$_5$ is optionally substituted phenyl, this reaction is preferably carried out in the presence of a carbodiimide (1-(3-dimethylaminopropyl)-3-ethylcarbodiimide or N,N'-dicyclohexylcarbodiimide for example), in an inert solvent such as an imide (dimethylformamide) or a chlorinated solvent (methylene chloride, 1,2-dichloroethane or chloroform for example), at a temperature of between 0° C. and the boiling temperature of the reaction mixture.

The derivatives of formula (IX) for which R represents a chain C=C(SO$_2$R$_1$) R'$_2$ or C(OR')CH(SO$_2$R$_1$) R'$_2$, R', R$_1$, R'$_2$, R'$_3$ and R'$_4$ have the same meanings as the substituents R', R$_1$, R$_2$, R$_3$ and R$_4$ of the formula (I) with the proviso that at least one of the substituents R'$_2$, R'$_3$ and R'$_4$ represents an aromatic or a heteroaromatic substituted with carboxyl may be obtained according to the methods described above for the preparation of the compounds of formula (I) from the corresponding intermediates and in particular according to the method described in Example 29.

The compounds of formula (I) for which R$_2$ and/or R$_3$ and/or R$_4$ represent an aromatic or a heteroaromatic substituted with alkylthioalkyl may also be prepared by reaction of a derivative of formula (IX) for which R represents a chain C=C(SO$_2$R$_1$)R'$_2$ or C(OR')CH(SO$_2$R$_1$)R'$_2$, R', R$_1$, R'$_2$, R'$_3$ and R'$_4$ have the same meanings as the substituents R', R$_1$, R$_2$, R$_3$ and R$_4$ of the formula (I) with the proviso that at least one of the substituents R'$_2$, R'$_3$ and R'$_4$ represents an aromatic or a heteroaromatic substituted with haloalkyl with sodium alkylthiolate.

This reaction is generally carried out in an inert solvent such as an amide (dimethylformamide for example), at a temperature close to 20° C.

The derivatives of formula (IX) for which R represents a chain C=C(SO$_2$R$_1$)R'$_2$ or C(OR') CH(SO$_2$R$_1$)R'$_2$, R', R$_1$, R'$_2$, R'$_3$ and R'$_4$ have the same meanings as the substituents R', R$_1$, R$_2$, R$_3$ and R$_4$ of the formula (I) with the proviso that at least one of the substituents R'$_2$, R'$_3$ and R'$_4$ represents an aromatic or a heteroaromatic substituted with haloalkyl may be obtained by reacting a phosphorus trihalide (preferably phosphorus tribromide) with a corresponding compound of formula (I) for which R$_2$ and/or R$_3$ and/or R$_4$ represent an aromatic or a heteroaromatic substituted with hydroxyalkyl, in an inert solvent such as a chlorinated solvent (carbon tetrachloride or chloroform for example), at a temperature close to 20° C.

The compounds of formula (I) for which R$_2$ and/or R$_3$ and/or R$_4$ represent an aromatic substituted with hydroxyalkyl in which the alkyl contains one carbon atom may also be prepared by reducing a compound of formula (I) for which at least one of the substituents R$_2$, R$_3$ and R$_4$ represents an aromatic substituted with formyl.

This reaction is generally carried out using sodium borohydride, in a 1-4C aliphatic alcohol (methanol or ethanol for example), at a temperature close to 0° C.

The compounds of formula (I) for which R$_3$ and/or R$_4$ represents an aromatic substituted with -alk-NR$_6$R$_7$ for which alk is an alkyl containing one carbon atom may also be prepared by reacting a compound of formula (I) for which at least one of the substituents R$_3$ and R$_4$ represents an aromatic substituted with formyl with an amine HNR$_6$R$_7$ in which R$_6$ and R$_7$ have the same meanings as in formula (I).

This reaction is generally carried out in an inert solvent such as a chlorinated solvent (dichloroethane for example), at a temperature close to 20° C. in the presence of sodium triacetoxyborohydride or sodium cyanoborohydride.

The compounds of formula (I) for which R$_2$ represents an aromatic or a heteroaromatic substituted with —CONHR$_9$ and/or R$_3$ and/or R$_4$ represents an aromatic or heteroaromatic substituted with —CO—NR$_{10}$R$_{11}$ may also be prepared by reacting a derivative of formula (IX) for which R represents a chain C=C(SO$_2$R$_1$)R'$_2$ or C(OR')CH(SO$_2$R$_1$) R'$_2$, R', R$_1$, R'$_2$, R'$_3$ and R'$_4$ have the same meanings as the substituents R', R$_1$, R$_2$, R$_3$ and R$_4$ of the formula (I) with the proviso that at least one of the substituents R'$_2$, R'$_3$ and R'$_4$ represents an aromatic or a heteroaromatic substituted with carboxyl with respectively an amine H$_2$NR$_9$ or HNR$_{10}$R$_{11}$ in which R$_9$, R$_{10}$ and R$_{11}$ have the same meanings as in formula (I).

This reaction is preferably carried out in the presence of a condensing agent which is used in peptide chemistry such as a carbodiimide (for example 1-(3-dimethylaminopropyl)-3-ethylcarbodiimide or N,N'-dicyclohexylcarbodiimide) or N,N'-carbonyldiimidazole, in an inert solvent such as an ether (tetrahydrofuran or dioxane for example), an amide (dimethylformamide) or a chlorinated solvent (methylene chloride, 1,2-dichloroethane or chloroform for example) at a temperature of between 0° C. and the boiling temperature of the reaction mixture, or after prior binding of the acid to a resin of the TFP type of formula:

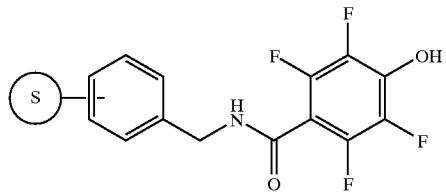

in which S represents an aminopolystyrene resin, in an inert solvent such as dimethylformamide, in the presence of 4-dimethylaminopyridine, at a temperature close to 20° C. The binding to the resin is generally carried out in dimethylformamide, in the presence of 4-dimethylaminopyridine and 1,3-diisopropyl-carbodiimide, at a temperature close to 20° C.

The compounds of formula (I) for which R$_2$ and/or R$_3$ and/or R$_4$, represent an aromatic or a heteroaromatic substituted with —CO—NH—NR$_6$R$_7$ may also be prepared by reacting a corresponding compound of formula (I) for which R$_2$ and/or R$_3$ and/or R$_4$ represent an aromatic or a heteroaromatic substituted with —COOR$_5$ and R$_5$ represents an alkyl or phenyl radical optionally substituted with halogens, with a hydrazine H$_2$N—NR$_6$R$_7$ for which R$_6$ and R$_7$ have the same meanings as in formula (I).

This reaction is generally carried out in an inert solvent such as dimethylformamide, at a temperature close to 20° C.

The compounds of formula (I) for which $R_2$ represents an aromatic or a heteroaromatic substituted with —CO—NHR$_9$ in which $R_9$ represents a hydrogen atom and/or $R_3$ and/or $R_4$ represent an aromatic or a heteroaromatic substituted with —CO—NR$_{10}$R$_{11}$ in which $R_{10}$ and $R_{11}$ are hydrogen atoms may also be prepared by hydrolysis of a corresponding compound of formula (I) for which $R_2$ and/or $R_3$ and/or $R_4$ represent an aromatic or a heteroaromatic substituted with cyano.

This reaction is carried out by any known method which makes it possible to pass from a nitrile to the corresponding carbamoyl without affecting the rest of the molecule. Preferably, the procedure is carried out using hydrochloric acid, in acetic acid, at a temperature close to 20° C.

The compounds of formula (I) for which $R_2$ represents an aromatic substituted with —O-alk-NR$_{12}$R$_{13}$ may also be prepared by reacting a derivative of formula (IX) for which R represents a chain C=C(SO$_2$R$_1$)—R'$_2$ or C(OR')CH (SO$_2$R$_1$)R'$_2$, R', R$_1$, R$_2$', R$_3$' and R$_4$' have the same meanings as the substituents R', R$_1$, R$_2$, R$_3$ and R$_4$ of the formula (I) with the proviso that at least one of the substituents R$_2$', R$_3$' or R$_4$' represents an aromatic substituted with —O-alk-Hal in which alk represents an alkyl radical and Hal represents a halogen atom and, preferably, a chlorine or bromine atom, with an amine HNR$_{12}$R$_{13}$ in which R$_{12}$R$_{13}$ have the same meanings as in formula (I).

This reaction is generally carried out in an inert solvent such as acetonitrile, in the presence of an alkali metal carbonate (potassium carbonate for example), at a temperature close to 20° C.

The derivatives of formula (IX) for which R represents a chain C=C(SO$_2$R$_1$) R'$_2$ or C(OR') CH(SO$_2$R$_1$) R'$_2$, R', R$_1$, R$_2$', R$_3$' and R$_4$' have the same meanings as the substituents R', R$_1$, R$_2$, R$_3$ and R$_4$ of the formula (I) with the proviso that at least one of the substituents R$_2$', R$_3$' or R$_4$' represents an aromatic substituted with —O-alk-Hal in which alk represents an alkyl radical and Hal represents a halogen atom may be obtained by reacting a corresponding compound of formula (I) for which $R_2$ represents an aromatic substituted with hydroxide with a Hal-alk-Hal derivative in which Hal represents a halogen.

This reaction is generally carried out in an inert solvent such as a ketone (methyl ethyl ketone for example), in the presence of a base such as an alkali metal carbonate (potassium carbonate for example), at the boiling temperature of the reaction medium.

The compounds of formula (I) for which $R_3$ and/or $R_4$ represents an aromatic substituted with -alk-NR$_6$R$_7$ may also be prepared by reacting a derivative of formula (IX) for which R represents a chain C=C(SO$_2$R$_1$)R'$_2$ or C(OR') CH(SO$_2$R$_1$) R'$_2$, R', R$_1$, R$_2$', R$_3$' and R$_4$' have the same meanings as the substituents R', R$_1$, R$_2$, R$_3$ and R$_4$ of the formula (I) with the proviso that at least one of the substituents R$_3$' or R$_4$' represents a substituted aromatic -alk-Cl in which alk represents an alkyl radical with an amine HNR$_6$R$_7$ in which R$_6$R$_7$ have the same meanings as in formula (I).

This reaction is generally carried out in an inert solvent such as a chlorinated solvent (dichloromethane for example), optionally in the presence of a nitrogen base such as dimethylaminopyridine, diisopropylethylamine, at a temperature of between 5 and 25° C.

The derivatives of formula (IX) in which R represents a chain C=C(SO$_2$R$_1$)R'$_2$ or C(OR') CH(SO$_2$R$_1$)R$_2$, R', R$_1$, R$_2$', R$_3$' and R$_4$' have the same meanings as the substituents R', R$_1$, R$_2$, R$_3$ and R$_4$ of the formula (I) with the proviso that at least one of the substituents R$_3$' or R$_4$' represents an aromatic substituted with -alk-Cl may be obtained by reacting thionyl chloride with a corresponding compound of formula (I) for which at least one of the substituents R$_3$ or R$_4$ represents an aromatic substituted with one or more hydroxyalkyl radicals.

This reaction is generally carried out in an inert solvent such as a chlorinated solvent (dichloromethane for example), at a temperature of between 10 and 30° C.

The compounds of formula (I) for which R represents a chain B, R' represents a hydrogen atom and R$_3$ and/or R$_4$ represents an aromatic substituted with hydroxyalkyl in which the alkyl residue contains one carbon atom may also be prepared by reacting diisobutylaluminum hydride with a corresponding compound of formula (I) for which R represents a chain B, R' represents a hydrogen atom and R$_3$ and/or R$_4$ represents an aromatic substituted with one or more —COOR$_5$ radicals, in which R$_5$ is an alkyl radical.

This reaction is generally carried out in toluene, at a temperature of between −30° C. and 0° C.

The compounds of formula (I) for which $R_2$ represents a phenyl radical substituted with —NR$_6$R$_7$ representing a 1-piperazinyl ring substituted at the 4 position with an alkyl radical may also be prepared by reacting a corresponding compound of formula (I) for which $R_2$ represents a phenyl radical substituted with a radical —NR$_6$R$_7$ representing a 1-piperazinyl ring with an alk-CHO derivative in which alk represents a straight- or branched-chain alkyl radical containing 1 to 5 carbon atoms.

This reaction is generally carried out in an inert solvent such as a chlorinated solvent (dichloroethane or chloroform for example), in the presence of NaBH(OCOCH$_3$)$_3$, at a temperature close to 20° C.

The compounds of formula (I) for which $R_2$ represents a phenyl radical substituted with —NR$_6$R$_7$ representing a 1-piperazinyl ring substituted at the 4 position with a radical —COOalk may also be prepared by reacting a corresponding compound of formula (I) for which $R_2$ represents a phenyl radical substituted with a radical —NR$_6$R$_7$ representing a 1-piperazinyl ring with a derivative of formula Hal-COOalk in which alk represents an alkyl radical and Hal represents a halogen atom and, preferably, a chlorine atom.

This reaction is generally carried out in pyridine, at a temperature close to 20° C.

The compounds of formula (I) for which $R_2$ represents a phenyl radical substituted with —NR$_6$R$_7$ representing a 1-piperazinyl ring substituted at the 4 position with a radical —CO—NHalk or —CS—NHalk may also be prepared by reacting a corresponding compound of formula (I) for which $R_2$ represents a phenyl radical substituted with —NR$_6$R$_7$ representing a 1-piperazinyl ring with a derivative of formula Y=C=Nalk in which alk represents a straight- or branched-chain alkyl radical containing 1 to 6 carbon atoms and Y represents a sulfur or oxygen atom.

This reaction is generally carried out in an inert solvent such as a chlorinated solvent (dichloromethane for example), at a temperature close to 20° C.

The compounds of formula (I) for which $R_2$ represents a phenyl radical substituted with a radical —NR$_6$R$_7$ representing a 1-piperazinyl ring substituted at the 4 position with a radical —CO-alk-NR$_{14}$R$_{15}$ may also be prepared by reacting a corresponding compound of formula (I) for which $R_2$ represents a phenyl radical substituted with a radical —NR$_6$R$_7$ representing a 1-piperazinyl ring with an acid of formula R$_{15}$R$_{14}$N-alk-COOH in which alk represents an alkyl radical and R$_{14}$ and R$^{15}$ have the same meanings as in formula (I), optionally followed by deprotection of the product for which $R_{14}$ is a tert-butoxycarbonyl radical in order to obtain the compounds for which $R_{14}$ is a hydrogen atom.

This reaction is generally carried out in an inert solvent such as a chlorinated solvent (dichloroethane for example), at a temperature close to 20° C. The deprotection is carried out using formic acid at a temperature close to 20° C.

The compounds of formula (I) for which $R_2$ represents a phenyl radical substituted with a radical —$NR_6R_7$ representing a 1-piperazinyl ring substituted at the 4 position with a radical —CO-alk in which alk represents a methyl radical may also be prepared by reacting a corresponding compound of formula (I) for which $R_2$ represents a phenyl radical substituted with a radical —$NR_6R_7$ representing a 1-piperazinyl ring with acetic anhydride.

This reaction is generally carried out in the presence of pyridine, at a temperature close to 20° C.

It is understood for persons skilled in the art that, to carry out the processes according to the invention which are described above, it may be necessary to introduce groups protecting amino, hydroxyl and carboxyl functions in order to avoid side reactions. These groups are those which allow removal without affecting the rest of the molecule. As examples of groups protecting the amino function, there may be mentioned tert-butyl or methylcarbamates which may be regenerated using iodotrimethylsilane or allyl using palladium catalysts. As examples of groups protecting the hydroxyl function, there may be mentioned triethylsilyl and tert-butyldimethylsilyl which may be regenerated using tetrabutylammonium fluoride or alternatively asymmetric acetals (methoxymethyl or tetrahydropyranyl for example) with regeneration using hydrochloric acid. As groups protecting carboxyl functions, there may be mentioned esters (allyl or benzyl for example), oxazoles and 2-alkyl-1,3-oxazolines. Other protecting groups which can be used are described by GREENE T. W. et al., Protecting Groups in Organic Synthesis, second edition, 1991, John Wiley & Sons.

The compounds of formula (I) may be purified by the customary known methods, for example by crystallization, chromatography or extraction.

The enantiomers of the compounds of formula (I) may be obtained by resolution of the racemates for example by chromatography on a chiral column according to PIRCKLE W. H. et al., Asymmetric synthesis, Vol. 1, Academic Press (1983) or by formation of salts or by synthesis from chiral precursors. The diastereoisomers may be prepared according to known conventional methods (crystallization, chromatography or from chiral precursors).

The compounds of formula (I) may be optionally converted to addition salts with an inorganic or organic acid by the action of such an acid in an organic solvent such as an alcohol, a ketone, an ether or a chlorinated solvent. These salts also form part of the invention.

As examples of pharmaceutically acceptable salts, the following salts may be mentioned: benzenesulfonate, hydrobromide, hydrochloride, citrate, ethanesulfonate, fumarate, gluconate, iodate, isethionate, maleate, methane sulfonate, methylene-bis-β-oxynaphtoate, nitrate, oxalate, pamoate, phosphate, salicylate, succinate, sulfate, tartrate, theophyllineacetate and p-toluenesulfonate.

The compounds of formula (I) exhibit advantageous pharmacological properties. These compounds possess a high affinity for the cannabinoid receptors and particularly those of the CB1 type. They are CBI receptor antagonists and are therefore useful in the treatment and prevention of disorders affecting the central nervous system, the immune system, the cardiovascular or endocrine system, the respiratory system, the gastrointestinal apparatus and reproductive disorders (Hollister, Pharm. Rev.; 38, 1986, 1–20, Reny and Sinha, Prog. Drug Res., 36, 71–114 (1991), Consroe and Sandyk, in Marijuana/Cannabinoids, Neurobiology and Neurophysiology, 459, Murphy L. and Barthe A. Eds, CRC Press, 1992) of bacterial, viral and parasitic infections.

Accordingly, these compounds may be used for the treatment or prevention of psychoses including schizophrenia, anxiety disorders, depression, epilepsy, neurodegeneration, cerebellar and spinocerebellar disorders, cognitive disorders, cranial trauma, panic attacks, peripheral neuropathies, glaucomas, migraine, Parkinson's disease, Alzeimer's disease, Huntington's chorea, Raynaud's syndrome, tremor, obsessive-compulsive disorder, senile dementia, thymic disorders, Tourette's syndrome, tardive dyskinesia, bipolar disorders, cancers, movement disorders induced by medicaments, dystonia, endotoxemic shocks, hemorrhagic shocks, hypotension, insomnia, immunological diseases, multiple sclerosis, vomiting, asthma, appetite disorders (bulimia, anorexia), obesity, memory disorders, in weaning from chronic treatments and alcohol or drug abuse (opiods, barbiturates, cannabis, cocaine, amphetamine, phencyclide, hallucinogens, benzodiazepines for example), as analgesics or potentiators of the analgesic activity of the narcotic and nonnarcotic drugs. They may also be used for the treatment or prevention of intestinal transit disorders, as antibacterial, antiviral and antiparasitic agents.

The affinity of the compounds of formula (I) for the cannabis receptors has been determined according to the method described by KUSTER J. E., STEVENSON J. I., WARD S. J., D'AMBRA T. E., HAYCOCK D. A. in J. Pharmacol. Exp. Ther., 264 1352–1363 (1993).

In this test, the $IC_{50}$ of the compounds of formula (I) is less than or equal to 100 nM.

Their antagonist activity has been shown by means of the model of hypothermia induced by an agonist of the cannabis receptors (CP-55940) in mice, according to the method described by Pertwee R. G. in Marijuana, Harvey D. J. eds, 84 Oxford IRL Press, 263–277 (1985).

In this text the ED50 of the compounds of formula (I) is less than or equal to 50 mg/kg.

The compounds of formula (I) exhibit low toxicity. Their $LD_{50}$ is greater than 40 mg/kg by the subcutaneous route in mice.

The preferred compounds of formula (I) are those for which

R represents a chain (A) or (B) and R' represents a hydrogen atom or a —COalk radical, $R_1$ represents a methyl or ethyl radical, $R_2$ represents either an aromatic chosen from phenyl and naphthyl, these aromatics being nonsubstituted or substituted with one or more halogens, alkyl, alkoxy, hydroxyl, —$COOR_5$, trifluoromethyl, trifluoromethylsulfanyl, trifluoromethoxy, —$NR_6R_7$, —CO—NH—$NR_6R_7$, cyano, —$CONHR_9$, alkylsulfanyl, hydroxyalkyl, nitro, —CO—$NR_{16}R_{17}$, —O-alk$NR_{12}R_{13}$ or alkylthioalkyl or a heteroaromatic chosen from isoquinolyl, pyridyl, quinolyl, 1,2,3,4-tetrahydroisoquinolyl, 1,2,3,4-tetrahydroquinolyl and thienyl, these heteroaromatics being unsubstituted or substituted with a halogen, alkyl, alkoxy, —$COOR_5$, trifluoromethyl, trifluoromethylsulfanyl, trifluoromethoxy, —$NR_6R_7$, —CO—NH—$NR_6R_7$, cyano, —$CONHR_9$, alkylsulfanyl, hydroxyalkyl, nitro or alkylthioalkyl, $R_3$ and $R_4$, which are identical or different, represent either an aromatic chosen from phenyl or naphthyl, these aromatics being nonsubstituted or substituted with one or more halogens, alkyl, alkoxy, trifluoromethyl, trifluoromethoxy, —CONR$_{10}$R$_{11}$, -alk-NR$_6$R$_7$, hydroxyalkyl, formyl or —COOR$_5$, or a heteroaromatic chosen from thiazolyl or thienyl rings, these heteroaromatics being unsubstituted or substituted with a halogen, alkyl, alkoxy, —CONR$_{10}$R$_{11}$, -alk-NR$_6$R$_7$, hydroxyalkyl or —COOR$_5$.

R$_5$ is alkyl or phenyl which is optionally substituted with one or more halogens, R$_6$ and R$_7$, which are identical or different, represent a hydrogen atom or an alkyl, —COOalk, cycloalkyl, alkylcycloalkyl,-alk-O-alk or hydroxyalkyl radical or alternatively R$_6$ and R$_7$ together form with the nitrogen atom to which they are attached a 3- to 10-membered saturated or unsaturated mono- or bicyclic heterocycle optionally containing another heteroatom chosen from oxygen, sulfur and nitrogen and being optionally substituted with one or more alkyl, —COalk, —COOalk, —CO—NHalk, —CS—NHalk, —CO-alk-NR$_{14}$R$_{15}$, oxo, hydroxyalkyl, alk-O-alk or —CO—NH$_2$ radicals, R$_9$ represents a hydrogen atom or an alkyl radical or an alkyl radical substituted with dialkylamino, phenyl, cycloalkyl (optionally substituted with —COOalk) or a 3- to 10-membered saturated or unsaturated mono- or bicyclic heterocycle optionally containing one or more heteroatoms chosen from oxygen, sulfur and nitrogen and being optionally substituted with one or more alkyl radicals, R$_{10}$ and R$_{11}$, which are identical or different, represent a hydrogen atom or an alkyl radical or alternatively R$_{10}$ and R$_{11}$ together form with the nitrogen atom to which they are attached a 3- to 10-membered saturated mono- or bicyclic heterocycle optionally containing another heteroatom chosen from oxygen, sulfur and nitrogen and being optionally substituted with an alkyl radical, R$_{12}$ and R$_{13}$, which are identical or different, represent a hydrogen atom or an alkyl or cycloalkyl radical or alternatively R$_{12}$ and R$_{13}$ together form with the nitrogen atom to which they are attached a 3- to 10-membered saturated mono- or bicyclic heterocycle optionally containing another heteroatom chosen from oxygen, sulfur and nitrogen and being optionally substituted with an alkyl, —COalk, —COOalk, —CO—NHalk, —CS—NHalk or —CO-alk-NR$_{14}$R$_{15}$ radical or a 3- to 10-membered saturated mono- or bicyclic heterocycle containing a heteroatom chosen from oxygen, sulfur and nitrogen, R$_{14}$ and R$_{15}$, which are identical or different, represent a hydrogen atom or an alkyl or —COOalk radical, R$_{16}$ and R$_{17}$ together form with the nitrogen atom to which they are attached a 3- to 10-membered saturated mono- or bicyclic heterocycle optionally containing another heteroatom chosen from oxygen, sulfur and nitrogen, alk represents an alkyl or alkylene radical, their optical isomers and their salts with an inorganic or organic acid.

The compounds of formula (I) which are particularly preferred are those for which R represents a chain (A) or (B), R' representing a hydrogen atom or a radical —COalk, R$_1$ represents a methyl or ethyl radical, R$_2$ represents either an aromatic chosen from naphthyl, phenyl, phenyl substituted with one or more halogen, alkyl, alkoxy, hydroxyl, —COOR$_5$, (in which R$_5$, represents an alkyl or phenyl radical optionally substituted with several halogens) trifluoromethyl, trifluoromethylsulfanyl, trifluoromethoxy, —NR$_6$R$_7$ (in which R$_6$ and R$_7$, which are identical or different, represent a hydrogen atom or an alkyl or —COOalk radical or alternatively R$_6$ and R$_7$ together form with the nitrogen atom to which they are attached a heterocycle chosen from pyrrolidinyl, piperidyl, piperazinyl or piperazinyl substituted with one or more alkyl, —COalk, —COOalk, —CO—NHalk, —CS—NHalk or —CO-alk-NR$_{14}$R$_{15}$ radicals, in which R$_{14}$ and R$_{15}$, which are identical or different, represent a hydrogen atom or an alkyl radical), —CO—NH—NR$_6$R$_7$ (R$_6$ and R$_7$, which are identical or different, represent a hydrogen atom or an alkyl radical or alternatively R$_6$ and R$_7$ together form with the nitrogen atom to which they are attached a heterocycle chosen from piperidyl, piperazinyl or piperazyl substituted with one or more alkyl radicals), cyano, —CONHR$_9$ (in which R$_9$ represents a hydrogen atom or an alkyl radical or an alkyl radical substituted with dialkylamino, phenyl, cycloalkyl (optionally substituted with —COOalk) or a heterocycle chosen from pyrrolidinyl (optionally substituted with alkyl), tetrahydrofuryl, or morpholinyl), alkylsulfanyl, hydroxyalkyl, nitro, —CO—NR$_{16}$R$_{17}$, (in which R$_{16}$ and R$_{17}$ together form with the nitrogen atom to which they are attached a piperidyl ring), —O-alkNR$_{12}$R$_{13}$ (in which R$_{12}$ and R$_{13}$ together form with the nitrogen atom to which they are attached a morpholino ring) or alkylthioalkyl, or a heteroaromatic chosen from isoquinolyl, pyridyl, quinolyl, 1,2,3,4-tetrahydroisoquinolyl, 1,2,3,4-tetrahydroquinolyl, thienyl, or thienyl substituted with a —COOR$_5$ (in which R$_5$ represents an alkyl radical) or —CONHR$_9$, (in which R$_9$ represents an alkyl radical), R$_3$ and R$_4$, which are identical or different, represent either an aromatic chosen from phenyl or phenyl substituted with one or more halogen, alkyl, alkoxy, trifluoromethyl, trifluoromethoxy, hydroxyalkyl, formyl, —COOR$_5$ (in which R$_5$ is an alkyl radical), —CONR$_{10}$R$_{11}$ (in which R$_{10}$ and R$_{11}$, which are identical or different, represent a hydrogen atom or an alkyl radical), -alk-NR$_6$R$_7$ (in which R$_6$ and R$_7$, which are identical or different, represent a hydrogen atom or an alkyl, cycloalkyl, -alk-O-alk or hydroxyalkyl radical or alternatively R$_6$ and R$_7$ together form with the nitrogen atom to which they are attached a heterocycle chosen from piperidyl (optionally substituted with alkyl or oxo), pyrrolidinyl (optionally substituted with alkyl, hydroxyalkyl, -alk-O-alk or —CO—NH$_2$), thiomorpholinyl, morpholinyl, pyrrolyl, piperazinyl optionally substituted with oxo, alkyl, hydroxyalkyl, —COOR$_5$ (in which R$_5$ is an alkyl radical), or a heteroaromatic chosen from thiazolyl or thienyl, alk represents an alkyl or alkylene radical, their optical isomers and their salts with an inorganic or organic acid.

Preferably, R$_2$ is a substituted phenyl radical, the latter is monosubstituted and, in particular, at the 3-position or alternatively disubstituted and, in particular at the 3,5, 2,5 or 2,3-positions.

Preferably, when R$_3$ is a substituted phenyl radical, the latter is monosubstituted and, in particular, at the 4-position or disubstituted and, in particular, at the 2,4-positions.

Preferably, when R$_4$ is a substituted phenyl radical, the latter is monosubstituted and, in particular, at the 4-position or disubstituted and, in particular, at the 2,4-positions.

The following compounds may be mentioned among the preferred compounds:
1-benzhydryl-3-[(methylsulfonyl)(phenyl)methylene]azetidine,
1-benzhydryl-3-[(3-methylphenyl)(methylsulfonyl)methylene]azetidine,
1-benzhydryl-3-[(3-chlorophenyl)(methylsulfonyl)methylene]azetidine,
1-benzhydryl-3-[(3,5-dichlorophenyl)(methylsulfonyl)methylene]azetidine,
1-benzhydryl-3-[(2,5-dichlorophenyl)(methylsulfonyl)methylene]azetidine,
1-benzhydryl-3-[(2,3-dichlorophenyl)(methylsulfonyl)methylene]azetidine,
1-benzhydryl-3-[(3-fluorophenyl)(methylsulfonyl)methylene]azetidine,
1-benzhydryl-3-[(3,5-difluorophenyl)(methylsulfonyl)methylene]azetidine,
1-benzhydryl-3-[(3-bromophenyl)(methylsulfonyl)methylene]azetidine,
1-benzhydryl-3-[(3-iodophenyl)(methylsulfonyl)methylene]azetidine,
1-benzhydryl-3-[(methylsulfonyl)(3-trifluoromethoxyphenyl)methylene]azetidine,
1-benzhydryl-3-[(methylsulfonyl)(3-trifluoromethylphenyl)methylene]azetidine,
1-benzhydryl-3-{[3,5-bis(trifluoromethyl)phenyl]-(methylsulfonyl)methylene}azetidine,
1-benzhydryl-3-[(3,5-dibromophenyl)(methylsulfonyl)methylene]azetidine,
1-benzhydryl-3-[(3-methoxycarbonylphenyl)(methylsulfonyl)methylene]azetidine,
1-benzhydryl-3-[(3-cyanophenyl)(methylsulfonyl)methylene]azetidine,
1-benzhydryl-3-[(3-cyanophenyl)(methylsulfonyl)methylene]azetidine,
1-benzhydryl-3-[(3-carbamoylphenyl)(methylsulfonyl)methylene]azetidine,
1-benzhydryl-3-[(methylsulfonyl)(naphth-1-yl)(methylsulfonyl)methylene]azetidine,
1-[bis(4-chlorophenyl)methyl]-3-[(3,5-difluorophenyl)(methylsulfonyl)methylene]azetidine,
1-[bis(4-methoxyphenyl)methyl]-3-[(3,5-difluorophenyl)(methylsulfonyl)methylene]azetidine,
1-[bis(4-methylphenyl)methyl]-3-[(3,5-difluorophenyl)(methylsulfonyl)methylene]azetidine,
(RS)-3-[(3,5-difluorophenyl)(methylsulfonyl)methylene]-1-[(4-methoxyphenyl)(phenyl)methyl)]azetidine,
(R)-3-[(3,5-difluorophenyl)(methylsulfonyl)methylene]-1-[(4-methoxyphenyl)(phenyl)methyl)]azetidine,
(S)-3-[(3,5-difluorophenyl)(methylsulfonyl)methylene]-1-[(4-methoxyphenyl)(phenyl)methyl)]azetidine,
1-[bis(4-trifluoromethoxyphenyl)methyl]-3-[(3,5-difluorophenyl(methylsulfonyl)methylene]azetidine,
1-[bis(4-trifluoromethylphenyl)methyl]-3-[(3,5-difluorophenyl(methylsulfonyl)methylene]azetidine,
1-[bis(4-chlorophenyl)methyl]-3-{[(3,5-bis(trifluoromethyl)phenyl]methylsulfonylmethylene}azetidine,
(RS)-1-[(4-chlorophenyl)(2,4-dichlorophenyl)methyl]-3-[(3,5-difluorophenyl)(methylsulfonyl)methylene]azetidine,
(R)-1-[(4-chlorophenyl)(2,4-dichlorophenyl)methyl]-3-[(3,5-difluorophenyl)(methylsulfonyl)methylene]azetidine,
(S)-1-[(4-chlorophenyl)(2,4-dichlorophenyl)methyl]-3-[(3,5-difluorophenyl)(methylsulfonyl)methylene]azetidine,
(RS)-1-{(4-chlorophenyl)[4-hydroxymethyl)phenyl]methyl}-3-[(3,5-difluorophenyl)(methylsulfonyl)methylene]azetidine,
(R)-1-{(4-chlorophenyl)[4-(hydroxymethyl)phenyl]methyl}-3-[(3,5-difluorophenyl)(methylsulfonyl)methylene]azetidine,
(S)-1-{(4-chlorophenyl)[4-(hydroxymethyl)phenyl]methyl}-3-[(3,5-difluorophenyl)(methylsulfonyl)methylene]azetidine,
(RS)-1-{(4-chlorophenyl)[4-(pyrrolidylmethyl)phenyl]methyl}-3-[(3,5-difluorophenyl)(methylsulfonyl)methylene]azetidine,
(R)-1-{(4-chlorophenyl)[4-(pyrrolidylmethyl)phenyl]methyl}-3-[(3,5-difluorophenyl)(methylsulfonyl)methylene]azetidine,
(S)-1-{(4-chlorophenyl)[4-(pyrrolidylmethyl)phenyl]methyl}-3-[(3,5-difluorophenyl)(methylsulfonyl)methylene]azetidine,
1-{(RS)-(4-chlorophenyl)[4-(3,3-dimethylpiperidin-1-yl-methyl)phenyl]methyl}-3-[(3,5-difluorophenyl)(methylsulfonyl)methylene]azetidine,
1-{(R)-(4-chlorophenyl)[4-(3,3-dimethylpiperidin-1-yl-methyl)phenyl]methyl}-3-[(3,5-difluorophenyl)(methylsulfonyl)methylene]azetidine,
1-{(S)-(4-chlorophenyl)[4-(3,3-dimethylpiperidin-1-yl-methyl)phenyl]methyl}-3-[(3,5-difluorophenyl)(methylsulfonyl)methylene]azetidine,
1-{(RS)-(4-chlorophenyl)[4-(thiomorpholin-4-ylmethyl)phenyl]methyl}-3-[(3,5-difluorophenyl)(methylsulfonyl)methylene]azetidine,
1-{(R)-(4-chlorophenyl)[4-(thiomorpholin-4-ylmethyl)phenyl]methyl}-3-[(3,5-difluorophenyl)(methylsulfonyl)methylene]azetidine,
1-{(S)-(4-chlorophenyl)[4-(thiomorpholin-4-ylmethyl)phenyl]methyl}-3-[(3,5-difluorophenyl)(methylsulfonyl)methylene]azetidine,
1-{(RS)-(4-chlorophenyl)[4-(N-ethyl-N-cyclohexylaminomethyl)phenyl]methyl}-3-[(3,5-difluorophenyl)(methylsulfonyl)methylene]azetidine,
1-{(R)-(4-chlorophenyl)[4-(N-ethyl-N-cyclohexylaminomethyl)phenyl]methyl}-3-[(3,5-difluorophenyl)(methylsulfonyl)methylene]azetidine,
1-{(S)-(4-chlorophenyl)[4-(N-ethyl-N-cyclohexylaminomethyl)phenyl]methyl}-3-[(3,5-difluorophenyl)(methylsulfonyl)methylene]azetidine,
1-{{(RS)-(4-chlorophenyl){4-[(4-ethoxycarbonylpiperazinyl)methyl]phenyl}methyl}}-3-[(3,5-difluorophenyl)(methylsulfonyl)methylene]azetidine,
1-{{(R)-(4-chlorophenyl){4-[(4-ethoxycarbonylpiperazinyl)methyl]phenyl}methyl}}-3-[(3,5-difluorophenyl)(methylsulfonyl)methylene]azetidine,
1-{{(S)-(4-chlorophenyl){4-[(4-ethoxycarbonylpiperazinyl)methyl]phenyl}methyl}}-3-[(3,5-difluorophenyl)(methylsulfonyl)methylene]azetidine,
1-{(RS)-(4-chlorophenyl)[4-(N-cyclopropyl-N-propyl-aminomethyl)phenyl]methyl}-3-[(3,5-difluorophenyl)(methylsulfonyl)methylene]azetidine,
1-{(R)-(4-chlorophenyl)[4-(N-cyclopropyl-N-propyl-aminomethyl)phenyl]methyl}-3-[(3,5-difluorophenyl)(methylsulfonyl)methylene]azetidine,
1-{(S)-(4-chlorophenyl)[4-(N-cyclopropyl-N-propyl-aminomethyl)phenyl]methyl}-3-[(3,5-difluorophenyl)(methylsulfonyl)methylene]azetidine,
1-{(RS)-(4-chlorophenyl)[4-(diisopropylaminomethyl)phenyl]methyl}-3-[(3,5-difluorophenyl)(methylsulfonyl)methylene]azetidine,
1-{(R)-(4-chlorophenyl)[4-(diisopropylaminomethyl)phenyl]methyl}-3-[(3,5-difluorophenyl)(methylsulfonyl)methylene]azetidine, 1-{(S)-(4-chlorophenyl)[4-(diisopropylaminomethyl)phenyl]methyl}-3-(3,5-difluorophenyl)(methylsulfonyl)methylene]azetidine,
1-{{(RS)-(4-chlorophenyl){4-[bis-(2-methoxyethyl)aminomethyl]phenyl}methyl}}-3-[(3,5-difluorophenyl)(methylsulfonyl)methylene]azetidine,
1-{{(R)-(4-chlorophenyl){4-[bis-(2-methoxyethyl)aminomethyl]phenyl}methyl}}-3-[(3,5-difluorophenyl)(methylsulfonyl)methylene]azetidine,
1-{{(S)-(4-chlorophenyl){4-[bis-(2-methoxyethyl)aminomethyl]phenyl}methyl}}-3-[(3,5-difluorophenyl)(methylsulfonyl)methylene]azetidine,
1-{(RS)-(4-chlorophenyl)[4-(di-n-propylaminomethyl)phenyl]methyl}-3-[(3,5-difluorophenyl)(methylsulfonyl)methylene]azetidine,
1-{(R)-(4-chlorophenyl)[4-(di-n-propylaminomethyl)phenyl]methyl}-3-[(3,5-difluorophenyl)(methylsulfonyl)methylene]azetidine,
1-{(S)-(4-chlorophenyl)[4-(di-n-propylaminomethyl)phenyl]methyl}-3-[(3,5-difluorophenyl)(methylsulfonyl)methylene]azetidine,
1-{(RS)-(4-chlorophenyl)[4-(piperidin-1-ylmethyl)phenyl]methyl}-3-[(3,5-difluorophenyl)(methylsulfonyl)methylene]azetidine,
1-{(R)-(4-chlorophenyl)[4-(piperidin-1-ylmethyl)phenyl]methyl}-3-[(3,5-difluorophenyl)(methylsulfonyl)methylene]azetidine,
1-{(S)-(4-chlorophenyl)[4-(piperidin-1-ylmethyl)phenyl]methyl}-3-[(3,5-difluorophenyl)(methylsulfonyl)methylene]azetidine,
1-{(RS)-(4-chlorophenyl)[4-(4-methylpiperazin-1-yl-methyl)phenyl]methyl}-3-[(3,5-difluorophenyl)(methylsulfonyl)methylene]azetidine,
1-{(R)-(4-chlorophenyl)[4-(4-methylpiperazin-1-yl-methyl)phenyl]methyl}-3-[(3,5-difluorophenyl)(methylsulfonyl)methylene]azetidine,
1-{(S)-(4-chlorophenyl)[4-(4-methylpiperazin-1-yl-methyl)phenyl]methyl}-3-[(3,5-difluorophenyl)(methylsulfonyl)methylene]azetidine,
1-{(RS)-(4-chlorophenyl)[4-(morpholin-4-yl-methyl)phenyl]methyl}-3-[(3,5-difluorophenyl)(methylsulfonyl)methylene]azetidine,
1-{(R)-(4-chlorophenyl)[4-(morpholin-4-yl-methyl)phenyl]methyl}-3-[(3,5-difluorophenyl)(methylsulfonyl)methylene]azetidine,
1-{(S)-(4-chlorophenyl)[4-(morpholin-4-yl-methyl)phenyl]methyl}-3-[(3,5-difluorophenyl)(methylsulfonyl)methylene]azetidine,
1-{(RS)-(4-chlorophenyl)[4-(diethylaminomethyl)phenyl]methyl}-3-[(3,5-difluorophenyl)(methylsulfonyl)methylene]azetidine,
1-{(R)-(4-chlorophenyl)[4-(diethylaminomethyl)phenyl]methyl}-3-[(3,5-difluorophenyl)(methylsulfonyl)methylene]azetidine,
1-{(S)-(4-chlorophenyl)[4-(diethylaminomethyl)phenyl]methyl}-3-[(3,5-difluorophenyl)(methylsulfonyl)methylene]azetidine,
1-{(RS)-(4-chlorophenyl)[4-(piperazin-2-on-4-yl-methyl)phenyl]methyl}-3-[3,5-difluorophenyl)(methylsulfonyl)methylene]azetidine,
1-{(R)-(4-chlorophenyl)[4-(piperazin-2-on-4-yl-methyl)phenyl]methyl}-3-[(3,5-difluorophenyl)(methylsulfonyl)methylene]azetidine,
1-{(S)-(4-chlorophenyl)[4-(piperazin-2-on-4-yl-methyl)phenyl]methyl}-3-[3,5-difluorophenyl)(methylsulfonyl)methylene]azetidine,
1-{(RS)-(4-chlorophenyl)[4-(imidazol-1-yl-methyl)phenyl]methyl}-3-[(3,5-difluorophenyl)(methylsulfonyl)methylene]azetidine,
1-{(R)-(4-chlorophenyl)[4-(imidazol-1-yl-methyl)phenyl]methyl}-3-[(3,5-difluorophenyl)(methylsulfonyl)methylene]azetidine,
1-{(S)-(4-chlorophenyl)[4-(imidazol-1-yl-methyl)phenyl]methyl}-3-[(3,5-difluorophenyl)(methylsulfonyl)methylene]azetidine,
(RS)-1-{(4-chlorophenyl)[4-(N,N-dimethylcarbamoyl)phenyl]methyl}-3-[(3,5-difluorophenyl)(methylsulfonyl)methylene]azetidine,
(R)-1-{(4-chlorophenyl)[4-(N,N-dimethylcarbamoyl)phenyl]methyl}-3-[(3,5-difluorophenyl)(methylsulfonyl)methylene]azetidine,
(S)-1-{(4-chlorophenyl)[4-(N,N-dimethylcarbamoyl)phenyl]methyl}-3-[(3,5-difluorophenyl)(methylsulfonyl)methylene]azetidine,
(RS)-1-{(4-chlorophenyl)[4-(N-ethylcarbamoyl)phenyl]methyl}-3-[(3,5-difluorophenyl)(methylsulfonyl)methylene]azetidine,
(R)-1-{(4-chlorophenyl)[4-(N-ethylcarbamoyl)phenyl]methyl}-3-[(3,5-difluorophenyl)(methylsulfonyl)methylene]azetidine,
(S)-1-{(4-chlorophenyl)[4-(N-ethylcarbamoyl)phenyl]methyl}-3-[(3,5-difluorophenyl)(methylsulfonyl)methylene]azetidine,
(RS)-1-[(4-carbamoylphenyl)(4-chlorophenyl)methyl]-3-[(3,5-difluorophenyl)(methylsulfonyl)methylene]azetidine,
(R)-1-[(4-carbamoylphenyl)(4-chlorophenyl)methyl]-3-[(3,5-difluorophenyl)(methylsulfonyl)methylene]azetidine,
(S)-1-[(4-carbamoylphenyl)(4-chlorophenyl)methyl]-3-[(3,5-difluorophenyl)(methylsulfonyl)methylene]azetidine,
1-[bis(4-chlorophenyl)methyl]-3-[(3,5-dichlorophenyl)(methylsulfonyl)methylene]azetidine,
1-benzhydryl-3-[(3-methylsulfanylphenyl)(methylsulfonyl)methylene]azetidine,
1-benzhydryl-3-[(3-methylsulfanylmethyl)phenyl)]-(methylsulfonyl)methylene]azetidine,
1-[bis(4-chlorophenyl)methyl]-3-[(3-cyanophenyl)(methylsulfonyl)methylene]azetidine,
1-[bis(4-chlorophenyl)methyl]-3-[(3-carbamoylphenyl)(methylsulfonyl)methylene]azetidine,
1-[bis(4-chlorophenyl)methyl]-3-[(3-methoxyphenyl)(methylsulfonyl)methylene]azetidine,
1-[bis(4-chlorophenyl)methyl]-3-[(3-hydroxyphenyl)(methylsulfonyl)methylene]azetidine,
1-[bis(4-chlorophenyl)methyl]-3-[(3-methylsulfonyl)(3-pyrrolidinylphenyl)methylene]azetidine,
1-[bis(4-chlorophenyl)methyl]-3-[(3-hydroxymethylphenyl)(methylsulfonyl)methylene]azetidine,
1-[bis(4-chlorophenyl)methyl]3-{(methylsulfonyl)[3-(N-piperidylcarbamoyl)phenyl]methylene}azetidine,
1-[bis(4-chlorophenyl)methyl]-3-[(methylsulfonyl)(3-trifluoromethylsulfanylphenyl)(methylsulfonyl)methylene]azetidine,
1-[bis(4-fluorophenyl)methyl]-3-[(3,5-difluorophenyl)(methylsulfonyl)methylene]azetidine,
1-[bis(2-fluorophenyl)methyl]-3-[(3,5-difluorophenyl)(methylsulfonyl)methylene]azetidine,
1-[bis(3-fluorophenyl)methyl]-3-[(3,5-difluorophenyl)(methylsulfonyl)methylene]azetidine,
(RS)-1-[(4-chlorophenyl)(thiazol-2-yl)methyl]-3-[(methylsulfonyl)(phenyl)methylene]azetidine,
(R)-1-[(4-chlorophenyl)(thiazol-2-yl)methyl]-3-[(methylsulfonyl)(phenyl)methylene]azetidine,
(S)-1-[(4-chlorophenyl)(thiazol-2-yl)methyl]-3-[(methylsulfonyl)(phenyl)methylene]azetidine, (RS)-1-[(4-chlorophenyl)(thien-2-yl)methyl]-3-[(3,5-difluorophenyl)(methylsulfonyl)methylene]azetidine,
(R)-1-[(4-chlorophenyl)(thien-2-yl)methyl]-3-[(3,5-difluorophenyl)(methylsulfonyl)methylene]azetidine,
(S)-1-[(4-chlorophenyl)(thien-2-yl)methyl]-3-[(3,5-difluorophenyl)(methylsulfonyl)methylene]azetidine,
1-benzhydryl-3-[(ethylsulfonyl)(phenyl)methylene]azetidine,
1-[bis(4-chlorophenyl)methyl]-3-{{3-[N-(4-methylpiperazinyl)carbamoyl]phenyl}(methylsulfonyl)methylene]azetidine,
1-[bis(4-chlorophenyl)methyl]-3-{[3-(2,2-dimethylcarbohydrazido)phenyl](methylsulfonyl)methylene}azetidine,
1-[bis(thien-2-yl)methyl]-3-[3,5-difluorophenyl)(methylsulfonyl)methylene]azetidine,
1-[bis(p-tolyl)methyl]-3-[(methylsulfonyl)(phenyl)methylene]azetidine,
1-[4-chlorophenyl)(4-hydroxymethylphenyl)methyl]-3-[(3,5-difluorophenyl)(methylsulfonyl)methylene]azetidine,
1-[bis(4-chlorophenyl)methyl]-3-[(3-methylaminophenyl)(methylsulfonyl)methylene]azetidine,
(RS)-1-[(4-chlorophenyl)(thiazol-2-yl)methyl]-3-[(3,5-difluorophenyl)(methylsulfonyl)methylene]azetidine,
(R)-1-[(4-chlorophenyl)(thiazol-2-yl)methyl]-3-[(3,5-difluorophenyl)(methylsulfonyl)methylene]azetidine,
(S)-1-[(4-chlorophenyl)(thiazol-2-yl)methyl]-3-[(3,5-difluorophenyl)(methylsulfonyl)methylene]azetidine,
1-[bis(4-chlorophenyl)methyl]-3-[(methylsulfonyl)(2-methoxycarbonylthien-5-yl)methylene]azetidine,
1-[bis(4-chlorophenyl)methyl]-3-hydroxy-3-[(methylsulfonyl)(2-methoxycarbonylthien-5-yl)methyl]azetidine (RS),
1-[bis(4-chlorophenyl)methyl]-3-[(2-isobutyl-aminocarbonylthien-5-yl)(methylsulfonyl)methylene]azetidine,
1-[bis(4-chlorophenyl)methyl]-3-[(3-methoxycarbonylphenyl)(methylsulfonyl)methyl-(RS)azetidin-3-ol,
1-[bis(4-chlorophenyl)methyl]-3-[(methylsulfonyl)(pyridin-4-yl)methyl-(RS)azetidin-3-ol,
1-[bis(4-chlorophenyl)methyl]-3-[(methylsulfonyl)(pyridin-3-yl)methyl-(RS)azetidin-3-ol,
3-({1-[bis(4-chlorophenyl)methyl]azetidin-3-ylidene}-methanesulfonylmethyl)-N-(3-morpholin-4-yl-propyl)benzamide,
3-({1-[bis(4-chlorophenyl)methyl]azetidin-3-ylidene}-methanesulfonylmethyl)-N-(3-dimethylaminopropyl)benzamide,
3-({1-[bis(4-chlorophenyl)methyl]azetidin-3-ylidene}-methanesulfonylmethyl)-N-(2-pyrrolidin-1-ylethyl)benzamide,
3-({1-[bis(4-chlorophenyl)methyl]azetidin-3-ylidene}-methanesulfonylmethyl)-N-(2-dimethylamino-1-methylethyl)benzamide,
3-({1-[bis(4-chlorophenyl)methyl]azetidin-3-ylidene}-methanesulfonylmethyl)-N-piperidin-1-ylbenzamide,
3-({1-[bis(4-chlorophenyl)methyl]azetidin-3-ylidene}-methanesulfonylmethyl)-N-isobutylbenzamide,
3-({1-[bis(4-chlorophenyl)methyl]azetidin-3-ylidene}-methanesulfonylmethyl)-N-(3-imidazol-1-ylpropyl)benzamide,
3-({1-[bis(4-chlorophenyl)methyl]azetidin-3-ylidene}-methanesulfonylmethyl)-N-(2-dimethylaminoethyl)benzamide,
3-({1-[bis-(4-chlorophenyl)methyl]azetidin-3-ylidene}methanesulfonylmethyl)benzoic acid N'-methylhydrazide,
3-({1-[bis-(4-chlorophenyl)methyl]azetidin-3-ylidene}-methanesulfonylmethyl)-N-(2-morpholin-4-ylethyl)benzamide,
3-({1-[bis-(4-chlorophenyl)methyl]azetidin-3-ylidene}-methanesulfonylmethyl)-N-(1-ethylpyrrolidin-2-ylmethyl)benzamide,
3-({1-[bis-(4-chlorophenyl)methyl]azetidin-3-ylidene}-methanesulfonylmethyl)-N-(2,2-dimethylpropyl)benzamide,
3-({1-[bis-(4-chlorophenyl)methyl]azetidin-3-ylidene}-methanesulfonylmethyl)-N-cyclohexylmethylbenzamide,
3-({1-[bis-(4-chlorophenyl)methyl]azetidin-3-ylidene}-methanesulfonylmethyl)-N-cyclopropylmethylbenzamide,
3-({1-[bis-(4-chlorophenyl)methyl]azetidin-3-ylidene}-methanesulfonylmethyl)-N-(2-methylbutyl)benzamide,
3-({1-[bis-(4-chlorophenyl)methyl]azetidin-3-ylidene}-methanesulfonylmethyl)-N-(2-phenylpropyl)benzamide,
3-({1-[bis-(4-chlorophenyl)methyl]azetidin-3-ylidene}-methanesulfonylmethyl)-N-(tetrahydrofuran-2-ylmethyl)benzamide,
3-({1-[bis-(4-chlorophenyl)methyl]azetidin-3-ylidene}-methanesulfonylmethyl)-N-(2,2-diphenylethyl)benzamide,
3-({1-[bis-(4-chlorophenyl)methyl]azetidin-3-ylidene}-methanesulfonylmethyl)-N-(2-ethylbutyl)benzamide,
4-{[3-({1-[bis(4-chlorophenyl)methyl]azetidin-3-ylidene}methanesulfonylmethyl)benzoylamino]methyl}cyclohexanecarboxylic acid methyl ester,
2-amino-1-{4-[3-({1-[bis-(4-chlorophenyl]methyl]azetidin-3-ylidene}methanesulfonylmethyl)phenyl]piperazin-1-yl}ethanone,
(2-{4-[3-({1-[bis(4-chlorophenyl)methyl]azetidin-3-ylidene}methanesulfonylmethyl)phenyl]piperazin-1-yl}-2-oxoethyl)carbamic acid tert-butyl ester,
1-{4-[3-({1-[bis-(4-chlorophenyl)methyl]azetidin-3-ylidene}methanesulfonylmethyl)phenyl]piperazin-1-yl}-2-methylaminoethanone,
(2-{4-[3-({1-[bis(4-chlorophenyl)methyl]azetidin-3-ylidene}methanesulfonylmethyl)phenyl]piperazin-1-yl}-2-oxoethyl)-N-methylcarbamic acid tert-butyl ester,
4-[3-({1-[bis(4-chlorophenyl)methyl]azetidin-3-ylidene}methanesulfonylmethyl)phenyl]piperazine-1-carbothioic acid N-methylamide,
4-[3-({1-[bis(4-chlorophenyl)methyl]azetidin-3-ylidene}methanesulfonylmethyl)phenyl]piperazine-1-carboxylic acid N-methylamide,
4-[3-({1-[bis(4-chlorophenyl)methyl]azetidin-3-ylidene}methanesulfonylmethyl)phenyl]piperazine-1-carboxylic acid methyl ester,
1-[3-({1-[bis(4-chlorophenyl)methyl]azetidin-3-ylidene}methanesulfonylmethyl)phenyl]-4-isobutylpiperazine,
1-[3-({1-[bis(4-chlorophenyl)methyl]azetidin-3-ylidene}methanesulfonylmethyl)phenyl]-4-ethylpiperazine,
4-acetyl 1-[3-({1-[bis(4-chlorophenyl)methyl]azetidin-3-ylidene}methanesulfonylmethyl)phenyl]piperazine,
1-{4-[3-({1-[bis(4-chlorophenyl)methyl]azetidin-3-ylidene}methanesulfonylmethyl)phenyl]piperazin-1-yl}-2-dimethylaminoethanone,
1-[3-({1-[bis(4-chlorophenyl)methyl]azetidin-3-ylidene}methanesulfonylmethyl)phenyl]piperazine,
4-[3-({1-[bis(4-chlorophenyl)methyl]azetidin-3-ylidene}methanesulfonylmethyl)phenyl]piperazine-1-carboxylic acid tert-butyl ester,
1-[bis(4-methoxycarbonylphenyl)methyl]-3-[(3,5-difluorophenyl)(methylsulfonyl)methylene]azetidine, 3-acetoxy-1-[bis(4-methoxycarbonylphenyl)methyl]-3-[(3,5-difluorophenyl)(methylsulfonyl)methyl-(RS)azetidine,
(RS)-4-[4-((4-chlorophenyl){3-[(3,5-difluorophenyl)methanesulfonylmethylene]azetidin-1-yl}methyl)benzyl]morpholine,
4-(4-{3-[(1-benzhydrylazetidin-3-ylidene)methanesulfonylmethyl]phenoxy}butyl)morpholine,
4-(4-{3-[(1-benzhydrylazetidin-3-ylidene)methanesulfonylmethyl]phenoxy}propyl)morpholine,
their optical isomers and their esters.

Among these compounds, the following compounds are particularly preferred;
1-[bis(4-chlorophenyl)methyl]-3-[(3,5-difluorophenyl)(methylsulfonyl)methylene]azetidine,
1-[bis(4-chlorophenyl)methyl]-3-[(3,5-difluorophenyl)(methylsulfonyl)methylene(RS)]azetidin-3-ol,
3-acetoxy-1-[bis(4-chlorophenyl)methyl]-3-[(3,5-difluorophenyl)(methylsulfonyl)methyl)methylsulfonylmethyl(RS)]azetidine
their optical isomers and their salts with an inorganic or organic acid.

The following examples illustrate the invention without limiting it.

EXAMPLE 1

0.3 cm$^3$ of methanesulfonyl chloride is added to a solution of 1 g of 1-benzhydryl-3-[(methylsulfonyl)(phenyl)methyl-(RS)]azetidin-3-ol in 10 cm$^3$ of pyridine, cooled to 5° C. The mixture is stirred for 2 hours at 5° C. and then 1 g of 4-dimethylaminopyridine is added in 10 cm$^3$ of dichloromethane at 5° C. The solution is stirred for 15 hours at room temperature and then concentrated to a dryness under reduced pressure (2.7 kPa). The residue obtained is chomatographed on a silica gel column (particle size 0.04–0.06 mm, diameter 3 cm, height 25 cm), eluting at a nitrogen pressure of 0.5 bar with dichloromethane and collecting 80 cm$^3$ fractions. Fractions 17 to 20 are combined and then concentrated to dryness under reduced pressure (2.7 kPa). The residue is crystallized from 10 cm$^3$ of ethyl ether. 0.14 g of 1-benzhydryl-3-[(methylsulfonyl)(phenyl)methylene]azetidine is obtained melting at 210° C. [NMR spectrum in DMSO-d6, T=300K, δ in ppm (300 MHz): 2.95 (3H, s, SCH$_3$), 3.80 (2H, s, NCH$_2$), 4.20 (2H, s, NCH$_2$), 4.75 (1H, s, NCH), 7.20 (2H, t, J=7 Hz, 2CH arom.), 7.30 (4H, t, J=7 Hz, 4CH arom.), between 7.40 and 7.60 (9H, m, 9 CH arom.)].

1-Benzhydryl-3-[(methylsulfonyl)(phenyl)methyl-(RS)]azetidin-3-ol may be obtained in the following manner: 6.25 cm$^3$ of 1.6 N n-butyllithium in solution in hexane are added to a solution of 1.4 cm$^3$ of diisopropylamine in 10 cm$^3$ of tetrahydrofuran, under an argon atmosphere, cooled to 0° C., and then the mixture is cooled to −70° C. A mixture of 1.7 g of benzyl methyl sulfone in 30 cm$^3$ of tetrahydrofuran are then added and the stirring is maintained for 45 minutes at −70° C. 2.4 g of 1-benzhydrylazetidin-3-one are added and then the mixture is stirred for 20 minutes while allowing the mixture to return to room temperature. The reaction mixture is filtered and then concentrated to dryness under reduced pressure (2.7 kPa). The residue is taken up in 50 cm$^3$ of ethyl acetate, 30 cm$^3$ of water and 20 cm$^3$ of normal hydrochloric acid. The precipitate is filtered, washed with 30 cm$^3$ of distilled water, drained and dried. 2 g of 1-benzhydryl-3-[(methylsulfonyl)(phenyl)methyl-(RS)]azetidin-3-ol are obtained melting at 260° C.

1-Benzhydrylazetidin-3-one may be prepared according to the procedure described by KATRITZKY A. R. et al. in J. Heterocycl. Chem., 271 (1994).

EXAMPLE 2

On carrying out the operation according to the procedure of Example 1 starting with 1.9 g of 1-benzhydryl-3-[(3-methylphenyl)(methylsulfonyl)methyl-(RS)]azetidin-3-ol, 0.52 cm$^3$ of methanesulfonyl chloride and 1.7 g of 4-dimethylaminopyridine, the residue obtained is purified by chromatography on a silica gel column (particle size 0.04–0.06 mm, diameter 3 cm, height 17 cm) at a nitrogen pressure of 0.5 bar with dichloromethane and then a dichloromethane and ethanol mixture (98.5/1.5 by volume) as eluents and collecting 100 cm$^3$ fractions. Fractions 5 and 6 are combined and concentrated to dryness under reduced pressure (2.7 kPa). The solid obtained is crystallized from 2 cm$^3$ of dichloromethane and 20 cm$^3$ of diisopropyl ether. 0.9 g of 1-benzhydryl-3-[(3-methylphenyl)(methylsulfonyl)methylene]azetidine is obtained melting at 180° C. [NMR spectrum in DMSO-d6, T=300K, δ in ppm (300 MHz): 2.35 (3H, s, PhCH$_3$), 2.95 (3H, s, SCH$_3$), 3.80 (2H, s, NCH$_2$), 4.20 (2H, s, NCH$_2$), 4.75 (1H, s, NCH), 7.20 (5H, m, 5CH arom.), 7.30 (5H, t, J=7 Hz, 5CH arom.), 7.50 (4H, d, J=7 Hz, 4 CH arom.)].

1-Benzhydryl-3-[(3-methylphenyl)(methylsulfonyl)methyl-(RS)]azetidin-3-ol may be obtained in the following manner: on carrying out the operation according to the procedure of Example 1 starting with 2.8 g of methyl(3-methylbenzyl)sulfone and 3.6 g of 1-benzhydrylazetidin-3-one, 2.6 g of a solid are obtained after purification on a silica gel column (particle size 0.04–0.06 mm, diameter 3 cm, height 25 cm) at a nitrogen pressure of 0.5 bar with a dichloromethane and ethanol mixture (98.5/1.5 by volume) as eluent. The solid is taken up in 25 cm$^3$ of diisopropyl ether. After filtration, draining and drying, 1.9 g of 1-benzhydryl-3-[(3-methylphenyl)(methylsulfonyl)methyl-(RS)]azetidin-3-ol are obtained melting at 170° C.

Methyl(3-methylbenzyl)sulfone may be prepared in the following manner: 10.5 g of oxone$^R$ and then 2.6 g of methyl(3-methylbenzyl)sulfide and 30 cm$^3$ of ethanol are added, at room temperature, to a solution of 30 cm$^3$ of water, 30 cm$^3$ of acetic acid and 15 cm$^3$ of 36 N sulfuric acid. The mixture is stirred for 48 hours at room temperature and then taken up in 100 cm$^3$ of water and 100 cm$^3$ of ethyl acetate. The organic phase is washed with a saturated aqueous sodium bicarbonate solution, decanted off, dried over magnesium sulfate and concentrated to dryness under reduced pressure (2.7 kPa). 2.8 g of methyl(3-methylbenzyl)sulfone are obtained in the form of a gum.

Methyl(3-methylbenzyl)sulfide may be prepared in the following manner: 1.7 g of sodium methylthiolate are added, while the temperature is kept below 30° C., to a solution of 3.7 g of 3-methylbenzyl bromide in 25 cm$^3$ of dimethylformamide. The mixture is stirred for 2 hours at a temperature close to 20° C. and then taken up in 50 cm$^3$ of ethyl acetate. The organic phase is washed with 3 times 100 cm$^3$ of water, dried over magnesium sulfate and concentrated to dryness under reduced pressure (2.7 kPa). 2.6 g of methyl(3-methylbenzyl)sulfide are obtained in the form of an oil.

EXAMPLE 3

0.3 cm$^3$ of methanesulfonyl chloride is added to a solution of 3.3 g of 1-benzhydryl-3-[(4-methylphenyl)(methylsulfonyl)methyl-(RS)]azetidin-3-ol in 10 cm$^3$ of pyridine, cooled to 5° C. The mixture is stirred for 2 hours at 5° C. and then 1 g of 4-dimethylaminopyridine is added in 10 cm$^3$ of dichloromethane at 5° C. The solution is stirred for 15 hours at room temperature and then concentrated to dryness under reduced pressure (2.7 kPa). The residue obtained is chromatographed on a silica gel column (particle size 0.04–0.06 mm, diameter 3 cm, height 25 cm), eluting at a nitrogen pressure of 0.5 bar with dichloromethane and collecting 80 cm³ fractions. Fractions 17 to 20 are combined and then concentrated to dryness under reduced pressure (2.7 kPa). The solid obtained is crystallized from 30 cm³ of acetonitrile. 0.14 g of 1-benzhydryl-3-[(4-methylphenyl)(methylsulfonyl)methylene]azetidine is obtained melting at 210° C. [NMR spectrum in DMSO-d6, T=300K, δ in ppm (300 MHz): 2.30 (3H, s, PhCH₃), 2.95 (3H, s, SCH₃), 3.80 (2H, s, NCH₂), 4.20 (2H, s, NCH₂), 4.75 (1H, s, NCH), 7.20 (4H, m, 4CH arom.), 7.30 (6H, t, J=7 Hz, 6CH arom.), 7.45 (4H, d, J=7 Hz, 4 CH arom.)].

1-Benzhydryl-3-[(4-methylphenyl)(methylsulfonyl)methyl-(RS)]azetidin-3-ol may be obtained in the following manner: on carrying out the operation according to the procedure of Example 1 starting with 4 g of methyl(4-methylbenzyl)sulfone and 5.1 g of 1-benzhydrylazetidin-3-one, 3 g of 1-benzhydryl-3-[(4-methylphenyl)(methylsulfonyl)methyl-(RS)]azetidin-3-ol are obtained melting at 226° C.

Methyl(4-methylbenzyl)sulfone may be prepared in the following manner: on carrying out the operation according to the procedure of Example 2 starting with 3.5 g of methyl(4-methylbenzyl)sulfide and 12.3 g of oxone$^R$, 3.5 g of methyl(4-methylbenzyl)sulfone are obtained in the form of a solid.

Methyl(4-methylbenzyl)sulfide may be prepared in the following manner: on carrying out the operation according to the procedure of Example 2 starting with 5.6 g of 4-methylbenzyl bromide and 2.3 g of sodium methylthiolate, 4.7 g of methyl(4-methylbenzyl)sulfide are obtained in the form of a solid.

EXAMPLE 4

0.7 cm³ of methanesulfonyl chloride and then 3.8 g of 4-dimethylaminopyridine are added to a solution of 3.3 g of 1-benzhydryl-3-[(2-methylphenyl)(methylsulfonyl)methyl-(RS)]azetidin-3-ol in 50 cm³ of dichloromethane, at room temperature. The solution is stirred for 3 hours under reflux and then taken up in twice 50 cm³ of water. The organic phase is decanted off, dried and concentrated to dryness under reduced pressure (2.7 kPa). The residue obtained is chromatographed on a silica gel column (particle size 0.04–0.06 mm, diameter 3 cm, height 25 cm), eluting at a nitrogen pressure of 0.5 bar with dichloromethane and then with a dichloromethane and ethanol mixture (99/1 by volume mixture) and collecting 100 cm³ fractions. Fractions 6 to 17 are combined and then concentrated to dryness under reduced pressure (2.7 kPa). The solid obtained is crystallized from 50 cm³ of ethyl ether. 2.6 g of 1-benzhydryl-3-[(2-methylphenyl)(methylsulfonyl)methylene]azetidine are obtained in the form of a foam [NMR spectrum in DMSO-d6, T=300K, δ in ppm (300 MHz): 2.30 (3H, s, PhCH₃), 2.95 (3H, s, SCH₃), 3.50 (2H, s, NCH₂), 4.20 (2H, s, NCH₂), 4.70 (1H, s, NCH) between 7.10 and 7.35 (10H, m, 10CH arom.), 7.45 (4H, m, 4CH arom.)].

1-Benzhydryl-3-[(2-methylphenyl)(methylsulfonyl)methyl-(RS)]azetidin-3-ol may be obtained in the following manner: on carrying out the operation according to the procedure of Example 1 starting with 3.4 g of methyl(2-methylbenzyl)sulfone and 4.3 g of 1-benzhydrylazetidin-3-one, 3.4 g of 1-benzhydryl-3-[(2-methylphenyl)(methylsulfonyl)methyl-(RS)]azetidin-3-ol are obtained melting at 218° C.

Methyl(2-methylbenzyl)sulfone may be prepared in the following manner: by carrying out the operation according to the procedure of Example 2 starting with 4.5 g of methyl(2-methylbenzyl)sulfide and 16.2 g of oxone$^R$, 3.4 g of methyl(2-methylbenzyl)sulfone are obtained in the form of a solid.

Methyl(2-methylbenzyl)sulfide may be prepared in the following manner: on carrying out the operation according to the procedure of Example 2 but starting with 5.6 g of 2-methylbenzyl bromide and 2.1 g of sodium methylthiolate, 4.5 g of methyl(2-methylbenzyl)sulfide are obtained in the form of a solid.

EXAMPLE 5

On carrying out the operation according to the procedure of Example 4 but starting with 2.1 g of 1-benzhydryl-3-[(2-chlorophenyl)(methylsulfonyl)methyl-(RS)]azetidin-3-ol, 0.55 cm³ of methanesulfonyl chloride and 2.3 g of 4-dimethylaminopyridine, the residue obtained is purified by chromatography on a silica gel column (particle size 0.04–0.06 mm, diameter 3 cm, height 25 cm) at a nitrogen pressure of 0.5 bar with dichloromethane as eluent and collecting 100 cm³ fractions. Fractions 12 to 18 are combined and concentrated to dryness under reduced pressure (2.7 kPa). The solid obtained is crystallized from a mixture of 3 cm³ of dichloromethane and 40 cm³ of ethyl ether. 1.1 g of 1-benzhydryl-3-[(2-chlorophenyl)(methylsulfonyl)methylene]azetidine are obtained melting at 204° C. [NMR spectrum in DMSO-d6, T=300K, δ in ppm (300 MHz): 2.95 (3H, s, SCH₃), 3.60 (2H, s, NCH₂) 4.20 (2H, s, NCH₂), 4.70 (1H, s, NCH), 7.20 (2H, t, J=7 Hz, 2CH arom.), 7.30 (4H, t, J=7 Hz, 4CH arom.), 7.45 (7H, m, 7CH arom.), 7.55 (1H, d, J=7 Hz, CH arom.)].

1-Benzhydryl-3-[(2-chlorophenyl)(methylsulfonyl)methyl-(RS)]azetidin-3-ol may be obtained in the following manner: on carrying out the operation according to the procedure of Example 1 starting with 4 g of (2-chlorobenzyl)methylsulfone and 4.6 g of 1-benzhydrylazetidin-3-one, the residue obtained is taken up in 50 cm³ of ethyl acetate, filtered and dried. 2.4 g of 1-benzhydryl-3-[(2-chlorophenyl)(methylsulfonyl)methyl-(RS)]azetidin-3-ol are obtained in the form of a white solid.

(2-Chlorobenzyl)methylsulfone may be prepared in the following manner: on carrying out the operation according to the procedure of Example 2 starting with 3.4 g of (2-chlorobenzyl)methylsulfide and 12 g of oxone$^R$, 4 g of (2-chlorobenzyl)methylsulfone are obtained in the form of an oil which crystallizes.

(2-Chlorobenzyl)methylsulfide may be prepared in the following manner: on carrying out the operation according to the procedure of Example 2 but starting with 4 g of 2-chlorobenzyl bromide and 1.5 g of sodium methylthiolate, 3.4 g of (2-chlorobenzyl)methylsulfide are obtained in the form of an oil.

EXAMPLE 6

On carrying out the operation according to the procedure of Example 4 starting with 3 g of 1-benzhydryl-3-[(3-chlorophenyl)(methylsulfonyl)methyl-(RS)]azetidin-3-ol, 0.79 cm³ of methanesulfonyl chloride and 3.3 g of 4-dimethylaminopyridine, the residue obtained is purified by chromatography on a silica gel column (particle size 0.04–0.06 mm, diameter 3 cm, height 25 cm) at a nitrogen pressure of 0.5 bar with dichloromethane as eluent and collecting 100 cm³ fractions. Fractions 2 to 5 are combined and concentrated to dryness under reduced pressure (2.7 kPa). The solid obtained is crystallized from 40 cm³ of ethyl ether. 1.7 g of 1-benzhydryl-3-[(3-chlorophenyl)

(methylsulfonyl)methylene]azetidine are obtained melting at 205° C. [NMR spectrum in DMSO-d6, T=300K, δ in ppm (300 MHz): 2.95 (3H, s, SCH$_3$), 3.80 (2H, s, NCH$_2$), 4.20 (2H, s, NCH$_2$), 4.70 (1H, s, NCH), 7.20 (2H, t, J=7 Hz, 2CH arom.), 7.30 (4H, t, J=7 Hz, 4CH arom.), 7.45 (8H, m, 8CH arom.)].

1-benzhydryl-3-[(3-chlorophenyl)(methylsulfonyl) methyl-(RS)]azetidin-3-ol may be obtained in the following manner: on carrying out the operation according to the procedure of Example 1 starting with 3.1 g of (3-chlorobenzyl)methylsulfone and 3.4 g of 1-benzhydrylazetidin-3-one, 3.4 g of 1-benzhydryl-3-[(3-chlorophenyl)(methylsulfonyl)methyl-(RS)]azetidin-3-ol are obtained in the form of a white solid.

(3-Chlorobenzyl)methylsulfone may be prepared in the following manner: on carrying out the operation according to the procedure of Example 2 starting with 3.2 g of (3-chlorobenzyl)methylsulfide and 12 g of oxone$^R$, 3.2 g of (3-chlorobenzyl)methylsulfone are obtained in the form of a white solid.

(3-Chlorobenzyl)methylsulfide may be prepared in the following manner: on carrying out the operation according to the procedure of Example 2 starting with 4 g of 3-chlorobenzyl bromide and 1.5 g of sodium methylthiolate, 3.2 g of 3-chlorobenzylmethylsulfide are obtained in the form of an oil.

EXAMPLE 7

On carrying out the operation according to the procedure of Example 4 starting with 3.3 g of 1-benzhydryl-3-[(4-chlorophenyl)(methylsulfonyl)methyl-(RS)]azetidin-3-ol, 0.87 cm$^3$ of methanesulfonyl chloride and 3.6 g of 4-dimethylaminopyridine, the residue obtained is purified by chromatography on a silica gel column (particle size 0.04–0.06 mm, diameter 3 cm, height 25 cm) at a nitrogen pressure of 0.5 bar with dichloromethane as eluent and collecting 100 cm$^3$ fractions. Fractions 8 to 12 are combined and concentrated to dryness under reduced pressure (2.7 kPa). The solid obtained is crystallized from a mixture of 3 cm$^3$ and 30 cm$^3$ of ethyl ether. 0.5 g of 1-benzhydryl-3-[(4-chlorophenyl)(methylsulfonyl)methylene]azetidine is obtained melting at 192° C. [NMR spectrum in DMSO-d6, T=300K, δ in ppm (300 MHz): 2.95 (3H, s, SCH$_3$), 3.80 (2H, s, NCH$_2$), 4.20 (2H, s, NCH$_2$), 4.70 (1H, s, NCH), 7.20 (2H, t, J=7 Hz, 2CH arom.), 7.30 (4H, t, J=7 Hz, 4CH arom.), between 7.40 and 7.55 (8H, m, 8CH arom.)].

1-Benzhydryl-3-[(4-chlorophenyl)(methylsulfonyl) methyl-(RS)]azetidin-3-ol may be obtained in the following manner: on carrying out the operation according to the procedure of Example 1 starting with 2.8 g of (4-chlorobenzyl)methylsulfone and 3.24 g of 1-benzhydrylazetidin-3-one, 3.4 g of 1-benzhydryl-3-[(4-chlorophenyl)(methylsulfonyl)methyl-(RS)]azetidin-3-ol are obtained in the form of a white solid after crystallization from 80 cm$^3$.

(4-Chlorobenzyl)methylsulfone may be prepared in the following manner: on carrying out the operation according to the procedure of Example 2 starting with 3.5 g of (4-chlorobenzyl)methylsulfide and 12.3 g of oxone$^R$, 3.5 g of (4-chlorobenzyl)methylsulfone are obtained in the form of a solid.

EXAMPLE 8

On carrying out the operation according to the procedure of Example 4 starting with 3.1 g of 1-benzhydryl-3-[(3,5-dichlorophenyl)(methylsulfonyl)methyl-(RS)]azetidin-3-ol, 0.75 cm$^3$ of methanesulfonyl chloride and 3.1 g of 4-dimethylaminopyridine, the residue obtained is purified by chromatography on a silica gel column (particle size 0.04–0.06 mm, diameter 3 cm, height 25 cm) at a nitrogen pressure of 0.5 bar with dichloromethane as eluent and collecting 100 cm$^3$ fractions. Fractions 6 to 10 are combined and concentrated to dryness under reduced pressure (2.7 kPa). The solid obtained is crystallized from a mixture of 2 cm$^3$ of dichloromethane and 30 cm$^3$ of ethyl ether. 0.8 g of 1-benzhydryl-3-[(3,5-dichlorophenyl)(methylsulfonyl) methylene]azetidine is obtained melting at 204° C. [NMR spectrum in DMSO-d6, T=300K, δ in ppm (300 MHz): 2.95 (3H, s, SCH$_3$), 3.85 (2H, s, NCH$_2$), 4.20 (2H, s, NCH$_2$), 4.75 (1H, s, NCH), 7.20 (2H, t, J=7 Hz, 2CH arom.), 7.30 (4H, t, J=7 Hz, 4CH arom.), 7.45 (6H, m, 6CH arom.), 7.70 (1H, s, CH arom.)].

1-Benzhydryl-3-[(3,5-dichlorophenyl)(methylsulfonyl) methyl-(RS)]azetidin-3-ol may be obtained in the following manner: on carrying out the operation according to the procedure of Example 1 starting with 4 g of (3,5-dichlorobenzyl)methylsulfone and 4 g of 1-benzhydrylazetidin-3-one, 3.2 g of 1-benzhydryl-3-[(3,5-dichlorophenyl)(methylsulfonyl)methyl-(RS)]azetidin-3-ol are obtained in the form of a white solid.

(3,5-Dichlorobenzyl)methylsulfone may be prepared in the following manner: on carrying out the operation according to the procedure of Example 2 starting with 5.3 g of (3,5-dichlorobenzyl)methylsulfide and 17 g of oxone$^R$, 5 g of (3,5-dichlorobenzyl)methylsulfone are obtained in the form of a white solid.

(3,5-Dichlorobenzyl)methylsulfide may be prepared in the following manner: on carrying out the operation according to the procedure of Example 2 starting with 5 g of 3,5-dichlorobenzyl chloride and 2 g of sodium methylthiolate, 5.3 g of (3,5-dichlorobenzyl)methylsulfide are obtained in the form of an oil.

EXAMPLE 9

On carrying out the operation according to the procedure of Example 4 starting with 5 g of 1-benzhydryl-3-[(3,4-dichlorophenyl)(methylsulfonyl)methyl-(RS)]azetidin-3-ol, 1.2 cm$^3$ of methanesulfonyl chloride and 3.8 g of 4-dimethylaminopyridine, the residue obtained is purified by chromatography on a silica gel column (particle size 0.04–0.06 mm, diameter 4 cm, height 35 cm) at a nitrogen pressure of 0.5 bar with a mixture of cyclohexane and ethyl acetate (70/30 by volume) as eluent and collecting 35 cm$^3$ fractions. Fractions 30 to 55 are combined and concentrated to dryness under reduced pressure (2.7 kPa). The solid obtained is crystallized from 50 cm$^3$ of ethyl ether. 1.5 g of 1-benzhydryl-3-[(3,4-dichlorophenyl)(methylsulfonyl) methylene]azetidine are obtained melting at 170° C. [NMR spectrum in DMSO-d6, T=300K, δ in ppm (300 MHz): 2.95 (3H, s, SCH$_3$), 3.80 (2H, s, NCH$_2$), 4.20 (2H, s, NCH$_2$), 4.70 (1H, s, NCH), 7.20 (2H, t, J=7 Hz, 2CH arom.), 7.30 (4H, t, J=7 Hz, 4CH arom.), between 7.35 and 7.50 (5H, m, 5CH arom.), 7.65 (2H, m, 2CH arom.)].

1-Benzhydryl-3-[(3,4-dichlorophenyl)(methylsulfonyl) methyl-(RS)]azetidin-3-ol may be obtained in the following manner: on carrying out the operation according to the procedure of Example 1 starting with 4.5 g of (3,4-dichlorobenzyl)methylsulfone and 4.3 g of 1-benzhydrylazetidin-3-one, 5 g of 1-benzhydryl-3-[(3,4-dichlorophenyl)(methylsulfonyl)methyl-(RS)]azetidin-3-ol are obtained in the form of a white solid.

(3,4-Dichlorobenzyl)methylsulfone may be prepared in the following manner: on carrying out the operation according to the procedure of Example 2 starting with 4.3 g of (3,4-dichlorobenzyl)methylsulfide and 13 g of oxone$^R$, 4.7 g of (3,4-dichlorobenzyl)methylsulfone are obtained in the form of a white solid.

(3,4-Dichlorobenzyl)methylsulfide may be prepared in the following manner: on carrying out the operation according to the procedure of Example 2 starting with 2.8 cm$^3$ of 3,4-dichlorobenzyl chloride and 1.5 g of sodium methylthiolate, 4.3 g of (3,4-dichlorobenzyl)methylsulfide are obtained in the form of an oil.

EXAMPLE 10

On carrying out the operation according to the procedure of Example 4 starting with 1.8 g of 1-benzhydryl-3-[(2,5-dichlorophenyl)(methylsulfonyl)methyl-(RS)]azetidin-3-ol, 0.4 cm$^3$ of methanesulfonyl chloride and 1.8 g of 4-dimethylaminopyridine, the residue obtained is purified by chromatography on a silica gel column (particle size 0.04–0.06 mm, diameter 3 cm, height 25 cm) at a nitrogen pressure of 0.5 bar with dichloromethane as eluent and collecting 100 cm$^3$ fractions. Fractions 8 to 14 are combined and concentrated to dryness under reduced pressure (2.7 kPa). The solid obtained is crystallized from a mixture of 2 cm$^3$ of dichloromethane and 30 cm$^3$ of ethyl ether. 1.2 g of 1-benzhydryl-3-[(2,5-dichlorophenyl)(methylsulfonyl) methylene]azetidine are obtained melting at 202° C. [NMR spectrum in DMSO-d6, T=300K, δ in ppm (250 MHz): 3.00 (3H, s, SCH$_3$), 3.70 (2H, m, NCH$_2$) 4.25 (2H, m, NCH$_2$), 4.70 (1H, s, NCH), 7.20 (2H, t, J=7 Hz, 2CH arom.), 7.30 (4H, t, J=7 Hz, 4CH arom.), 7.45 (4H, d, J=7 Hz, 4CH arom.), between 7.55 and 7.70 (3H, m, 3CH arom.)].

1-Benzhydryl-3-[(2,5-dichlorophenyl)(methylsulfonyl) methyl-(RS)]azetidin-3-ol may be obtained in the following manner: on carrying out the operation according to the procedure of Example 1 starting with 1.2 g of (2,5-dichlorobenzyl)methylsulfone and 1.2 g of 1-benzhydrylazetidin-3-one, 1.8 g of 1-benzhydryl-3-[(2,5-dichlorophenyl)(methylsulfonyl)methyl-(RS)]azetidin-3-ol are obtained in the form of a white solid.

(2,5-Dichlorobenzyl)methylsulfone may be prepared in the following manner: 1.9 g of sodium methanesulfinate are added, at room temperature, to a solution of 2.7 g of 2,5-dichlorobenzyl chloride in 30 cm$^3$ of ethanol. The mixture is heated under reflux for 5 hours, cooled to room temperature and then taken up in 50 cm$^3$ of water and 50 cm$^3$ of ethyl acetate. The organic phase is decanted off, washed with 20 cm$^3$ of a saturated aqueous sodium chloride solution, dried over magnesium sulfate and concentrated to dryness under reduced pressure (2.7 kPa). 1.2 g of (2,5-dichlorobenzyl)methylsulfone are obtained in the form of a white solid.

EXAMPLE 11

On carrying out the operation according to the procedure of Example 4 starting with 9.1 g of 1-benzhydryl-3-[(2,4-dichlorophenyl)(methylsulfonyl)methyl-(RS)]azetidin-3-ol, 2.2 cm$^3$ of methanesulfonyl chloride and 7 g of 4-dimethylaminopyridine, the residue obtained is purified by chromatography on a silica gel column (particle size 0.04–0.06 mm, diameter 5.5 cm, height 30 cm) at a nitrogen pressure of 0.5 bar with dichloromethane as eluent and collecting 40 cm$^3$ fractions. Fractions 27 to 39 are combined and concentrated to dryness under reduced pressure (2.7 kPa). The solid obtained is crystallized from 20 cm$^3$ of ethyl ether. 1.5 g of 1-benzhydryl-3-[(2,4-dichlorophenyl) (methylsulfonyl)methylene]azetidine are obtained melting at 165° C. [NMR spectrum in DMSO-d6, T=300K, δ in ppm (250 MHz): 3.00 (3H, s, SCH$_3$), 3.65 (2H, m, NCH$_2$), 4.25 (2H, m, NCH$_2$), 4.75 (1H, s, NCH), 7.20 (2H, t, J=7 Hz, 2CH arom.), 7.30 (4H, t, J=7 Hz, 4CH arom.), 7.45 (6H, m, 6CH arom.), 7.80 (1H, s, CH arom.)].

1-Benzhydryl-3-[(2,4-dichlorophenyl)(methylsulfonyl) methyl-(RS)]azetidin-3-ol may be obtained in the following manner: on carrying out the operation according to the procedure of Example 1 starting with 4.8 g of (2,4-dichlorobenzyl)methylsulfone and 4.7 g of 1-benzhydrylazetidin-3-one, 9.1 g of 1-benzhydryl-3-[(2,4-dichlorophenyl)(methylsulfonyl)methyl-(RS)]azetidin-3-ol are obtained in the form of a brown foam.

(2,4-Dichlorobenzyl)methylsulfone may be prepared in the following manner: on carrying out the operation according to the procedure of Example 2 starting with 4 g of (2,4-dichlorobenzyl)methylsulfide and 13 g of oxone$^R$, 4.8 g of (2,4-dichlorobenzyl)methylsulfone are obtained in the form of a white solid melting at 111° C.

(2,4-Dichlorobenzyl)methylsulfide may be prepared in the following manner: on carrying out the operation according to the procedure of Example 2 starting with 2.8 cm$^3$ of 2,4-dichlorobenzyl chloride and 1.5 g of sodium methylthiolate, 4 g of (2,4-dichlorobenzyl)methylsulfide are obtained in the form of an oil.

EXAMPLE 12

On carrying out the operation according to the procedure of Example 4 starting with 3 g of 1-benzhydryl-3-[(2,3-dichlorophenyl)(methylsulfonyl)methyl-(RS)]azetidin-3-ol, 1.1 g of methanesulfonyl chloride and 3 g of 4-dimethylaminopyridine, the residue obtained is purified by chromatography on a silica gel column (particle size 0.04–0.06 mm, diameter 3 cm, height 30 cm) at a nitrogen pressure of 0.5 bar with a mixture of dichloromethane and ethanol (98/2 by volume) as eluent and collecting 100 cm$^3$ fractions. Fractions 10 to 20 are combined and concentrated to dryness under reduced pressure (2.7 kPa). The solid obtained is crystallized from 40 cm$^3$ of ethyl ether. 1.6 g of 1-benzhydryl-3-[(2,3-dichlorophenyl)(methylsulfonyl) methylene]azetidine are obtained melting at 201° C. [NMR spectrum in DMSO-d6, T=300K, δ in ppm (300 MHz): 3.00 (3H, s, SCH$_3$), 3.60 (2H, m, NCH$_2$), 4.20 (2H, m, NCH$_2$), 4.70 (1H, s, NCH), 7.20 (2H, t, J=7 Hz, 2CH arom.), 7.30 (4H, t, J=7 Hz, 4CH arom.), 7.45 (6H, m, 6CH arom.), 7.70 (1H, dd, J=8 and 2 Hz, CH arom.)].

1-Benzhydryl-3-[(2,3-dichlorophenyl)(methylsulfonyl) methyl-(RS)]azetidin-3-ol may be obtained in the following manner: on carrying out the operation according to the procedure of Example 1 starting with 3.6 g of (2,3-dichlorobenzyl)methylsulfone and 3.6 g of 1-benzhydrylazetidin-3-one, 5.4 g of 1-benzhydryl-3-[(2,3-dichlorophenyl)(methylsulfonyl)methyl-(RS)]azetidin-3-ol are obtained in the form of a white solid.

(2,3-Dichlorobenzyl)methylsulfone may be prepared in the following manner: on carrying out the operation according to the procedure of Example 10 starting with 3 g of 2,3-dichlorobenzyl chloride and 2.4 g of sodium methanesulfinate, 3.6 g of (2,3-dichlorobenzyl) methylsulfonate are obtained in the form of a white solid.

EXAMPLE 13

On carrying out the operation according to the procedure of Example 4 starting with 2.5 g of 1-benzhydryl-3-[(3- fluorophenyl)(methylsulfonyl)methyl-(RS)]azetidin-3-ol, 0.72 cm³ of methanesulfonyl chloride and 2.9 g of 4-dimethylaminopyridine, the residue obtained is purified by chromatography on a silica gel column (particle size 0.04–0.06 mm, diameter 3 cm, height 25 cm) at a nitrogen pressure of 0.5 bar with dichloromethane as eluent, collecting 100 cm³ fractions. Fractions 2 to 6 are combined and concentrated to dryness under reduced pressure (2.7 kPa). The solid obtained is crystallized from 40 cm³ of ethyl ether. 1.5 g of 1-benzhydryl-3-[(3-fluorophenyl)(methylsulfonyl) methylene]azetidine are obtained melting at 210° C. [NMR spectrum in DMSO-d6, T=300K, δ in ppm (300 MHz): 2.95 (3H, s, SCH₃), 3.80 (2H, m, NCH₂), 4.20 (2H, s, NCH₂), 4.70 (1H, s, NCH), between 7.10 and 7.30 (9H, m, 9CH arom.), 7.45 (5H, m, 5CH arom.)].

1-Benzhydryl-3-[(3-fluorophenyl)(methylsulfonyl) methyl-(RS)]azetidin-3-ol may be obtained in the following manner: on carrying out the operation according to the procedure of Example 1 starting with 2.6 g of 3-fluorobenzyl methyl sulfone and 3.3 g of 1-benzhydrylazetidin-3-one, 2.9 g of 1-benzhydryl-3-[(3-fluorophenyl)(methylsulfonyl) methyl-(RS)]azetidin-3-ol are obtained in the form of a white solid melting at 200° C.

(3-Fluorobenzyl) methyl sulfone may be prepared in the following manner: on carrying out the operation according to the procedure of Example 2 starting with 3.1 g of 3-fluorobenzyl methyl sulfide and 13 g of oxone$^R$, 2.7 g of 3-fluorobenzyl methyl sulfone are obtained in the form of a white solid.

(3-Fluorobenzyl) methyl sulfide may be prepared in the following manner: on carrying out the operation according to the procedure of Example 2 starting with 2.6 cm³ of 3-fluorobenzyl bromide and 1.6 g of sodium methylthiolate, 3.1 g of 3-fluorobenzylmethyl sulfide are obtained in the form of an oil.

EXAMPLE 14

On carrying out the operation according to the procedure of Example 4 starting with 4.3 g of 1-benzhydryl-3-[(2-fluorophenyl)(methylsulfonyl)methyl-(RS)]azetidin-3-ol, 1.2 cm³ of methanesulfonyl chloride and 3.7 g of 4-dimethylaminopyridine, the residue obtained is purified by chromatography on a silica gel column (particle size 0.04–0.06 mm, diameter 4.5 cm, height 30 cm) at a nitrogen pressure of 0.5 bar with dichloromethane as eluent and collecting 30 cm³ fractions. Fractions 28 to 58 are combined and concentrated to dryness under reduced pressure (2.7 kPa). The solid obtained is crystallized from 100 cm³ of ethyl ether. 2.3 g of 1-benzhydryl-3-[(2-fluorophenyl) (methylsulfonyl)methylene]azetidine are obtained melting at 188° C. [NMR spectrum in DMSO-d6, T=300K, δ in ppm (300 MHz): 3.00 (3H, s, SCH₃), 3.65 (2H, m, NCH₂) 4.20 (2H, m, NCH₂), 4.75 (1H, s, NCH), 7.20 (2H, t, J=7 Hz, 2CH arom.), 7.30 (6H, m, 6CH arom.), 7.50 (6H, m, 6CH arom.)].

1-Benzhydryl-3-[(2-fluorophenyl)(methylsulfonyl) methyl-(RS)]azetidin-3-ol may be obtained in the following manner: on carrying out the operation according to the procedure of Example 1 starting with 3.4 g of 2-fluorobenzyl methyl sulfone and 4.2 g of 1-benzhydrylazetidin-3-one, 4.3 g of 1-benzhydryl-3-[(3-fluorophenyl)(methylsulfonyl) methyl-(RS)]azetidin-3-ol are obtained in the form of a white solid.

(2-Fluorobenzyl) methyl sulfone may be prepared in the following manner: on carrying out the operation according to the procedure of Example 2 starting with 3 g of 2-fluorobenzyl methyl sulfide and 13 g of oxone$^R$, 3.6 g of 3-fluorobenzyl methyl sulfone are obtained in the form of a white solid.

(2-Fluorobenzyl) methyl sulfide may be prepared in the following manner: on carrying out the operation according to the procedure of Example 2 starting with 2.4 cm³ of 2-fluorobenzyl bromide and 1.5 g of sodium methylthiolate, 3 g of 2-fluorobenzyl methyl sulfide are obtained in the form of an oil.

EXAMPLE 15

On carrying out the operation according to the procedure of Example 4 starting with 1 g of 1-benzhydryl-3-[(4-fluorophenyl)(methylsulfonyl)methyl-(RS)]azetidin-3-ol, 0.3 cm³ of methanesulfonyl chloride and 0.9 g of 4-dimethylaminopyridine, the residue obtained is purified by chromatography on a silica gel column (particle size 0.04–0.06 mm, diameter 3 cm, height 35 cm) at a nitrogen pressure of 0.5 bar with dichloromethane as eluent and collecting 30 cm³ fractions. Fractions 20 to 35 are combined and concentrated to dryness under reduced pressure (2.7 kPa). The solid obtained is crystallized from 50 cm³ of ethyl ether. 0.4 g of 1-benzhydryl-3-[(4-fluorophenyl) (methylsulfonyl)methylene]azetidine are obtained melting at 186° C. [NMR spectrum in DMSO-d6, T=300K, δ in ppm (300 MHz): 2.95 (3H, s, SCH₃), 3.80 (2H, m, NCH₂), 4.20 (2H, m, NCH₂), 4.75 (1H, s, NCH), between 7.15 and 7.35 (8H, m, 8CH arom.), 7.45 (6H, m, 6CH arom.)].

1-Benzhydryl-3-[(4-fluorophenyl)(methylsulfonyl) methyl-(RS)]azetidin-3-ol may be obtained in the following manner: on carrying out the operation according to the procedure of Example 1 starting with 2.8 g of 4-fluorobenzyl methyl sulfone and 3.6 g of 1-benzhydrylazetidin-3-one, 1 g of 1-benzhydryl-3-[(4-fluorophenyl)(methylsulfonyl) methyl-(RS)]azetidin-3-ol is obtained in the form of a white solid.

(4-Fluorobenzyl) methyl sulfone may be prepared in the following manner: on carrying out the operation according to the procedure of Example 2 starting with 3 g of 4-fluorobenzyl methyl sulfide and 13 g of oxone$^R$, 3 g of 4-fluorobenzyl methyl sulfone are obtained in the form of a white solid melting at 110° C.

(4-Fluorobenzyl) methyl sulfide may be prepared in the following manner: on carrying out the operation according to the procedure of Example 2 starting with 2.5 cm³ of 4-fluorobenzyl chloride and 1.5 g of sodium methylthiolate, 3 g of 4-fluorobenzyl methyl sulfide are obtained in the form of an oil.

EXAMPLE 16

On carrying out the operation according to the procedure of Example 4 starting with 3.8 g of 1-benzhydryl-3-[(3,5-difluorophenyl)(methylsulfonyl)methyl-(RS)]azetidin-3-ol, 1 cm³ of methanesulfonyl chloride and 4.2 g of 4-dimethylaminopyridine, the residue obtained is purified by chromatography on a silica gel column (particle size 0.04–0.06 mm, diameter 3 cm, height 30 cm) at a nitrogen pressure of 0.5 bar with dichloromethane as eluent, collecting 100 cm³ fractions. Fractions 5 to 10 are combined and concentrated to dryness under reduced pressure (2.7 kPa). The solid obtained is crystallized from 30 cm³ of ethyl ether. 0.8 g of 1-benzhydryl-3-[(3,5-difluorophenyl) (methylsulfonyl)methylene]azetidine are obtained melting at 172° C. [NMR spectrum in DMSO-d6, T=300K, δ in ppm (250 MHz): 3.00 (3H, s, SCH₃), 3.85 (2H, m, NCH₂), 4.20 (2H, m, NCH₂), 4.75 (1H, s, NCH), between 7.10 and 7.40 (9H, m, 9CH arom.), 7.50 (4H, d, J=7 Hz, 4CH arom.)].

1-Benzhydryl-3-[(3,5-difluorophenyl)(methylsulfonyl) methyl-(RS)]azetidin-3-ol may be obtained in the following manner: on carrying out the operation according to the procedure of Example 1 starting with 3.2 g of 3,5-difluorobenzyl methyl sulfone and 3.7 g of 1-benzhydrylazetidin-3-one, 3.9 g of 1-benzhydryl-3-[(3,5-difluorophenyl)(methylsulfonyl)methyl-(RS)]azetidin-3-ol are obtained in the form of a white solid.

(3,5-Difluorobenzyl) methyl sulfone may be prepared in the following manner: on carrying out the operation according to the procedure of Example 2 starting with 4.2 g of 3,5-difluorobenzyl methyl sulfide and 16 g of oxone$^R$, 3.3 g of 3,5-difluorobenzyl methyl sulfone are obtained in the form of a white solid.

(3,5-Difluorobenzyl) methyl sulfide may be prepared in the following manner: on carrying out the operation according to the procedure of Example 2 starting with 5 g of 3,5-difluorobenzyl bromide and 2 g of sodium methylthiolate, 4.9 g of 3,5-difluorobenzyl methyl sulfide are obtained in the form of an oil.

EXAMPLE 17

On carrying out the operation according to the procedure of Example 4 starting with 5.2 g of 1-benzhydryl-3-[(2,3-difluorophenyl)(methylsulfonyl)methyl-(RS)]azetidin-3-ol, 2.3 cm$^3$ of methanesulfonyl chloride and 7.3 g of 4-dimethylaminopyridine, the residue obtained is purified by chromatography on a silica gel column (particle size 0.04–0.06 mm, diameter 6 cm, height 40 cm) at a nitrogen pressure of 0.5 bar with a mixture of dichloromethane and methanol (98/2 by volume) as eluent and collecting 50 cm$^3$ fractions. Fractions 65 to 87 are combined and concentrated to dryness under reduced pressure (2.7 kPa). The solid obtained is crystallized from 75 cm$^3$ of ethyl ether. 2.5 g of 1-benzhydryl-3-[(2,3-difluorophenyl)(methylsulfonyl) methylene]azetidine are obtained melting at 208° C. [NMR spectrum in DMSO-d6, T=300K, δ in ppm (400 MHz): 3.05 (3H, s, SCH$_3$), 3.70 (2H, s, NCH$_2$), 4.25 (2H, s, NCH$_2$), 4.75 (1H, s, NCH), between 7.15 and 7.55 (13H, m, 13CH arom.)].

1-Benzhydryl-3-[(2,3-difluorophenyl)(methylsulfonyl) methyl-(RS)]azetidin-3-ol may be obtained in the following manner: on carrying out the operation according to the procedure of Example 1 starting with 4 g of (2,3-difluorobenzyl) methyl sulfone and 4.8 g of 1-benzhydrylazetidin-3-one, 5.5 g of 1-benzhydryl-3-[(2,3-difluorophenyl)(methylsulfonyl)methyl-(RS)]azetidin-3-ol are obtained in the form of a beige solid.

(2,3-Difluorobenzyl) methyl sulfone may be prepared in the following manner: on carrying out the operation according to the procedure of Example 10 starting with 4.1 g of 2,3-difluorobenzyl bromide and 4.1 g of sodium methanesulfinate, 4 g of (2,3-difluorobenzyl) methyl sulfone are obtained in the form of a white solid.

EXAMPLE 18

On carrying out the operation according to the procedure of Example 4 starting with 5.2 g of 1-benzhydryl-3-[(2,5-difluorophenyl)(methylsulfonyl)methyl-(RS)]azetidin-3-ol, 2.3 cm$^3$ of methanesulfonyl chloride and 7.3 g of 4-dimethylaminopyridine, the residue obtained is purified by chromatography on a silica gel column (particle size 0.04–0.06 mm, diameter 6 cm, height 40 cm) at a nitrogen pressure of 0.5 bar with a mixture of dichloromethane and methanol (98/2 by volume) as eluent and collecting 50 cm$^3$ fractions. Fractions 73 to 90 are combined and concentrated to dryness under reduced pressure (2.7 kPa). The solid obtained is crystallized from 75 cm$^3$ of ethyl ether. 2.6 g of 1-benzhydryl-3-[(2,5-difluorophenyl)(methylsulfonyl) methylene]azetidine are obtained melting at 176° C.

1-Benzhydryl-3-[(2,5-difluorophenyl)(methylsulfonyl) methyl-(RS)]azetidin-3-ol may be obtained in the following manner: on carrying out the operation according to the procedure of Example 1 starting with 4 g of (2,5-difluorobenzyl) methyl sulfone and 4.8 g of 1-benzhydrylazetidin-3-one, 5.9 g of 1-benzhydryl-3-[(2,5-difluorophenyl)(methylsulfonyl)methyl-(RS)]azetidin-3-ol are obtained in the form of a cream-colored solid.

(2,5-Difluorobenzyl) methyl sulfone may be prepared in the following manner: on carrying out the operation according to the procedure of Example 10 starting with 4.1 g of 2,5-difluorobenzyl bromide and 4.1 g of sodium methanesulfinate, 4.8 g of (2,5-difluorobenzyl) methyl sulfone are obtained in the form of a white solid melting at 95° C.

EXAMPLE 19

On carrying out the operation according to the procedure of Example 4 starting with 7.7 g of 1-benzhydryl-3-[(3-bromophenyl)(methylsulfonyl)methyl-(RS)]azetidin-3-ol, 1.8 cm$^3$ of methanesulfonyl chloride and 5.8 g of 4-dimethylaminopyridine, the residue obtained is purified by chromatography on a silica gel column (particle size 0.04–0.06 mm, diameter 3 cm, height 35 cm) at a nitrogen pressure of 0.5 bar with dichloromethane and then a dichloromethane and ethanol mixture (99.5/0.5 by volume) as eluents and collecting 100 cm$^3$ fractions. Fractions 17 to 28 are combined and concentrated to dryness under reduced pressure (2.7 kPa). The solid obtained is crystallized from a mixture of 5 cm$^3$ of dichloromethane and 50 cm$^3$ of ethyl ether. 3.5 g of 1-benzhydryl-3-[(3-bromophenyl) (methylsulfonyl)methylene]azetidine are obtained melting at 200° C. [NMR spectrum in DMSO-d6, T=300K, δ in ppm (300 MHz): 2.95 (3H, s, SCH$_3$), 3.80 (2H, s, NCH$_2$), 4.20 (2H, s, NCH$_2$), 4.75 (1H, s, NCH), 7.20 (2H, t, J=7 Hz, 2CH arom.), 7.30 (4H, t, J=7 Hz, 4CH arom.), between 7.35 and 7.55 (6H, m, 6CH arom.), 7.65 (2H, m, 2CH arom.)].

1-Benzhydryl-3-[(3-bromophenyl)(methylsulfonyl) methyl-(RS)]azetidin-3-ol may be obtained in the following manner: on carrying out the operation according to the procedure of Example 1 starting with 8 g of 3-bromobenzyl methyl sulfone and 7.6 g of 1-benzhydrylazetidin-3-one, 8 g of 1-benzhydryl-3-[(3-bromophenyl)(methylsulfonyl) methyl-(RS)]azetidin-3-ol are obtained in the form of a white solid.

3-Bromobenzyl methyl sulfone may be prepared in the following manner: on carrying out the operation according to the procedure of Example 2 starting with 9 g of 3-bromobenzyl methyl sulfide and 27 g of oxone$^R$, 8.2 g of 3-bromobenzyl methyl sulfone are obtained in the form of a white solid.

3-Bromobenzyl methyl sulfide may be prepared in the following manner: on carrying out the operation according to the procedure of Example 2 starting with 10 g of 3-bromobenzyl bromide and 3.1 g of sodium methylthiolate, 9 g of 3-bromobenzyl methyl sulfide are obtained in the form of an oil.

EXAMPLE 20

On carrying out the operation according to the procedure of Example 4 starting with 1.5 g of 1-benzhydryl-3-[(3- iodophenyl)(methylsulfonyl)methyl-(RS)]azetidin-3-ol, 0.3 cm³ of methanesulfonyl chloride and 1.4 g of 4-dimethylaminopyridine, the residue obtained is purified by chromatography on a silica gel column (particle size 0.04–0.06 mm, diameter 3 cm, height 35 cm) at a nitrogen pressure of 0.5 bar with dichloromethane and then a mixture of dichloromethane and ethanol (99.7/0.3 by volume) as eluents and collecting 100 cm³ fractions. Fractions 16 to 24 are combined and concentrated to dryness under reduced pressure (2.7 kPa). The solid obtained is crystallized from a mixture of 1.5 cm³ of dichloromethane and 25 cm³ of ethyl ether. 0.5 g of 1-benzhydryl-3-[(3-iodophenyl)(methylsulfonyl)methylene]azetidine is obtained melting at 198° C. [NMR spectrum in DMSO-d6, T=300K, δ in ppm (300 MHz): 2.95 (3H, s, SCH₃), 3.80 (2H, s, NCH₂), 4.20 (2H, s, NCH₂), 4.75 (1H, s, NCH), between 7.10 and 7.30 (7H, m, 7CH arom.), 7.45 (5H, m, 5CH arom.), 7.80 (2H, m, 2CH arom.)].

1-Benzhydryl-3-[(3-iodophenyl)(methylsulfonyl)methyl-(RS)]azetidin-3-ol may be obtained in the following manner: on carrying out the operation according to the procedure of Example 1 starting with 3.7 g of 3-iodobenzyl methyl sulfone and 3 g of 1-benzhydrylazetidin-3-one, 1.5 g of 1-benzhydryl-3-[(3-iodophenyl)(methylsulfonyl)methyl-(RS)]azetidin-3-ol are obtained in the form of a white solid.

3-Iodobenzyl methyl sulfone may be prepared in the following manner: on carrying out the operation according to the procedure of Example 2 starting with 3.6 g of 3-iodobenzyl methyl sulfide and 10.3 g of oxone$^R$, 3.7 g of 3-iodobenzyl methyl sulfone are obtained in the form of a white solid.

3-Iodobenzyl methyl sulfide may be prepared in the following manner: on carrying out the operation according to the procedure of Example 2 starting with 5 g of 3-iodobenzyl bromide and 1.3 g of sodium methylthiolate, 4 g of 3-iodobenzyl methyl sulfide are obtained in the form of an oil.

EXAMPLE 21

On carrying out the operation according to the procedure of Example 4 starting with 2.4 g of 1-benzhydryl-3-[(methylsulfonyl)(3-trifluoromethoxyphenyl)methyl-(RS)]azetidin-3-ol, 0.6 cm³ of methanesulfonyl chloride and 2.3 g of 4-dimethylaminopyridine, the residue obtained is purified by chromatography on a silica gel column (particle size 0.04–0.06 mm, diameter 3 cm, height 35 cm) at a nitrogen pressure of 0.5 bar with dichloromethane and then a mixture of dichloromethane and ethanol (99.7/0.3 by volume) as eluents and collecting 100 cm³ fractions. Fractions 12 to 25 are combined and concentrated to dryness under reduced pressure (2.7 kPa). The solid obtained is crystallized from a mixture of 2 cm³ of dichloromethane and 30 cm³ of ethyl ether. 0.7 g of 1-benzhydryl-3-[(methylsulfonyl)(3-trifluoromethoxyphenyl)methylene]azetidine is obtained melting at 162° C. [NMR spectrum in DMSO-d6, T=300K, δ in ppm (250 MHz): 3.00 (3H, s, SCH₃), 3.80 (2H, s, NCH₂), 4.20 (2H, s, NCH₂), 4.75 (1H, s, NCH), between 7.15 and 7.40 (6H, m, 6CH arom.), between 7.45 and 7.55 (7H, m, 7CH arom.), 7.60 (1H, t, J=7 Hz, CH arom.)].

1-Benzhydryl-3-[(methylsulfonyl)(3-trifluoromethoxyphenyl)methyl-(RS)]azetidin-3-ol may be obtained in the following manner: on carrying out the operation according to the procedure of Example 1 starting with 2.4 g of methyl(3-trifluoromethoxybenzyl)sulfone and 2.2 g of 1-benzhydrylazetidin-3-one, 2.4 g of 1-benzhydryl-3-[(methylsulfonyl)(3-trifluoromethoxyphenyl)methyl-(RS)]azetidin-3-ol are obtained in the form of a white solid.

Methyl(3-fluoromethoxybenzyl)sulfone may be prepared in the following manner: on carrying out the operation according to the procedure of Example 2 starting with 2.6 g of methyl(3-trifluoromethoxybenzyl)sulfide and 7.2 g of oxone$^R$, 2.4 g of methyl-(3-trifluoromethoxybenzyl)sulfone are obtained in the form of a white solid.

Methyl(3-trifluoromethoxybenzyl)sulfide may be prepared in the following manner: on carrying out the operation according to the procedure of Example 2 starting with 3 g of 3-trifluoromethoxybenzyl bromide and 1 g of sodium methylthiolate, 3.3 g of methyl-(3-trifluoromethoxybenzyl)sulfide are obtained in the form of an oil.

EXAMPLE 22

On carrying out the operation according to the procedure of Example 4 starting with 4.1 g of 1-benzhydryl-3-[(methylsulfonyl)(3-trifluoromethylphenyl)methyl-(RS)]azetidin-3-ol, 1 cm³ of methanesulfonyl chloride and 4.2 g of 4-dimethylaminopyridine, the residue obtained is purified by chromatography on a silica gel column (particle size 0.04–0.06 mm, diameter 3 cm, height 35 cm) at a nitrogen pressure of 0.5 bar with dichloromethane as eluent, collecting 100 cm³ fractions. Fractions 10 to 14 are combined and concentrated to dryness under reduced pressure (2.7 kPa). The solid obtained is crystallized from a mixture of 2 cm³ of dichloromethane and 30 cm³ of ethyl ether. 1.2 g of 1-benzhydryl-3-[(methylsulfonyl)(3-trifluoromethylphenyl)methylene]azetidine are obtained melting at 178° C. [NMR spectrum in DMSO-d6, T=300K, δ in ppm (300 MHz): 3.00 (3H, s, SCH₃), 3.80 (2H, s, NCH₂), 4.15 (2H, s, NCH₂), 4.70 (1H, s, NCH), 7.20 (2H, t, J=7 Hz, 2CH arom.), 7.30 (4H, t, J=7 Hz, 4CH arom.), 7.45 (4H, d, J=7 Hz, 4CH arom.), between 7.60 and 7.80 (4H, m, 4CH arom.)].

1-Benzhydryl-3-[(methylsulfonyl)(3-trifluoromethylphenyl)methyl-(RS)]azetidin-3-ol may be obtained in the following manner: on carrying out the operation according to the procedure of Example 1 starting with 3.4 g of methyl(3-trifluoromethylbenzyl)sulfone and 3.4 g of 1-benzhydrylazetidin-3-one, 4.2 g of 1-benzhydryl-3-[(methylsulfonyl)(3-trifluoromethylphenyl)methyl-(RS)]azetidin-3-ol are obtained in the form of a white solid.

Methyl(3-trifluoromethylbenzyl)sulfone may be prepared in the following manner: on carrying out the operation according to the procedure of Example 2 starting with 3.3 g of methyl(3-trifluoromethylbenzyl)sulfide and 10 g of oxone$^R$, 3.4 g of methyl(3-trifluoromethylbenzyl)sulfone are obtained in the form of a white solid.

Methyl(3-trifluoromethylbenzyl)sulfide may be prepared in the following manner: on carrying out the operation according to the procedure of Example 2 starting with 3.9 g of 3-trifluoromethylbenzyl bromide and 1.4 g of sodium methylthiolate, 3.3 g of methyl-(3-trifluoromethylbenzyl)sulfide are obtained in the form of an oil.

EXAMPLE 23

On carrying out the operation according to the procedure of Example 4 starting with 2.7 g of 1-benzhydryl-3-{[3,5-bis(trifluoromethyl)phenyl]-(methylsulfonyl)methyl-(RS)}azetidin-3-ol, 0.6 cm³ of methanesulfonyl chloride and 2.4 g of 4-dimethylaminopyridine, the residue obtained is purified by chromatography on a silica gel column (particle size 0.04–0.06 mm, diameter 6 cm, height 40 cm) at a nitrogen pressure of 0.5 bar with dichloromethane as eluent, collecting 100 cm³ fractions. Fractions 7 to 12 are combined and concentrated to dryness under reduced pressure (2.7 kPa). The solid obtained is crystallized from 10 cm³ of ethyl ether.

1 g of 1-benzhydryl-3-{[3,5-bis(trifluoromethyl)phenyl](methylsulfonyl)methylene}azetidine is obtained melting at 192° C. [NMR spectrum in DMSO-d6, T=300K, δ in ppm (300 MHz): 3.00 (3H, s, SCH$_3$), 3.85 (2H, s, NCH$_2$), 4.15 (2H, s, NCH$_2$), 4.70 (1H, s, NCH), 7.15 (2H, t, J=7 Hz, 2CH arom.), 7.30 (4H, t, J=7 Hz, 4CH arom.), 7.40 (4H, d, J=7 Hz, 4CH arom.), 8.05 (2H, s, 2CH arom.), 8.15 (1H, s, CH arom.)].

1-Benzhydryl-3-{[3,5-bis(trifluoromethyl)phenyl](methylsulfonyl)methylene}azetidin-3-ol may be obtained in the following manner: on carrying out the operation according to the procedure of Example 1 starting with 3.1 g of methyl[3,5-bis(trifluoromethyl)benzyl]sulfone and 2.4 g of 1-benzhydrylazetidin-3-one, 2.8 g of 1-benzhydryl-3-{[(3,5-bis(trifluoromethyl)phenyl](methylsulfonyl)methylene}azetidin-3-ol are obtained in the form of a white solid.

Methyl[3,5-bis(trifluoromethyl)benzylsulfone may be prepared in the following manner: on carrying out the operation according to the procedure of Example 10 starting with 3 g of 3,5-bis(trifluoromethyl)benzyl chloride and 2 g of sodium methanesulfinate, 3.1 g of methyl[3,5-bis(trifluoromethyl)benzyl]sulfone are obtained in the form of a white solid melting at 132° C.

EXAMPLE 24

On carrying out the operation according to the procedure of Example 4 starting with 10.7 g of 1-benzhydryl-3-[(3,5-dibromophenyl)(methylsulfonyl)methyl-(RS)]azetidin-3-ol, 2.2 cm$^3$ of methanesulfonyl chloride and 7 g of 4-dimethylaminopyridine, the residue obtained is purified by chromatography on a silica gel column (particle size 0.04–0.06 mm, diameter 5.5 cm, height 30 cm) at a nitrogen pressure of 0.5 bar with dichloromethane as eluent and collecting 35 cm$^3$ fractions. Fractions 40 to 58 are combined and concentrated to dryness under reduced pressure (2.7 kPa). The solid obtained is crystallized from 50 cm$^3$ of ethyl ether. 1.5 g of 1-benzhydryl-3-[3,5-dibromophenyl)(methylsulfonyl)methylene]azetidine are obtained melting at 209° C. [NMR spectrum in DMSO-d6, T=300K, δ in ppm (250 MHz): 3.00 (3H, s, SCH$_3$), 3.88 (2H, s, NCH$_2$), 4.22 (2H, s, NCH$_2$), 4.75 (1H, s, NCH), 7.22 (2H, t, J=7 Hz, 2CH arom.), 7.33 (4H, t, J=7 Hz, 4CH arom.), 7.48 (4H, d, J=7 Hz, 4CH arom.), 7.68 (2H, s, 2CH arom.), 7.95 (1H, s, CH arom.)].

1-Benzhydryl-3-[(3,5-dibromophenyl)(methylsulfonyl)methyl-(RS)]azetidin-3-ol may be obtained in the following manner: on carrying out the operation according to the procedure of Example 1 starting with 6.2 g of (3,5-dibromobenzyl)methylsulfone and 4.5 g of 1-benzhydrylazetidin-3-one, 10.7 g of 1-benzhydryl-3-[3,5-dibromophenyl)(methylsulfonyl)methyl-(RS)]azetidin-3-ol are obtained in the form of a foam.

(3,5-Dibromobenzyl)methylsulfone may be prepared in the following manner: on carrying out the operation according to the procedure of Example 2 starting with 5.8 g of (3,5-dibromobenzyl)methylsulfide and 13 g of oxone$^R$, 6.2 g of (3,5-dibromobenzyl)methylsulfone are obtained in the form of a white solid.

(3,5-Dibromobenzyl)methylsulfide may be prepared in the following manner: on carrying out the operation according to the procedure of Example 2 starting with 6.6 g of 3,5-dibromobenzyl bromide and 1.5 g of sodium methylthiolate, 5.8 g of (3,5-dibromobenzyl)methylsulfide are obtained in the form of an oil.

EXAMPLE 25

On carrying out the operation according to the procedure of Example 4 starting with 4.2 g of 1-benzhydryl-3-[(methylsulfonyl)(3-nitrophenyl)methyl-(RS)]azetidin-3-ol, 1.1 cm$^3$ of methanesulfonyl chloride and 2.5 g of 4-dimethylaminopyridine, the residue obtained is purified by chromatography on a silica gel column (particle size 0.04–0.06 mm, diameter 4 cm, height 35 cm) at a nitrogen pressure of 0.5 bar with a mixture of cyclohexane and ethyl acetate (50/50 by volume) as eluents, collecting 400 cm$^3$ fractions. Fractions 17 to 33 are combined and concentrated to dryness under reduced pressure (2.7 kPa). The solid obtained is recrystallized from 15 cm$^3$ of ethyl acetate. 0.6 g of 1-benzhydryl-3-[(methylsulfonyl)(3-nitrophenyl)methylene]azetidine is obtained melting at 184° C. [NMR spectrum in DMSO-d6, T=300K, δ in ppm (300 MHz): 3.00 (3H, s, SCH$_3$), 3.85 (2H, s, NCH$_2$), 4.25 (2H, s, NCH$_2$), 4.75 (1H, s, NCH), 7.20 (2H, t, J=7 Hz, 2CH arom.), 7.30 (4H, t, J=7 Hz, 4CH arom.), 7.45 (4H, d, J=7 Hz, 4CH arom.), 7.75 (1H, t, J=7 Hz, CH arom.), 7.85 (1H, d, J=7 Hz, CH arom.), 8.25 (2H, m, 2CH arom.)].

1-Benzhydryl-3-[(methylsulfonyl)(3-nitrophenyl)methyl-(RS)]azetidin-3-ol may be obtained in the following manner: on carrying out the operation according to the procedure of Example 1 starting with 3.9 g of methyl(3-nitrobenzyl)sulfone and 4.2 g of 1-benzhydrylazetidin-3-one, 4.2 g of 1-benzhydryl-3-[(methylsulfonyl)(3-nitrophenyl)methyl-(RS)]azetidin-3-ol are obtained in the form of a foam.

Methyl(3-nitrobenzyl)sulfone may be prepared in the following manner: on carrying out the operation according to the procedure of Example 2 but starting with 18.1 g of methyl(3-nitrobenzyl)sulfide and 68 g of oxone$^R$, 13.9 g of methyl(3-nitrobenzyl)sulfone are obtained in the form of a foam.

Methyl(3-nitrobenzyl)sulfide may be prepared in the following manner: on carrying out the operation according to the procedure of Example 2 starting with 17.2 g of 3-nitrobenzyl chloride and 7.7 g of sodium methylthiolate, 18.2 g of methyl (3-nitrobenzyl) sulfide are obtained in the form of an oil.

EXAMPLE 26

A mixture of 0.34 g of 1-benzhydryl-3-[(methylsulfonyl)(3-nitrophenyl)methylene]azetidine, 16 cm$^3$ of 1 N hydrochloric acid in 8 cm$^3$ of ethanol and 16 cm$^3$ of tetrahydrofuran is heated under reflux. 0.17 g of iron powder is added and the reflux is maintained for 3 hours. The mixture is then cooled to room temperature and the insoluble matter is filtered off. The solution is taken up in 10 cm$^3$ of 1 N sodium hydroxide and 50 cm$^3$ of a saturated aqueous sodium chloride solution. The aqueous phase is extracted with 3 times 40 cm$^3$ of dichloromethane, the extracts are combined, dried over sodium sulfate and concentrated to dryness under reduced pressure (2.7 kPa). The residue is purified on a silica gel column (particle size 0.04–0.06 mm, diameter 3 cm, height 30 cm) at a nitrogen pressure of 0.5 bar with a mixture of cyclohexane and ethyl acetate (50/50 by volume) as eluent, collecting 20 cm$^3$ fractions. Fractions 13 to 31 are combined and concentrated to dryness under reduced pressure (2.7 kPa). The solid obtained is crystallized from 15 cm$^3$ of ethyl ether. 0.17 g of 3-[(3-aminophenyl)(methylsulfonyl)methylene]-1-benzhydrylazetidine is obtained melting at 197° C. [NMR spectrum in DMSO-d6, T=300K, δ in ppm (250 MHz): 2.95 (3H, s, SCH$_3$), 3.80 (2H, s, NCH$_2$), 4.20 (2H, s, NCH$_2$), 4.75 (1H, s, NCH), 5.25 (2H, s, NH$_2$), 6.55 (3H, m, 3CH arom.), 7.05 (1H, t, J=7 Hz, CH arom.), 7.20 (2H, t, J=7 Hz, 2CH arom.), 7.30 (4H, t, J=7 Hz, 4CH arom.), 7.45 (4H, d, J=7 Hz, 4CH arom.)].

EXAMPLE 27

On carrying out the operation according to the procedure of Example 4 starting with 1.2 g of 1-benzhydryl-3-[(3- methoxycarbonylphenyl)(methylsulfonyl)methyl-(RS)] azetidin-3-ol, 0.3 cm³ of methanesulfonyl chloride and 1.3 g of 4-dimethylaminopyridine, the residue obtained is purified by chromatography on a silica gel column (particle size 0.04–0.06 mm, diameter 3 cm, height 30 cm) at a nitrogen pressure of 0.5 bar with dichloromethane and then a mixture of dichloromethane and ethyl acetate (99.5/0.5 by volume) as eluents and collecting 100 cm³ fractions. Fraction 18 is concentrated to dryness under reduced pressure (2.7 kPa). The solid obtained is precipitated in 5 cm³ of ethyl ether. 0.13 g of 1-benzhydryl-3-[(3-methoxycarbonylphenyl) (methylsulfonyl)methylene]azetidine is obtained in the form of a foamy solid [NMR spectrum in DMSO-d6, T=300K, δ in ppm (300 MHz): 2.95 (3H, s, SCH₃), 3.80 (2H, s, NCH₂), 4.20 (2H, s, NCH₂), 4.75 (1H, s, NCH), 7.20 (2H, t, J=7 Hz, 2CH arom.), 7.30 (4H, t, J=7 Hz, 4CH arom.), 7.45 (4H, d, J=7 Hz, 4CH arom.), 7.60 (1H, t, J=7 Hz, CH arom.), 7.70 (1H, d, J=7 Hz, CH arom.), 8.00 (2H, m, 2CH arom.)].

1-Benzhydryl-3-[(3-methoxycarbonylphenyl) (methylsulfonyl)methyl-(RS)]azetidin-3-ol may be obtained in the following manner: on carrying out the operation according to the procedure of Example 1 starting with 3 g of (3-methoxycarbonylbenzyl)methylsulfone and 3.6 g of 1-benzhydrylazetidin-3-one, 1.2 g of 1-benzhydryl-3-[(3-methoxycarbonylphenyl)(methylsulfonyl)methyl-(RS)] azetidin-3-ol are obtained in the form of a foam after purification by chromatography on a silica gel column (particle size 0.04–0.06 mm, diameter 3 cm, height 30 cm) at a nitrogen pressure of 0.5 bar with dichloromethane and then a dichloromethane and ethanol mixture (99/1 by volume) as eluents.

(3-Methoxycarbonylbenzyl)methylsulfone may be prepared in the following manner: on carrying out the operation according to the procedure of Example 2 starting with 4.3 g of (3-methoxycarbonylbenzyl)methylsulfide and 13.4 g of oxone$^R$, 3.4 g of (3-methoxycarbonylbenzyl)methylsulfone are obtained in the form of a white solid.

(3-Methoxycarbonylbenzyl)methylsulfide may be prepared in the following manner: on carrying out the operation according to the procedure of Example 2 starting with 5 g of 3-methoxycarbonylbenzyl bromide and 1.7 g of sodium methylthiolate, 4.3 g of (3-methoxycarbonylbenzyl) methylsulfide are obtained in the form of an oil.

EXAMPLE 28

On carrying out the operation according to the procedure of Example 4 starting with 6.2 g of 1-benzhydryl-3-[(3-cyanophenyl)(methylsulfonyl)methyl-(RS)]azetidin-3-ol, 1.6 cm³ of methanesulfonyl chloride and 6.8 g of 4-dimethylaminopyridine, the residue obtained is purified by chromatography on a silica gel column (particle size 0.04–0.06 mm, diameter 3 cm, height 30 cm) at a nitrogen pressure of 0.5 bar with dichloromethane and then a dichloromethane and ethyl acetate mixture (99.5/0.5 by volume) as eluents and collecting 250 cm³ fractions. Fractions 10 to 15 are combined and concentrated to dryness under reduced pressure (2.7 kPa). The solid obtained is crystallized from a mixture of 5 cm³ of dichloromethane and 70 cm³ of ethyl ether. 2.9 g of 1-benzhydryl-3-[(3-cyanophenyl) (methylsulfonyl)methylene]azetidine are obtained melting at 152° C. [NMR spectrum in DMSO-d6, T=300K, δ in ppm (300 MHz): 3.00 (3H, s, SCH₃), 3.80 (2H, s, NCH₂), 4.20 (2H, s, NCH₂), 4.75 (1H, s, NCH), 7.20 (2H, t, J=7 Hz, 2CH arom.), 7.30 (4H, t, J=7 Hz, 4CH arom.), 7.45 (4H, d, J=7 Hz, 4CH arom.), 7.65 (1H, t, J=7 Hz, CH arom.), 7.75 (1H, d, J=7 Hz, CH arom.), 7.90 (2H, m, 2CH arom.)].

1-Benzhydryl-3-[(3-cyanophenyl)(methylsulfonyl) methyl-(RS)]azetidin-3-ol may be obtained in the following manner: on carrying out the operation according to the procedure of Example 1 starting with 3.9 g of (3-cyanobenzyl)methylsulfone and 4.7 g of 1-benzhydrylazetidin-3-one, 6.2 g of 1-benzhydryl-3-[(3-cyanophenyl)(methylsulfonyl)methyl-(RS)]azetidin-3-ol are obtained in the form of a white solid.

(3-Cyanobenzyl)methylsulfone may be prepared in the following manner: on carrying out the operation according to the procedure of Example 2 starting with 6.7 g of (3-cyanobenzyl)methylsulfide and 27.6 g of oxone$^R$, 3.9 g of (3-cyanobenzyl)methylsulfone are obtained in the form of a white solid.

(3-Cyanobenzyl)methylsulfide may be prepared in the following manner: on carrying out the operation according to the procedure of Example 2 starting with 8 g of 3-cyanobenzyl bromide and 3.1 g of sodium methylthiolate, 6.8 g of (3-cyanobenzyl)methylsulfide are obtained in the form of an oil.

EXAMPLE 29

A mixture of 3 g of 1-benzhydryl-3-[(3-carboxyphenyl) (methylsulfonyl)methylene]azetidine hydrochloride, 1.3 g of pentafluorophenol, 1.4 g of 1-(3-dimethylaminopropyl)-3-ethylcarbodiimide in 30 cm³ of dimethylformamide is stirred at room temperature for 15 hours. The mixture is taken up in 100 cm³ of water and 100 cm³ of a saturated aqueous sodium chloride solution and 50 cm³ of ethyl acetate. The organic phase is decanted off, dried over magnesium sulfate and concentrated to dryness under reduced pressure (2.7 kPa). The residue is purified by chromatography on a silica gel column (particle size 0.04–0.06 mm, diameter 3 cm, height 35 cm) at a nitrogen pressure of 0.5 bar with dichloromethane and then a dichloromethane and methanol mixture (99.4/0.6 by volume) as eluents and collecting 100 cm³ fractions. Fractions 13 to 16 are combined and concentrated to dryness under reduced pressure (2.7 kPa). The solid obtained is crystallized from 10 cm³ of ethyl ether. 0.6 g of 1-benzhydryl-3-[(methylsulfonyl)(3-pentafluorophenoxycarbonylphenyl) methylene]azetidine is obtained melting at 182° C. [NMR spectrum in DMSO-d6, T=300K, δ in ppm (400 MHz): 3.00 (3H, s, SCH₃), 3.85 (2H, s, NCH₂), 4.25 (2H, s, NCH₂), 4.75 (1H, s, NCH), 7.20 (2H, t, J=7 Hz, 2CH arom.), 7.30 (4H, t, J=7 Hz, 4CH arom.), 7.45 (4H, d, J=7 Hz, 4CH arom.), 7.70 (1H, t, J=7 Hz, CH arom.), 8.20 (2H, m, 2CH arom.)].

1-Benzhydryl-3-[(3-carboxyphenyl)(methylsulfonyl) methylene]azetidine hydrochloride may be prepared in the following manner: a mixture of 10 g of 1-benzhydryl-3-[(3-cyanophenyl)(methylsulfonyl)methylene]azetidine in 40 cm³ of acetic acid and 40 cm³ of concentrated hydrochloric acid (d=1.18) is heated at 45° C. for 7 days. The reaction medium is cooled on an ice-cold water bath and the precipitate formed is filtered on sintered glass. The solid is washed with 20 cm³ of a mixture of acetic acid and concentrated hydrochloric acid (50-50 by volume) and then with 3 times 20 cm³ of water and finally with 20 cm³ of ethanol. The white solid obtained is under reduced pressure (2.7 kPa) at 45° C. and 2.5 g of 1-benzhydryl-3-[(3-carboxyphenyl)(methylsulfonyl)methylene]azetidine hydrochloride are obtained in the form of a white solid.

EXAMPLE 30

A solution of 0.65 g of 1-benzhydryl-3-[(methylsulfonyl) (3-pentafluorophenoxycarbonylphenyl) methylene]

azetidine in 25 cm³ of 6.2 N ammoniacal ethanol is stirred for 4 hours at room temperature. The mixture is concentrated to dryness under reduced pressure (2.7 kPa) and then the residue is purified by chromatography on a silica gel column (particle size 0.04–0.06 mm, diameter 3 cm, height 30 cm) at a nitrogen pressure of 0.5 bar with a dichloromethane and ethanol mixture (99/1 by volume) and then a dichloromethane and ethanol mixture (98/2 by volume) as eluents and collecting 60 cm³ fractions. Fractions 18 to 30 are combined and concentrated to dryness under reduced pressure (2.7 kPa). 0.2 g of 1-benzhydryl-3-[(3-carbamoylphenyl)(methylsulfonyl)methylene]azetidine is obtained melting at 140° C. [NMR spectrum in DMSO-d6, T=300K, δ in ppm (300 MHz): 3.00 (3H, s, SCH₃), 3.80 (2H, s, NCH₂), 4.25 (2H, s, NCH₂), 4.75 (1H, s, NCH), 7.25 (2H, t, J=7 Hz, 2CH arom.), 7.30 (4H, t, J=7 Hz, 4CH arom.), between 7.45 and 7.65 (7H, m, 6CH arom. and 2 CONH₂), 7.95 (2H, m, 2CH arom.), 8.10 (1H, s, 2 CONH₂).

EXAMPLE 31

On carrying out the operation according to the procedure of Example 4 starting with 4.6 g of 1-benzhydryl-3-[(3-methoxyphenyl)(methylsulfonyl)methyl-(RS)]azetidin-3-ol, 1.2 cm³ of methanesulfonyl chloride and 3.8 g of 4-dimethylaminopyridine, 2.6 g of 1-benzhydryl-3-[(3-methoxyphenyl)(methylsulfonyl)methylene]azetidine are obtained, after recrystallization from 150 cm³ of acetonitrile, melting at 179° C. [NMR spectrum in DMSO-d6, T=300K, δ in ppm (250 MHz): 2.95 (3H, s, SCH₃), 3.75 (3H, s, OCH₃), 3.80 (2H, s, NCH₂), 4.20 (2H, s, NCH₂), 4.75 (1H, s, NCH), 7.00 (3H, m, 3 CH arom.), between 7.20 and 7.12 (11H, m, 10H phenyls and 1 CH arom.)].

1-Benzhydryl-3-[(3-methoxyphenyl)(methylsulfonyl)methyl-(RS)]azetidin-3-ol may be obtained in the following manner: on carrying out the operation according to the procedure of Example 1 starting with 3.4 g of (3-methoxybenzyl)methylsulfone and 4 g of 1-benzhydrylazetidin-3-one, 4.6 g of 1-benzhydryl-3-[(3-methoxyphenyl)(methylsulfonyl)methyl-(RS)]azetidin-3-ol are obtained in the form of a white solid.

(3-Methoxybenzyl)methylsulfone may be prepared in the following manner: on carrying out the operation according to the procedure of Example 2 starting with 3.4 g of (3-methoxybenzyl)methylsulfide and 13 g of oxone$^R$, 4 g of (3-methoxybenzyl)methylsulfone are obtained in the form of a white solid melting at 710° C.

(3-Methoxybenzyl)methylsulfide may be prepared in the following manner: on carrying out the operation according to the procedure of Example 2 starting with 3.1 g of 3-methoxybenzyl bromide and 1.5 g of sodium methylthiolate, 3.4 g of (3-methoxybenzyl)methylsulfide are obtained in the form of an oil.

EXAMPLE 32

10 cm³ of a 1 M solution of boron tetrabromide in dichloromethane are added, with stirring, to a solution of 1.3 g of 1-benzhydryl-3-[(3-methoxyphenyl)(methylsulfonyl)methylene]azetidine in 100 cm³ of dichloromethane. The stirring is maintained for 16 hours at room temperature. The reaction medium is taken up in 100 cm³ of ice-cold water. The organic phase is washed with 3 times 50 cm³ of water, dried over magnesium sulfate and concentrated to dryness under reduced pressure (2.7 kPa). The residue is precipitated in 150 cm³ of isopropyl ether and then dissolved in 50 cm³ of dichloromethane. The organic phase is washed with 3 times 30 cm³ of a saturated aqueous solution of sodium bicarbonate, decanted off, dried over magnesium sulfate and concentrated to dryness under reduced pressure (2.7 kPa). The residue is precipitated in 80 cm³ of ethyl ether. 0.36 g of 1-benzhydryl-3-[(3-hydroxyphenyl)(methylsulfonyl)methylene]azetidine is obtained from a solid melting at 248° C. [NMR spectrum in DMSO-d6, T=300K, δ in ppm (300 MHz): 2.95 (3H, s, SCH₃), 3.80 (2H, s, NCH₂), 4.20 (2H, s, NCH₂), 4.75 (1H, s, NCH), 6.85 (3H, m, 3 CH arom.), 7.25 (3H, m, 3 CH arom.), 7.35 (4H, t, J=7 Hz, 4CH arom.), 7.50 (4H, d, J=7 Hz, 4CH arom.), 9.50 (1H, s, OH)].

EXAMPLE 33

On carrying out the operation according to the procedure of Example 32 starting with 1.4 g of 1-benzhydryl-3-[(4-methoxyphenyl)(methylsulfonyl)methylene]azetidine, 10 cm³ of a 1 M boron tribromide solution and 100 cm³ of dichloromethane, the residue obtained is purified by chromatography on a silica gel column (particle size 0.04–0.06 mm, diameter 3.5 cm, height 24 cm) at a nitrogen pressure of 0.5 bar with a mixture of cyclohexane and ethyl acetate (50/50 by volume) as eluents and collecting 25 cm³ fractions. Fractions 21 to 37 are combined and concentrated to dryness under reduced pressure (2.7 kPa). The solid obtained is crystallized from a mixture of 30 cm³ of ethyl ether. 0.6 g of 1-benzhydryl-3-[(4-hydroxyphenyl)(methylsulfonyl)methylene]azetidine is obtained melting at 211° C. [NMR spectrum in DMSO-d6, T=300K, δ in ppm (300 MHz): 2.90 (3H, s, SCH₃), 3.80 (2H, s, NCH₂), 4.20 (2H, s, NCH₂), 4.75 (1H, s, NCH), 6.80 (2H, d, J=7 Hz, 2CH arom.), between 7.10 and 7.35 (8H, m, 8CH arom.), 7.48 (4H, d, J=7 Hz, 4CH arom.), 9.80 (1H, s, OH)].

1-Benzhydryl-3-[(4-methoxyphenyl)(methylsulfonyl)methylene]azetidine may be obtained in the following manner: on carrying out the operation according to the procedure of Example 4 starting with 3.5 g of 1-benzhydryl-3-[(4-methoxyphenyl)(methylsulfonyl)methyl-(RS)]azetidin-3-ol, 0.9 cm³ of methanesulfonyl chloride and 2.9 g of 4-dimethylaminopyridine, the residue obtained is purified by recrystallization from 100 cm³ of acetonitrile. 1 g of 1-benzhydryl-3-[(4-methoxyphenyl)(methylsulfonyl)methylene]azetidine is obtained melting at 181° C.

1-Benzhydryl-3-[(4-methoxyphenyl)(methylsulfonyl)methyl-(RS)]azetidin-3-ol may be obtained in the following manner: on carrying out the operation according to the procedure of Example 1 starting with 3.5 g of (4-methoxybenzyl)methylsulfone and 4 g of 1-benzhydrylazetidin-3-one, 3.6 g of 1-benzhydryl-3-[(4-methoxyphenyl)(methylsulfonyl)methyl-(RS)]azetidin-3-ol are obtained in the form of a white solid.

(4-Methoxybenzyl)methylsulfone may be prepared in the following manner: on carrying out the operation according to the procedure of Example 2 starting with 3.4 g of (4-methoxybenzyl)methylsulfide and 13 g of oxone$^R$, 3.5 g of (3-methoxybenzyl)methylsulfone are obtained in the form of a white solid melting at 113° C.

(4-Methoxybenzyl)methylsulfide may be prepared in the following manner: on carrying out the operation according to the procedure of Example 2 starting with 3.1 g of 4-methoxybenzyl chloride and 1.5 g of sodium methylthiolate, 3.4 g of (4-methoxybenzyl)methylsulfide are obtained in the form of an oil.

EXAMPLE 34

On carrying out the operation according to the procedure of Example 32 starting with 1.4 g of 1-benzhydryl-3-[(2-methoxyphenyl)(methylsulfonyl)methylene]azetidine, 10 cm³ of a 1 M solution of boron tribromide and 100 cm³ of dichloromethane, the residue obtained is purified by chromatography on a silica gel column (particle size 0.04–0.06 mm, diameter 4 cm, height 30 cm) at a nitrogen pressure of 0.5 bar with dichloromethane as eluent and collecting 40 cm³ fractions. Fractions 15 to 34 are combined and concentrated to dryness under reduced pressure (2.7 kPa). The solid obtained is crystallized from 40 cm³ of ethyl ether. 0.7 g of 1-benzhydryl-3-[(2-hydroxyphenyl)(methylsulfonyl)methylene]azetidine is obtained melting at 196° C. [NMR spectrum in DMSO-d6, T=300K, δ in ppm (300 MHz): 3.00 (3H, s, SCH₃), 3.60 (2H, s, NCH₂), 4.20 (2H, s, NCH₂), 4.75 (1H, s, NCH), 6.85 (1H, t, J=7 Hz, CH arom.), 6.90 (1H, d, J=7 Hz, CH arom.), 7.20 (4H, m, 4CH arom.), 7.30 (4H, t, J=7 Hz, 4CH arom.), 7.48 (4H, d, J=7 Hz, 4CH arom.), 9.90 (1H, s, OH)].

1-Benzhydryl-3-[(2-methoxyphenyl)(methylsulfonyl)methylene]azetidine may be obtained in the following manner: on carrying out the operation according to the procedure of Example 4 starting with 4.2 g of 1-benzhydryl-3-[(2-methoxyphenyl)(methylsulfonyl)methyl-(RS)]azetidin-3-ol, 1.1 cm³ of methanesulfonyl chloride and 3.5 g of 4-dimethylaminopyridine, the residue obtained is purified by chromatography on a silica gel column (particle size 0.04–0.06 mm, diameter 4 cm, height 30 cm) at a nitrogen pressure of 0.5 bar with a mixture of dichloromethane and ethyl acetate (50/50 by volume) as eluents and collecting 40 cm³ fractions. Fractions 23 to 54 are combined and concentrated to dryness under reduced pressure (2.7 kPa). The solid obtained is crystallized from 40 cm³ of ethyl ether. 1.9 g of 1-benzhydryl-3-[(2-methoxyphenyl)(methylsulfonyl)methylene]azetidine are obtained melting at 204° C.

1-Benzhydryl-3-[(2-methoxyphenyl)(methylsulfonyl)methyl-(RS)]azetidin-3-ol may be obtained in the following manner: on carrying out the operation according to the procedure of Example 1 starting with 4 g of (2-methoxybenzyl)methylsulfone and 4.5 g of 1-benzhydrylazetidin-3-one, 4.3 g of 1-benzhydryl-3-[(2-methoxyphenyl)(methylsulfonyl)methyl-(RS)]azetidin-3-ol are obtained in the form of a brown foam.

(2-Methoxybenzyl)methylsulfone may be prepared in the following manner: on carrying out the operation according to the procedure of Example 10 starting with 3.1 g of (2-methoxybenzyl) chloride and 4.1 g of sodium methanesulfinate, 4 g of (2-methoxybenzyl)methylsulfone are obtained in the form of a white solid.

EXAMPLE 35

On carrying out the operation according to the procedure of Example 4 starting with 2.1 g of 1-benzhydryl-3-[(methylsulfonyl)(naphth-2-yl)methyl-(RS)]azetidin-3-ol, 0.5 cm³ of methanesulfonyl chloride and 2.2 g of 4-dimethylaminopyridine, the residue obtained is purified by chromatography on a silica gel column (particle size 0.04–0.06 mm, diameter 4 cm, height 30 cm) at a nitrogen pressure of 0.5 bar with dichloromethane as eluent and collecting 100 cm³ fractions. Fractions 6 to 10 are combined and concentrated to dryness under reduced pressure (2.7 kPa). The solid obtained is crystallized from 20 cm³ of ethyl ether. 0.6 g of 1-benzhydryl-3-[(methylsulfonyl)(naphth-2-yl)methylene]azetidine is obtained melting at 178° C. [NMR spectrum in DMSO-d6, T=300K, δ in ppm (300 MHz): 3.00 (3H, s, SCH₃), 3.80 (2H, s, NCH₂), 4.20 (2H, s, NCH₂), 4.75 (1H, s, NCH), 7.20 (4H, m, 4CH arom.), 7.30 (4H, t, J=7 Hz, 4CH arom.), 7.45 (4H, d, J=7 Hz, 4CH arom.), 7.52 (3H, m, 3CH arom.), 7.90 (4H, m, 4CH arom.)].

1-Benzhydryl-3-[(methylsulfonyl)(naphth-2-yl)methyl-(RS)]azetidin-3-ol may be obtained in the following manner: on carrying out the operation according to the procedure of Example 1 starting with 3.5 g of methyl(naphth-2-ylmethyl)sulfone and 3.8 g of 1-benzhydrylazetidin-3-one, 2.2 g of 1-benzhydryl-3-[(methylsulfonyl)(naphth-2-yl)methyl-(RS)]azetidin-3-ol are obtained in the form of a white solid melting at 196° C.

Methyl(naphth-2-ylmethyl)sulfone may be prepared in the following manner: on carrying out the operation according to the procedure of Example 2 starting with 4.2 g of methyl(naphth-2-ylmethyl)sulfide and 13.7 g of oxone$^R$, 3.6 g of methyl(naphth-2-ylmethyl)sulfone are obtained in the form of a cream-colored solid.

Methyl(naphth-2-ylmethyl)sulfide may be prepared in the following manner: on carrying out the operation according to the procedure of Example 2 starting with 5 g of (2-bromomethyl)naphthalene and 1.8 g of sodium methylthiolate, 4.2 g of methyl(naphth-2-ylmethyl)sulfide are obtained in the form of an oil.

EXAMPLE 36

On carrying out the operation according to the procedure of Example 4 starting with 4.3 g of 1-benzhydryl-3-[(methylsulfonyl)(naphth-1-yl)methyl-(RS)]azetidin-3-ol, 1.1 cm³ of methanesulfonyl chloride and 4.6 g of 4-dimethylaminopyridine, the residue obtained is purified by chromatography on a silica gel column (particle size 0.04–0.06 mm, diameter 4 cm, height 30 cm) at a nitrogen pressure of 0.5 bar with dichloromethane as eluent and collecting 100 cm³ fractions. Fractions 6 to 14 are combined and concentrated to dryness under reduced pressure (2.7 kPa). The solid obtained is crystallized from 30 cm³ of ethyl ether. 2.5 g of 1-benzhydryl-3-[(methylsulfonyl)(naphth-1-yl)methylene]azetidine are obtained melting at 196° C. [NMR spectrum in DMSO-d6, T=300K, δ in ppm (300 MHz): 3.00 (3H, s, SCH₃), 3.35 and 3.50 (1H each, dd, J=16 and 3 Hz, NCH₂), 4.35 (2H, m, NCH₂), 4.75 (1H, s, NCH), between 7.10 and 7.70 (14H, m, 14CH arom.), 8.00 (3H, m, 3CH arom.)].

1-Benzhydryl-3-[(methylsulfonyl)(naphth-1-yl)methyl-(RS)]azetidin-3-ol may be obtained in the following manner: on carrying out the operation according to the procedure of Example 1 starting with 4.1 g of methyl(naphth-1-ylmethyl)sulfone and 4.4 g of 1-benzhydrylazetidin-3-one, 4.3 g of 1-benzhydryl-3-[(methylsulfonyl)(naphth-1-yl)methyl-(RS)]azetidin-3-ol are obtained in the form of a solid.

Methyl(naphth-1-ylmethyl)sulfone may be prepared in the following manner: on carrying out the operation according to the procedure of Example 2 starting with 4.3 g of methyl(naphth-1-ylmethyl)sulfide and 13.9 g of oxone$^R$, 4.1 g of methyl(naphth-1-yl-ethyl)sulfone are obtained in the form of a white solid.

Methyl(naphth-1-ylmethyl)sulfide may be prepared in the following manner: on carrying out the operation according to the procedure of Example 2 starting with 4 g of 1-chloromethylnaphthalene chloride and 1.8 g of sodium methylthiolate, 4.5 g of methyl(naphth-1-ylmethyl)sulfide are obtained in the form of an oil.

EXAMPLE 37

On carrying out the operation according to the procedure of Example 4 starting with 0.6 g of 1-benzhydryl-3-[(methylsulfonyl)(3-pyrrolidinophenyl)methyl-(RS)]azetidin-3-ol, 0.15 cm³ of methanesulfonyl chloride and 0.6 g of 4-dimethylaminopyridine, the residue obtained is purified by chromatography on a silica gel column (particle size 0.04–0.06 mm, diameter 2 cm, height 30 cm) at a nitrogen pressure of 0.5 bar with a dichloromethane and methanol mixture (98/2 by volume) as eluents and collecting 20 cm$^3$ fractions. Fractions 8 to 13 are combined and concentrated to dryness under reduced pressure (2.7 kPa). The solid obtained is crystallized from 8 cm$^3$ of ethyl ether. 0.36 g of 1-benzhydryl-3-[(methylsulfonyl)(3-pyrrolidinophenyl)methylene]azetidine is obtained melting at 153° C. [NMR spectrum in DMSO-d6, T=300K, δ in ppm (250 MHz): 1.95 (4H, m, 2 CH$_2$), 2.95 (3H, s, SCH$_3$), 3.20 (4H, m, 2 NCH$_2$), 3.80 (2H, S, NCH$_2$), 4.20 (2H, s, NCH$_2$), 4.75 (1H, s, NCH), 6.60 (3H, m, 3CH arom.), 7.20 (3H, m, 3CH arom.), 7.30 (4H, t, J=7 Hz, 4CH arom.), 7.48 (4H, d, J=7 Hz, 4CH arom.)].

1-Benzhydryl-3-[(methylsulfonyl)(3-pyrrolidinophenyl)methyl-(RS)]azetidin-3-ol may be obtained in the following manner: on carrying out the operation according to the procedure of Example 1 starting with 0.77 g of 3-pyrrolidinobenzyl methyl sulfone and 0.76 g of 1-benzhydrylazetidin-3-one, 0.6 g of 1-benzhydryl-3-[(methylsulfonyl)(3-pyrrolidinophenyl)methyl-(RS)]azetidin-3-ol is obtained in the form of a solid.

Methyl(3-pyrrolidinobenzyl)sulfone may be prepared in the following manner: on carrying out the operation according to the procedure of Example 2 starting with 1 g of methyl(3-pyrrolidinobenzyl)sulfide and 3.3 g of oxone$^R$, 0.8 g of methyl(3-pyrrolidinobenzyl)sulfone is obtained in the form of a solid.

Methyl(3-pyrrolidinobenzyl)sulfide may be prepared in the following manner: a mixture of 2 g of (3-iodobenzyl)methylsulfide, 1.3 cm$^3$ of pyrrolidine, 1.1 g of sodium tert-butoxide, 0.28 g of 1,1'-bis(diphenylphosphino)ferrocenyl palladium chloride, 0.63 g of 1,1'-bis(diphenylphosphino)ferrocene and 60 cm$^3$ of tetrahydrofuran is heated under reflux, under a nitrogen stream, for 3 hours. The reaction medium is cooled to room temperature and filtered on sintered glass. The precipitate is washed with 20 cm$^3$ of tetrahydrofuran and 10 cm$^3$ of dichloromethane and then the filtrate is concentrated to dryness under reduced pressure (2.7 kPa). The residue is taken up with 30 cm$^3$ of ethyl acetate and 30 cm$^3$ of 3 N hydrochloric acid. The aqueous phase is decanted off, neutralized (pH=7–8) with 35 cm$^3$ of 3 N sodium hydroxide and taken up in 50 cm$^3$ of ethyl acetate. The organic phase is extracted; 4 g of silica are added and then the mixture is concentrated to dryness under reduced pressure (2.5 kPa). The powder obtained is eluted on sintered glass containing 20 g of silica with a mixture of cyclohexane and ethyl acetate (90/10 by volume). The filtrate is concentrated to dryness under reduced pressure (2.7 kPa). 1.2 g of methyl(3-pyrrolidinobenzyl)sulfide are obtained in the form of an oil.

1,1'-Bis(diphenylphosphino)ferrocenyl palladium chloride may be prepared according to Hayashi T. et al., J. Am. Chem. Soc., 106, 158 (1984).

EXAMPLE 38

Method 1

0.65 cm$^3$ of methanesulfonyl chloride is added to a solution of 2.94 g of 1-[bis(4-chlorophenyl)methyl]-3-[(3,5-difluorophenyl)(methylsulfonyl)methyl-(RS)]azetidin-3-ol in 250 cm$^3$ of dichloromethane at 22° C., followed, in small portions over 15 minutes, by 2.42 g of 4-dimethylaminopyridine; the orange-colored solution is stirred for 2 hours at room temperature. The reaction mixture is washed 3 times with 150 cm$^3$ of distilled water and once with 150 cm$^3$ of a saturated sodium chloride solution and then dried with magnesium sulfate, filtered and concentrated to dryness under reduced pressure (2.7 kPa). The residue obtained is chromatographed on a silica gel column (particle size 0.04–0.06 mm, diameter 5.5 cm, height 15 cm), at an argon pressure of 0.5 bar with a mixture of ethyl acetate and cyclohexane (1/9 by volume) as eluents and collecting 70 cm$^3$ fractions. Fractions 15 to 36 are combined and then concentrated to dryness under reduced pressure (2.7 kPa). 1.86 g of white foam are obtained, which foam is crystallized from isopropyl ether in order to obtain a solid melting at 190° C. A recrystallization from 145 cm$^3$ of ethanol gives 1.08 g of 1-[bis(4-chlorophenyl)methyl]-3-[(3,5-difluorophenyl)(methylsulfonyl)methylene]azetidine melting at 206° C. [NMR spectrum in DMSO-d6, T=300K, δ in ppm (300 MHz): 3.00 (3H, s, SCH$_3$), 3.87 (2H, s, NCH$_{12}$), 4.20 (2H, s, NCH$_2$), 4.75 (1H, s, NCH), 7.15 (2H, d, J=8 Hz, 2CH arom.), 7.30 (5H, m, 5CH arom.), 7.45 (4H, d, J=7 Hz, 4CH arom.)].

Method 2

0.80 g of ground sodium hydroxide is added to a solution of 2.2 g of 3-acetoxy-1-[bis-(4-chlorophenyl)methyl]-3-[(3,5-difluorophenyl)(methylsulfonyl)methyl-(RS)]azetidine in 25 cm$^3$ of dioxane at room temperature. After 16 hours at room temperature, 50 cm$^3$ of water and 100 cm$^3$ of ethyl acetate are added. The mixture is separated after settling out, the organic phase rewashed with 100 cm$^3$ of water, dried over magnesium sulfate, filtered and concentrated to dryness under reduced pressure (2.7 kPa). A white foam is obtained which is crystallized from isopropyl ether in order to obtain 0.85 g of a solid melting at 190° C. Recrystallization from 20 cm$^3$ of ethanol gives 0.70 g of 1-[bis-(4-chlorophenyl)methyl]-3-[(3,5-difluorophenyl)(methylsulfonyl)methylene]azetidine melting at 205° C.

EXAMPLE 39

6.75 g of 3-[(3,5-difluorophenyl)(methylsulfonyl)methyl-(RS)]azetidin-3-ol hydrochloride and then 2.97 g of potassium carbonate are added to a solution of 6.8 g of bis(4-chlorophenyl)bromomethane in 300 cm$^3$ of acetonitrile. The reaction mixture is heated for 1 hour under reflux, cooled to room temperature, filtered and concentrated to dryness under reduced pressure (2.7 kPa). The residue obtained is chromatographed on a silica gel column (particle size 0.04–0.06 mm, diameter 8.5 cm, height 22 cm), at an argon pressure of 0.5 bar with a mixture of ethyl acetate and cyclohexane (25/75 by volume) as eluents and collecting 250 cm$^3$ fractions. Fractions 11 to 48 are combined and then concentrated to dryness under reduced pressure (2.7 kPa). 5.3 g of 1-[bis(4-chlorophenyl)methyl]-3-[(3,5-difluorophenyl)(methylsulfonyl)methyl-(RS)]azetidin-3-ol are obtained. [$^1$H NMR spectrum (300 MHz, (CD$_3$)$_2$SO-d6, δ in ppm): 2.00 (s, 3H), 2.94 (s, 3H), 3.25 (mt, 2H), 3.48 (d, J=9 Hz, 1H), 3.80 (d, J=9 Hz, 1H), 4.54 (s, 1H), 5.34 (s, 1H), 7.15 (d, J=8.5 Hz, 2H), from 7.20 to 7.40 (mt, 8H), 7.50 (broad t, J=9 Hz, 1H)].

Bis(4-chlorophenyl)bromomethane may be prepared according to the procedure described by BACHMANN W. E., J. Am. Chem. Soc., 2135 (1933).

3-[(3,5-Difluorophenyl)(methylsulfonyl)methyl-(RS)]azetidin-3-ol hydrochloride may be obtained in the following manner: 160 cm$^3$ of a 6.2 N hydrochloric acid solution in dioxane are added to a solution of 37 g of 3-[(3,5-difluorophenyl)(methylsulfonyl)methyl-(RS)]-1-(vinyloxycarbonyl)azetidin-3-ol in 160 cm$^3$ of dioxane. After 16 hours at room temperature, the reaction mixture is concentrated to dryness under reduced pressure (2.7 kPa).

The residue obtained is taken up in 320 cm³ of ethanol, heated for 1 hour under reflux and cooled in an ice-cold water bath. The solid which appears is filtered, washed with ethyl ether and dried at 40° C. under reduced pressure (2.7 kPa). 29.85 g of white crystals are obtained whose melting point is greater than 260° C.

3-[(3,5-Difluorophenyl)(methylsulfonyl)methyl-(RS)]-1-(vinyloxycarbonyl)azetidin-3-ol may be obtained in the following manner: a solution of 14.0 cm³ of vinyl chloroformate in 35 cm³ of dichloromethane is added at 5° C. to a solution of 60.18 g of 1-benzhydryl-3-[(3,5-difluorophenyl)(methylsulfonyl)methyl-(RS)]azetidin-3-ol in 1000 cm³ of dichloromethane. After 20 hours at room temperature, the reaction mixture is concentrated to dryness under reduced pressure (2.7 kPa). The residue obtained is chromatographed on a silica gel column (particle size 0.04–0.06 mm, diameter 11 cm, height 32 cm), at an argon pressure of 0.5 bar with a mixture of ethyl acetate and cyclohexane (3/7 by volume) as eluents and collecting 1000 cm³ fractions. Fractions 8 to 18 are combined and then concentrated to dryness under reduced pressure (2.7 kPa). 37 g of 3-[(3,5-difluorophenyl)(methylsulfonyl)methyl-(RS)]-1-(vinyloxycarbonyl)azetidin-3-ol are obtained in the form of white crystals melting at 195° C.

EXAMPLE 40

14 cm³ of a 1.6 N n-butyllithium solution in hexane are added at −70° C. to a solution of 4.77 g of (3,5-difluorobenzyl)methylsulfone in 70 cm³ of tetrahydrofuran under an argon atmosphere. After 1 hour at −70° C. , a solution of 6.8 g of 1-[bis(4-chlorophenyl)methyl]azetidin-3-one in 30 cm³ of tetrahydrofuran is added and then, 1 hour later, a solution of 2.34 cm³ of acetyl chloride in 20 cm³ of tetrahydrofuran and the temperature of the reaction mixture is raised to 20° C. for 1 hour. 50 cm³ of water and 200 cm³ of ethyl acetate are added. The mixture is separated after settling out, the organic phase washed with 100 cm³ of water, 100 cm³ of a saturated sodium chloride solution, dried over magnesium sulfate, filtered and concentrated to dryness under reduced pressure (2.7 kPa). 14.4 g of 3-acetoxy-1-[bis(4-chlorophenyl)methyl]-3-[(3,5-difluorophenyl)(methylsulfonyl)methyl)methylsulfonylmethyl-(RS)]azetidine are obtained in the form of a yellow oil [$^1$H NMR spectrum (400 MHz, CDCl$_3$, δ in ppm): 2.79 (s, 3H), 3.04 (AB, J=9 Hz, 2H), 3.27 (d, J=9 Hz, 1H), 3.45 (s, 1H), 3.81 (d, J=9 Hz, 1H), 4.32 (s, 1H), 4.49 (s, 1H), 6.88 (tt, J=9 and 2.5 Hz, 1H), from 7.20 to 7.35 (mt, 10H)].

1-[Bis(4-chlorophenyl)methyl]azetidin-3-one may be prepared according to the following procedure: a solution of 8.1 cm³ of dimethyl sulfoxide in 17.6 cm³ of dichloromethane is added to a solution of 5.0 cm³ of oxalyl chloride in 73 cm³ of dichloromethane cooled to −78° C. After 0.5 hour at −78° C. , a solution of 16.0 g of 1-[bis(4-chlorophenyl)methyl]azetidin-3-ol dissolved in 50 cm³ of dichloromethane is poured in. After 5 hours at −78° C. , 26.6 cm³ of triethylamine are added dropwise and the reaction mixture is allowed to return to room temperature. After 16 hours, the reaction mixture is washed with 4 times 200 cm³ of water and then with 200 cm³ of a saturated sodium chloride solution, dried over magnesium sulfate, filtered and concentrated to dryness under reduced pressure (2.7 kPa). The residue obtained is chromatographed on a silica gel column (particle size 0.04–0.06 mm, diameter 9.2 cm, height 21 cm) at an argon pressure of 0.5 bar with a mixture of ethyl acetate and cyclohexane (40/60 by volume) as eluents and collecting 200 cm³ fractions. Fractions 15 to 25 are combined and then concentrated to dryness under reduced pressure (2.7 kPa). 8.9 g of 1-[bis(4-chlorophenyl)methyl]azetidin-3-one are obtained in the form of pale yellow crystals melting at 111° C.

1-[Bis(4-chlorophenyl)methyl]azetidin-3-ol may be prepared according to the procedure described by KATRITZKY A. R. et al., J. Heterocycl. Chem., (1994), 271 starting with 35.5 g of [bis(4-chlorophenyl)methyl]amine hydrochloride and 11.0 cm³ of epichlorohydrin. 9.0 g of 1-[bis(4-chlorophenyl)methyl]azetidin-3-ol are isolated.

[Bis(4-chlorophenyl)methyl]amine hydrochloride may be prepared according to the method described by GRISAR M. et al., J. Med. Chem., 885 (1973).

EXAMPLE 41

On carrying out the operation according to the procedure of Example 38 (Method 1), starting with 0.72 g of 1-[bis(4-methoxyphenyl)methyl]-3-[(3,5-difluorophenyl)(methylsulfonyl)methyl-(RS)]azetidin-3-ol and after chromatography on a silica gel column (particle size 0.04–0.06 mm, diameter 4.0 cm, height 16.5 cm) at an argon pressure of 0.5 bar with a mixture of ethyl acetate and cyclohexane (2/8 by volume) as eluent and collecting 40 cm³ fractions, 0.10 g of a white foam is obtained. After crystallization from a mixture of ethyl acetate and cyclohexane, 60 mg of 1-[bis(4-methoxyphenyl)methyl]-3-[(3,5-difluorophenyl)(methylsulfonyl)methylene]azetidine are obtained in the form of a solid melting at 180° C. [NMR spectrum in DMSO-d6, T=300K, δ in ppm (250 MHz): 3.00 (3H, s, SCH$_3$), 3.70 (6H, s, 2 OCH$_3$), 3.80 (2H, s, NCH$_2$), 4.15 (2H, s, NCH$_2$), 4.58 (1H, s, NCH), 6.85 (4H, d, J=7 Hz, 4CH arom.), 7.15 (2H, d, J=8 Hz, 2CH arom.), 7.30 (5H, m, 5CH arom.)].

1-[Bis(4-methoxyphenyl)methyl]-3-[(3,5-difluorophenyl)(methylsulfonyl)methyl-(RS)]azetidin-3-ol may be obtained in the following manner: on carrying out the operation according to Example 39 starting with 1.2 g of bis(4-methoxyphenyl)bromomethane and 1.2 g of 3-[(3,5-difluorophenyl)(methylsulfonyl)methyl-(RS)]azetidin-3-ol hydrochloride and after chromatography on a silica gel column (particle size 0.04–0.06 mm, diameter 4.8 cm, height 18 cm), at an argon pressure of 0.5 bar with a mixture of ethyl acetate and cyclohexane (25/75 by volume) as eluent and collecting 50 cm³ fractions, fractions 9 to 18 are combined and then concentrated to dryness under reduced pressure (2.7 kPa). 0.55 g of 1-[bis(4-methoxyphenyl)methyl]-3-[(3,5-difluorophenyl)(methylsulfonyl)methyl-(RS)]azetidin-3-ol is obtained.

Bis(4-methoxyphenyl)bromomethane may be prepared according to the procedure described by BACHMANN W. E., J. Am. Chem. Soc. , 2135 (1933).

EXAMPLE 42

On carrying out the operation according to Example 38 (Method 1), starting with 0.47 g of 1-[bis-(4-methylphenyl)methyl]-3-[(3,5-difluorophenyl)(methylsulfonyl)methyl-(RS)]azetidin-3-ol and after chromatography on a silica gel column (particle size 0.04–0.06 mm, diameter 3.2 cm, height 18.5 cm), at an argon pressure of 0.5 bar with a mixture of ethyl acetate and cyclohexane (1/9 by volume) as eluent and collecting 35 cm³ fractions, 0.30 g of a white solid is obtained. After crystallization from diisopropyl ether, 0.20 g of 1-[bis(4-methylphenyl)methyl]-3-[(3,5-difluorophenyl)(methylsulfonyl)methylene]azetidine is obtained in the form of white needles melting at 200° C.

1-[Bis(4-methylphenyl)methyl]-3-[(3,5-difluorophenyl)(methylsulfonyl)methyl-(RS)]azetidin-3-ol may be obtained in the following manner: on carrying out the operation as in Example 39 starting with 0.7 g of bis(4-methylphenyl)bromomethane and 0.8 g of 3-[(3,5-difluorophenyl)(methylsulfonyl)methyl-(RS)]azetidin-3-ol hydrochloride and after chromatography on a silica gel column (particle size 0.04–0.06 mm, diameter 4.0 cm, height 19 cm), at an argon pressure of 0.5 bar with a mixture of ethyl acetate and cyclohexane (2/8 by volume) as eluent and collecting 40 cm$^3$ fractions, fractions 35 to 40 are combined and then concentrated to dryness under reduced pressure (2.7 kPa). 0.47 g of 1-[bis(4-methylphenyl)methyl]-3-[(3,5-difluorophenyl)(methylsulfonyl)methyl-(RS)]azetidin-3-ol is obtained.

Bis(4-methylphenyl)bromomethane may be prepared according to the procedure described by BACHMANN W. E., J. Am. Chem. Soc., 2135 (1933).

EXAMPLE 43

On carrying out the operation according to Example 38 (Method 1), starting with 1.42 g of 3-[(3,5-difluorophenyl)(methylsulfonyl)methyl-(RS)]-1-[(4-methoxyphenyl)(phenyl)methyl-(RS)]azetidin-3-ol, a mixture of the two diastereoisomers, and after chromatography on a silica gel column (particle size 0.04–0.06 mm, diameter 4.0 cm, height 21 m), at an argon pressure of 0.5 bar with a mixture of ethyl acetate and cyclohexane (2/8 by volume) as eluent and collecting 40 cm$^3$ fractions, 0.10 g of a white solid is obtained. After crystallization from diisopropyl ether, 50 mg of (RS)-3-[(3,5-difluorophenyl)(methylsulfonyl)methylene]-1-(4-methoxyphenyl)(phenyl)methyl]azetidine are obtained in the form of a white solid [NMR spectrum in DMSO-d6, T=300K, δ in ppm (300 MHz): 2.23 (6H, s, 2 PhCH$_3$), 3.00 (3H, s, SCH$_3$), 3.80 (2H, s, NCH$_2$), 4.12 (2H, s, NCH$_2$), 4.58 (1H, s, NCH), 7.08 (4H, d, J=7 Hz, 4CH arom.), 7.15 (2H, d, J=8 Hz, 2CH arom.), 7.25 (5H, m, 5CH arom.)]

The mixture of diastereoisomers 3-[(3,5-difluorophenyl)(methylsulfonyl)methyl-(RS)]-1-[(4-methoxyphenyl)(phenyl)methyl-(RS)]azetidin-3-ol may be obtained in the following manner: on carrying out the operation according to Example 39 starting with 2.52 g (RS)-bromo(4-methoxyphenyl)(phenyl)methane and 2.85 g of 3-[(3,5-difluorophenyl)(methylsulfonyl)methyl-(RS)]azetidin-3-ol hydrochloride and after chromatography on a silica gel column (particle size 0.04–0.06 mm, diameter 5.6 cm, height 19 cm), at an argon pressure of 0.5 bar with a mixture of ethyl acetate and cyclohexane (25/75 by volume) as eluent and collecting 100 cm$^3$ fractions, fractions 11 to 18 are combined and then concentrated to dryness under reduced pressure (2.7 kPa). 1.16 g of the mixture of diastereoisomers 3-[(3,5-difluorophenyl)(methylsulfonyl)methyl-(RS)]-1-[(4-methoxyphenyl)(phenyl)methyl-(RS)]azetidin-3-ol are obtained.

(RS)-bromo(4-methoxyphenyl)(phenyl)methane may be prepared according to the procedure described by BACHMANN W. E., J. Am. Chem. Soc., 2135 (1933).

EXAMPLE 44

On carrying out the operation as in Example 38 (Method 1), starting with 0.47 g of 1-[bis-(4-trifluoromethoxyphenyl)methyl]-3-[(3,5-difluorophenyl)(methylsulfonyl)methyl-(RS)]azetidin-3-ol, and after chromatography on a silica gel column (particle size 0.04–0.06 mm, diameter 4.2 cm, height 14 cm), at an argon pressure of 0.5 bar with a mixture of ethyl acetate and cyclohexane (2/8 by volume) as eluent and collecting 25 cm$^3$ fractions, 0.28 g of 1-[bis-(4-trifluoromethoxyphenyl)methyl]-3-[(3,5-difluorophenyl)(methylsulfonyl)methylene]azetidine is obtained in the form of a solid [NMR spectrum in DMSO-d6, T=300K, δ in ppm (300 MHz): 3.05 (3H, s, SCH$_3$), 3.95 (2H, s, NCH$_2$), 4.25 (2H, s, NCH$_2$), 4.90 (1H, s, NCH), 7.20 (2H, d, J=8 Hz, 2CH arom.), 7.32 (5H, m, 5CH arom.), 7.60 (4H, d, J=7 Hz, 4CH arom.)].

1-[Bis(4-trifluoromethoxyphenyl)methyl]-3-[(3,5-difluorophenyl)(methylsulfonyl)methyl-(RS)]azetidin-3-ol may be obtained in the following manner: on carrying out the operation as in Example 39 starting with 1.59 g of bis(4-trifluoromethoxyphenyl)bromomethane and 1.2 g of 3-[(3,5-difluorophenyl)(methylsulfonyl)methyl-(RS)]azetidin-3-ol hydrochloride and after chromatography on a silica gel column (particle size 0.04–0.06 mm, diameter 4.8 cm, height 17 cm), at an argon pressure of 0.5 bar with a mixture of ethyl acetate and cyclohexane (25/75 by volume) as eluent and collecting 50 cm$^3$ fractions, fractions 15 to 23 are combined and then concentrated to dryness under reduced pressure (2.7 kPa). 0.49 g of 1-[bis-(4-trifluoromethoxyphenyl)methyl]-3-[(3,5-difluorophenyl)(methylsulfonyl)methyl]azetidin-3-ol is obtained.

Bis(4-trifluoromethoxyphenyl)bromomethane may be prepared according to the procedure described by BACHMANN W. E., J. Am. Chem. Soc., 2135 (1933), starting with 1.39 g of bis(4-trifluoromethoxyphenyl)methanol, 3 cm$^3$ of 33% hydrobromic acid in acetic acid and 0.6 cm$^3$ of acetyl bromide. 1.59 g of bis(4-trifluoromethoxyphenyl)bromomethane are obtained in the form of a brown oil.

Bis(4-trifluoromethoxyphenyl)methanol is prepared according to PAVIA M. R. et al., J. Med. Chem., 4238 (1992).

EXAMPLE 45

On carrying out the operation as in Example 38 (Method 1), starting with 0.25 g of 1-[bis-(4-trifluoromethylphenyl)methyl]-3-[(3,5-difluorophenyl)(methylsulfonyl)methyl-(RS)]azetidin-3-ol, and after chromatography on a silica gel column (particle size 0.04–0.06 mm, diameter 2.4 cm, height 14 cm), at an argon pressure of 0.5 bar with a mixture of ethyl acetate and cyclohexane (2/8 by volume) as eluent and collecting 20 cm$^3$ fractions, 0.12 g of 1-[bis-(4-trifluoromethylphenyl)methyl]-3-[(3,5-difluorophenyl)(methylsulfonyl)methylene]azetidine is obtained in the form of a white solid [NMR spectrum in DMSO-d6, T=300K, δ in ppm (300 MHz): 3.05 (3H, s, SCH$_3$), 3.95 (2H, s, NCH$_2$), 4.25 (2H, s, NCH$_2$), 4.90 (1H, s, NCH), 7.20 (2H, d, J=8 Hz, 2CH arom.), 7.32 (5H, m, 5CH arom.), 7.60 (4H, d, J=7 Hz, 4CH arom.)].

1-[Bis(4-trifluoromethylphenyl)methyl]-3-[(3,5-difluorophenyl)(methylsulfonyl)methyl-(RS)]azetidin-3-ol may be obtained in the following manner: on carrying out the operation as in Example 39 starting with 1.46 g of bis(4-trifluoromethylphenyl)bromomethane and 1.2 g of 3-[(3,5-difluorophenyl)(methylsulfonyl)methyl-(RS)]azetidin-3-ol hydrochloride and after chromatography on a silica gel column (particle size 0.04–0.06 mm, diameter 4.8 cm, height 17 cm), at an argon pressure of 0.5 bar with a mixture of ethyl acetate and cyclohexane (30/70 by volume) as eluent and collecting 50 cm$^3$ fractions, fractions 9 to 14 are combined and then concentrated to dryness under reduced pressure (2.7 kPa). 0.25 g of 1-[bis-(4-trifluoromethylphenyl)methyl]-3-[(3,5-difluorophenyl)(methylsulfonyl)methyl-(RS)]azetidin-3-ol is obtained.

Bis(4-trifluoromethylphenyl)bromomethane may be prepared according to the procedure described by BACH- MANN W. E., J. Am. Chem. Soc., 2135 (1933), starting with 2.5 g of bis(4-trifluoromethylphenyl)methanol, 6 cm³ of 33% hydrobromic acid in acetic acid and 1.2 cm³ of acetyl bromide. 2.9 g of bis(4-trifluoromethylphenyl) bromomethane are obtained in the form of a brown oil.

Bis(4-trifluoromethylphenyl)methanol is prepared according to PAVIA M. R. et al., J. Med. Chem., 4238 (1992).

EXAMPLE 46

On carrying out the operation according to Example 38 (Method 2), starting with 3.16 g of 3-acetoxy-1-[bis(4-chlorophenyl)methyl]-3-{[3,5-bis(trifluoromethyl)phenyl](methylsulfonyl)methyl-(RS)}azetidine and 0.96 g of ground sodium hydroxide, a yellow foam is obtained, after 16 hours at room temperature, which is chromatographed on a silica gel column (particle size 0.04–0.06 mm, diameter 4.8 cm, height 14 cm), at an argon pressure of 0.5 bar with a mixture of ethyl acetate and cyclohexane (15/85 by volume) as eluent and collecting 40 cm³ fractions. 1.49 g of 1-[bis(4-chlorophenyl)methyl]-3-{[3,5-bis-(trifluoromethyl)phenyl](methylsulfonyl) methylene}azetidine are thus obtained in the form of a white foam [NMR spectrum in DMSO-d6, T=300K, δ in ppm (300 MHz): 3.05 (3H, s, SCH₃), 3.90 (2H, s, NCH₂), 4.30 (2H, s, NCH₂), 4.80 (1H, s, NCH), 7.40 (2H, d, J=7 Hz, 2CH arom.), 7.50 (2H, d, J=7 Hz, 2CH arom.), 8.10 (2H, s, 2CH arom.), 8.20 (1H, s, CH arom.)].

3-Acetoxy-1-[bis(4-chlorophenyl)methyl]-3-{[3,5-bis(trifluoromethyl)phenyl](methylsulfonyl)methyl-(RS)}azetidine may be obtained in the following manner: on carrying out the operation as in Example 40 starting with 2.0 g of [3,5-bis(trifluoromethyl)benzyl]methylsulfone, 4.1 cm³ of a 1.6 N solution of n-butyllithium in hexane, 2.0 g of 1-[bis(4-chlorophenyl)methyl]azetidin-3-one and 0.77 cm³ of acetyl chloride in 20 cm³ of anhydrous diisopropyl ether, 3.56 g of 3-acetoxy-1-[bis(4-chlorophenyl)methyl]-3-{[3,5-bis(trifluoromethyl)phenyl](methylsulfonyl)methyl-(RS)}azetidine are obtained in the form of a white foam after chromatography on a silica gel column (particle size 0.04–0.06 mm, diameter 5.6 cm, height 16 cm), at an argon pressure of 0.5 bar with a mixture of ethyl acetate and cyclohexane (1/9 by volume) as eluent and collecting 100 cm³ fractions.

[3,5-Bis(trifluoromethyl)benzyl]methylsulfone is prepared in the following manner: on carrying out the operation according to Example 10 starting with 1.8 g of 3,5-bis(trifluoromethyl)benzyl chloride and 1.22 g of sodium methanesulfinate, 1.86 g of [3,5-bis-(trifluoromethyl)benzyl]methylsulfone are obtained in the form of a white solid.

EXAMPLE 47

On carrying out the operation as in Example 38 (Method 1), starting with 0.27 g of the mixture of the two diastereoisomers 1-[(4-chlorophenyl)(2,4-dichlorophenyl)methyl-(RS)]-3-[(3,5-difluorophenyl)(methylsulfonyl)methyl-(RS)] azetidin-3-ol and after chromatography on a silica gel column (particle size 0.04–0.06 mm, diameter 2.4 cm, height 7.5 cm), at an argon pressure of 0.5 bar with a mixture of ethyl acetate and cyclohexane (15/85 by volume) as eluent and collecting 20 cm³ fractions, 0.10 g of (RS)-1-[(4-chlorophenyl)(2,4-dichlorophenyl)methyl]-3-[(3,5-difluorophenyl)(methylsulfonyl)methylene]azetidine is obtained in the form of a white solid [NMR spectrum in DMSO-d6, T=300K, δ in ppm (250 MHz): 3.02 (3H, s, SCH₃), 3.82 (1H, dd, J=3 and 16 Hz, NCHH), 4.04 (1H, dd, J=3 and 16 Hz, NCHH), 4.10 (1H, dd, J=3 and 16 Hz, NCHH), 4.35 (1H, dd, J=3 and 16 Hz, NCHH), 5.12 (1H, s, NCH), 7.18 (2H, d, J=8 Hz, 2CH arom.), 7.32 (1H, t, J=8 Hz, CH arom.), 7.38 (2H, d, J=7 Hz, 2CH arom.), 7.45 (2H, d, J=7 Hz, 2CH arom.), 7.48 (1H, dd, J=2 and 7 Hz, CH arom.), 7.58 (1H, d, J=2 Hz, CH arom.), 7.80 (1H, d, J=7 Hz, CH arom.)].

The mixture of the two diastereoisomers 1-[(4-chlorophenyl)(2,4-dichlorophenyl)methyl-(RS)]-3-[(3,5-difluorophenyl)(methylsulfonyl)methyl-(RS)]azetidin-3-ol may be obtained in the following manner: on carrying out the operation according to Example 39 starting with 0.56 g of (RS)-bromo(4-chlorophenyl)(2,4-dichlorophenyl) methane and 0.50 g of 3-[(3,5-difluorophenyl)(methylsulfonyl)methyl-(RS)]azetidin-3-ol hydrochloride and after chromatography on a silica gel column (particle size 0.04–0.06 mm, diameter 4.0 cm, height 13 cm), at an argon pressure of 0.5 bar with a mixture of ethyl acetate and cyclohexane (20/80 by volume) as eluent and collecting 40 cm³ fractions, fractions 9 to 14 are combined and then concentrated to dryness under reduced pressure (2.7 kPa). 0.27 g of the mixture of the two diastereoisomers 1-[(4-chlorophenyl)(2,4-dichlorophenyl)methyl-(RS)]-3-[(3,5-difluorophenyl)(methylsulfonyl)methyl-(RS)]azetidin-3-ol is obtained.

(RS)-bromo(4-chlorophenyl)(2,4-dichlorophenyl) methane may be prepared according to the procedure described by BACHMANN W. E., J. Am. Chem. Soc., 2135 (1933) starting with 4.05 g of (RS)-(4-chlorophenyl)(2,4-dichlorophenyl)methanol, 10 cm³ of 33% hydrobromic acid in acetic acid and 2.1 cm³ of acetyl bromide. 4.6 g of (RS)-bromo(4-chlorophenyl)(2,4-dichlorophenyl)methane are obtained in the form of a greenish oil.

(RS)-(4-chlorophenyl)(2,4-dichlorophenyl)methanol is prepared according to PAVIA M. R. et al., J. Med. Chem., 4238 (1992).

EXAMPLE 48

75.6 cm³ of 5 N hydrochloric acid are added to a solution of 18.9 g of 1-{(4-chlorophenyl)[4-(1,3-dioxolan-2-yl) phenyl]methyl-(RS)}-3-[(3,5-difluorophenyl)(methylsulfonyl)methylene]azetidine in 80 cm³ of tetrahydrofuran. After 3 hours at room temperature, the mixture is taken up in dichloromethane and distilled water and then adjusted to pH 14 by addition of 30% sodium hydroxide and separated after settling out. The organic phase is washed twice with 100 cm³ of water and then 100 cm³ of a saturated aqueous sodium chloride solution, dried over magnesium sulfate, filtered and concentrated to dryness under reduced pressure (2.7 kPa). 16 g of (RS)-1-[(4-chlorophenyl)(4-formylphenyl)methyl]-3-[(3,5-difluorophenyl)(methylsulfonyl)methylene]azetidine are obtained in the form of a white foam [Spectrum in DMSO-d6, T=300K, δ in ppm (300 MHz): 3.06 (3H, s, SCH₃), 3.95 (2H, m, NCH₂), 4.26 (2H, m, NCH₂), 4.91 (1H, s, NCH), 7.20 (2H, d, J=8 Hz, 2CH arom.), 7.36 (1H, t, J=8 Hz, 1CH arom.), 7.40 and 7.52 (4H, 2d, J=7.5 Hz, 4CH arom.), 7.70 and 7.88 (4H, 2d, J=7.5 Hz, 4CH arom.), 9.97 (1H, s, CH aldehydic)].

1-{(4-Chlorophenyl)[4-(1,3-dioxolan-2-yl)phenyl] methyl-(RS)}-3-[(3,5-difluorophenyl)(methylsulfonyl) methylene]azetidine may be prepared according to the following method: 13.0 cm³ of 1,8-diazabicyclo[5.4.0]undec-7-ene are added dropwise to a solution of 34.45 g of the mixture of the two diastereoisomers 3-acetoxy-1-{(4-chlorophenyl)[4-(1,3-dioxolan-2-yl)phenyl]methyl-(RS)}-

3-[(3,5-difluorophenyl)(methylsulfonyl)methyl-(RS)]azetidine in 400 cm³ of tetrahydrofuran under argon at 0° C., and after customary treatment, 16.6 g of 1-{(4-chlorophenyl)[4-(1,3-dioxolan-2-yl)phenyl]methyl-(RS)}-3-[(3,5-difluorophenyl)(methylsulfonyl)methylene]azetidine are obtained in the form of a white solid after chromatography on a silica gel column (particle size 0.04–0.06 mm, diameter 10.2 cm, height 23 cm), at an argon pressure of 0.5 bar with a mixture of ethyl acetate and cyclohexane (2/8 by volume) as eluent and collecting 250 cm³ fractions.

The mixture of the two diastereoisomers 3-acetoxy-1-{(4-chlorophenyl)[4-(1,3-dioxolan-2-yl)phenyl]methyl-(RS)}-3-[(3,5-difluorophenyl)(methylsulfonyl)methyl-(RS)]azetidine may be obtained in the following manner: on carrying out the operation according to Example 40, starting with 11.6 g of (3,5-difluorobenzyl)methylsulfone, 35.1 cm³ of a 1.6 N solution of n-butyllithium in hexane, 19.3 g of 1-{(4-chlorophenyl)[4-(1,3-dioxolan-2-yl)phenyl]methyl-(RS)}azetidin-3-one and 8.8 cm³ of acetyl chloride in 500 cm³ of tetrahydrofuran, 37.8 g of the mixture of the two diastereoisomers 3-acetoxy-1-{(4-chlorophenyl)[4-(1,3-dioxolan-2-yl)phenyl]methyl-(RS)}-3-[(3,5-difluorophenyl)(methylsulfonyl)methyl-(RS)]azetidine are obtained in the form of a white foam.

1-{(4-Chlorophenyl)[4-(1,3-dioxolan-2-yl)phenyl]methyl-(RS)}azetidin-3-one may be prepared in the following manner: 46 cm³ of triethylamine are added at room temperature to a solution of 28.32 g of 1-{(4-chlorophenyl)[4-(1,3-dioxolan-2-yl)phenyl]methyl-(RS)}azetidin-3-ol in 200 cm³ of dimethyl sulfoxide, and then a solution of 34 g of sulfur trioxide-pyridine complex in 100 cm³ of dimethyl sulfoxide are added dropwise. After 0.25 hour at room temperature, the reaction mixture is poured over ice, extracted with ethyl acetate, washed with 3 times 400 cm³ of water and then with 400 cm³ of a saturated sodium chloride solution, dried over magnesium sulfate, filtered and concentrated to dryness under reduced pressure (2.7 kPa). The residue obtained is chromatographed on a silica gel column (particle size 0.04–0.06 mm, diameter 9.2 cm, height 21 cm), at an argon pressure of 0.5 bar with a mixture of ethyl acetate and cyclohexane (20/80 by volume) as eluent and collecting 250 cm³ fractions. Fractions 9 to 18 are combined and then concentrated to dryness under reduced pressure (2.7 kPa). 20.4 g of 1-{(4-chlorophenyl)[4-(1,3-dioxolan-2-yl)phenyl]methyl-(RS)}azetidin-3-one are obtained in the form of a yellow oil.

1-{(4-Chlorophenyl)[4-(1,3-dioxolan-2-yl)phenyl]methyl-(RS)}azetidin-3-ol may be prepared according to the procedure described by KATRITZKY A. R. et al., J. Heterocycl. Chem., 271 (1994) starting with 35.0 g of {(4-chlorophenyl)[4-(1,3-dioxolan-2-yl)phenyl]methyl}amine, 8.3 g of epibromohydrin, 5.1 g of sodium hydrogen carbonate and 400 cm³ of ethanol. 30.3 g of 1-{(4-chlorophenyl)[4-(1,3-dioxolan-2-yl)phenyl]methyl-(RS)}azetidin-3-ol are isolated.

{(4-Chlorophenyl)[4-(1,3-dioxolan-2-yl)phenyl]methyl-(RS)}amine hydrochloride may be prepared according to the method described by GRISAR M. et al., J. Med. Chem., 885 (1973) starting with 67.2 g of 4-(1,3-dioxolan-2-yl)benzonitrile, 88.2 g of 1-bromo-4-chlorobenzene, 11 g of magnesium and 600 cm³ of ethyl ether. 42.3 g of {(4-chlorophenyl)[4-(1,3-dioxolan-2-yl)phenyl]methyl-(RS)}amine are obtained in the form of a yellow oil.

EXAMPLE 49

0.020 g of sodium borohydride is added to a solution of 0.50 g of (RS)-1-{(4-chlorophenyl)(4-formylphenyl)methyl}-3-[(3,5-difluorophenyl)(methylsulfonyl)methylene]azetidine in 15 cm³ of methanol at 0° C. After 1 hour at 0° C. , 40 cm³ of water are added and the product extracted with 100 cm³ of dichloromethane. The organic phase is washed twice with 40 cm³ of water and then 40 cm³ of a saturated sodium chloride solution, dried over magnesium sulfate, filtered and concentrated to dryness under reduced pressure (2.7 kPa). The residue obtained is chromatographed on a silica gel column (particle size 0.04–0.06 mm, diameter 3.2 cm, height 14 cm), at an argon pressure of 0.5 bar with a mixture of ethyl acetate and cyclohexane (30/70 by volume) and collecting 20 cm³ fractions. Fractions 20 to 25 are combined and then concentrated to dryness under reduced pressure (2.7 kPa). 0.29 g of (RS)-1-{(4-chlorophenyl)[4-(hydroxymethyl)phenyl]methyl}-3-[(3,5-difluorophenyl)(methylsulfonyl)methylene]azetidine is obtained in the form of a white foam [NMR spectrum in DMSO-d6, T=300K, δ in ppm (250 MHz): 3.02 (3H, s, SCH₃), 3.90 (2H, s, NCH₂), 4.20 (2H, s, NCH₂), 4.42 (2H, d, J=5 Hz, OCH₂), 4.75 (1H, s, NCH), 5.10 (1H, t, J=5 Hz, OH), between 7.10 and 7.50 (11H, m, 11CH arom.)].

EXAMPLE 50

0.75 g of (RS)-1-{(4-chlorophenyl)(4-formylphenyl)methyl}-3-[(3,5-difluorophenyl)(methylsulfonyl)methylene]azetidine and then 0.68 g of sodium triacetoxyborohydride are added to a solution of 0.10 g of pyrrolidine in 20 cm³ of 1,2-dichloroethane. After 20 hours at room temperature, 2 cm³ of 1 N sodium hydroxide are added, the product is extracted with 100 cm³ of dichloromethane, the organic phase is washed twice with 50 cm³ of water and then 50 cm³ of a saturated sodium chloride solution, dried over magnesium sulfate, filtered and concentrated to dryness under reduced pressure (2.7 kPa). The residue obtained is chromatographed on a silica gel column (particle size 0.04–0.06 mm, diameter 4.1 cm, height 13 cm), at an argon pressure of 0.5 bar with acetate as eluent and collecting 20 cm³ fractions. Fractions 10 to 18 are combined and then concentrated to dryness under reduced pressure (2.7 kPa). 0.39 g of (RS)-1-{(4-chlorophenyl)[4-(pyrrolidylmethyl)phenyl]methyl}-3-[(3,5-difluorophenyl)(methylsulfonyl)methylene]azetidine is obtained in the form of a white foam [NMR spectrum in DMSO-d6, T=300K, δ in ppm (300 MHz): 1.65 (4H, m, 2CH₂), 2.40 (4H, m, 2NCH₂), 3.02 (3H, s, SCH₃), 3.50 (2H, s, NCH₂Ph), 3.85 (2H, s, NCH₂), 4.20 (2H, s, NCH₂), 4.75 (1H, s, NCH), between 7.15 and 7.40 (9H, m, 9CH arom.), 7.48 (2H, d, J=7 Hz, 2CH arom.)].

EXAMPLE 51

On carrying out the operation as in Example 50 starting with 0.93 cm³ of a 2 M solution of dimethylamine in methanol, 30 cm³ of 1,2-dichloroethane, 0.75 g of (RS)-1-{(4-chlorophenyl)(4-formylphenyl)methyl}-3-[(3,5-difluorophenyl)(methylsulfonyl)methylene]azetidine and then 0.9 g of sodium triacetoxyborohydride, there is obtained after chromatography on a silica gel column (particle size 0.04–0.06 mm, diameter 4 cm, height 17.5 cm), at an argon pressure of 0.5 bar with a mixture of ethyl acetate and cyclohexane (30/70 by volume) as eluent and collecting 40 cm³ fractions, 0.46 g of (RS)-1-[(4-chlorophenyl)(4-dimethylaminomethyl)methyl]-3-[(3,5-difluorophenyl)(methylsulfonyl)methylene]azetidine in the form of a white solid [NMR spectrum in DMSO-d6, T=300K, δ in ppm (300 MHz): 2.12 (6H, s, N(CH₃)₂), 3.02 (3H, s, SCH₃), 3.32 (2H, s, NCH₂Ph), 3.90 (2H, s, NCH₂), 4.20 (2H, s, NCH₂), 4.75 (1H, s, NCH), 7.18 (2H, d, J=8 Hz, 2CH arom.), 7.22 (2H, d, J=8 Hz, 2CH arom.), 7.35 (1H, t, J=8 Hz, CH arom.), 7.39 (4H, m, 4CH arom.), 7.48 (4H, d, J=7 Hz, 4CH arom.)].

EXAMPLE 52

A solution of 0.5 g of (RS)-1-{(4-carboxyphenyl)(4-chlorophenyl)methyl]-3-[(3,5-difluorophenyl)(methylsulfonyl)methylene]azetidine in 10 cm$^3$ of dichloromethane at 0° C. is stirred with 0.5 cm$^3$ of a solution (2 M) of dimethylamine in ethanol. 13 mg of hydroxybenzotriazole, 0.2 g of 1,3-dimethylaminopropyl-3-ethylcarbodiimide hydrochloride and 0.18 cm$^3$ of diisopropylethylamine are then added. After 20 hours at room temperature, the reaction mixture is diluted with dichloromethane, washed twice with 80 cm$^3$ of water and then 80 cm$^3$ of a saturated sodium chloride solution, dried over magnesium sulfate, filtered and concentrated to dryness under reduced pressure (2.7 kPa). The residue obtained is chromatographed on a silica gel column (particle size 0.04–0.06 mm, diameter 4.1 cm, height 13 cm), at an argon pressure of 0.5 bar with a dichloromethane/acetonitrile/methanol (98/1/1 by volume) mixture as eluent and collecting 15 cm$^3$ fractions. Fractions 13 to 15 are combined and then concentrated to dryness under reduced pressure (2.7 kPa). 0.16 g of a cream-colored solid is obtained which, after taking up in isopropyl ether and drying, gives 0.11 g of (RS)-1-{(4-chlorophenyl)[4-N,N-dimethylcarbamoyl)phenyl]methyl}-3-[(3,5-difluorophenyl) (methylsulfonyl)methylene]azetidine in the form of a solid [NMR spectrum in DMSO-d6, T=300K, δ in ppm (300 MHz): 2.85 (3H, broad s, NCH$_3$), 2.95 (3H, broad s, NCH$_3$), 3.00 (3H, s, SCH$_3$), 3.90 (2H, s, NCH$_2$), 4.20 (2H, s, NCH$_2$), 4.80 (1H, s, NCH), 7.15 (2H, d, J=8 Hz, 2CH arom.), 7.30 (1H, t, J=8 Hz, CH arom.), 7.35 (4H, m, 4CH arom.), 7.50 (4H, d, J=7 Hz, 4CH arom.)].

(RS)-1-{(4-carboxyphenyl)(4-chlorophenyl)methyl]-3-[(3,5-difluorophenyl)(methylsulfonyl)methylene]azetidine may be prepared in the following manner: 1.0 cm$^3$ of Jones reagent is added to a solution of 0.50 g of (RS)-1-{(4-chlorophenyl)(4-formylphenyl)methyl}-3-[(3,5-difluorophenyl)(methylsulfonyl)methylene]azetidine in 10 cm$^3$ acetone at 0° C. After 5 hours, the reaction mixture is poured into distilled water, the product is extracted with 50 cm$^3$ of ethyl acetate, the organic phase is washed twice with 50 cm$^3$ of water and then 50 cm$^3$ of a saturated sodium chloride solution, dried over magnesium sulfate, filtered and concentrated to dryness under reduced pressure (2.7 kPa). The solid obtained is crystallized from an ethyl acetate-cyclohexane mixture, filtered and dried. 0.50 g of (RS)-1-{(4-carboxyphenyl)(4-chlorophenyl)methyl-(RS)]-3-[(3,5-difluorophenyl)(methylsulfonyl)methylene]azetidine is obtained in the form of a white solid.

EXAMPLE 53

The operation is carried out as in Example 52, starting with 1 g of (RS)-1-{(4-carboxyphenyl)(4-chlorophenyl)methyl]-3-[(3,5-difluorophenyl)(methylsulfonyl)methylene]azetidine, 0.38 g of 1,3-dimethylaminopropyl-3-ethylcarbodiimide hydrochloride, 22 mg of hydroxybenzotriazole hydrate, 30 cm$^3$ of dichloromethane and 0.83 cm$^3$ of a 2 M ethylamine solution in THF, chromatographing on a silica gel column (particle size 0.04–0.06 mm, diameter 4.1 cm, height 15 cm), at an argon pressure of 0.5 bar with a mixture of ethyl acetate and cyclohexane (45/55 by volume) as eluent and collecting 30 cm$^3$ fractions. Fractions 22 to 32 are combined and then concentrated to dryness under reduced pressure (2.7 kPa). 0.29 g of (RS)-1-{(4-chlorophenyl)[4-(N-ethylcarbamoyl)phenyl]methyl}-3-[(3,5-difluorophenyl)(methylsulfonyl)methylene] azetidine is obtained in the form of a white solid [NMR spectrum in DMSO-d6, T=300K, δ in ppm (300 MHz): 1.07 (3H, t, J=6 Hz, CH$_3$), 3.00 (3H, s, SCH$_3$), 3.35 (2H, m, NCH$_2$), 3.90 (2H, s, NCH$_2$), 4.20 (2H, s, NCH$_2$), 4.80 (1H, s, NCH), 7.15 (2H, d, J=8 Hz, 2CH arom.), 7.30 (1H, t, J=8 Hz, CH arom.), 7.35 (2H, d, J=7 Hz, 2CH arom.), 7.48 (4H, m, 4CH arom.), 7.74 (2H, d, J=7 Hz, 2CH arom.), 8.37 (1H, t, CONH)].

EXAMPLE 54

The operation is carried out as in Example 52, starting with 1 g of (RS)-1-{(4-carboxyphenyl)(4-chlorophenyl)methyl]-3-[(3,5-difluorophenyl)(methylsulfonyl)methylene]azetidine, 0.38 g of 1,3-dimethylaminopropyl-3-ethylcarbodiimide hydrochloride, 22 mg of hydroxybenzotriazole hydrate, 40 cm$^3$ of dichloromethane and 0.24 cm$^3$ of a 7 N solution of ammonium hydroxide in methanol and chromatographing on a silica gel column (particle size 0.04–0.06 mm, diameter 4.1 cm, height 15 cm), at an argon pressure of 0.5 bar with a mixture of ethyl acetate and cyclohexane (60/40 by volume) as eluent and collecting 35 cm$^3$ fractions. Fractions 38 to 48 are combined and then concentrated to dryness under reduced pressure (2.7 kPa). 0.29 g of a solid is obtained which, after taking up in isopropyl ether and drying, gives 0.22 g of (RS)-1-[(4-carbamoylphenyl)(4-chlorophenyl)methyl-(RS)]-3-[(3,5-difluorophenyl)(methylsulfonyl)methylene]azetidine in the form of a white solid [NMR spectrum in DMSO-d6, T=300K, δ in ppm (300 MHz): 3.00 (3H, s, SCH$_3$, 3.90 (2H, s, NCH$_2$), 4.20 (2H, s, NCH$_2$), 4.82 (1H, s, NCH), 7.17 (2H, d, J=8 Hz, 2CH arom.), 7.30 (1H, t, J=8 Hz, CH arom.), 7.38 (2H, d, J=7 Hz, 2CH arom.), 7.50 (5H, m, 4CH arom. and 2 CONH$_2$), 7.80 (2H, d, J=7 Hz, 2CH arom.), 7.90 (1H, s, 2 CONH$_2$)].

EXAMPLE 55

The operation is carried out according to the procedure of Example 4 starting with 1.7 g of 1-[bis-(4-chlorophenyl)methyl]-3-[(3,5-difluorophenyl)(methylsulfonyl)methyl-(RS)]azetidin-3-ol, 0.35 cm$^3$ of methanesulfonyl chloride and 1.5 g of 4-dimethylaminopyridine. The residue obtained is purified by chromatography on a silica gel column (particle size 0.04–0.06 mm, diameter 3 cm, height 35 cm), at a nitrogen pressure of 0.5 bar with a mixture of dichloromethane and ethanol (99.5/0.5 by volume) as eluent and collecting 100 cm$^3$ fractions. Fractions 7 to 10 are combined and then concentrated to dryness under reduced pressure (2.7 kPa). The solid is crystallized from 15 cm$^3$ of ethyl ether. 0.2 g of 1-[bis(4-chlorophenyl)methyl]-3-[(3,5-difluorophenyl)(methylsulfonyl)methylene]azetidine is obtained melting at 200° C. [NMR spectrum in DMSO-d6, T=300K, δ in ppm (300 MHz): 3.00 (3H, s, SCH$_3$), 3.80 (2H, s, NCH$_2$), 4.20 (2H, s, NCH$_2$), 4.75 (1H, s, NCH), 7.35 (4H, d, J=7 Hz, 4CH arom.), 7.45 (6H, m, 6CH arom.), 7.67 (1H, s, CH arom.)].

1-[Bis(4-chlorophenyl)methyl]-3-[(3,5-dichlorophenyl)(methylsulfonyl)methyl-(RS)]azetidin-3-ol may be obtained in the following manner: on carrying out the operation according to the procedure of Example 39 starting with 4 g of bis(4-chlorophenyl)bromomethane and 3 g of 3-[(3,5-dichlorophenyl)(methylsulfonyl)methyl-(RS)]azetidin-3-ol hydrochloride, the residue obtained is purified by chromatography on a silica gel column (particle size 0.04–0.06 mm, diameter 3 cm, height 40 cm), at a nitrogen pressure of 0.5 bar with dichloromethane and then a mixture of dichloromethane and ethanol (99/1 by volume) as eluent and collecting 100 cm³ fractions. Fractions 15 to 19 are combined and concentrated to dryness under reduced pressure (2.7 kPa). 1.7 g of 1-[bis(4-chlorophenyl)methyl]-3-[(3,5-dichlorophenyl)(methylsulfonyl)methyl-(RS)]azetidin-3-ol are obtained in the form of a foam.

Bis(4-chlorophenyl)bromomethane may be prepared according to the procedure described by BACHMANN W. E., J. Am. Chem. Soc., 2135 (1933).

3-[(3,5-Dichlorophenyl)(methylsulfonyl)methyl-(RS)]azetidin-3-ol hydrochloride may be obtained in the following manner: on carrying out the operation according to the procedure of Example 39 starting with 5.6 g of 3-[(3,5-dichlorophenyl)(methylsulfonyl)methyl-(RS)]-1-(vinyloxycarbonyl)azetidin-3-ol and 56 cm³ of a 6.2 N solution of hydrochloric dioxane in 56 cm³ of dioxane, 5.1 g of 3-[(3,5-dichlorophenyl)(methylsulfonyl)methyl-(RS)]azetidin-3-ol hydrochloride are obtained in the form of a foam.

3-[(3,5-Dichlorophenyl)(methylsulfonyl)methyl-(RS)]-1-(vinyloxycarbonyl)azetidin-3-ol may be prepared in the following manner: on carrying out the operation according to the procedure of Example 39 starting with 7.4 g of 1-benzhydryl-3-[(3,5-dichlorophenyl)(methylsulfonyl)methyl-(RS)]azetidin-3-ol and 1.6 cm³ of vinyl chloroformate in 75 cm³ of dichloromethane, the residue obtained is purified by chromatography on a silica gel column (particle size 0.04–0.06 mm, diameter 3 cm, height 40 cm), at a nitrogen pressure of 0.5 bar with a mixture of ethyl acetate and cyclohexane (30/70 by volume) as eluent and collecting 100 cm³ fractions. Fractions 4 to 10 are combined and concentrated to dryness under reduced pressure (2.7 kPa). 5.6 g of 3-[(3,5-dichlorophenyl)(methylsulfonyl)methyl-(RS)]-1-(vinyloxycarbonyl)azetidin-3-ol are obtained in the form of a foam.

EXAMPLE 56

On carrying out the operation according to the procedure of Example 4 starting with 0.5 g of 1-benzhydryl-3-[(3-dimethylaminophenyl)(methylsulfonyl)methyl-(RS)]azetidin-3-ol, 0.1 cm³ of methanesulfonyl chloride and 0.5 g of 4-dimethylaminopyridine, the residue obtained is purified by chromatography on silica gel column (particle size 0.04–0.06 mm, diameter 2 cm, height 30 cm), at a nitrogen pressure of 0.5 bar with a mixture of dichloromethane and ethanol (98/2 by volume) as eluent and collecting 20 cm³ fractions. Fractions 8 to 13 are combined and concentrated to dryness under reduced pressure (2.7 kPa). The solid obtained is crystallized from 8 cm³ of ethyl ether. 0.3 g of 1-benzhydryl-3-[(3-dimethylaminophenyl)(methylsulfonyl)methylene]azetidine is obtained melting at 176° C. [NMR spectrum in DMSO-d6, T=300K, δ in ppm (250 MHz): 2.90 (6H, s, N(CH₃)₂), 2.95 (3H, s, SCH₃), 3.80 (2H, s, NCH₂), 4.20 (2H, s, NCH₂), 4.75 (1H, s, NCH), 6.70 (3H, m, 3CH arom.), 7.20 (3H, m, 3CH arom.), 7.30 (4H, t, J=7 Hz, 4CH arom.), 7.48 (4H, d, J=7 Hz, 4CH arom.)].

1-Benzhydryl-3-[(3-dimethylaminophenyl)(methylsulfonyl)methyl-(RS)]azetidin-3-ol may be obtained in the following manner: on carrying out the operation according to the procedure of Example 1 starting with 0.4 g of (3-dimethylaminobenzyl)methylsulfone, 0.4 g of 1-benzhydrylazetidin-3-one and 1.2 cm³ of a 1.6 M solution of n-butyllithium in hexane, 0.5 g of 1-benzhydryl-3-[(3-dimethylaminophenyl)(methylsulfonyl)methyl-(RS)]azetidin-3-ol is obtained in the form of a solid melting at 185° C.

(3-Dimethylaminobenzyl)methylsulfone may be prepared in the following manner: on carrying out the operation according to the procedure of Example 2 starting with 1.4 g of (3-dimethylaminobenzyl)methylsulfide and 5.1 g of oxone$^R$, 1.1 g of (3-dimethylaminobenzyl)methylsulfone are obtained in the form of a white solid melting at 195° C.

(3-Dimethylaminobenzyl)methylsulfide may be prepared in the following manner: on carrying out the operation according to the procedure of Example 37 starting with 4 g of (3-iodobenzyl)methylsulfide, 1.4 g of dimethylamine in solution in 5 cm³ of tetrahydrofuran, 2.9 g of sodium tert-butoxide, 0.56 g of 1,1-bis(diphenylphosphino)ferrocenylpalladium chloride and 1.3 g of 1,1'-bis(diphenylphosphino)ferrocene in 35 cm³ of tetrahydrofuran, 0.9 g of (3-dimethylaminobenzyl)methylsulfide is obtained in the form of an oil.

EXAMPLE 57

On carrying out the operation according to the procedure of Example 4 starting with 1.3 g of 1-benzhydryl-3-[(3-methylsulfanylphenyl)(methylsulfonyl)methyl-(RS)]azetidin-3-ol, 0.3 cm³ of methanesulfonyl chloride and 1.4 g of 4-dimethylaminopyridine, the residue obtained is purified by chromatography on a silica gel column (particle size 0.04–0.06 mm, diameter 2 cm, height 30 cm), at a nitrogen pressure of 0.5 bar with a mixture of dichloromethane and ethanol (98/2 by volume) as eluent and collecting 20 cm³ fractions. Fractions 11 to 13 are combined and concentrated to dryness under reduced pressure (2.7 kPa). The solid obtained is crystallized from 15 cm³ of ethyl ether. 0.6 g of 1-benzhydryl-3-[(3-methylsulfanylphenyl)(methylsulfonyl)methylene]azetidine is obtained melting at 146° C. [NMR spectrum in DMSO-d6, T=300K, δ in ppm (300 MHz): 2.45 (3H, s, PhSCH₃), 2.95 (3H, s, SCH₃), 3.80 (2H, s, NCH₂), 4.20 (2H, s, NCH₂), 4.75 (1H, s, NCH), between 7.10 and 7.50 (14H, m, 14CH arom.)].

1-Benzhydryl-3-[(3-methylsulfanylphenyl)(methylsulfonyl)methyl-(RS)]azetidin-3-ol may be obtained in the following manner: on carrying out the operation according to the procedure of Example 1 starting with 1.1 g of methyl(3-methylsulfanylbenzyl)sulfone, 1.2 g of 1-benzhydrylazetidin-3-one, 1.3 g of 1-benzhydryl-3-[(3-methylsulfanylphenyl)(methylsulfonyl)methyl-(RS)]azetidin-3-ol are obtained in the form of a solid.

Methyl(3-methylsulfanylbenzyl)sulfone may be prepared in the following manner: a mixture of 5 g of (3-iodobenzyl)methylsulfone and 1 g of tetrakis-triphenylphosphinepalladium in 250 cm³ of dimethyl sulfoxide is heated at a temperature close to 100° C., under a nitrogen stream, for 1 hour. 2.5 g of sodium methylthiolate are added and then the heating at 100° C. is maintained for 18 hours. The reaction medium is cooled to room temperature and taken up in 700 cm³ of ethyl acetate and 500 cm³ of water. The organic phase is decanted off, washed with 10 times 500 cm³ of water, 500 cm³ of a saturated aqueous sodium chloride solution, filtered on sintered glass and concentrated to dryness under reduced pressure (2.7 kPa). The residue obtained is purified by chromatography on a silica gel column (particle size 0.04–0.06 mm, diameter 3 cm, height 30 cm), at a nitrogen pressure of 0.5 bar with a mixture of cyclohexane and ethyl acetate (70/30 and then 60/40 and then 50/50 by volume) as eluent and collecting 30 cm³ fractions. Fractions 26 to 30 are combined and concentrated to dryness under reduced pressure (2.7 kPa). 1.2 g of methyl(3-methylsulfanylbenzyl)methylsulfone are obtained in the form of an oil.

EXAMPLE 58

4 cm³ of a 1 M solution of tetrabutylammonium fluoride in tetrahydrofuran are added to a solution, cooled to 5° C., of 1.1 g 1-benzhydryl-3-{[3-(tert-butyldimethylsiloxymethyl)phenyl](methylsulfonyl)methylene}azetidine in 10 cm³ of tetrahydrofuran. The mixture is stirred for 3 hours at a temperature close to 20° C. and then taken up in 100 cm³ of ethyl acetate and twice 50 cm³ of water. The organic phase is decanted off, extracted, dried over anhydrous magnesium sulfate and concentrated to dryness under reduced pressure (2.7 kPa). The residue obtained is purified by chromatography on a silica gel column (particle size 0.04–0.06 mm, diameter 2 cm, height 30 cm), at a nitrogen pressure of 0.5 bar with a mixture of dichloromethane and ethanol (95/5 by volume) as eluent and collecting 60 cm³ fractions. Fractions 4 to 6 are combined and concentrated to dryness under reduced pressure (2.7 kPa). 0.5 g of 1-benzhydryl-3-[(3-hydroxymethylphenyl)(methylsulfonyl)methylene]azetidine is obtained in the form of a white solid melting at 152° C. [NMR spectrum in DMSO-d6, T=300K, δ in ppm (300 MHz): 2.95 (3H, s, $SCH_3$), 3.80 (2H, s, $NCH_2$), 4.20 (2H, s, $NCH_2$), 4.50 (2H, d, J=5 Hz, $OCH_2$), 4.75 (1H, s, NCH), 5.25 (1H, t, J=5 Hz, OH), 7.20 (2H, t, J=7 Hz, 2CH arom.), 7.30 (8H, m. 8CH arom.), 7.45 (4H, d, J=7 Hz, 4 CH arom.)].

1-Benzhydryl-3-{[3-(tert-butyldimethylsilyloxymethyl)phenyl](methylsulfonyl)methylene}azetidine may be prepared in the following manner: on carrying out the operation according to the procedure of Example 4 starting with 1.6 g of 1-benzhydryl-3-{[3-(tert-butyldimethylsilyloxymethyl)phenyl](methylsulfonyl)methyl-(RS)]azetidin-3-ol, 0.3 cm³ of methanesulfonyl chloride and 1.4 g of 4-dimethylaminopyridine, the residue obtained is purified by chromatography on a silica gel column (particle size 0.04–0.06 mm, diameter 3 cm, height 30 cm), at a nitrogen pressure of 0.5 bar with dichloromethane as eluent and collecting 60 cm³ fractions. Fractions 15 to 30 are combined and concentrated to dryness under reduced pressure (2.7 kPa). 1.1 g of 1-benzhydryl-3-{[3-(tert-butyldimethylsiloxymethyl)phenyl](methylsulfonyl)methylene}azetidine are obtained in the form of a white solid melting at 148° C.

1-Benzhydryl-3-{[3-(tert-butyldimethylsilyloxymethyl)phenyl](methylsulfonyl)methyl-(RS)]azetidin-3-ol may be obtained in the following manner: on carrying out the operation according to the procedure of Example 1 starting with 2 g of [3-(tert-butyldimethylsilyloxymethyl)benzyl]methylsulfone and 1.5 g of 1-benzhydrylazetidin-3-one, 1.6 g of 1-benzhydryl-3-{[3-(tert-butyldimethylsilyloxymethyl)phenyl](methylsulfonyl)methyl-(RS)]azetidin-3-ol are obtained in the form of a white solid melting at 175° C.

[(3-(Tert-butyldimethylsilyloxymethyl)benzyl]methylsulfone may be prepared in the following manner: a mixture of 13.4 g of (3-hydroxymethylbenzyl)methylsulfone, 11 g of imidazole and 12 g of tert-butyldimethylsilane chloride is stirred for 18 hours at a temperature close to 20° C. The solution is concentrated to dryness under reduced pressure (2.7 kPa). The residue obtained is purified by chromatography on a silica gel column (particle size 0.04–0.06 mm, diameter 5 cm, height 50 cm), at a nitrogen pressure of 0.5 bar with dichloromethane as eluent and collecting 100 cm³ fractions. Fractions 7 to 14 are combined and concentrated to dryness under reduced pressure (2.7 kPa). 5.7 g of [3-(tert-butyldimethylsilyloxymethyl)benzyl]methylsulfone are obtained in the form of a white solid melting at 80° C.

(3-Hydroxymethylbenzyl)methylsulfone may be prepared in the following manner: a mixture of 26 g of 3-(methylsulfonylmethyl)benzoic acid and 4.6 g of lithium aluminium hydride in 600 cm³ of tetrahydrofuran is stirred for 18 hours at a temperature close to 20° C. The solution is cooled to 0° C. and then 15 cm³ of ethyl acetate, 5 cm³ of water, 5 cm³ of a 15% aqueous solution of sodium hydroxide and finally 30 cm³ of water are added successively. The mixture is filtered on celite, the filtrate taken up in 600 cm³ of ethyl acetate. The organic phase is taken up in 500 cm³ of water and then 200 cm³ of a saturated aqueous sodium chloride solution, decanted off, dried over anhydrous magnesium sulfate, filtered and concentrated to dryness under reduced pressure (2.7 kPa). 10.4 g of (3-hydroxymethylbenzyl)methylsulfone are obtained in the form of a gum.

3-(Methylsulfonylmethyl)benzoic acid may be prepared in the following manner: on carrying out the operation according to the procedure of Example 10 starting with 23.3 g of 3-chloromethylbenzoic acid and 23.3 g of sodium methanesulfinate, 26 g of 3-(methylsulfonylmethyl)benzoic acid are obtained in the form of a white solid melting at 210° C.

EXAMPLE 59

0.13 g of sodium methylthiolate is added, while the temperature is maintained below 30° C., to a solution of 0.8 g of 1-benzhydryl-3-[(3-bromomethylphenyl)(methylsulfonyl)methylene]azetidine in 8 cm³ of dimethylformamide. The mixture is stirred for 18 hours at a temperature close to 20° C. and then taken up in 30 cm³ of ethyl acetate and 50 cm³ of water. The organic phase is decanted off, extracted and washed with 3 times 50 cm³ of water, dried over magnesium sulfate and concentrated to dryness under reduced pressure (2.7 kPa). The residue obtained is purified by chromatography on a silica gel column (particle size 0.04–0.06 mm, diameter 2 cm, height 28 cm) at a nitrogen pressure of 0.5 bar with a mixture of cyclohexane and ethyl acetate (90/10 by volume) as eluent and collecting 50 cm³ fractions. Fractions 8 to 14 are combined and concentrated to dryness under reduced pressure (2.7 kPa). 0.3 g of 1-benzhydryl-3-{[3-(methylsulfanylmethyl)phenyl](methylsulfonyl)methylene]}azetidine is obtained in the form of a white solid melting at 150° C. [NMR spectrum in DMSO-d6, T=300K, δ in ppm (300 MHz): 1.95 (3H, s, $SCH_3$), 2.95 (3H, s, $SCH_3$), 3.75 (2H, s, $SCH_2$), 3.80 (2H, s, $NCH_2$), 4.20 (2H, s, $NCH_2$), 4.75 (1H, s, NCH), 7.20 (2H, t, J=7 Hz, CH arom.), 7.30 (8H, d, J=7 Hz, 8CH arom.), 7.45 (4H, d, J=7 Hz, 4 CH arom.)].

1-Benzhydryl-3-[(3-bromomethylphenyl)(methylsulfonyl)methylene]azetidine may be prepared in the following manner: 0.23 cm³ of phosphorus tribromide and then a drop of pyridine are added, at a temperature close to 20° C., to a mixture of 1 g of 1-benzhydryl-3-[(3-hydroxymethylphenyl)(methylsulfonyl)methylene]azetidine in 10 cm³ of dichloromethane. The stirring is maintained for 18 hours at the same temperature. The reaction medium is taken up in 20 cm³ of water and 10 cm³ of a saturated aqueous sodium chloride solution. The organic phase is decanted off, extracted, dried over anhydrous magnesium sulfate, filtered and concentrated to dryness under reduced pressure (2.7 kPa). 1 g of 1-benzhydryl-3-[(3-bromomethylphenyl)(methylsulfonyl)methylene]azetidine is obtained in the form of a foam used in the crude state in subsequent syntheses.

EXAMPLE 60

On carrying out the operation according to the procedure of Example 4 starting with 6.6 g of 1-benzhydryl-3-

[(methylsulfonyl)(quinol-8-yl)methyl-(RS)]azetidin-3-ol, 1.7 cm³ of methanesulfonyl chloride and 5.2 g of 4-dimethylaminopyridine, the residue obtained is purified by chromatography on a silica gel column (particle size 0.04–0.06 mm, diameter 6.5 cm, height 35 cm), at a nitrogen pressure of 0.5 bar with a dichloromethane and methanol mixture (95/5 by volume) as eluent and collecting 40 cm³ fractions. Fractions 7 to 15 are combined and concentrated to dryness under reduced pressure (2.7 kPa). The solid obtained is crystallized from 100 cm³ of ethyl ether. 4.4 g of 1-benzhydryl-3-[(methylsulfonyl)(quinol-8-yl)methylene]azetidine are obtained melting at 212° C. [NMR spectrum in DMSO-d6, T=300K, δ in ppm (250 MHz): 3.15 (3H, s, SCH₃), 3.55 (2H, broad s, NCH₂), 4.30 (2H, s, NCH₂), 4.70 (1H, s, NCH), 7.18 (2H, t, J=7 Hz, 2CH arom.), 7.25 (4H, t, J=7 Hz, 4CH arom.), 7.43 (4H, d, J=7 Hz, 4 CH arom.), 7.62 (2H, m, 2CH quinoline), 7.75 (1H, dd, J=2 and 7 Hz, CH quinoline), 8.05 (1H, dd, J=2 and 7 Hz, CH quinoline), 8.43 (1H, dd, J=2 and 8 Hz, CH quinoline), 9.00 (1H, dd, J=2 and 5 Hz, CH quinoline)].

1-Benzhydryl-3-[(methylsulfonyl)(quinol-8-yl)methyl-(RS)]azetidin-3-ol may be obtained in the following manner: on carrying out the operation according to the procedure of Example 1 starting with 5.5 g of methyl(quinol-8-ylmethyl)sulfone, 5.9 g of 1-benzhydrylazetidin-3-one and 18.8 cm³ of a 1.6 M solution of n-butyllithium in hexane, 6.6 g of 1-benzhydryl-3-[(methylsulfonyl)(quinol-8-yl)methyl-(RS)]azetidin-3-ol are obtained in the form of a beige solid.

Methyl(quinol-8-ylmethyl)sulfone may be prepared in the following manner: on carrying out the operation according to the procedure of Example 10 starting with 4.5 g of 8-chloromethylquinoline and 4.4 g of sodium methanesulfinate, 5.7 g of methyl(quinol-8-ylmethyl)sulfone are obtained in the form of a beige solid.

8-Chloromethyl quinoline may be prepared in the following manner: 6.7 g of N-chlorosuccinimide and then 250 mg of benzoyl peroxide are added, at a temperature close to 20° C., to a mixture of 7.1 g of 8-methylquinoline in 250 cm³ of carbon tetrachloride. The reaction medium is heated at the reflux temperature of the solvent for 36 hours and then cooled to 20° C. The mixture is filtered on sintered glass and the filtrate is concentrated to dryness under reduced pressure (2.7 kPa). The residue obtained is purified by chromatography on a silica gel column (particle size 0.04–0.06 mm, diameter 5.5 cm, height 32 cm), at a nitrogen pressure of 0.5 bar with dichloromethane as eluent and collecting 40 cm³ fractions. Fractions 21 to 40 are combined and concentrated to dryness under reduced pressure (2.7 kPa). 4.5 g of 8-chloromethylquinoline are obtained in the form of a brown oil which is used in the crude state in subsequent syntheses.

EXAMPLE 61

On carrying out the operation according to the procedure of Example 4 starting with 6.2 g of 1-[bis(4-chlorophenyl)methyl]-3-[(3-cyanophenyl)(methylsulfonyl)methyl-(RS)]azetidin-3-ol, 1.4 cm³ of methanesulfonyl chloride and 6.1 g of 4-dimethylaminopyridine, the residue obtained is purified by chromatography on a silica gel column (particle size 0.04–0.06 mm, diameter 4 cm, height 60 cm), at a nitrogen pressure of 0.5 bar with dichloromethane as eluent and collecting 100 cm³ fractions. Fractions 4 to 7 are combined and concentrated to dryness under reduced pressure (2.7 kPa). The solid obtained is crystallized from 25 cm³ of ethyl ether. 0.7 g of 1-[bis(4-chlorophenyl)methyl]-3-[(3-cyanophenyl)(methylsulfonyl)methylene]azetidine is obtained in the form of a solid melting at 178° C. [NMR spectrum in DMSO-d6, T=300K, δ in ppm (300 MHz): 3.00 (3H, s, SCH₃), 3.80 (2H, s, NCH₂) 4.20 (2H, s, NCH₂), 4.75 (1H, s, NCH), 7.30 (4H, d, J=7 Hz, 4CH arom.), 7.40 (4H, d, J=7 Hz, 4CH arom.), 7.60 (1H, t, J=7 Hz, CH arom.), 7.70 (1H, d, J=7 Hz, CH arom.), 7.85 (2H, m, 2CH arom.)].

1-[Bis(4-chlorophenyl)methyl]-3-[(3-cyanophenyl)(methylsulfonyl)methyl-(RS)]azetidin-3-ol may be obtained in the following manner: on carrying out the operation according to the procedure of Example 1 starting with 5.5 g of (3-cyanophenyl)methylsulfone, 6.1 g of 1-[bis(4-chlorophenyl)methyl]azetidin-3-one and 13.8 cm³ of a 1.6 M solution of n-butyllithium in hexane, 6.3 g of 1-[bis-(4-chlorophenyl)methyl]-3-[(3-cyanophenyl)(methylsulfonyl)methyl-(RS)]azetidin-3-ol are obtained in the form of a foam.

EXAMPLE 62

A mixture of 4.5 g of 1-[bis(4-chlorophenyl)methyl]-3-[(3-cyanophenyl)(methylsulfonyl)methylene]azetidine in 50 cm³ of acetic acid and 50 cm³ of concentrated hydrochloric acid (d=1.18) is heated at 50° C. for 20 hours. The reaction medium is cooled to room temperature and concentrated to dryness under reduced pressure (2.7 kPa). The oil obtained is taken up in 100 cm³ of ethanol and then the solution is concentrated to dryness under reduced pressure (2.7 kPa). The residue is precipitated in 60 cm³ of ethyl ether. The solid obtained is purified by chromatography on a silica gel column (particle size 0.04–0.06 mm, diameter 25 cm, height 40 cm) at a nitrogen pressure of 0.5 bar with dichloromethane and then a dichloromethane and ethanol mixture (99.5/0.5 by volume) as eluent and collecting 30 cm³ fractions. Fractions 35 to 46 are combined and concentrated to dryness under reduced pressure (2.7 kPa). The solid obtained is crystallized from 15 cm³ of ethyl ether. 0.2 g of 1-[bis(4-chlorophenyl)methyl]-3-[(3-carbamoylphenyl)(methylsulfonyl)methylene]azetidine is obtained in the form of a solid melting at 192° C. [NMR spectrum in DMSO-d6, T=300K, δ in ppm (300 MHz): 2.95 (3H, s, SCH₃), 3.80 (2H, s, NCH₂), 4.20 (2H, s, NCH₂), 4.80 (1H, s, NCH), 7.35 (4H, d, J=7 Hz, 4CH arom.), 7.45 (5H, d, J=7 Hz, 4CH arom. and 2 CONH₂), 7.50 (2H, m, 2CH arom.), 7.85 (2H, m, 2CH arom.)].

EXAMPLE 63

On carrying out the operation according to the procedure of Example 1 starting with 0.8 g of 1-benzhydryl-3-{[3-(N-tert-butyloxycarbonyl-N-methylamino)phenyl](methylsulfonyl)methyl-(RS)}azetidin-3-ol, 0.2 cm³ of methanesulfonyl chloride and 0.7 g of 4-dimethylaminopyridine, the residue obtained is purified by chromatography on a silica gel column (particle size 0.04–0.06 mm, diameter 2 cm, height 30 cm), at a nitrogen pressure of 0.5 bar with a dichloromethane and ethanol mixture (98/2 by volume) as eluent, collecting 20 cm³ fractions. Fractions 4 to 8 are combined and concentrated to dryness under reduced pressure (2.7 kPa). The solid obtained is recrystallized from 10 cm³ of ethyl acetate. 0.5 g of 1-benzhydryl-3-{[3-(N-tert-butyloxycarbonyl-N-methylamino)phenyl](methylsulfonyl)methylene}azetidine is obtained in the form of a solid melting at 161° C. [NMR spectrum in DMSO-d6, T=300K, δ in ppm (300 MHz): 1.30 (9H, s, (CH₃)₃), 2.95 (3H, s, SCH₃), 3.15 (3H, s, NCH₃), 3.75 (2H, s, SCH₂), 3.80 (2H, s, NCH₂), 4.20 (2H, s, NCH₂), 4.75 (1H, s, NCH), between 7.15 and 7.50 (14H, m, 14CH arom.)].

1-Benzhydryl-3-{[3-(N-tert-butyloxycarbonyl-N-methylamino)phenyl](methylsulfonyl)methyl- (RS)}azetidin-3-ol may be obtained in the following manner: on carrying out the operation according to the procedure of Example 1 starting with 1.6 g of [3-(N-tert-butyloxycarbonyl-N-methylamino)benzyl]methylsulfone, 1.3 g of 1-benzhydrylazetidin-3-one and 3.8 cm$^3$ of a 1.6 M solution of n-butyllithium in hexane, 0.8 g of 1-benzhydryl-3-{[3-(N-tert-butyloxycarbonyl-N-methylamino)phenyl](methylsulfonyl)methyl-(RS)}azetidin-3-ol is obtained in the form of a white solid.

[3-(N-tert-butyloxycarbonyl-N-methylamino)benzyl]methylsulfone may be prepared in the following manner: 2.5 g of di-tert-butyl dicarbonate in 40 cm$^3$ of dioxane are added to a solution, cooled to 0° C. of methyl(3-methylaminobenzyl)sulfone in 30 cm$^3$ of dioxane. The stirring is maintained for 18 hours at room temperature. The reaction medium is taken up in 75 cm$^3$ of dichloromethane; the organic phase is washed with 75 cm$^3$ of water and then with 75 cm$^3$ of a saturated aqueous sodium chloride solution. The organic phase is decanted off, extracted, dried over anhydrous sodium sulfate, filtered and concentrated to dryness under reduced pressure (2.7 kPa). The residue obtained is purified by chromatography on a silica gel column (particle size 0.04–0.06 mm, diameter 2 cm, height 35 cm) at a nitrogen pressure of 0.5 bar with a cyclohexane and ethyl acetate mixture (50/50 by volume) as eluent, collecting 20 cm$^3$ fractions. Fractions 5 to 10 are combined and concentrated to dryness under reduced pressure (2.7 kPa). 1.8 g of [3-(N-tertbutyloxycarbonyl-N-methylamino)benzyl]methylsulfone are obtained in the form of a colorless oil.

Methyl(3-methylaminobenzyl)sulfone may be prepared in the following manner: a mixture of 9.7 cm$^3$ of formic acid (d=1.22) and 19.6 cm$^3$ of acetic anhydride (d=1.08) is heated for 3 hours at 50° C. and then the solution is allowed to return to room temperature. 40 cm$^3$ of tetrahydrofuran are added and the mixture is cooled to −20° C. 14.8 g of (3-aminobenzyl)methylsulfone and 200 cm$^3$ of tetrahydrofuran are then added. The stirring is maintained for 2 hours at −20° C. and then 48 hours at room temperature. The mixture is filtered on sintered glass, the precipitate is washed with 3 times 50 cm$^3$ of disopropyl ether and then dried. The filtrate is concentrated to half its volume (2.7 kPa), the precipitate obtained is filtered on sintered glass and washed with 3 times 30 cm$^3$ of diisopropyl ether and then dried. The two precipitates are combined and dissolved in 375 cm$^3$ of tetrahydrofuran. The solution is cooled to 0° C.; 100 cm$^3$ of a 2 M solution of borane dimethyl sulfide in tetrahydrofuran added and then heated under reflux for 3 hours. The mixture is cooled to 5° C. and then 60 cm$^3$ of methanol are added over 20 minutes. The stirring is maintained for 1 hour at room temperature. A stream of hydrogen chloride is bubbled in the solution for 5 minutes. The reaction medium is then heated under reflux for 1 hour, cooled to room temperature and taken up in 300 cm$^3$ of water. The solution is alkalinized with 3N sodium hydroxide and then with a saturated aqueous sodium bicarbonate solution. The organic phase is extracted with twice 250 cm$^3$ of ethyl acetate, washed with 300 cm$^3$ of a saturated aqueous sodium bicarbonate solution and twice 300 cm$^3$. It is concentrated to dryness under reduced pressure (2.7 kPa). The oil obtained is taken up in 100 cm$^3$ of 4 N hydrochloric acid and then with 100 cm$^3$ of ethyl acetate. The aqueous phase is alkalinized with 120 cm$^3$ of 3 N sodium hydroxide, and then with an aqueous sodium bicarbonate solution. The organic phase is extracted with twice 75 cm$^3$ of ethyl acetate, dried over anhydrous magnesium sulfate, filtered and concentrated to dryness under reduced pressure (2.7 kPa). 9 g of methyl(3-methylaminobenzyl)sulfone are obtained in the form of a pink solid.

(3-Aminobenzyl)methylsulfone may be prepared in the following manner: a mixture of 23.7 g of methyl(3-nitrobenzyl)sulfone, 65 cm$^3$ of hydrochloric acid (d=1.18) and 150 cm$^3$ of methanol is heated under reflux for 15 minutes. 18.5 g of iron are added over 10 minutes and the reflux is maintained for 4 hours and then 18 hours at room temperature. The reaction medium is alkalinized with an aqueous solution of ammonium hydroxide and then with an aqueous sodium bicarbonate solution. The organic phase is extracted with 3 times 250 cm$^3$ of ethyl acetate, dried over magnesium sulfate, filtered on sintered glass and concentrated to dryness under reduced pressure (2.7 kPa). 14.9 g of (3-aminobenzyl)methylsulfone are obtained in the form of a beige solid which is used in the crude state in subsequent syntheses.

EXAMPLE 64

A mixture of 0.3 g of 1-benzhydryl-3-{[3-(N-tert-butyloxycarbonyl-N-methylamino)phenyl](methylsulfonyl)methylene}azetidine, 4 cm$^3$ of a 4.7 N solution of hydrochloric dioxane and 4 cm$^3$ of dioxane is stirred for 18 hours at room temperature. The reaction medium is concentrated to dryness under reduced pressure (2.7 kPa). The residue is taken up in 100 cm$^3$ of water and 20 cm$^3$ of diethyl ether. The aqueous phase is alkalinized with 30 cm$^3$ of an aqueous sodium bicarbonate solution. The organic phase is extracted with twice 40 cm$^3$ of ethyl acetate, washed with twice 30 cm$^3$ of water, decanted off, dried over anhydrous magnesium sulfate, filtered and concentrated to dryness under reduced pressure (2.7 kPa). The residue is crystallized from 20 cm$^3$ of diethyl ether. 0.16 g of 1-benzhydryl-3-[(3-methylaminophenyl)(methylsulfonyl)methylene]azetidine is obtained in the form of a solid melting at 161° C. [NMR spectrum in DMSO-d6, T=300K, δ in ppm (250 MHz): 2.65 (3H, d, J=5 Hz, NCH$_3$), 2.95 (3H, s, SCH$_3$), 3.80 (2H, s, NCH$_2$), 4.20 (2H, s, NCH$_2$), 4.75 (1H, s, NCH), 5.80 (1H, q, J=5 Hz, NH), 6.60 (3H, m, 3CH arom.), 7.15 (1H, t, J=7 Hz, CH arom.), 7.22 (2H, t, J=7 Hz, 2CH arom.), 7.30 (4H, t, J=7 Hz, 4CH arom.), 7.48 (4H, d, J=7 Hz, 4 CH arom.)].

EXAMPLE 65

On carrying out the operation according to the procedure of Example 4 starting with 11.3 g of 1-[bis(4-chlorophenyl)methyl]-3-[(3-methoxyphenyl)(methylsulfonyl)methyl-(RS)]azetidin-3-ol, 2.6 cm$^3$ of methanesulfonyl chloride and 10.9 g of 4-dimethylaminopyridine, 5 g of 1-[bis(4-chlorophenyl)methyl]-3-[(3-methoxyphenyl)(methylsulfonyl)methylene]azetidine are obtained after recrystallization from 20 cm$^3$ of diethyl ether, melting at 181° C. [NMR spectrum in DMSO-d6, T=300K, δ in ppm (300 MHz): 2.95 (3H, s, SCH$_3$), 3.77 (3H, s, OCH$_3$), 3.80 (2H, s, NCH$_2$), 4.20 (2H, s, NCH$_2$), 4.80 (1H, s, NCH), 6.95 (3H, m, 3CH arom.), 7.35 (5H, m, 5CH arom.), 7.45 (4H, d, J=7 Hz, 4CH arom.)].

1-[Bis(4-chlorophenyl)methyl]-3-[(3-methoxyphenyl)(methylsulfonyl)methyl-(RS)]azetidin-3-ol may be obtained in the following manner: on carrying out the operation according to the procedure of Example 1 starting with 6.6 g of (3-methoxybenzyl)methylsulfone, 10 g of 1-[bis(4-chlorophenyl)methyl]azetidin-3-one and 23 cm$^3$ of a 1.6 N solution of n-butyllithium in hexane, 11.4 g of 1-[bis(4-chlorophenyl)methyl]-3-[(3-methoxyphenyl)(methylsulfonyl)methyl-(RS)]azetidin-3-ol are obtained in the form of a white solid melting at 130° C.

EXAMPLE 66

On carrying out the operation according to the procedure of Example 32 starting with 4.8 g of 1-[bis(4-chlorophenyl)

methyl]-3-[(3-methoxyphenyl)(methylsulfonyl)methylene]azetidine, 32 cm³ of a 1 M solution of boron tribromide in dichloromethane, the residue obtained is purified by chromatography on a silica gel column (particle size 0.04–0.06 mm, diameter 3 cm, height 30 cm), at a nitrogen pressure of 0.5 bar with a mixture of dichloromethane and ethanol (98/2 by volume) as eluent and collecting 20 cm³ fractions. Fractions 16 to 17 are concentrated to dryness under reduced pressure (2.7 kPa). 0.1 g 1-[bis(4-chlorophenyl)methyl]-3-[(3-hydroxyphenyl)(methylsulfonyl)methylene]azetidine is obtained, after recrystallization from 5 cm³ of diethyl ether, in the form of a solid melting at 114° C. [NMR spectrum in DMSO-d6, T=300K, δ in ppm (250 MHz): 2.92 (3H, s, SCH₃), 3.80 (2H, s, NCH₂), 4.20 (2H, s, NCH₂), 4.80 (1H, s, NCH), 6.80 (3H, m, 3CH arom.), 7.20 (1H, t, J=7 Hz, CH arom.), 7.37 (4H, t, J=7 Hz, 4CH arom.), 7.47 (4H, d, J=7 Hz, 4 CH arom.)].

EXAMPLE 67

On carrying out the operation according to the procedure of Example 4 starting with 0.6 g of 1-[bis(4-chlorophenyl)methyl]-3-[(methylsulfonyl)(3-pyrrolidinylphenyl)methyl-(RS)]azetidin-3-ol, 0.1 cm³ of methanesulfonyl chloride and 0.5 g of 4-dimethylaminopyridine, the residue obtained is purified by chromatography on a silica gel column (particle size 0.04–0.06 mm, diameter 2 cm, height 30 cm) at a nitrogen pressure of 0.5 bar with a dichloromethane and ethanol mixture as eluent (98.5/1.5 by volume) and collecting 10 cm³ fractions. Fraction 4 is concentrated to dryness under reduced pressure (2.7 kPa). 0.5 g 1-[bis(4-chlorophenyl)methyl]-3-[(methylsulfonyl)(3-pyrrolidinylphenyl)methylene]azetidine is obtained, after recrystallization from 5 cm³ of diethyl ether, in the form of a solid melting at 133° C. [NMR spectrum in DMSO-d6, T=300K, δ in ppm (400 MHz): 2.00 (4H, m, 2 CH₂), 2.95 (3H, s, SCH₃), 3.20 (4H, m, 2 NCH₂), 3.80 (2H, s, NCH₂), 4.20 (2H, s, NCH₂), 4.80 (1H, s, NCH), 6.50 (1H, s, CH arom.), 6.60 (1H, d, J=7 Hz, CH arom.), 6.65 (1H, d, J=7 Hz, CH arom), 7.20 (1H, t, J=7 Hz, CH arom.), 7.40 (4H, d, J=7 Hz, 4 CH arom.), 7.50 (4H, d, J=7 Hz, 4 CH arom.)].

1-[Bis(4-chlorophenyl)methyl]-3-[(methylsulfonyl)(3-pyrrolidinylphenyl)methyl-(RS)]azetidin-3-ol may be obtained in the following manner: on carrying out the operation according to the procedure of Example 1 starting with 0.5 g of methyl(3-pyrrolidinylbenzyl)sulfone, 0.6 g of 1-[bis-(4-chlorophenyl)methyl]azetidin-3-one and 1.4 cm³ of a 1.6 N solution of n-butyllithium in hexane, 0.6 g of 1-[bis(4-chlorophenyl)methyl]-3-[(methylsulfonyl)(3-pyrrolidinylphenyl)methyl-(RS)]azetidin-3-ol is obtained in the form of a cream-colored solid.

EXAMPLE 68

On carrying out the operation according to the procedure of Example 58 starting with 5.1 g of 1-[bis(4-chlorophenyl)methyl]-3-{[3-(tert-butyldimethylsilyloxymethyl)phenyl](methylsulfonyl)methylene}azetidine and 17 cm³ of a 1 M solution of tetrabutylammonium fluoride in tetrahydrofuran, the residue obtained is purified by chromatography on a silica gel column (particle size 0.04–0.06 mm, diameter 2 cm, height 30 cm), at a nitrogen pressure of 0.5 bar with a dichloromethane and ethanol mixture (97/3 by volume) as eluent and collecting 100 cm³ fractions. Fractions 10 to 14 are combined, concentrated to dryness under reduced pressure (2.7 kPa). The yellow solid obtained is taken up in 2 cm³ of dichloromethane and 10 cm³ of ethyl acetate and then filtered on sintered glass and washed with 2 cm³ of ethyl acetate. 1.6 g of 1-[bis(4-chlorophenyl)methyl]-3-[(3-hydroxymethylphenyl)(methylsulfonyl)methylene]azetidine are obtained in the form of a white solid melting at 214° C. [NMR spectrum in DMSO-d6, T=300K, δ in ppm (400 MHz): 2.95 (3H, s, SCH₃), 3.80 (2H, s, NCH₂), 4.20 (2H, s, NCH₂), 4.50 (2H, d, J=5 Hz, OCH₂), 4.80 (1H, s, NCH), 5.25 (1H, t, J=5 Hz, OH), 7.30 (1H, d, J=7 Hz, CH arom.), between 7.35 and 7.45 (7H, m, 7CH arom.), 7.50 (4H, d, J=7 Hz, 4CH arom.)].

1-[Bis(4-chlorophenyl)methyl]-3-{[3-(tert-butyldimethylsilyloxymethyl)phenyl](methylsulfonyl)methylene}azetidine may be prepared in the following manner: on carrying out the operation according to the procedure of Example 4 starting with 10.8 g of 1-[bis-(4-chlorophenyl)methyl]-3-{[3-(tert-butyldimethylsilyloxymethyl)phenyl](methylsulfonyl)methyl-(RS)}azetidin-3-ol, 2 cm³ of methanesulfonyl chloride and 8.5 g of 4-dimethylaminopyridine, the residue obtained is purified by chromatography on a silica gel column (particle size 0.04–0.06 mm, diameter 4 cm, height 40 cm) at a nitrogen pressure of 0.5 bar with dichloromethane as eluent and collecting 100 cm³ fractions. Fractions 12 to 29 are combined, concentrated to dryness under reduced pressure (2.7 kPa). 5.2 g of 1-[bis(4-chlorophenyl)methyl]-3-{[3-(tert-butyldimethylsilyloxymethyl)phenyl](methylsulfonyl)methylene}azetidine are obtained in the form of a gum.

1-[Bis(4-chlorophenyl)methyl]-3-{[3-(tert-butyldimethylsilyloxymethyl)phenyl](methylsulfonyl)methyl-(RS)}azetidin-3-ol may be obtained in the following manner: on carrying out the operation according to the procedure of Example 1 starting with 5.8 g of [3-(tert-butylsilyloxymethyl)benzyl]methylsulfone and 5.6 g of 1-[bis(4-chlorophenyl)methyl]azetidin-3-one, 10.8 g of 1-[bis(4-chlorophenyl)methyl]-3-{[3-(tert-butyldimethylsilyloxymethyl)phenyl](methylsulfonyl)methyl-(RS)}azetidin-3-ol are obtained in the form of a gum.

EXAMPLE 69

A mixture of 0.45 g of 1-[bis(4-chlorophenyl)methyl]-3-{(methylsulfonyl)[3-(pentafluorophenoxycarbonyl)phenyl]methylene}azetidine, 0.07 cm³ of 1-aminopiperidine in 4 cm³ of dimethylformamide is stirred for 18 hours at room temperature. The mixture is taken up in 30 cm³ of ethyl acetate. The organic phase is washed with 3 times 50 cm³ of water, dried over magnesium sulfate, filtered and concentrated to dryness under reduced pressure (2.7 kPa). 0.2 g of 1-[bis-(4-chlorophenyl)methyl]-3-{(methylsulfonyl)[3-(N-piperidylcarbamoyl)phenyl]methylene}azetidine is obtained melting at 175° C. [NMR spectrum in DMSO-d6, T=300K, δ in ppm (400 MHz): 1.40 (2H, m, CH₂), 1.60 (4H, m, 2CH₂), 2.85 (4H, m, 2NCH₂), 3.00 (3H, s, SCH₃), 3.80 (2H, s, NCH₂), 4.20 (2H, s, NCH₂), 4.80 (1H, s, NCH), between 7.45 and 7.60 (10H, m, 10CH arom.), 7.75 (2H, m, 2CH arom.), 9.45 (1H, s, NH)].

1-[bis(4-chlorophenyl)methyl]-3-{(methylsulfonyl)[3-(pentafluorophenoxycarbonyl)phenyl]methylene}azetidine may be prepared in the following manner: on carrying out the operation according to the procedure of Example 29 starting with 2.6 g of 1-[bis-(4-chlorophenyl)methyl]-3-[(3-carboxyphenyl)(methylsulfonyl)methylene]azetidine hydrochloride, 0.9 g of pentafluorophenol, 0.9 g of 1-(3-dimethylaminopropyl)-3-ethylcarbodiimide hydrochloride in 25 cm³ of dimethylformamide, the residue obtained is purified by chromatography on a silica gel column (particle size 0.04–0.06 mm, diameter 2 cm, height 30 cm), at a nitrogen pressure of 0.5 bar with a mixture of dichloromethane and ethanol (99/1 by volume) as eluent and collecting 30 cm³ fractions. Fractions 7 to 12 are combined and concentrated to dryness under reduced pressure (2.7 kPa). 0.9 g of 1-[bis(4-chlorophenyl)methyl]-3-{(methylsulfonyl)[3-(pentafluorophenoxycarbonyl)phenyl]methylene}azetidine is obtained in the form of a foam.

1-[Bis(4-chlorophenyl)methyl]-3-[(3-carboxyphenyl)(methylsulfonyl)methylene]azetidine may be prepared in the following manner: 2 cm³ of Jones reagent are added to a mixture of 0.5 g of 1-[bis-(4-chlorophenyl)methyl]-3-[(3-hydroxymethylphenyl)(methylsulfonyl)methylene]azetidine in 9 cm³ of acetone, cooled to 5° C. This stirring is maintained for 2 hours at this temperature and then 50 cm³ of a mixture of water and ice and 50 cm³ of ethyl acetate are added. The organic phase is decanted off, washed with 50 cm³ of a saturated aqueous sodium chloride solution, dried over magnesium sulfate, filtered and concentrated to dryness under reduced pressure (2.7 kPa). The residue obtained is purified by chromatography on a silica gel column (particle size 0.04–0.06 mm, diameter 3 cm, height 25 cm), at a nitrogen pressure of 0.5 bar with a mixture of dichloromethane and ethanol as eluent and collecting 60 cm³ fractions. Fractions 12 to 14 are combined, concentrated to dryness under reduced pressure (2.7 kPa). The solid obtained is crystallized from 10 cm³ of ethyl ether. 32 mg of 1-[bis(4-chlorophenyl)methyl]-3-[(3-carboxyphenyl)(methylsulfonyl)methylene]azetidine are obtained in the form of a solid melting at 205° C. [NMR spectrum in DMSO-d6, T=300K, δ in ppm (400 MHz): 2.90 (3H, s, SCH₃), 3.80 (2H, s, NCH₂), 4.20 (2H, s, NCH₂), 4.80 (1H, s, NCH), 7.33 (4H, d, J=7 Hz, 4CH arom.), 7.39 (1H, d, J=7 Hz, CH arom.), 7.42 (4H, d, J=7 Hz, 4CH arom.), 7.49 (1H, t, J=7 Hz, CH arom.), 7.57 (1H, d, J=7 Hz, CH arom.), 7.90 (2H, s, CH arom. and NH⁺)].

EXAMPLE 70

On carrying out the operation according to the procedure for Example 4 starting with 0.8 g of 1-[bis(4-chlorophenyl)methyl]-3-[(methylsulfonyl)(3-trifluoromethylsulfanylphenyl)methyl(RS)]azetidin-3-ol, 0.24 g of methanesulfonyl chloride and 0.7 g of 4-dimethylaminopyridine, the residue obtained is purified by chromatography on a silica gel column (particle size 0.04–0.06 mm, diameter 2 cm, height 18 cm) at a nitrogen pressure of 0.5 bar with dichloromethane as eluent and collecting 50 cm³ fractions. Fractions 12 to 17 are combined, concentrated to dryness under reduced pressure (2.7 kPa). The residue obtained is again purified by chromatography on a silica gel column (particle size 0.04–0.06 mm, diameter 2 cm, height 20 cm), at a nitrogen pressure of 0.5 bar with dichloromethane as eluent and collecting 30 cm³ fractions. Fractions 15 to 28 are combined, concentrated to dryness under reduced pressure (2.7 kPa). 0.25 g of 1-[bis(4-chlorophenyl)methyl]-3-[(methylsulfonyl)(3-trifluoromethylsulfanylphenyl)methylene]azetidine is obtained melting at 70° C. [NMR spectrum in DMSO-d6+ CD₃CO₂D, T=300K, δ in ppm (300 MHz): 3.00 (3H, s, SCH₃), 3.80 (2H, s, NCH₂), 4.20 (2H, s, NCH₂), 4.80 (1H, s, NCH), 7.35 (4H, d, J=7 Hz, 4CH arom.), 7.45 (4H, d, J=7 Hz, 4 CH arom.), 7.60 (2H, m, 2CH arom), 7.75 (2H, m, 2CH arom.)].

1-[Bis(4-chlorophenyl)methyl]-3-[(methylsulfonyl)(3-trifluoromethylsulfanylphenyl)methyl-(RS)]azetidin-3-ol may be obtained in the following manner: on carrying out the operation according to the procedure of Example 1 starting with 2 g of methyl(3-trifluoromethylsulfanylbenzyl)sulfone, 2.3 g of 1-[bis(4-chlorophenyl)methyl]azetidin-3-one and 5.5 cm³ of a 1.6 M solution of n-butyllithium in hexane, 0.9 g of 1-benzhydryl-3-[(methylsulfonyl)(3-trifluoromethylsulfanylphenyl)methyl-(RS)]azetidin-3-ol is obtained in the form of a white solid.

Methyl(3-trifluoromethylsulfanylbenzyl)sulfone may be prepared in the following manner: on carrying out the operation according to the procedure of Example 10 starting with 5 g of 3-trifluoromethylsulfanylbenzyl chloride and 3.2 g of sodium methanesulfinate, 5.2 g of methyl(3-trifluoromethylsulfanylbenzyl)sulfone are obtained in the form of a white solid melting at 125° C.

EXAMPLE 71

On carrying out the operation as in Example 38 (Method 1), starting with 0.72 g of 1-[bis(4-fluorophenyl)methyl]-3-[(3,5-difluorophenyl)(methylsulfonyl)methyl-(RS)]azetidin-3-ol, 0.18 cm³ of methanesulfonyl chloride and 0.66 g of 4-dimethylaminopyridine, 0.42 g of 1-[bis(4-fluorophenyl)methyl]-3-[(3,5-difluorophenyl)(methylsulfonyl)methylene]azetidine is obtained, after chromatography on a silica gel column (particle size 0.04–0.06 mm, diameter 2.5 cm, height 15 cm), at an argon pressure of 1 bar with a mixture of ethyl acetate and cyclohexane (15/85 by volume) as eluent and collecting 25 cm³ fractions, in the form of a white foam [NMR spectrum in DMSO-d6, T=300K, δ in ppm (250 MHz): 3.05 (3H, s, SCH₃), 3.90 (2H, s, NCH₂), 4.20 (2H, s, NCH₂), 4.80 (1H, s, NCH), 7.15 (6H, m, 6CH arom.), 7.35 (1H, t, J=8 Hz, CH arom.), 7.50 (4H, dd, J=6 and 8 Hz, 4CH arom.)].

1-[Bis(4-fluorophenyl)methyl]-3-[(3,5-difluorophenyl)(methylsulfonyl)methyl-(RS)]azetidin-3-ol may be obtained in the following manner: the operation is carried out as in Example 39 starting with 2.25 g of bis(4-fluorophenyl)bromomethane, 1.1 g of potassium carbonate and 2.5 g of 3-[(3,5-difluorophenyl)(methylsulfonyl)methyl-(RS)]azetidin-3-ol hydrochloride. After chromatography on a silica gel column (particle size 0.04–0.06 mm, diameter 4.4 cm, height 25 cm), at an argon pressure of 0.9 bar with a mixture of ethyl acetate and cyclohexane (2/8 by volume) as eluent and collecting 60 cm³ fractions, fractions 23 to 39 are combined and then concentrated to dryness under reduced pressure (2.7 kPa). 0.72 g of 1-[bis(4-fluorophenyl)methyl]-3-[(3,5-difluorophenyl)(methylsulfonyl)methyl-(RS)]azetidin-3-ol is obtained in the form of a white solid.

Bis(4-fluorophenyl)bromomethane may be prepared according to the procedure described by BACHMANN W. E., J. Am. Chem. Soc., 2135 (1933) starting with 4 g of 4,4'-difluorobenzydrol, 2.70 cm³ of acetal bromide and 14 cm³ of a 33% hydrobromic acid solution in acetic acid.

EXAMPLE 72

On carrying out the operation as in Example 38 (Method 1), starting with 1.22 g of 1-[bis(2-fluorophenyl)methyl]-3-[(3,5-difluorophenyl)(methylsulfonyl)methyl-(RS)]azetidin-3-ol, 0.29 cm³ of methanesulfonyl chloride and 1.1 g of 4-dimethylaminopyridine, 0.177 g of 1-[bis(2-fluorophenyl)methyl]-3-[(3,5-difluorophenyl)(methylsulfonyl)methylene]azetidine is obtained, after chromatography on a silica gel column (particle size 0.04–0.06 mm, diameter 3 cm, height 23 cm), at an argon pressure of 1 bar with a mixture of ethyl acetate and cyclohexane (15/85 by volume) as eluent and collecting 60 cm³ fractions, in the form of a white foam [NMR spectrum in DMSO-d6, T=300K, δ in ppm (300 MHz): 3.05 (3H, s, SCH₃), 3.95 (2H, s, NCH₂), 4.25 (2H, s, NCH₂), 5.35 (1H, s, NCH), 7.20 (6H, m, 6CH arom.), 7.35 (3H, m, 3CH arom.), 7.55 (2H, m, 2CH arom.)].

1-[Bis(2-fluorophenyl)methyl]-3-[(3,5-difluorophenyl)(methylsulfonyl)methyl-(RS)]azetidin-3-ol may be obtained in the following manner: the operation is carried out as in Example 39 starting with 2 g of bis(2-fluorophenyl)bromomethane, 1.0 g of potassium carbonate and 2.22 g of 3-[(3,5-difluorophenyl)(methylsulfonyl)methyl-(RS)]azetidin-3-ol hydrochloride. After chromatography on a silica gel column (particle size 0.04–0.06 mm, diameter 3 cm, height 17 cm), at an argon pressure of 1 bar with a mixture of ethyl acetate and cyclohexane (2/8 by volume) as eluent and collecting 60 cm$^3$ fractions, fractions 6 to 10 are combined and then concentrated to dryness under reduced pressure (2.7 kPa). 1.22 g of 1-[bis(2-fluorophenyl)methyl]-3-[(3,5-difluorophenyl)(methylsulfonyl)methyl-(RS)]azetidin-3-ol are obtained in the form of a whitish solid.

Bis(2-fluorophenyl)bromomethane may be prepared according to the procedure described by BACHMANN W. E., J. Am. Chem. Soc., 2135 (1933), starting with 1.80 g of 2,2'-difluorobenzydrol, 1.22 cm$^3$ of acetyl bromide and 6.5 cm$^3$ of a 33% solution of hydrobromic acid in acetic acid.

2,2'-difluorobenzydrol may be prepared according to the following method: 32 cm$^3$ of a 1.6 M solution of n-butyllithium in hexane are poured dropwise into a solution, cooled to −70° C. under argon, of 8.8 g of 2-bromofluorobenzene in 100 cm$^3$ of tetrahydrofuran. After stirring for 10 minutes at −70° C., 2.1 cm$^3$ of ethyl formate are added slowly and then the mixture is stirred at −70° C. for 30 minutes. The reaction medium is then brought to 0° C. and then supplemented with 50 cm$^3$ of ethyl acetate and 100 cm$^3$ of saturated ammonium chloride solution. After stirring, the organic phase is separated, dried over magnesium sulfate, concentrated to dryness at 55° C., under reduced pressure (2.7 Kpa). 3.63 g of 2,2'-difluorobenzydrol are obtained in the form of a yellow oil.

EXAMPLE 73

On carrying out the operation as in Example 38 (Method 1), starting with 1.15 g of 1-[bis-(3-fluorophenyl)methyl]-3-[(3,5-difluorophenyl)(methylsulfonyl)methyl-(RS)]azetidin-3-ol, 0.264 cm$^3$ of methanesulfonyl chloride, and 0.98 g of 4-dimethylaminopyridine, 0.55 g of 1-[bis(3-fluorophenyl)methyl]-3-[(3,5-difluorophenyl)(methylsulfonyl)methylene]azetidine is obtained, after chromatography on a silica gel column (particle size 0.06–0.200 mm, diameter 2.8 cm, height 25 cm), at an argon pressure of 1 bar with a mixture of ethyl acetate and cyclohexane (15/85 by volume) as eluent and collecting 60 cm$^3$ fractions, in the form of a white solid melting at 178° C. [NMR spectrum in DMSO-d6, T=300K, δ in ppm (250 MHz): 3.05 (3H, s, SCH$_3$), 3.95 (2H, s, NCH$_2$), 4.25 (2H, s, NCH$_2$), 4.80 (1H, s, NCH), 7.10 (2H, m, 2CH arom.), 7.20 (2H, m, 2CH arom.), between 7.30 and 7.50 (7H, m, 7CH arom.)].

1-[Bis(3-fluorophenyl)methyl]-3-[(3,5-difluorophenyl)(methylsulfonyl)methyl-(RS)]azetidin-3-ol may be prepared in the following manner: on carrying out the operation according to Example 1 starting with 1.2 g of (3,5-difluorobenzyl)methylsulfone and 1.5 g of 1-[bis(3-fluorophenyl)methyl]azetidin-3-one, 1.95 g of 1-[bis(3-fluorophenyl)methyl]-3-[(3,5-difluorophenyl)(methylsulfonyl)methyl-(RS)]azetidin-3-ol are obtained, after purification on a silica gel column (particle size 0.06–0.200 mm, diameter 3.2 cm, height 30 cm), at an argon pressure of 1 bar with a mixture of ethyl acetate and cyclohexane (2/8 by volume) as eluent and collecting 60 cm$^3$ fractions, in the form of a white solid melting at 170° C. (decomposition).

1-[Bis(3-fluorophenyl)methyl]azetidin-3-one may be prepared by carrying out the operation in a manner identical to the procedure described by KATRITZKY A. R. et al., J. Heterocycl. Chem., 271 (1994), starting with 4.9 g of [bis(3-fluorophenyl)methyl]amine and 1.78 cm$^3$ of epichlorohydrin.

[Bis(3-fluorophenyl)methyl]amine may be prepared in the following manner: a solution of 5.17 g of 3,3'-difluorobenzophenone oxime in 30 cm$^3$ of tetrahydrofuran is poured, under an argon atmosphere over 30 minutes, into a suspension of 1.27 g of lithium aluminum hydride in 80 cm$^3$ of tetrahydrofuran. After stirring for 5 hours under reflux, 1.3 cm$^3$ of water, 1.3 cm$^3$ of 4 N sodium hydroxide, 2.6 cm$^3$ of water and then 50 cm$^3$ of ethyl acetate are added successively. After drying over magnesium sulfate and concentrating to dryness under reduced pressure (2.7 kPa), 4.9 g of [bis(3-fluorophenyl)methyl]amine are obtained in the form of a yellow oil.

3-3'-Difluorobenzophenone oxime may be prepared according to the following procedure: a solution of 1.6 g of hydroxylamine hydrochloride in 8 cm$^3$ of water is poured dropwise into a solution of 5.0 g of 3,3'-difluorobenzophenone in 10 cm$^3$ of ethanol, and then 1.2 g of sodium hydroxide pellets are added in small fractions. The reaction mixture, heated under reflux for 10 minutes, is cooled to 20° C. and then acidified with 7.5 cm$^3$ of 4 N hydrochloric acid. Once triturated, the oily precipitate obtained becomes a white solid which is filtered, washed with water and then dried at 35° C. under reduced pressure (2.7 kPa). 5.17 g of 3,3'-difluorobenzophenone oxime are obtained in the form of a white solid.

EXAMPLE 74

On carrying out the operation as in Example 1, starting with 1.30 g of a mixture of two diastereoisomers 1-[(4-chlorophenyl)(thiazol-2-yl)methyl-(RS)]-3-[(methylsulfonyl)(phenyl)methyl-(RS)]azetidin-3-ol, 0.35 cm$^3$ of methanesulfonyl chloride and 1.22 g of 4-dimethylaminopyridine, 0.7 g of (RS)-1-[(4-chlorophenyl)(thiazol-2-yl)methyl]-3-[(methylsulfonyl)(phenyl)methylene]azetidine is obtained, after chromatography on a silica gel column (particle size 0.06–0.200 mm, diameter 2.4 cm, height 25 cm), at an argon pressure of 1 bar with a mixture of ethyl acetate and cyclohexane (1/1 by volume) as eluent and collecting 30 cm$^3$ fractions, in the form of a pinkish solid [NMR spectrum in DMSO-d6, T=300K, δ in ppm (300 MHz): 2.95 (3H, s, SCH$_3$), 3.95 (2H, m, NCH$_2$), 4.35 (2H, m, NCH$_2$), 5.25 (1H, s, NCH), 7.45 (9H, m, 9CH arom.), 7.65 (1H, d, J=2 Hz, CH thiazole), 7.70 (1H, d, J=2 Hz, CH thiazole)].

The mixture of the two diastereoisomers 1-[(4-chlorophenyl)(thiazol-2-yl)methyl-(RS)]-3-[(methylsulfonyl)(phenyl)methyl-(RS)]azetidin-3-ol may be obtained in the following manner: on carrying out the operation as in Example 39 starting with 4.47 g of (RS)-bromo(4-chlorophenyl)(thiazol-2-yl)methane and 4.31 g of 3-[(methylsulfonyl)(phenyl)methyl-(RS)]azetidin-3-ol hydrochloride and after chromatography on a silica gel column (particle size 0.06–0.200 mm, diameter 5.6 cm, height 40 cm), at an argon pressure of 0.5 bar with a mixture of ethyl acetate and cyclohexane (25/75 by volume) up to fraction 35 and then with pure ethyl acetate as eluent and collecting 60 cm$^3$ fractions, fractions 38 to 40 are combined and then concentrated to dryness under reduced pressure (2.7 kPa). 1.3 g of the mixture of the two diastereoisomers 1-[(4-chlorophenyl)(thiazol-2-yl)methyl-(RS)]-3-

[(methylsulfonyl)(phenyl)methyl-(RS)]azetidin-3-ol are obtained in the form of a whitish solid.

(RS)-bromo(4-chlorophenyl)(thiazol-2-yl)methane may be prepared according to the procedure described by BACHMANN W. E., J. Am. Chem. Soc., 2135 (1933), starting with 3.5 g of (RS)-(4-chlorophenyl)(2-thiazolyl)methanol, 3.81 g of acetyl bromide and 12.0 cm³ of a 33% solution of hydrobromic acid in acetic acid.

(RS)-(4-chlorophenyl)(thiazol-2-yl)methanol may be prepared according to the procedure described by G. EVAN BOSWELL et al., J. Heterocyclic Chem., 32, 1801 (1995), starting with 4.22 g of 4-chlorobenzaldehyde and 4.92 g of 2-bromothiazole.

EXAMPLE 75

On carrying out the operation as in Example 1, starting with 0.52 g of a mixture of the two diastereoisomers 1-[(4-chlorophenyl)(thien-2-yl)methyl-(RS)]-3-[(3,5-difluorophenyl)(methylsulfonyl)methyl-(RS)]azetidin-3-ol, 0.14 cm³ of methanesulfonyl chloride and 0.49 g of 4-dimethylaminopyridine, 0.32 g of (RS)-1-[(4-chlorophenyl)(thien-2-yl)methyl]-3-[(3,5-difluorophenyl)(methylsulfonyl)methylene]azetidine is obtained, after chromatography on a silica gel column (particle size 0.06–0.200 mm, diameter 2.4 cm, height 20 cm), at an argon pressure of 0.5 bar with a mixture of ethyl acetate and cyclohexane (20/80 by volume) as eluent and collecting 30 cm³ fractions, in the form of a white solid melting at 176° C. [NMR spectrum in DMSO-d6, T=300K, δ in ppm (300 MHz): 2.98 (3H, s, $SCH_3$), 3.90 (2H, m, $NCH_2$), 4.20 (2H, s, $NCH_2$), 5.03 (1H, s, NCH), 6.85 (1H, dd, J=3 and 5 Hz, CH thiophene), 7.08 (3H, m, 2CH arom. and 1CH thiophene), 7.22 (1H, t, J=8 Hz, CH arom.),7.32 (3H, m, 2CH arom. and 1CH thiophene), 7.40 (2H, d, J=7 Hz, 2CH arom.)].

The mixture of the two diastereoisomers 1-[(4-chlorophenyl)(thien-2-yl)methyl-(RS)]-3-[(3,5-difluorophenyl)(methylsulfonyl)methyl-(RS)]azetidin-3-ol may be prepared in the following manner: on carrying out the operation as in Example 1 starting with 1.60 cm³ of 1.6 N n-butyllithium in solution in hexane, 0.83 g of (3,5-difluorobenzyl)methylsulfone and 1.06 g of 1-[(4-chlorophenyl)(thien-2-yl)methyl-(RS)]-azetidin-3-one, 0.55 g of the mixture of diastereoisomers 1-[4-chlorophenyl)(thien-2-yl)methyl-(RS)]-3-[(3,5-difluorophenyl)(methylsulfonyl)methyl-(RS)]azetidin-3-ol is obtained, after purification on a silica gel column (particle size 0.06–0.200 mm, diameter 2.8 cm, height 30 cm), at an argon pressure of 0.5 bar with a mixture of ethyl acetate and cyclohexane (25/75 by volume) as eluent and collecting 40 cm³ fractions, in the form of an off-white solid.

1-[(4-Chlorophenyl)(thien-2-yl)methyl-(RS)]azetidin-3-one may be prepared by carrying out the operation in the following manner: 3.04 cm³ of dimethyl sulfoxide are poured over 10 minutes into a solution, cooled to −70° C., of 1.83 cm³ of oxalyl chloride in 20 cm³ of dichloromethane under argon. After stirring for 30 minutes at −60° C., a solution of 5.2 g of 1-[(4-chlorophenyl)(thien-2-yl)methyl-(RS)]azetidin-3-ol in 80 cm³ of dichloromethane is poured in over 20 minutes, the mixture is stirred for 3 hours at a temperature of between −60° and −70° C. and then 9.12 cm³ of triethylamine are added. The mixture is then allowed to return to room temperature and then diluted with water. The organic phase is separated, dried over magnesium sulfate and then concentrated to dryness under reduced pressure. The residue is chromatographed on a silica gel column (particle size 0.06–0.200 mm, diameter 4 cm, height 36 cm), at an argon pressure of 0.5 bar with a mixture of ethyl acetate and cyclohexane (1/9 by volume) as eluent and collecting 60 cm³ fractions. 3.3 g of 1-[(4-chlorophenyl)(thien-2-yl)methyl-(RS)]zetidin-3-one are obtained in the form of a yellow oil which crystallizes at room temperature.

1-[(4-Chlorophenyl)(thien-2-yl)methyl-(RS)]azetidin-3-ol may be prepared in the following manner: 4.12 g of sodium bicarbonate are added to a solution of 11.0 g of [(4-chlorophenyl)(thien-2-yl)methyl-(RS)]amine in 80 cm³ of ethanol. The mixture is heated at 65° C. and supplemented with 4.03 cm³ of epibromohydrin. After stirring for 20 hours at 65° C., the cooled mixture is filtered and the filtrate concentrated to dryness under reduced pressure (2.7 Kpa). The residue is chromatographed on a silica gel column (particle size 0.06–0.200 mm, diameter 3.6 cm, height 32 cm), at an argon pressure of 0.5 bar with a mixture of ethyl acetate and cyclohexane (25/75 by volume) as eluent and collecting 60 cm³ fractions. 6.3 g of 1-[(4-chlorophenyl)(thien-2-yl)methyl-(RS)]azetidin-3-ol are obtained in the form of a pale yellow oil.

[(4-Chlorophenyl)(thien-2-yl)methyl-(RS)]amine may be prepared in the following manner: a solution of 10.92 g of 2-thiophenecarbonitrile in 80 cm³ of ethyl ether is poured slowly into a suspension, cooled to 10° C., of 4-chlorophenylmagnesium bromide (prepared from 19.15 g of 4-bromochlorobenzene and 2.43 g of magnesium) in 120 cm³ of anhydrous ethyl ether. After refluxing for one hour, the mixture is cooled to 10° C., supplemented slowly with 40 cm³ of methanol and then filtered on supercel. 4.54 g of sodium borohydride are added under argon and in small fractions over 15 minutes and then the reaction medium is stirred for 20 hours at 20° C. The mixture obtained is diluted with ethyl acetate and then washed with water. The organic phase is dried over magnesium sulfate, concentrated to dryness at 50° C. under reduced pressure (2.7 kPa). The residue is chromatographed on a silica gel column (particle size 0.06–0.200 mm, diameter 5 cm, height 42 cm), at an argon pressure of 0.5 bar with a mixture of ethyl acetate and cyclohexane (4/6 by volume) as eluent and collecting 100 cm³ fractions. Fractions 6 to 12, concentrated to dryness, correspond to 13 g of imine in the form of a yellow oil which is taken up in 100 cm³ of methanol. The solution obtained is supplemented with 2.4 g of sodium borohydride and stirred for one hour at 5° C. The mixture obtained is diluted with ethyl acetate and then washed with water. The organic phase is dried over magnesium sulfate, concentrated to dryness at 50° C. under reduced pressure (2.7 Kpa). The residue is chromatographed on a silica gel column (particle size 0.06–0.200 mm, diameter 3.2 cm, height 40 cm), at an argon pressure of 0.5 bar with a mixture of ethyl acetate and cyclohexane (4/6 by volume) as eluent and collecting 60 cm³ fractions. 11.0 g of [(4-chlorophenyl)(thien-2-yl)methyl-(RS)]amine are obtained in the form of a yellow oil.

EXAMPLE 76

On carrying out the operation as described in Example 75, starting with 1.66 g of the mixture of the two chiral diastereoisomers 1-[(4-chlorophenyl)(thien-2-yl)methyl-(R*)]-3-[(3,5-difluorophenyl)(methylsulfonyl)methyl-(R*)]azetidin-3-ol and 1-[(4-chlorophenyl)(thien-2-yl)methyl-(R*)]-3-[(3,5-difluorophenyl)(methylsulfonyl)methyl-(S*)]azetidin-3-ol, 50 cm³ of dichloromethane, 0.45 cm³ of methanesulfonyl chloride, and 1.64 g of 4-dimethylaminopyridine, 0.6 g of (+)-1-[(4-chlorophenyl)(thien-2-yl)methyl]-3-[(3,5-difluorophenyl)(methylsulfonyl)methylene]azetidine is obtained in the form of white crystals melting at 136° C., $[\alpha]^{20}_D$=+3.2° (c=0.5% in dichloromethane).

The mixture of the two chiral diastereoisomers 1-[(4-chlorophenyl)(thien-2-yl)methyl-(R*)]-3-[(3,5-difluorophenyl)(methylsulfonyl)methyl-(R*)]azetidin-3-ol and 1-[(4-chlorophenyl)(thien-2-yl)methyl-(R*)]-3-[(3,5-difluorophenyl)(methylsulfonyl)methyl-(S*)]azetidin-3-ol may be prepared as described in Example 75, starting with 1.06 g of (+)-1-[(4-chlorophenyl)(thien-2-yl)methyl]azetidin-3-one, 0.82 g of (3,5-difluorobenzyl)methylsulfone, 2.5 cm$^3$ of 1.6 N solution of n-butyllithium in hexane, and 25 cm$^3$ of tetrahydrofuran. 1.7 g of the mixture of the two chiral diastereoisomers 1-[(4-chlorophenyl)(thien-2-yl)methyl-(R*)]-3-[(3,5-difluorophenyl)(methylsulfonyl)methyl-(R*)]azetidin-3-ol and 1-[(4-chlorophenyl)(thien-2-yl)methyl-(R*)]-3-[(3,5-difluorophenyl)(methylsulfonyl)methyl-(S*)]azetidin-3-ol are obtained, after purification by chromatography, in the form of a white solid.

(+)-1-[(4-Chlorophenyl)(thien-2-yl)methyl]azetidin-3-one may be prepared as described in Example 75, starting with 12.4 g of (+)-1-[(4-chlorophenyl)(thien-2-yl)methyl]azetidin-3-ol, 220 cm$^3$ of dichloromethane, 7.1 cm$^3$ of dimethyl sulfoxide, 4.4 cm$^3$ of oxalyl chloride and 21.5 cm$^3$ of triethylamine. 9.2 g of (+)-1-[(4-chlorophenyl)(thien-2-yl)methyl]azetidin-3-one are obtained in the form of a pale yellow oil crystallizing at 20° C.

(+)-1-[(4-Chlorophenyl)(thien-2-yl)methyl]azetidin-3-ol may be prepared as described in Example 75, starting with 16.1 g of (+)-[(4-chlorophenyl)(thien-2-yl)methyl]amine, 130 cm$^3$ of ethanol, 5.9 cm$^3$ of epibromohydrin and 6.05 g of sodium bicarbonate. 11.5 g of (+)-1-[(4-chlorophenyl)(thien-2-yl)methyl]azetidin-3-ol are obtained, after purification by chromatography, in the form of a cream-colored oil.

(+)-4-[(Chlorophenyl)(thien-2-yl)methyl]amine may be prepared in the following manner: 73 g of D-(−)-tartaric acid are added to a solution of 109 g of [(4-chlorophenyl)(thien-2-yl)methyl-(RS)]amine in 500 cm$^3$ of methanol. The mixture is concentrated to dryness under reduced pressure (2.7 kPa). The foam obtained is taken up in 2.05 liters of an ethanol-water 90/10 by volume mixture. After stirring slowly for 20 hours at 20° C., the crystalline suspension obtained is filtered, the crystals washed with a minimum amount of the same mixture of solvents, and then dried. Another recrystallization is carried out under the same conditions with 1.5 liters of the same mixture of solvents. 44.9 g of crystals of the acid tartrate of the amine are obtained. [a]$^{20}_D$=+10.3° (c=0.5% in dimethylformamide). This compound is recrystallized from 600 cm$^3$ of an ethanol-water 80/20 by volume mixture (the crystals are filtered and washed with twice 30 cm$^3$ of the same mixture of solvents and then drained) and then recrystallized under the same conditions with 400 cm$^3$ of an ethanol-water 78/22 mixture. 28.2 g of acid D-(−)-tartrate of (+)-[(4-chlorophenyl)thien-2-yl)methyl]amine are obtained in the form of white crystals [a]$^{20}_D$=+10.8° (c=0.5% in dimethylformamide).

This salt is taken up in 400 cm$^3$ of a 1 N aqueous solution of sodium hydroxide and with 100 cm$^3$ of ethyl acetate. The organic phase is separated, washed with 100 cm$^3$ of water, dried over magnesium sulfate and then concentrated to dryness under reduced pressure (2.7 kPa). 16.1 g of (+)-[(4-chlorophenyl)(thien-2-yl)methyl]amine are obtained in the form of an oil which crystallizes at 20° C. [a]$^{20}_D$=+32.7° (c=0.5% in dichloromethane).

EXAMPLE 77

On carrying out the operation as described in Example 75, starting with 1.30 g of the mixture of the two chiral diastereoisomers 1-[(4-chlorophenyl)(thien-2-yl)methyl-(S*)]-3-[(3,5-difluorophenyl)(methylsulfonyl)methyl-(R*)]azetidin-3-ol and 1-[(4-chlorophenyl)(thien-2-yl)methyl-(S*)]-3-[(3,5-difluorophenyl)(methylsulfonyl)methyl-(S*)]azetidin-3-ol, 40 cm$^3$ of dichloromethane, 0.35 cm$^3$ of methanesulfonyl chloride and 1.28 g of 4-dimethylaminopyridine, 0.97 g of (−)-1-[(4-chlorophenyl)(thien-2-yl)methyl]-3-[(3,5-difluorophenyl)(methylsulfonyl)methylene]zetidine is obtained in the form of white crystals melting at 135° C., [a]$^{20}_D$=−3.4° (c=0.5% in dichloromethane).

The mixture of the two chiral diastereoisomers 1-[(4-chlorophenyl)(thien-2-yl)methyl-(S*)]-3-[(3,5-difluorophenyl)(methylsulfonyl)methyl-(R*)]azetidin-3-ol and 1-[(4-chlorophenyl)(thien-2-yl)methyl-(S*)]-3-[(3,5-difluorophenyl)(methylsulfonyl)methyl-(S*)]azetidin-3-ol may be prepared as described in Example 75, starting with 1.06 g of (−)-1-[(4-chlorophenyl)(thien-2-yl)methyl]azetidin-3-one, 0.82 g of (3,5-difluorobenzyl)methylsulfone, 2.5 cm$^3$ of 1.6 N solution of n-butyllithium in hexane, and 25 cm$^3$ of tetrahydrofuran. 1.3 g of the mixture of the two chiral diastereoisomers 1-[(4-chlorophenyl)(thien-2-yl)methyl-(S*)]-3-[(3,5-difluorophenyl)(methylsulfonyl)methyl-(R*)]azetidin-3-ol and 1-[(4-chlorophenyl)(thien-2-yl)methyl-(S*)]-3-[(3,5-difluorophenyl)(methylsulfonyl)methyl-(S*)]azetidin-3-ol are obtained after purification by chromatography in the form of a white solid.

(−)-1-[(4-Chlorophenyl)(thien-2-yl)methyl]azetidin-3-one may be prepared as described in Example 75, starting with 11.4 g of (−)-1-[(4-chlorophenyl)(thien-2-yl)methyl]azetidin-3-ol, 200 cm$^3$ of dichloromethane, 4.0 cm$^3$ of dimethyl sulfoxide, 4.0 cm$^3$ of oxalyl chloride and 19.5 cm$^3$ of triethylamine. 8.3 g of (−)-1-[(4-chlorophenyl)(thien-2-yl)methyl]azetidin-3-one are obtained in the form of a pale yellow oil crystallizing at 20° C.

(−)-1-[(4-Chlorophenyl)(thien-2-yl)methyl]azetidin-3-ol may be prepared as described in Example 75, starting with 15.4 g of (−)-[(4-chlorophenyl)(thien-2-yl)methyl]amine, 120 cm$^3$ of ethanol, 5.8 cm$^3$ of epibromohydrin and 5.8 g of sodium bicarbonate. 10.7 g of (−)-1-[(4-chlorophenyl)(thien-2-yl)methyl]azetidin-3-ol are obtained, after purification by chromatography, in the form of a cream-colored oil.

(−)-[(4-Chlorophenyl)(thien-2-yl)methyl]amine may be prepared in the following manner: 29 g of L-(+)-tartaric acid are added to a solution of 43 g of [(4-chlorophenyl)(thien-2-yl)methyl-(RS)]amine in 200 cm$^3$ of methanol. The mixture obtained crystallizes in 2 hours at room temperature. The crystals are filtered, washed with twice 10 cm$^3$ of methanol. Recrystallization is carried out with 500 cm$^3$ of an ethanol-water 80/20 by volume mixture, the crystals are filtered, washed with twice 30 cm$^3$ of the same mixture of solvents and then dried under vacuum at 45° C. A final recrystallization is carried out with 350 cm$^3$ of an ethanol-water 78/22 by volume mixture, allowing the mixture to be stirred for 20 hours at 20° C. The crystals obtained are drained, dried under reduced pressure (2.7 kPa). 26 g of acid L-(+)-tartrate of (−)-[(4-chlorophenyl)(thien-2-yl)methyl]amine are obtained. [a]$^{20}_D$=−10.7° (c=0.5% in dimethylformamide).

This salt is taken up in 400 cm$^3$ of a 1 N aqueous sodium hydroxide solution and with 100 cm$^3$ of ethyl acetate. The organic phase is separated, washed with 100 cm$^3$ of water, dried over magnesium sulfate and then concentrated to dryness under reduced pressure (2.7 kPa). 15.4 g of (−)-[(4-chlorophenyl)(thien-2-yl)methyl]amine are obtained in the form of an oil which crystallizes at 20° C. [a]$^{20}_D$=−31.7° (c=0.5% in dichloromethane).

EXAMPLE 78

On carrying out the operation according to the procedure of Example 1 starting with 3.4 g of 1-benzhydryl-3-[(ethylsulfonyl)(phenyl)methyl-(RS)]azetidin-3-ol, 0.72 cm³ of methanesulfonyl chloride and 3.8 g of 4-dimethylaminopyridine, 1.9 g of 1-benzhydryl-3-[(ethylsulfonyl)(phenyl)methylene]azetidine are obtained, after recrystallization from 40 cm³ of acetonitrile, in the form of crystals melting at 210° C. [[NMR spectrum in DMSO-d6, T=300K, δ in ppm (300 MHz): 1.15 (3H, t, J=6 Hz, CH₃), 2.92 (2H, q, J=6 Hz, CH₂), 3.83 (2H, s, NCH₂), 4.20 (2H, s, NCH₂), 4.75 (1H, s, NCH), between 7.20 and 7.50 (15H, m, 3 phenyls)].

1-Benzhydryl-3-[(ethylsulfonyl)(phenyl)methyl-(RS)] azetidin-3-ol may be obtained by carrying out the operation according to the procedure described in Example 1 starting with 2.4 g of benzylethylsulfone, 2.2 cm³ of diisopropylamine, 10 cm³ of 1.6 N n-butyllithium in solution in hexane, 65 cm³ of tetrahydrofuran and 3.1 g of 1-benzhydrylazetidin-3-one. 3.6 g of 1-benzhydryl-3-[(ethylsulfonyl)(phenyl)methyl-(RS)]azetidin-3-ol are obtained, after recrystallization from 30 cm³ of acetonitrile, in the form of white crystals melting at 222° C.

Benzylethylsulfone may be prepared by carrying out the operation according to the procedure of Example 2 starting with 6.3 g of benzylethylsulfide, 50 cm³ of acetic acid, 50 cm³ of water, 25 cm³ of 36 N sulfuric acid and 24.8 g of oxone$^R$. 3.2 g of benzylethylsulfone are obtained, by recrystallization from 20 cm³ of ethyl ether, in the form of a solid melting at 86° C.

Benzylethylsulfide may be prepared in the following manner: 1.2 g of sodium hydride are added in small portions to a solution of 5 g of benzylmercaptan in 50 cm³ of dimethylformamide under argon, and then 3.36 cm³ of ethyl iodide are poured in, while the temperature is maintained below 45° C. The mixture is stirred for 2 hours and then taken up in 200 cm³ of ethyl ether. The organic phase is washed with 200 cm³ of water and then with 3 times 100 cm³ of water, dried over magnesium sulfate and concentrated to dryness under reduced pressure (2.7 kPa). 6.3 g of benzylethylsulfide are obtained in the form of a pale yellow liquid.

EXAMPLE 79

0.083 g of 1-amino-4-methylpiperazine is added to a solution of 0.45 g of 1-[bis(4-chlorophenyl)methyl]-3-{(methylsulfonyl)[3-(pentafluorophenoxycarbonyl)phenyl]methylene]azetidine in 5 cm³ of dimethylformamide. The mixture is stirred for 20 hours at room temperature and then 40 cm³ of ethyl acetate are added. The organic phase is washed with 4 times 20 cm³ of water, dried over magnesium sulfate and concentrated to dryness under reduced pressure (2.7 kPa). The residue is triturated with 10 cm³ of ethyl ether, filtered and then dried. 0.2 g of 1-[bis(4-chlorophenyl) methyl]-3-{(methylsulfonyl)[(N-4-methylpiperazinylcarbamoyl)phenyl]methylene}azetidine is obtained in the form of a yellow solid melting at 162° C. [NMR spectrum in DMSO-d6, T=300K, δ in ppm (300 MHz): 2.20 (3H, s, NCH₃), 2.40 (4H, m, 2 NCH₂), 2.90 (4H, m, 2 NCH₂), 2.95 (3H, s, SCH₃), 3.80 (2H, s, NCH₂), 4.20 (2H, s, NCH₂), 4.80 (1H, s, NCH), 7.40 (4H, d, J=7 Hz, 4CH arom.), 7.50 (4H, d, J=7 Hz, 4CH arom.), 7.55 (2H, m, 2CH arom.), 7.80 (2H, m, 2CH arom.), 9.50 (1H, s, CONH)].

1-[Bis(4-chlorophenyl)methyl]-3-{(methylsulfonyl)[3-(pentafluorophenoxycarbonyl)phenyl]methylene]azetidine may be prepared in the following manner: 0.94 g of N-(3-dimethylaminopropyl)-N'-ethylcarbodiimide hydrochloride and 0.89 g of pentafluorophenol are added to a solution of 2.9 g of 1-[bis(4-chlorophenyl)methyl]-3-[(3-carboxyphenyl)(methylsulfonyl)methylene]azetidine in 25 cm³ of dimethylformamide. The mixture is stirred for 20 hours at room temperature and then taken up in 50 cm³ of ethyl acetate. The organic phase is washed with 100 cm³ of water, 200 cm³ of a saturated aqueous sodium bicarbonate solution and then with twice 50 cm³ of distilled water, dried over magnesium sulfate and concentrated to dryness under reduced pressure (2.7 kpa). The residue is chromatographed on a silica column (particle size 0.04–0.006 mm, diameter 2 cm), eluting with a mixture of dichloromethane and ethanol (99/1 by volume). 0.92 g of 1-[bis(4-chlorophenyl)methyl]-3-{(methylsulfonyl)[3-(pentafluorophenoxycarbonyl)phenyl]methylene]azetidine is obtained in the form of a white foam.

1-[Bis(4-chlorophenyl)methyl]-3-[(3-carboxyphenyl)(methylsulfonyl)methylene]azetidine may be prepared in the following manner: a 36% solution of hydrochloric acid at a temperature of 50° C. is added to a solution of 3.8 g of 1-[bis(4-chlorophenyl)methyl]-3-[(3-cyanophenyl)(methylsulfonyl)methylene]azetidine in 5 cm³ of acetic acid. The heating is continued for 48 hours and then the mixture is evaporated to dryness under reduced pressure (2.7 Kpa). The residue is taken up in 30 cm³ of ethanol and again evaporated to dryness. The residue is triturated in 35 cm³ of ethyl ether. 3.8 g of 1-[bis(4-chlorophenyl)methyl]-3-[(3-carboxyphenyl)(methylsulfonyl)methylene)]azetidine are obtained in the form of a beige solid.

1-[Bis(4-chlorophenyl)methyl]-3-[(3-cyanophenyl)(methylsulfonyl)methylene]azetidine may be prepared according to the procedure of Example 4, starting with 11 g of 1-[bis(4-chlorophenyl)methyl]-3-[(3-cyanophenyl)(methylsulfonyl)methyl-(RS)]azetidin-3-ol, 150 cm³ of dichloromethane, 2.54 cm³ of methanesulfonyl chloride and 10.7 g of 4-dimethylaminopyridine, at room temperature for 3 hours. The residue obtained is purified by chromatography on a silica gel column (particle size 0.04–0.06 mm, diameter 4.5 cm) and eluted with dichloromethane and then with a mixture of dichloromethane and ethanol (99.6/0.4 by volume). The fractions are evaporated to dryness under reduced pressure (2.7 Kpa). 3.8 g of 1-[bis(4-chlorophenyl) methyl]-3-[(3-cyanophenyl)(methylsulfonyl)methylene] azetidine are obtained in the form of a white foam.

1-[Bis(4-chlorophenyl)methyl]-3-[(3-cyanophenyl)(methylsulfonyl)methyl-(RS)]azetidin-3-ol may be prepared in the following manner: a solution of 5 g of 3-cyanobenzyl methyl sulfone in 500 cm³ of tetrahydrofuran is added over 15 minutes to a solution of 17.6 cm³ of 1.6 M n-butyllithium in hexane, in 30 cm³ of tetrahydrofuran under argon, and cooled to −70° C. The mixture is stirred for 1 hour 30 minutes. Next, a solution of 7.8 g of 1-[bis(4-chlorophenyl) methyl]azetidin-3-one in 80 cm³ of tetrahydrofuran is poured in over 10 minutes. After stirring for 1 hour 30 minutes, 60 cm³ of a saturated aqueous ammonium chloride solution are poured in and then the mixture is allowed to return to room temperature. The mixture is taken up in 300 cm³ of ethyl acetate, the organic phase washed with 200 cm³ of a saturated aqueous sodium chloride solution, dried over magnesium sulfate and evaporated under reduced pressure (2.7 Kpa). 11 g of 1-[bis(4-chlorophenyl)methyl]-3-[(3-cyanophenyl)(methylsulfonyl)methyl-(RS)]azetidin-3-ol are obtained in the form of a foam.

(3-Cyanobenzyl)methylsulfone may be prepared in the following manner: starting with a solution of 20.2 g of 3-chloromethylbenzonitrile in 200 cm³ of ethanol, 17.4 g of 85% sodium methanesulfinate are added. The mixture is stirred for 20 hours under reflux and then taken up in 500 cm³ of ethyl acetate and 500 cm³ of water. The insoluble matter is filtered off, the organic phase in the filtrate is dried over magnesium sulfate and evaporated to dryness under reduced pressure (2.7 Kpa). The solid obtained is triturated with 100 cm³ of ethyl ether. After filtration and drying of the solid, 21 g of (3-cyanobenzyl)methylsulfone are obtained in the form of white crystals melting at 165° C.

3-Chloromethylbenzonitrile may be prepared in the following manner: 32 g of 3-chloromethylbenzoamide in 200 cm³ of phosphorus oxychloride are heated at 95° C. for 3 hours, and then 1 liter of ice is loaded, the mixture stirred for 1 hour and extracted with 500 cm³ of dichloromethane. The organic phase is washed with 200 cm³ of water, dried over magnesium sulfate and evaporated to dryness under reduced pressure (2.7 Kpa). 20.2 g of 3-chloromethylbenzonitrile are obtained in the form of a white solid.

3-Chloromethylbenzoamide may be prepared in the following manner: 150 cm³ of a solution of ammonium hydroxide (d=0.90) are poured into a solution of 50 g of 3-chloromethylbenzoyl chloride in 150 cm³ of ethyl ether, the mixture is cooled, stirred for 1 hour, filtered and washed with twice 200 cm³ of ethyl ether. 32 g of 3-chloromethylbenzoamide are obtained in the form of white crystals.

EXAMPLE 80

On carrying out the operation according to the procedure of Example 79 starting with 0.5 g of 1-[bis(4-chlorophenyl)methyl]-3-{(methylsulfonyl)[3-(pentafluorophenoxycarbonyl)phenyl]methylene}azetidine, 0.06 cm³, 1,1-dimethylhydrazine and 5 cm³ of dimethylformamide, 0.125 g of 1-[bis(4-chlorophenyl)methyl]-3-{(3-(2,2-dimethylcarbohydrazido)phenyl](methylsulfonyl)methylene}azetidine is obtained in the form of a white solid melting at 134° C. [NMR spectrum in DMSO-d6, T=300K, δ in ppm (300 MHz): 2.60 (6H, s, N(CH₃)₂), 2.95 (3H, s, SCH₃), 3.80 (2H, s, NCH₂), 4.20 (2H, s, NCH₂), 4.80 (1H, s, NCH), 7.35 (4H, d, J=7 Hz, 4CH arom.), 7.45 (4H, d, J=7 Hz, 4CH arom.), 7.50 (2H, m, 2CH arom.), 7.80 (2H, m, 2CH arom.), 9.50 (1H, s, CONH)].

EXAMPLE 81

On carrying out the operation according to the procedure described in Example 1 starting with 2.2 g of 1-[bis(thien-2-yl)methyl]-3-[(3,5-difluorophenyl)(methylsulfonyl)methyl-(RS)]azetidin-3-ol, 0.64 cm³ of methanesulfonyl chloride, 2.3 g of 4-dimethylaminopyridine and 75 cm³ of dichloromethane, 1.3 g of 1-[bis(thien-2-yl)methyl]-3-[(3,5-difluorophenyl)(methylsulfonyl)methylene]azetidine are obtained, after purification by chromatography and crystallization from diisopropyl ether, in the form of white crystals melting at 165° C. [NMR spectrum in DMSO-d6, T=300K, δ in ppm (300 MHz): 3.00 (3H, s, SCH₃), 3.92 (2H, s, NCH₂), 4.28 (2H, s, NCH₂), 5.40 (1H, s, NCH), 6.95 (2H, dd, J=5 and 2 Hz, 2CH thio.), 7.15 (2H, d, J=2 Hz, 2CH thio.), 7.20 (2H, m, 2CH arom.), 7.35 (1H, t, J=8 Hz, CH arom.), 7.50 (2H, d, J=5 Hz, 2CH thio.)].

1-[Bis(thien-2-yl)methyl]-3-[(3,5-difluorophenyl)(methylsulfonyl)methyl-(RS)]azetidin-3-ol may be obtained according to the procedure described in Example 1, starting with 1.5 g of 1-[bis(thien-2-yl)methyl]azetidin-3-one, 4 cm³ of 1.6 N n-butyllithium in hexane, 1.3 g of (3,5-dichlorobenzyl)methylsulfone and 40 cm³ of tetrahydrofuran. 2.2 g of 1-[bis(thien-2-yl)methyl]-3-[(3,5-difluorophenyl)(methylsulfonyl)methyl-(RS)]azetidin-3-ol are obtained, after purification by chromatography, in the form of white crystals melting at 145° C.

1-[Bis-thien-2-yl)methyl]azetidin-3-one may be prepared by carrying out the operation as described in Example 73, starting with 4 g of 1-[bis(thien-2-yl)methyl]azetidin-3-ol, 2.6 cm³ of dimethyl sulfoxide, 7.7 cm³ of triethylamine, 7.7 cm³ of oxalyl chloride, and 100 cm³ of dichloromethane. The residue obtained is purified by chromatography on a silica gel column (particle size 0.04–0.06 mm, diameter 3 cm, height 30 cm) with, as eluent, a mixture of cyclohexane/ethyl acetate (1/1 by volume). The fractions obtained are evaporated to dryness under reduced pressure (2.7 Kpa). 3.2 g of 1-[bis(thien-2-yl)methyl]azetidin-3-one are obtained in the form of cream-colored crystals melting at 70° C.

1-[Bis(thien-2-yl)methyl]azetidin-3-ol may be prepared by carrying out the operation as described in Example 73, starting with 6 g of 1-[bis(thien-2-yl)methyl]amine, 2.5 cm³ of epibromohydrin, 2.6 g of sodium bicarbonate and 50 cm³ of ethanol. 4 g of 1-[bis(thien-2-yl)methyl]azetidin-3-ol are obtained in the form of beige crystals melting at 115° C.

1-[Bis(thien-2-yl)methyl]amine may be prepared in the following manner: a solution of 5 cm³ of thien-2-ylcarbonitrile in 50 cm³ of diethyl ether is poured dropwise into a suspension, cooled under argon to 10° C., of thien-2-ylmagnesium bromide (prepared from 1.29 g of magnesium and 3.22 cm³ 2-bromothiophene in 75 cm³ of diethyl ether). After refluxing for 1 hour and 30 minutes, the reaction medium is cooled to 5° C. and then 20 cm³ of methanol are poured in dropwise, the suspension filtered and the solid washed with methanol. The filtrate obtained a brown solution. 2.45 g of sodium borohydride are added to this solution, under argon, in several portions. The mixture is stirred at room temperature for 16 hours and then diluted with ethyl acetate and supplemented with water slowly. The organic phase is extracted, washed with water, dried over magnesium sulfate and evaporated to dryness under reduced pressure (2.7 kpa) at 55° C. A brown oil is obtained which is chromatographed on a silica gel column (particle size 0.2–0.063 mm, diameter 8 cm, height 25 cm) and eluted with a mixture of cyclohexane/ethyl acetate (90/10 and then 85/15 by volume). Fractions 21 to 30 are combined and evaporated to dryness under reduced pressure (2.7 kpa). 11 g of 1-[bis(thien-2-yl)methyl]amine are obtained in the form of a crystallized solid.

EXAMPLE 82

On carrying out the operation according to the procedure described in Example 1 starting with 0.47 g of 4-dimethylaminopyridine, 0.13 cm³ of methanesulfonyl chloride, 25 cm³ of dichloromethane and 0.48 g of 1-(bis-p-tolylmethyl)-3-[(methylsulfonyl)(phenyl)methyl-(RS)]azetidin-3-ol, 0.25 g of 1-(bis-p-tolylmethyl)-3-[(methylsulfonyl)(phenyl)methylene]azetidine is obtained, after purification by chromatography and crystallization from diisopropyl ether, in the form of a white solid [NMR spectrum in DMSO-d6, T=300K, δ in ppm (250 MHz): 2.23 (6H, s, 2 PhCH₃), 2.98 (3H, s, SCH₃), 3.76 (2H, s, NCH₂), 4.20 (2H, s, NCH₂), 5.55 (1H, s, NCH), 7.10 (4H, d, J=7 Hz, 4 CH arom.), 7.32 (4H, d, J=7 Hz, 4 CH arom.), 7.43 (5H, s, phenyl)].

1-(Bis-p-tolylmethyl)-3-[(methylsulfonyl)(phenyl)methyl-(RS)]azetidin-3-ol may be prepared according to the procedure described in Example 39, starting with 0.59 g of bromo(bis-p-tolyl)methane, 20 cm³ of acetonitrile, 0.3 g of potassium carbonate and 0.6 g of 3-[(methylsulfonyl)

(phenyl)methyl-(RS)]azetidin-3-ol hydrochloride. The residue obtained is chromatographed on a silica gel column (particle size 0.04–0.06 mm, diameter 4 cm, height 16 cm) with, as eluent, a cyclohexane/ethyl acetate (7/3 by volume) mixture. The fractions are concentrated to dryness under reduced pressure (2.7 Kpa). 0.48 g of 1-(bis-p-tolylmethyl)-3-[(methylsulfonyl)(phenyl)methyl-(RS)]azetidin-3-ol is obtained in the form of a white solid.

Bromo(di-p-tolyl)methane may be prepared according to the procedure described by BACHMANN W. E., J. Am. Chem. Soc., 2135 (1933).

3-[(Methylsulfonyl)(phenyl)methyl-(RS)]azetidin-3-ol hydrochloride may be prepared according to the procedure described in Example 39 starting with 7 g of 3-[(methylsulfonyl)(phenyl)methyl-(RS)]-1-(vinyloxycarbonyl)azetidin-3-ol, 35 cm³ of dioxane, 35 cm³ of a 6.2 N solution of hydrochloric acid in dioxane. 5 g of 3-[(methylsulfonyl)(phenyl)methyl-(RS)]azetidin-3-ol hydrochloride are obtained in the form of a white solid.

3-[(Methylsulfonyl)(phenyl)methyl-(RS)]-1-(vinyloxycarbonyl)azetidin-3-ol may be prepared according to the procedure described in Example 38 (Method 1), starting with 10 g of 1-benzhydryl-3-[(methylsulfonyl)(phenyl)methyl-(RS)]azetidin-3-ol, 600 cm³ of dichloromethane and 2.52 cm³ of vinyl chloroformate. The residue is chromatographed on a silica gel column (particle size 0.06–0.2 mm, diameter 5.2 cm, height 36 cm with, as eluent, a cyclohexane/ethyl acetate (7/3 by volume) mixture. The fractions are evaporated to dryness under reduced pressure (2.7 Kpa). 7 g of 3-[(methylsulfonyl)(phenyl)methyl-(RS)]-1-(vinyloxycarbonyl)azetidin-3-ol are obtained in the form of a white solid.

EXAMPLE 83

A solution of 30 mg of sodium borohydride in 2 cm³ of methanol is poured into a solution of 0.77 g of (−)-1-[(4-chlorophenyl)(4-formylphenyl)methyl]-3-[(3,5-difluorophenyl)(methylsulfonyl)methylene]azetidine in 20 cm³ of methanol at 0° C. under argon. After stirring for 4 hours at 0° C., water is added and the mixture is then extracted with dichloromethane. The organic phase is washed with a saturated aqueous sodium chloride solution, dried over magnesium sulfate and then evaporated to dryness under reduced pressure (2.7 kpa). The white foam obtained is purified on a silica gel column (particle size 0.04–0.06 mm, diameter 3.2 cm, height 17 cm) with, as eluent, a cyclohexane/ethyl acetate (60/40 by volume) mixture. 0.1 g of (+)-1-[(4-chlorophenyl)(4-hydroxymethylphenyl)methyl]-3-[(3,5-difluorophenyl)(methylsulfonyl)methylene]azetidine is obtained, after crystallization from 1.5 cm³ of absolute ethanol, in the form of white crystals melting at 190° C., $[\alpha]^{20}_D$=+4.2° (c=0.5% in methanol) [NMR spectrum in DMSO-d6, T=300K, δ in ppm (300 MHz): 3.05 (3H, s, SCH₃), 3.95 (2H, s, NCH₂), 4.22 (2H, s, NCH₂), 4.48 (2H, d, J=6 Hz, CH₂O), 4.75 (1H, s, NCH), 5.15 (1H, t, J=6 Hz, OH), 7.20 (2H, m, 2CH arom.), 7.28 (2H, d, J=7 Hz, 2CH arom.), 7.40(5H, m, 5 CH arom.), 7.50 (2H, d, J=7 Hz, 2CH arom.)].

(−)-1-[(4-Chlorophenyl)(4-formylphenyl)methyl]-3-[(3,5-difluorophenyl)methylsulfonyl-methylene]azetidine may be prepared in the following manner: 3.32 cm³ of a 5 N solution of hydrochloric acid are poured into a solution of 0.83 g of (+)-1-{(4-chlorophenyl)[4-(1,3-dioxolan-2-yl)phenyl]methyl}-3-[(3,5-difluorophenyl)(methylsulfonyl)methylene]azetidine in 5 cm³ of tetrahydrofuran and then the mixture is kept stirring for 20 hours. Dichloromethane and water are added to the reaction medium followed by a 30% aqueous solution of sodium hydroxide until a pH=14 is obtained. The aqueous phase is extracted with dichloromethane, the organic phase is washed successively with water, with a saturated aqueous solution of sodium chloride, dried over magnesium sulfate, filtered and evaporated to dryness under reduced pressure (2.7 kpa). 0.8 g of (−)-1-[(4-chlorophenyl)(4-formylphenyl)methyl]-3-[(3,5-difluorophenyl)(methylsulfonyl)methylene]azetidine is obtained in the form of a white foam.

(+)-1-{(4-Chlorophenyl)[4-(1,3-dioxolan-2-yl)phenyl]methyl}-3-[(3,5-difluorophenyl)(methylsulfonyl)methylene]azetidine may be obtained in the following manner: 0.93 g of 1,8-Diazabicyclo[5-4-0]-undec-7-ene is poured dropwise into a solution of 2.42 g of the mixture of the two diastereoisomers 3-acetoxy-1-{(4-chlorophenyl)[4-(1,3-dioxolan-2-yl)phenyl]methyl-(R*)}-3-[(3,5-difluorophenyl)(methylsulfonyl)methyl-(R*)]azetidine and 3-acetoxy-1-{(4-chlorophenyl)[4-(1,3-dioxolan-2-yl)phenyl]methyl-(R*))-3-[(3,5-difluorophenyl)(methylsulfonyl)methyl-(S*)]azetidine in 25 cm³ of tetrahydrofuran under argon at 0° C. After stirring for 1 hour and 30 minutes at 0° C., the reaction medium is diluted with ethyl acetate, washed with water and with a saturated aqueous sodium chloride solution. The organic phase is dried over magnesium sulfate, filtered and evaporated to dryness under reduced pressure. The crude product is purified on a silica gel column (particle size 0.04–0.06 mm, diameter 4.8 cm, height 17.5 cm) with, as eluent, a cyclohexane/ethyl acetate (80/20 by volume) mixture. 1.21 g of (+)-1-{(4-chlorophenyl)[4-(1,3-dioxolan-2-yl)phenyl]methyl}-3-[(3,5-difluorophenyl)(methylsulfonyl)methylene]azetidine are obtained in the form of a yellow foam.

The mixture of the two diastereoisomers 3-acetoxy-1-{(4-chlorophenyl)[4-(1,3-dioxolan-2-yl)phenyl]methyl-(R*)}-3-[(3,5-difluorophenyl)(methylsulfonyl)methyl-(R*)]azetidine and 3-acetoxy-1-{(4-chlorophenyl)[4-(1,3-dioxolan-2-yl)phenyl]methyl-(R*)}-3-[(3,5-difluorophenyl)(methylsulfonyl)methyl-(S*)]azetidine may be prepared in the following manner: 3.27 cm³ of n-butyllithium are poured dropwise into a solution of 1.08 g of 3,5-difluorobenzyl methyl sulfone under argon, cooled to −70° C., and then the mixture is kept stirring for 1 hour at −70° C. and then a solution of 1.80 g of (+)-1-{(4-chlorophenyl)[4-(1,3-dioxolan-2-yl)phenyl]methyl}azetidin-3-one in 10 cm³ of tetrahydrofuran is poured in dropwise. After stirring for 3 hours at −70° C. and for 1 hour at −20° C., a solution of 0.74 cm³ of acetyl chloride in 10 cm³ of anhydrous diethyl ether at −20° C. is poured in and the mixture is stirred for 2 hours at −20° C. The reaction medium is thrown over water, the mixture is extracted with ethyl acetate, the organic phase washed with water and with a saturated aqueous sodium chloride solution, dried over magnesium sulfate and concentrated to dryness under reduced pressure (2.7 kpa). 2.42 g of the mixture of the two diastereoisomers 3-acetoxy-1-{(4-chlorophenyl)[4-(1,3-dioxolan-2-yl)phenyl]methyl-(R*)}-3-[(3,5-difluorophenyl)(methylsulfonyl)methyl-(R*)]azetidine and 3-acetoxy-1-{(4-chlorophenyl)-[4-(1,3-dioxolan-2-yl)phenyl]methyl-(R*)}-3-[(3,5-difluorophenyl)(methylsulfonyl)methyl-(S*)]azetidine are obtained in the form of a yellow oil.

(+)-1-{(4-Chlorophenyl)[4-(1,3-dioxolan-2-yl)phenyl]methyl}azetidin-3-one may be prepared in the following manner: 2.24 cm³ of triethylamine are poured into a solution of 1.38 g of (+)-1-{(4-chlorophenyl)[4-(1,3-dioxolan-2-yl)phenyl]methyl}azetidin-3-ol in 20 cm³ of anhydrous dimethyl sulfoxide under argon, followed dropwise by 1.65 g of a solution of sulfur trioxide pyridine complex in 20 cm³ of anhydrous dimethyl sulfoxide. After stirring for 1 hour and 15 minutes at room temperature, the reaction medium is thrown over ice, extracted with ethyl acetate, the organic phase washed with water, with a saturated aqueous sodium chloride solution, dried over magnesium sulfate, filtered and concentrated to dryness under reduced pressure (2.7 kpa). The oily residue obtained (1.31 g), combined with another batch of the same crude compound (1.21 g), are purified together on a silica gel column (particle size 0.04–0.06 mm, diameter 4.8 cm, height 18 cm), with, as eluent, a cyclohexane/ethyl acetate (80/20 by volume) mixture. 1.87 g of (+)-1-{(4-chlorophenyl)[4-(1,3-dioxolan-2-yl)phenyl]methyl}azetidin-3-one are obtained in the form of a yellow oil. [a]$^{20}$365 nm=+5.9° (c=0.5; methanol).

(+)-1-{(4-Chlorophenyl)[4-(1,3-dioxolan-2-yl)phenyl]methyl}azetidin-3-ol may be described according to the procedure described in Example 73, starting with 4.43 g of (+)-{(4-chlorophenyl)[4-(1,3-dioxolan-2-yl)phenyl]methyl}amine, 40 cm³ of absolute ethanol, 1.25 cm³ of epibromohydrin and 1.28 g of sodium bicarbonate. 1.66 g of (+)-1-{(4-chlorophenyl)[4-(1,3-dioxolan-2-yl)phenyl]methyl}azetidin-3-ol are obtained in the form of a yellow oil.

Chiral (+)-{(4-chlorophenyl)[4-(1,3-dioxolan-2-yl)phenyl]methyl}amine may be obtained in the following manner: 3.95 cm³ of ethylene glycol are poured into a suspension of 18.16 g of chiral (R*)-[(4-chlorophenyl)(4-formylphenyl)methyl]amine hydrochloride, in 1000 cm³ of toluene, and 0.82 g of para-toluenesulfonic acid monohydrate is added. After stirring for 20 hours at the reflux temperature, the reaction medium is cooled, washed with a saturated aqueous sodium bicarbonate solution, with water and with a saturated aqueous sodium chloride solution. The organic phase is dried over magnesium sulfate, filtered and concentrated to dryness under reduced pressure. The residue obtained is purified on a silica gel column (particle size 0.04–0.06 mm, diameter 8.4 cm, height 21.5 cm) with, as eluent, a cyclohexane/ethyl acetate (30/70 by volume) mixture, collecting 250 cm³ fractions. Fractions 23 to 30 are concentrated to dryness under reduced pressure (2.7 kpa). 1.39 g of chiral (+)-{(4-chlorophenyl)-[4-(1,3-dioxolan-2-yl)phenyl]methyl}amine are obtained in the form of a yellow oil.

Chiral (R*)-[(4-chlorophenyl)(4-formylphenyl)methyl]amine hydrochloride may be prepared in the following manner: 330 cm³ of methanol are poured into a solution of 51.4 g of the diastereoisomer N-{(4-chlorophenyl)[4-(diethoxymethyl)phenyl]methyl-(R*)}-(R)-2-phenylglycinol in 660 cm³ of anhydrous dichloromethane, the mixture cooled with an ice bath, 60.96 g of lead tetraacetate added, the mixture stirred for 5 minutes and then 1 liter of a phosphate buffer solution pH 7 poured in. After stirring for 30 minutes at room temperature, the mixture is filtered and the aqueous phase is extracted with dichloromethane. The organic phase is concentrated to dryness under reduced pressure (2.7 kpa). The residue is taken up in 1 liter of diethyl ether and supplemented with 1 liter of a 3 N aqueous solution of hydrochloric acid, the mixture is stirred for 15 minutes at room temperature, the aqueous phase is separated, washed with ethyl acetate and then concentrated to dryness under reduced pressure (2.7 kpa). 18.16 g of chiral (R*)-[(4-chlorophenyl)(4-formylphenyl)methyl]amine hydrochloride are obtained in the form of a white solid.

N-{(4-chlorophenyl)[4-(diethoxymethyl)phenyl]methyl-(R*)}-(R)-2-phenylglycinol may be prepared in the following manner: 286 cm³ of 1.6 M n-butyllithium in hexane are poured dropwise into a solution, cooled to −70° C., under argon, of 87.7 g of 4-bromochlorobenzene and the mixture is stirred for 15 minutes at −70° C. This solution obtained is then added dropwise to the following solution cooled to 0° C.: 30 g of (R)-N-[4-(diethoxymethyl)benzylidene]-2-phenylglycinol in 300 cm³ of diethyl ether. The mixture is stirred for 2 hours at 0° C. and then thrown over water. The organic phase is washed with water and then with a saturated aqueous sodium chloride solution, dried over magnesium sulfate, filtered and concentrated to dryness under reduced pressure (2.7 kpa). 71.5 g of a reddish oil are obtained, which oil is purified on a silica gel column (particle size 0.04–0.06 mm, diameter 11 cm, height 45 cm), with, as eluent, a cyclohexane/ethyl acetate (85/15 by volume, then 80/20 and 75/25) mixture, collecting 1 liter fractions. Fractions 11 to 17 are concentrated to dryness under reduced pressure (2.7 kpa). 39.85 g of the sole diastereoisomer N-{(4-chlorophenyl)[4-(diethoxymethyl)phenyl]methyl-(R*)}-(R)-2-phenylglycinol are obtained in the form of an orange red oil.

(R)-N-[4-(diethoxymethyl)benzylidene]-2-phenylglycinol may be prepared in the following manner: 35.9 cm³ of 4-(diethoxymethyl)benzaldehyde are poured into a white suspension of 24.7 g of (R)-(−)-2-phenylglycinol in 500 cm³ of toluene. The cloudy yellow solution is heated under reflux for 6 hours 30 minutes, and is then stirred at room temperature for 20 hours. After concentrating the reaction medium to dryness under reduced pressure (2.7 kpa), 61.6 g of (R)-N-[4-(diethoxymethyl)benzylidene]-2-phenylglycinol are obtained in the form of a yellow oil.

EXAMPLE 84

On carrying out the operation according to the procedure of Example 1, but starting with 5.6 g of 1-[bis(4-chlorophenyl)methyl]-3-{[3-(N-tert-butyloxycarbonyl-N-methylamino)phenyl](methylsulfonyl)methyl-(RS)}azetidin-3-ol, 100 cm³ of dichloromethane, 1.59 g of methanesulfonyl chloride and 4.5 g of 4-dimethylaminopyridine. The mixture is kept stirring for 3 hours at room temperature. The crude product obtained is purified by chromatography on a silica gel column (particle size 0.04–0.06 mm, diameter 4 cm³ and weight of silica 250 g), eluting at a nitrogen pressure of 0.5 bar with an ethyl acetate/cyclohexane (30/70 by volume) mixture and collecting 100 cm³ fractions. Fractions 12 to 18 are combined, concentrated to dryness under reduced pressure (2.7 kpa). 3.2 g of 1-[bis(4-chlorophenyl)methyl]-3-{[3-(N-tert-butyloxycarbonyl-N-methylamino)phenyl](methylsulfonyl)methylene}azetidine are obtained in the form of a white foam [NMR spectrum in DMSO-d6, T=300K, δ in ppm (300 MHz): 1.30 (9H, s, OC(CH$_3$)$_3$), 2.65 (3H, s, J=6 Hz, NCH$_3$), 2.85 (3H, s, SCH$_3$), 3.50 (2H, s, NCH$_2$), 3.90 (2H, s, NCH$_2$), 4.45 (1H, s, NCH) between 6.85 and 7.05 (8H, m, 8 CH arom.), 7.10 (4H, d, J=7 Hz, 4 CH arom.)].

1-[Bis(4-chlorophenyl)methyl]-3-{[3-(N-tert-butyloxycarbonyl-N-methylamino)phenyl]-(methylsulfonyl)methyl-(RS)}azetidin-3-ol may be prepared according to the procedure described in Example 1 starting with 3.8 g of [3-(N-tertbutyloxycarbonyl-N-methylamino)benzyl]methylsulfone, 50 cm³ of tetrahydrofuran, 9.5 cm³ of a 1.6 N solution of n-butyllithium in hexane, 3.82 g of 1-[bis(4-chlorophenyl)methyl]azetidin-3-one. The crude product is purified by chromatography on a silica gel column (particle size 0.04–0.06 mm, diameter 4 cm, weight of silica 250 g), eluting at a nitrogen pressure of 0.5 bar with dichloromethane and then with a dichloromethane and ethanol mixture (99/1 by volume) and collecting 500 cm³ fractions. Fractions 10 to 16 are combined, concentrated to dryness under reduced pressure (2.7 kPa). 5.6 g of 1-[bis(4-chlorophenyl)methyl]-3-{[3-(N-tertbutyloxycarbonyl-N-methylamino)phenyl](methylsulfonyl)methyl-(RS)}azetidin-3-ol, are obtained in the form of a foam.

EXAMPLE 85

2.7 g of 1-[bis(4-chlorophenyl)methyl]-3-{[3-(N-tertbutyloxycarbonyl-N-methylamino)phenyl](methylsulfonyl)methylene}azetidine in 30 cm³ of dioxane and 30 cm³ of a 4.7 N solution of hydrochloric dioxane are stirred for 20 hours. The reaction medium is evaporated to dryness under reduced pressure (2.7 kpa), taken up in 50 cm³ of water and 50 cm³ of ethyl acetate, stirred and neutralized carefully with a saturated aqueous sodium bicarbonate solution. The organic phase is separated, dried over magnesium sulfate, treated with animal charcoal and then concentrated under reduced pressure (2.7 kpa) to a volume of about 25 cm³, then filtered, concentrated to dryness under reduced pressure. 1.3 g of 1-[bis(4-chlorophenyl)methyl]-3-[(3-methylaminophenyl)(methylsulfonyl)methylene]azetidine are obtained in the form of white crystals melting at 228° C. [NMR spectrum in DMSO-d6, T=300K, δ in ppm (300 MHz): 2.65 (3H, s, J=6 Hz, NCH₃), 2.95 (3H, s, SCH₃), 3.80 (2H, s, NCH₂), 4.20 (2H, s, NCH₂), 4.80 (1H, s, NCH), 5.85 (1H, q, J=6 Hz, NH), 6.55 (3H, m, 3 CH arom.), 7.15 (1H, t, J=7 Hz, CH arom.), 7.40 (4H, d, J=7 Hz, 4CH arom.), 7.50 (4H, m, 4CH arom.)].

EXAMPLE 86

On carrying out the operation as in Example 1, starting with 0.40 g of a mixture of two diastereoisomers 1-[(4-chlorophenyl)(thiazol-2-yl)methyl-(RS)]-3-[3,5-difluorophenyl)(methylsulfonyl)methyl-(RS)]azetidin-3-ol, 0.10 cm³ of methanesulfonyl chloride and 0.37 g of 4-dimethylaminopyridine, 0.13 g of (RS)-1-[(4-chlorophenyl)(thiazol-2-yl)methyl]-3-[3,5-difluorophenyl)(methylsulfonyl)methylene]azetidine is obtained, after chromatography on a silica gel column (particle size 0.06–0.200 mm, diameter 1.2 cm, height 20 cm), at an argon pressure of 1 bar with a mixture of ethyl acetate and cyclohexane (40/60 by volume) as eluent and collecting 20 cm³ fractions, in the form of a pinkish solid [NMR spectrum in DMSO-d6, T=300K, δ in ppm (300 MHz): 3.05 (3H, s, SCH₃), 4.05 (2H, s, NCH₂), 4.35 (2H, m, NCH₂), 5.25 (1H, s, NCH), 7.20 (2H, d, J=8 Hz, 2CH arom.), 7.35 (1H, t, J=8 Hz, CH arom.), 7.45 (2H, d, J=7 Hz, 2CH arom.), 7.50 (2H, d, J=7 Hz, 2CH arom.), 7.70 (1H, d, J=2 Hz, CH thiazole), 7.75 (1H, d, J=2 Hz, CH thiazole)].

The mixture of the two diastereoisomers 1-[(4-chlorophenyl)(thiazol-2-yl)methyl-(RS)]-3-[3,5-difluorophenyl)(methylsulfonyl)methyl-(RS)]azetidin-3-ol may be obtained in the following manner: on carrying out the operation as in Example 72, starting with 1.01 g of (RS)-bromo(4-chlorophenyl)thiazol-2-ylmethane and 0.55 g of (RS)-3-[3,5-difluorophenyl)(methylsulfonyl)methyl] azetidin-3-ol hydrochloride and after chromatography on a silica gel column (particle size 0.06–0.200 mm, diameter 4.4 cm, height 38 cm), at an argon pressure of 0.5 bar and eluting with a mixture of ethyl acetate and cyclohexane (30/70 by volume and then 40/60 from fraction 16) and collecting 60 cm³ fractions, fractions 21 to 35 are combined and concentrated to dryness under reduced pressure (2.7 kPa). 0.40 g of the mixture of the two diastereoisomers 1-[(4-chlorophenyl)(thiazol-2-yl)methyl-(RS)]-3-[3,5-difluorophenyl)(methylsulfonyl)methyl-(RS)]azetidin-3-ol which is obtained in the form of a whitish solid.

EXAMPLE 87

50 mm³ of pyrrolidine are added to a solution of 0.32 g of 1-{(R*)-[4-(chloromethyl)phenyl](4-chlorophenyl) methyl}-3-[(3,5-difluorophenyl)(methylsulfonyl) methylene]azetidine, form A isomer, and 5 mg of sodium iodide in 10 cm³ of dichloromethane. After stirring for 20 hours at 20° C., 50 mm³ of pyrrolidine are added to the mixture, stirred for 8 hours and then 50 mm³ of pyrrolidine are again added and the mixture is stirred for 20 hours at 20° C. The reaction mixture is washed with water and then the organic phase is dried over magnesium sulfate and concentrated to dryness under vacuum (2.7 kPa). The residue obtained is chromatographed on a silica gel column (particle size 0.06–0.200 mm, diameter 1.2 cm, height 30 cm), at an argon pressure of 0.1 bar, eluting with dichloromethane and then with a dichloromethane and methanol mixture (97.5/2.5 by volume) and collecting 3 cm³ fractions. Fractions 12 to 40 are combined and then concentrated to dryness under reduced pressure (2.7 kPa). 0.18 g of 1-{(R*)-(4-chlorophenyl)[4-pyrrolidinylmethyl)phenyl]methyl}-3-[(3,5-difluorophenyl)(methylsulfonyl)methylene]azetidine, form A isomer, is obtained in the form of a white foam [a]$^{20}$365 nm=−22.5°+/−0.7 (c=0.5%; dichloromethane) [¹H NMR spectrum (300 MHz, CDCl₃, δ in ppm): 1.78 (mt, 4H), 2.51 (mt, 4H), 2.81 (s, 3H), 3.58 (s, 2H), 3.84 (mt, 2H), 4.33 (mt, 2H), 4.50 (s, 1H), 6.84 (tt, J=9 and 2.5 Hz, 1H), 6.98 (mt, 2H), from 7.20 to 7.40 (mt, 8H)].

1-{(R*)-[(4-chloromethyl)phenyl](4-chlorophenyl) methyl}-3-[(3,5-difluorophenyl)(methylsulfonyl) methylene]azetidine, form A isomer, may be prepared by carrying out the operation in the following manner: 12.4 cm³ of methanesulfonyl chloride are added to a solution of 28.0 g of the mixture of the 2 diastereoisomers (forms A) 1-{ (R*)-[(4-chloromethyl)phenyl](4-chlorophenyl)methyl}-3-[(R)-(3,5-difluorophenyl)(methylsulfonyl)methyl]azetidin-3-ol and 1-{(R*)-[(4-chloromethyl)phenyl](4-chlorophenyl) methyl}-3-[(S)-(3,5-difluorophenyl)(methylsulfonyl) methyl]azetidin-3-ol and 32 g of 4-dimethylaminopyridine, in 500 cm³ of dichloromethane. After stirring for 1 hour at 10° C. and then 1 hour at 20° C., the reaction mixture is washed with 500 cm³ of water, the organic phase is dried over magnesium sulfate and concentrated to dryness under reduced pressure (2.7 kPa). The residue is chromatographed on a silica gel column (particle size 0.06–0.200 mm, diameter 6 cm, height 30 cm), at an argon pressure of 0.2 bar, eluting with dichloromethane and collecting 250 cm³ fractions. Fractions 9 to 25 are combined and then concentrated to dryness under reduced pressure (2.7 kPa). 6.3 g of 1-{(R*)-[4-(chloromethyl)phenyl](4-chlorophenyl) methyl}-3-[(3,5-difluorophenyl)(methylsulfonyl) methylene]azetidine, form A isomer, are obtained in the form of a white foam.

The mixture of the 2 diastereoisomers (forms A) 1-{(R*)-[4-(chloromethyl)phenyl](4-chlorophenyl)methyl}-3-[(R)-(3,5-difluorophenyl)(methylsulfonyl)methyl)]azetidin-3-ol, and 1-{(R*)-[(4-chloromethyl)phenyl](4-chlorophenyl) methyl}-3-[(S)-(3,5-difluorophenyl)(methylsulfonyl) methyl)]azetidin-3-ol, may be prepared by carrying out the operation in the following manner: 60 mm³ of thionyl chloride are added to a solution of 0.20 g of the mixture of the 2 diastereoisomers (forms A) 1-{(R*)-[4-(chlorophenyl) [4-(hydroxymethyl)phenyl]methyl}-3-[(R)-(3,5- difluorophenyl)(methylsulfonyl)methyl)]azetidin-3-ol, and 1-{(R*)-(4-chlorophenyl)[4-(hydroxymethyl)phenyl]methyl}-3-(S)-(3,5-difluorophenyl)(methylsulfonyl)methyl]azetidin-3-ol, in 10 cm³ of dichloromethane. After stirring for 20 hours at 20° C., 5 cm³ of a saturated aqueous sodium hydrogen carbonate solution are added to the reaction mixture and then the mixture is stirred for 15 minutes. The mixture is separated after settling out, the organic phase is washed with water, dried over magnesium sulfate and then concentrated to dryness under reduced pressure (2.7 kPa). The residue is chromatographed on a silica gel column (particle size 0.04–0.06 mm, diameter 1.0 cm, height 20 cm), at an argon pressure of 0.2 bar, eluting with a cyclohexane and ethyl acetate mixture (75/25 by volume) and collecting 20 cm³ fractions. Fractions 4 to 7 are combined and then concentrated to dryness under reduced pressure (2.7 kPa). 0.17 g of the mixture of the 2 diastereoisomers (forms A) 1-{(R*)-[4-(chloromethyl)phenyl]-[4-chlorophenyl]methyl}-3-[(R)-(3,5-difluorophenyl)(methylsulfonyl)methyl)]azetidin-3-ol, and 1-{(R*)-[4-(chloromethyl)phenyl](4-chlorophenyl)methyl}-3-[(S)(3,5-difluorophenyl)(methylsulfonyl)methyl)]azetidin-3-ol is obtained in the form of a white foam.

The mixture of the 2 diastereoisomers (forms A) 1-{(R*)-4-(chlorophenyl)phenyl][4-(hydroxymethyl)phenyl]methyl}-3-[(R)-(3,5-difluorophenyl)(methylsulfonyl)methyl)]azetidin-3-ol, and 1-{(R*)-(4-chlorophenyl)[4-(hydroxymethyl)phenyl]methyl}-3-[(S)-(3,5-difluorophenyl)(methylsulfonyl)methyl]azetidin-3-ol, may be prepared by carrying out the operation in the following manner: 1.6 cm³ of a 1.5 M solution of diisobutylaluminum hydride in toluene are added to a solution, maintained under argon and cooled to −30° C., of 0.58 g of the mixture of the 2 diastereoisomers (forms A) 3-acetoxy-1-{(R*)-(4-chlorophenyl)[4-(methoxycarbonyl)phenyl]methyl}-3-[(R)-(3,5-difluorophenyl)(methylsulfonyl)methyl)]azetidine and 3-acetoxy-1-{(R*)-(4-chlorophenyl)[4-(methoxycarbonyl)phenyl]methyl}-3-[(S)-(3,5-difluorophenyl)(methylsulfonyl)methyl]azetidine, in 10 cm³ of anhydrous toluene. After stirring for 15 minutes at −30° C., 1.0 cm³ of this same hydride solution is again added and then the mixture is allowed to return to 0° C. After stirring for 30 minutes, the stirred mixture is supplemented with 3 cm³ of water and 6 cm³ of 1 N sodium hydroxide and then extracted with 25 cm³ of dichloromethane. The organic phase is washed with 5 cm³ of water, 5 cm³ of brine, and then dried over magnesium sulfate and concentrated to dryness under reduced pressure (2.7 kPa). The residue is chromatographed on a silica gel column (particle size 0.06–0.200 mm, diameter 1.2 cm, height 30 cm), at an argon pressure of 0.1 bar, eluting with a cyclohexane and ethyl acetate mixture (50/50 by volume) and collecting 30 cm³ fractions. Fractions 4 to 12 are combined and then concentrated to dryness under reduced pressure (2.7 kPa). 0.42 g of the mixture of the 2 diastereoisomers (forms A) 1-{(R*)-(4-chlorophenyl)[4-(hydroxymethyl)phenyl]methyl}-3-[(R)-(3,5-difluorophenyl)(methylsulfonyl)methyl)]azetidin-3-ol, and 1{(R*)-(4-chlorophenyl)[4-(hydroxymethyl)phenyl]methyl}-3-[(S)(3,5-difluorophenyl)(methylsulfonyl)methyl)]azetidin-3-ol is obtained in the form of a white lacquer.

The mixture of the 2 diastereomers (forms A) 3-acetoxy-1-{(R*)-(4-chlorophenyl)[4-(methoxycarbonyl)phenyl]methyl}-3-[(R)-(3,5-difluorophenyl)(methylsulfonyl)methyl)]azetidine and 3-acetoxy-1-{(R*)-(4-chlorophenyl)[4-(methoxycarbonyl)phenyl]methyl}-3-[(S)-(3,5-difluorophenyl)(methylsulfonyl)methyl)}azetidine may be prepared by carrying out the operation as described in Example 40, starting with 1.0 g of (3,5-difluorobenzyl)methylsulfone, 30 cm³ of tetrahydrofuran, 3 cm³ of a 1.6 N solution of n-butyllithium in hexane, 1.45 g of 1-{(R*)-(4-chlorophenyl)[4-(methoxycarbonyl)phenyl]methyl}azetidin-3-one, form A isomer, and 0.43 cm³ of acetyl chloride. 1.28 g of the mixture of the 2 diastereoisomers (forms A) 3-acetoxy-1-{(R*)-(4-chlorophenyl)[4-methoxycarbonyl)phenyl]methyl}-3-[(R)-(3,5-difluorophenyl)(methylsulfonyl)methyl)]azetidine and 3-acetoxy-1-{(R*)-(4-chlorophenyl)[4-methoxycarbonyl)phenyl]methyl}-3-[(S)-(3,5-difluorophenyl)(methylsulfonyl)methyl]azetidine are obtained in the form of a beige foam.

1-{(R*)-[(4-chlorophenyl)[4-(methoxycarbonyl)phenyl]methyl}azetidin-3-one, form A isomer, may be prepared by carrying out the operation as described in Example 40, starting with 0.55 cm³ of oxalyl chloride, 25 cm³ of dichloromethane, 0.90 cm³ of dimethyl sulfoxide, 1.75 g of 1-{(4-chlorophenyl)[4-(methoxycarbonyl)phenyl]methyl}azetidin-3-ol, and 2.70 cm³ of triethylamine. 1.45 g of 1-{(R*)-(4-chlorophenyl)[4-(methoxycarbonyl)phenyl]methyl}azetidin-3-one, form A isomer, are obtained in the form of a yellow foam.

1-{(R*)(4-chlorophenyl)[4-(methoxycarbonyl)phenyl]methyl}azetidin-3-ol, form A isomer, may be prepared by carrying out the operation according to the procedure described by KATRITZKY A. R. et al., in J. Heterocycl. Chem., (1994), 271 from 2.0 g of methyl (+)-4-[(R*)-amino-(4-chlorophenyl)methyl]benzoate, 30 cm³ of ethanol, 0.60 g of sodium hydrogen carbonate and 0.60 cm³ of epibromhydrin. 1.76 g of 1-{(R*)-(4-chlorophenyl)[4-(methoxycarbonyl)phenyl]methyl}azetidin-3-ol, form A isomer, are obtained in the form of a pasty solid.

Methyl (+)-4-[(R*)-amino-(4-chlorophenyl)methyl]benzoate may be prepared by carrying out the operation in the following manner: 2.51 g of D-(−)-tartaric acid are added to a solution of 9.2 g of methyl (4-[(RS)-amino-(4-chlorophenyl)methyl]benzoate in 10 cm³ of methanol. The solution is concentrated to dryness under reduced pressure (2.7 kPa). The cream-colored foam obtained is dissolved in 50 cm³ of ethanol containing 5% water and the resulting solution is allowed to crystallize for 20 hours at 20° C. The crystals are filtered, washed with ethanol containing 5% water, drained and then dried under reduced pressure (2.7 kPa). 3.4 g of white crystals are obtained which are called "A crystals" [and which are stored for the subsequent preparation of the second enantiomer, methyl (−)-4-[(R*)-amino-(4-chlorophenyl)methyl]benzoate]. The mother liquors are concentrated to dryness and a white foam (8.1 g) is obtained which is dissolved in 100 cm³ of ethyl acetate. The solution obtained is supplemented with 50 cm³ of 1 N sodium hydroxide, stirred and separated after settling out. The organic phase is washed with 50 cm³ of water and then dried over magnesium sulfate and concentrated to dryness under reduced pressure (2.7 kPa). A yellow solid is obtained which is dissolved in 100 cm³ of methanol. The solution obtained is supplemented with 1.85 g of L-(+)-tartaric acid and the resulting solution is concentrated to dryness under reduced pressure (2.7 kPa). A cream-colored foam is obtained which, once dissolved in 27 cm³ of ethanol containing 4% water, is allowed to crystallize for 20 hours at 20° C. The crystals are filtered, washed with ethanol containing 4% water, drained and then dried under reduced pressure (2.7 kPa). 3.4 g of methyl (+)-4-[(R*)-amino-(4-chlorophenyl)methyl]benzoate L-(+)-tartrate crystals are obtained which are recrystallized from 60 cm³ of ethanol containing 5% water.

After draining and then drying, 2.78 g of white crystals are obtained which are dissolved in 50 cm³ of ethyl acetate. The solution obtained is supplemented with 100 cm³ of 1 N sodium hydroxide, stirred and separated after settling out. The organic phase is washed with 50 cm³ of water and then dried over magnesium sulfate and concentrated to dryness under reduced pressure (2.7 kPa). 2.1 g of methyl (+)-4-[(R*)-amino-(4-chlorophenyl)methyl]benzoate are obtained in the form of a white solid.

Methyl 4-[(RS)-amino-(4-chlorophenyl)methyl]benzoate may be prepared by carrying out the operation in the following manner: 3.9 cm³ of hydrazine hydrate are added to a suspension of 16.3 g of methyl 4-[(RS)-phthalimido-(4-chlorophenyl)methyl]benzoate in 200 cm³ of methanol. After stirring for 5 hours at the reflux temperature and then for 20 hours at 20° C., the reaction mixture is filtered and the filtrate is concentrated to dryness under reduced pressure (2.7 kPa). The residue obtained is taken up in a mixture of 200 cm³ of water and 200 cm³ of ethyl acetate. After stirring for 15 minutes, the resulting suspension is filtered, the filtrate separated after settling out in a separating funnel, and the organic phase is washed with 50 cm³ of water, dried over magnesium sulfate and concentrated to dryness under reduced pressure (2.7 kPa). 8.4 g of methyl 4-[(RS)-amino-(4-chlorophenyl)methyl]benzoate are obtained in the form of a pale yellow oil.

Methyl 4-[(RS)-phthalimido-(4-chlorophenyl)methyl]benzoate may be prepared by carrying out the operation in the following manner: 12.6 g of potassium phthalimide are added to a solution of 11.6 g of methyl 4-[(RS)-bromo-(4-chlorophenyl)methyl]benzoate in 70 cm³ of dimethylformamide. After stirring for 3 hours at the reflux temperature, the reaction mixture is cooled to 20° C. and then supplemented with 300 cm³ of ethyl acetate and 300 cm³ of water. After stirring, the mixture is separated after settling out, the aqueous phase reextracted with twice 100 cm³ of ethyl acetate, the combined organic phases are washed with twice 400 cm³ of water and then dried over magnesium sulfate and concentrated to dryness under reduced pressure (2.7 kPa). 16.3 g of methyl 4-[(RS)-phthalimido-(4-chlorophenyl)methyl]benzoate are obtained in the form of a pasty yellow solid.

Methyl 4-[(RS)-bromo-(4-chlorophenyl)methyl]benzoate may be prepared by carrying out the operation in the following manner: 10.18 g of N,N'-carbonyldiimidazole and 54.3 cm³ of allyl bromide are added to a solution of 17.4 g of methyl 4-[(RS)-(4-chlorophenyl)(hydroxy)methyl]benzoate in 200 cm³ of acetonitrile. After stirring for 30 minutes at 20° C., the reaction mixture is heated under reflux for 2 hours, stirred for 20 hours at 20° C. and concentrated to dryness under reduced pressure (2.7 kPa). The mixture, taken up in dichloromethane, is chromatographed on a silica gel column (particle size 0.06–0.200 mm, diameter 7 cm, height 30 cm), at an argon pressure of 0.5 bar, eluting with dichloromethane and collecting 500 cm³ fractions. Fractions 3 to 6 are combined and then concentrated to dryness under reduced pressure (2.7 kPa). 11.6 g of methyl 4-[(RS)-bromo-(4-chlorophenyl)methyl]benzoate are obtained in the form of an oil which will be used as it is in the next step.

Methyl 4-[(RS)-(4-chlorophenyl)(hydroxy)methyl]benzoate may be prepared by carrying out the operation in the following manner: 1.21 g of sodium borohydride are slowly added in small fractions to a suspension of 2.75 g of methyl 4-(4-chlorobenzoyl)benzoate in 200 cm³ of methanol at 20° C. (heating of the medium up to 50° C. occurs). After stirring for 20 hours at 20° C., the reaction mixture is concentrated to a reduced volume and then supplemented with 150 cm³ of dichloromethane and, while stirring, with 100 cm³ of 0.5 N hydrochloric acid. After separating after settling out, the organic phase is dried over magnesium sulfate and concentrated to dryness under reduced pressure (2.7 kPa). 2.5 g of methyl 4-[(RS)-(4-chlorophenyl)(hydroxy)methyl]benzoate are obtained in the form of a colorless oil which slowly crystallizes at 20° C., and which will be used as it is in the next step.

Methyl 4-(4-chlorobenzoyl)benzoate may be prepared by carrying out the operation in the following manner: 27.4 cm³ of tri-n-butylphosphine are added, under argon, to a solution, cooled to −22° C., of 19.3 g of terephthalic acid chloride monomethyl ester in 200 cm³ of tetrahydrofuran. After stirring for 20 minutes at −22° C., a solution of 4-chlorophenylmagnesium bromide (prepared from 19.15 g of 4-bromochlorobenzene, 2.43 g of magnesium and an iodine crystal in 100 cm³ of diethyl ether under reflux) is poured in while this temperature is maintained. After stirring for 30 minutes at −22° C., 150 cm³ of 1 N hydrochloric acid are slowly added, the mixture is allowed to return to 20° C. and then the medium is diluted with 200 cm³ of diethyl ether. The white suspension obtained is filtered, the solid is washed with twice 50 cm³ of water and then with twice 50 cm³ of diethyl ether. 16.2 g of methyl 4-(4-chlorobenzoyl)benzoate are obtained, after draining and then drying under reduced pressure (2.7 kPa), in the form of a white solid melting at 170° C.

EXAMPLE 88

The operation is carried out as described in Example 87, starting with 0.05 g of 1-{(R*)-[4-(chloromethyl)phenyl]-(4-chlorophenyl)methyl}-3-[(3,5-difluorophenyl)(methylsulfonyl)methylene]azetidine, form A isomer, 1.0 cm³ of dichloromethane and 0.025 g of 3,3-dimethylpiperidine. The crude product is chromatographed on a silica gel column (particle size 0.06–0.200 mm, diameter 8 mm, height 8 cm), eluting with 80 cm³ of dichloromethane and then eluting with a dichloromethane and methanol mixture (95/5 by volume), collecting 2.5 cm³ fractions immediately after using this eluent mixture. Fractions 3 to 8 are combined and then concentrated to dryness under reduced pressure (2.7 kPa). 0.040 g of 1-{(R*)-(4-chlorophenyl)[4-(3,3-dimethylpiperidin-1-ylmethyl)phenyl]methyl}-3-[(3,5-difluorophenyl)(methylsulfonyl)methylene]azetidine, form A isomer, is obtained in the form of a white foam [$^1$H NMR spectrum (300 MHz, CDCl$_3$, δ in ppm): 0.94 (s, 6H), 1.21 (mt, 2H), from 1.50 to 1.65 (mt, 2H), 1.99 (broad s, 2H), 2.27 (unresolved complex, 2H), 2.81 (s, 3H), 3.36 (s, 2H), 3.85 (mt, 2H), 4.33 (mt, 2H), 4.49 (s, 1H), 6.84 (tt, J=8.5 and 2.5 Hz, 1H), 6.98 (mt, 2H), from 7.20 to 7.40 (mt, 8H)].

EXAMPLE 89

The operation is carried out as described in Example 87, starting with 0.05 g of methylsulfonyl methyl 1-{(R*)-[4-(chloromethyl)phenyl](4-chlorophenyl)methyl}-3-[(3,5-difluorophenyl)(methylsulfonyl)methylene]azetidine, form A isomer, 1.0 cm³ of dichloromethane and 0.025 g of thiomorpholine. The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 3 to 8 are combined and then concentrated to dryness under reduced pressure (2.7 kPa). 0.038 g of 1-{(R*)-(4-chlorophenyl)[4-

(thiomorpholin-4-ylmethyl)phenyl]methyl}-3-[(3,5-difluorophenyl)(methylsulfonyl)methylene]azetidine, form A isomer, is obtained in the form of a white foam [$^1$H NMR spectrum (300 MHz, CDCl$_3$, δ in ppm): from 2.60 to 2.75 (mt, 8H), 2.80 (s, 3H), 3.44 (s, 2H), 3.84 (mt, 2H), 4.33 (mt, 2H), 4.50 (s, 1H), 6.83 (tt, J=8.5 and 2.5 Hz, 1H), 6.97 (mt, 2H), from 7.20 to 7.40 (mt, 8H)].

EXAMPLE 90

The operation is carried out as described in Example 87, starting with 0.05 g of 1-{(R*)-[4-(chloromethyl)phenyl](4-(chlorophenyl)methyl}-3-[(3,5-difluorophenyl)(methylsulfonyl)methylene]azetidine, form A isomer, 1.0 cm$^3$ of dichloromethane and 0.025 g of N-cyclohexyl-N-ethylamine. The crude product is chromatographed on a silica gel column (particle size 0.06–0.200 mm, diameter 8 mm, height 8 cm), eluting with 80 cm$^3$ of dichloromethane and then with a dichloromethane and ethanol mixture (95/5) by volume), collecting 2.5 cm$^3$ fractions immediately after using this eluent mixture. 0.022 g of 1-{(R*)-(4-chlorophenyl)[4-(N-ethyl-N-cyclohexylaminomethyl)phenyl]methyl}}-3-[(3,5-difluorophenyl)(methylsulfonyl)methylene]azetidine, form A isomer, is obtained in the form of a white foam [$^1$H NMR spectrum (300 MHz, CDCl$_3$ with addition of a few drops of CD$_3$COOD-d4, δ in ppm): from 1.15 to 1.25 (mt, 2H), 1.29 (t, J=7.5 Hz, 3H), from 1.45 to 1.65 (mt, 4H), 1.88 (mt, 2H), 2.17 (mt, 2H), 2.81 (s, 3H), 3.05 (q, J=7.5 Hz, 2H), 3.27 (mt, 1H), 3.95 (mt, 2H), 4.18 (s, 2H), 4.40 (mt, 2H), 4.66 (s, 1H), 6.82 (tt, J=8.5 and 2.5 Hz, 1H), 7.00 (mt, 2H), from 7.20 to 7.40 (mt, 4H), 7.41 (d, J=8 Hz, 2H), 7.53 (d, J=8 Hz, 2H)].

EXAMPLE 91

The procedure is carried out as described in Example 87, starting with 0.05 g of 1-{(R*)-[4-(chloromethyl)phenyl](4-(chlorophenyl)methyl}-3-[(3,5-difluorophenyl)(methylsulfonyl)methylene]azetidine, form A isomer, 1.0 cm$^3$ of dichloromethane and 0.032 g of 4-(ethoxycarbonyl)piperazine. The crude product is chromatographed on a silica gel column (particle size 0.06–0.200 mm, diameter 8 mm, height 8 cm), eluting with 80 cm$^3$ of dichloromethane and then with a dichloromethane and methanol mixture (95/5 by volume), collecting 2.5 cm$^3$ fractions immediately after using this eluent mixture. Fractions 2 to 8 are combined and then concentrated to dryness under reduced pressure (2.7 kPa). 0.021 g of 1-{{(R*)-(4-chlorophenyl){4-[(4-ethoxycarbonylpiperazinyl)methyl]phenyl}methyl}}-3-[(3,5-difluorophenyl)(methylsulfonyl)methylene]azetidine, form A isomer, is obtained in the form of a white foam [$^1$H NMR spectrum (400 MHz, CDCl$_3$, δ in ppm): 1.25 (t, J=7 Hz, 3H), 2.36 (mt, 4H), 2.80 (s, 3H), 3.44 (s, 2H), 3.46 (mt, 4H), 3.85 (mt, 2H), 4.13 (q, J=7 Hz, 2H), 4.34 (mt, 2H), 4.50 (s, 1H), 6.83 (tt, J=9 and 2.5 Hz, 1H), 6.98 (mt, 2H), from 7.20 to 7.40 (mt, 8H)].

EXAMPLE 92

The operation is carried out as described in Example 87, starting with 0.05 g of 1-{(R*)-[4-(chloromethyl)phenyl](4-chlorophenyl)methyl}-3-[(3,5-difluorophenyl)(methylsulfonyl)methylene]azetidine, form A isomer, 1.0 cm$^3$ of dichloromethane and 0.023 g of N-cyclopropyl-N-propylamine. The crude product is chromatographed on a silica gel column (particle size 0.06–0.200 mm, diameter 8 mm, height 8 cm), eluting with 80 cm$^3$ of dichloromethane and then with a dichloromethane and methanol mixture (95/5 by volume), collecting 2.5 cm$^3$ fractions immediately after using this eluent mixture. Fractions 3 to 9 are combined and then concentrated to dryness under reduced pressure (2.7 kPa). 0.026 g of 1-{(R*)-(4-chlorophenyl)[(4-N-cyclopropyl-N-propylaminomethyl)phenyl]methyl}-3-[(3,5-difluorophenyl)(methylsulfonyl)methylene]azetidine, form A isomer, is obtained in the form of a white foam [$^1$H NMR spectrum (400 MHz, CDCl$_3$ with addition of a few drops of CD$_3$COOD-d4, δ in ppm): 0.34 (mt, 2H), 0.70 (mt, 2H), 0.91 (t, J=7 Hz, 3H), 1.08 (mt, 1H), 1.76 (mt, 2H), 2.82 (s, 3H), 2.92 (d, J=7 Hz, 2H), 3.00 (mt, 2H), 3.90 (mt, 2H), 4.25 (s, 2H), 4.37 (mt, 2H), 4.59 (s, 1H), 6.83 (tt, J=9 and 2.5 Hz, 1H), 7.00 (mt, 2H), from 7.20 to 7.45 (mt, 8H)].

EXAMPLE 93

The operation is carried out as described in Example 87, but by stirring the reaction mixture for 6 days at 20° C., starting with 0.05 g of 1-{(R*)-[4-(chloromethyl)phenyl](4-(chlorophenyl)methyl}-3-[(3,5-difluorophenyl)(methylsulfonyl)methylene]azetidine, form A isomer, 1.0 cm$^3$ of dichloromethane, 5 mg of sodium iodide and 0.020 g of diisopropylamine. The crude product is chromatographed on a silica gel column (particle size 0.06–0.200 mm, diameter 8 mm, height 8 cm), eluting with 80 cm$^3$ of dichloromethane and then with a dichloromethane and methanol mixture (95/5 by volume), collecting 2.5 cm$^3$ fractions immediately after using this eluent mixture. Fractions 2 to 8 are combined and then concentrated to dryness under reduced pressure (2.7 kPa). 0.028 g of 1-{(R)-(4-chlorophenyl)[4-(diisopropylaminomethyl)phenyl]methyl}-3-[(3,5-difluorophenyl)(methylsulfonyl)methylene]azetidine, form A isomer, is obtained in the form of a white foam [$^1$H NMR spectrum (300 MHz, CDCl$_3$, δ in ppm): 1.00 (unresolved complex, 12H), 2.80 (s, 3H), from 2.90 to 3.10 (unresolved complex, 2H), 3.58 (mt, 2H), 3.84 (mt, 2H), 4.33 (mt, 2H), 4.48 (s, 1H), 6.82 (tt, J=8.5 and 2.5 Hz, 1H), 6.97 (mt, 2H), from 7.20 to 7.40 (mt, 8H)].

EXAMPLE 94

The operation is carried out as described in Example 87, starting with 0.05 g of 1-{(R*)-[4-(chloromethyl)phenyl](4-(chlorophenyl)methyl}-3-[(3,5-difluorophenyl)(methylsulfonyl)methylene]azetidine, form A isomer, 1.0 cm$^3$ of dichloromethane, and 0.027 g of bis(2-methoxyethyl)amine. The crude product is chromatographed on a silica gel column (particle size 0.06–0.200 mm, diameter 8 mm, height 8 cm), eluting with 80 cm$^3$ of dichloromethane and then with a dichloromethane and methanol mixture (95/5 by volume), collecting 2.5 cm$^3$ fractions immediately after using this eluent mixture. Fractions 3 to 10 are combined and then concentrated to dryness under reduced pressure (2.7 kPa). 0.014 g of 1-{{(R*)-(4-chlorophenyl){4-[bis(2-methoxyethyl)aminomethyl]phenyl}methyl}}-3-[(3,5-difluorophenyl)(methylsulfonyl)methylene]azetidine, form A isomer, is obtained in the form of a white foam [$^1$H NMR spectrum (300 MHz, CDCl$_3$, δ in ppm): 2.70 (broad t, J=5.5 Hz, 4H), 2.81 (s, 3H), 3.29 (s, 6H), 3.46 (broad t, J=5.5 Hz, 4H) 3.65 (broad s, 2H), 3.85 (mt, 2H), 4.33 (mt, 2H), 4.49 (s, 1H), 6.84 (tt, J=9 and 2.5 Hz, 1H), 6.98 (mt, 2H), from 7.20 to 7.40 (mt, 8H)].

EXAMPLE 95

The operation is carried out as described in Example 87, starting with 0.05 g of 1-{(R*)-[4-(chloromethyl)phenyl](4-chlorophenyl)methyl}-3-[(3,5-difluorophenyl)(methylsulfonyl)methylene]azetidine, form A isomer, 1.0 cm$^3$ of dichloromethane, and 0.020 g of di-n-propylamine.

The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 3 to 8 are combined and then concentrated to dryness under reduced pressure (2.7 kPa). 0.025 g of 1-{(R*)-(4-chlorophenyl)[4-(di-n-propylaminomethyl)phenyl]methyl}-3-[(3,5-difluorophenyl)(methylsulfonyl)methylene]azetidine, form A isomer, is obtained in the form of a white foam [¹H NMR spectrum (400 MHz, CDCl₃, δ in ppm): 0.85 (t, J=7 Hz, 6H) 1.45 (mt, 4H), 2.34 (t, J=7.5 Hz, 4H), 2.80 (s, 3H), 3.48 (s, 2H), 3.84 (mt, 2H), 4.33 (mt, 2H), 4.50 (s, 1H), 6.83 (tt, J=9 and 2.5 Hz, 1H), 6.98 (mt, 2H), from 7.20 to 7.40 (mt, 8H)].

EXAMPLE 96

The operation is carried out as described in Example 87, starting with 0.05 g of 1-{(R*)-[4-(chloromethyl)phenyl](4-chlorophenyl)methyl}-3-[(3,5-difluorophenyl)(methylsulfonyl)methylene]azetidine, form A isomer, 1.0 cm³ of dichloromethane, and 0.017 g of piperidine. The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 5 to 10 are combined and then concentrated to dryness under reduced pressure (2.7 kPa). 0.035 g of 1-{(R*)-(4-chlorophenyl)[4-(piperidin-1-ylmethyl)phenyl]methyl}-3-[(3,5-difluorophenyl)(methylsulfonyl)methylene]azetidine, form A isomer, is obtained in the form of a white foam [¹H NMR spectrum (300 MHz, CDCl₃, δ in ppm): from 1.35 to 1.65 (mt, 6H), 2.35 (unresolved complex, 4H), 2.80 (s, 3H), 3.41 (broad s, 2H), 3.84 (mt, 2H), 4.33 (mt, 2H), 4.50 (s, 1H), 6.84 (tt, J=8.5 and 2.5 Hz, 1H), 6.98 (mt, 2H), from 7.20 to 7.40 (mt, 8H)].

EXAMPLE 97

The operation is carried out as described in Example 87, starting with 0.05 g of 1-{(R*)-[4-(chloromethyl)phenyl](4-chlorophenyl)methyl}-3-[(3,5-difluorophenyl)(methylsulfonyl)methylene]azetidine, form A isomer, 1.0 cm³ of dichloromethane, and 0.020 g of N-methylpiperazine. The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 3 to 9 are combined and then concentrated to dryness under reduced pressure (2.7 kPa). 0.025 g of 1-{(R*)-(4-chlorophenyl)[4-(4-methylpiperazin-1-ylmethyl)phenyl]methyl}-3-[(3,5-difluorophenyl)(methylsulfonyl)methylene]azetidine, form A isomer, is obtained in the form of a white foam [¹H NMR spectrum (300 MHz, CDCl₃, δ in ppm): 2.28 (s, 3H), from 2.30 to 2.60 (unresolved complex, 8H), 2.80 (s, 3H), 3.45 (s, 2H), 3.84 (mt, 2H), 4.33 (mt, 2H), 4.50 (s, 1H), 6.84 (tt, J=8.5 and 2.5 Hz, 1H), 6.98 (mt, 2H), from 7.20 to 7.40 (mt, 8H)].

EXAMPLE 98

The operation is carried out as described in Example 87, starting with 0.05 g of 1-{(R*)-[4-(chloromethyl)phenyl](4-chlorophenyl)methyl}-3-[(3,5-difluorophenyl)(methylsulfonyl)methylene]azetidine, form A isomer, 1.0 cm³ of dichloromethane, and 0.018 g of morpholine. The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 3 to 8 are combined and then concentrated to dryness under reduced pressure (2.7 kPa). 0.022 g of 1-{(R*)-(4-chlorophenyl)[4-(morpholin-4-ylmethyl)phenyl]methyl}-3-[(3,5-difluorophenyl)(methylsulfonyl)methylene]azetidine, form A isomer, is obtained in the form of a white foam [¹H NMR spectrum (300 MHz, CDCl₃, δ in ppm): 2.41 (t, J=5 Hz, 4H), 2.80 (s, 3H), 3.43 (s, 2H), 3.69 (t, J=5 Hz, 4H), 3.85 (mt, 2H), 4.33 (mt, 2H), 4.50 (s, 1H), 6.84 (tt, J=8.5 and 2.5 Hz, 1H), 6.98 (mt, 2H), from 7.20 to 7.40 (mt, 8H)].

EXAMPLE 99

The operation is carried out as described in Example 87, starting with 0.05 g of 1-{(R*)-[4-(chloromethyl)phenyl](4-chlorophenyl)methyl}-3-[(3,5-difluorophenyl)(methylsulfonyl)methylene]azetidine, form A isomer, 1.0 cm³ of dichloromethane, and 0.020 cm³ of D-prolinol. The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 3 to 8 are combined and then concentrated to dryness under reduced pressure (2.7 kPa). 0.025 g of 1-{(R*)-(4-chlorophenyl)[4-((2R)-hydroxymethylpyrrolidin-1-ylmethyl)phenyl]methyl}-3-[(3,5-difluorophenyl)(methylsulfonyl)methylene]azetidine, form A isomer, is obtained in the form of a white foam [¹H NMR spectrum (300 MHz, (CD₃)₂SO-d6 with addition of a few drops of CD₃COOD-d4, δ in ppm): from 1.60 to 2.15 (mt, 4H), from 2.90 to 3.05 (mt, 1H), 2.98 (s, 3H), 3.13 (mt, 1H), 3.38 (mt, 1H), from 3.50 to 3.60 (mt, 1H), 3.56 (d, J=5 Hz, 2H), 3.90 (mt, 2H), 4.04 (d, J=13.5 Hz, 2H), 4.21 (mt, 2H), 4.40 (d, J=13.5 Hz, 2H), 4.78 (s, 1H), 7.14 (mt, 2H), 7.27 (tt, J=9 and 2.5 Hz, 1H), from 7.30 to 7.55 (mt, 8H)].

EXAMPLE 100

The operation is carried out as described in Example 87, starting with 0.05 g of 1-{(R*)-[4-(chloromethyl)phenyl](4-chlorophenyl)methyl}-3-[(3,5-difluorophenyl)(methylsulfonyl)methylene]azetidine, form A isomer, 1.0 cm³ of dichloromethane, and 0.015 g of diethylamine. The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 4 to 9 are combined and then concentrated to dryness under reduced pressure (2.7 kPa). 0.025 g of 1-{(R*)-(4-chlorophenyl)[4-(diethylaminomethyl)phenyl]methyl}-3-[(3,5-difluorophenyl)(methylsulfonyl)methylene]azetidine, form A isomer, is obtained in the form of a white foam [¹H NMR spectrum (400 MHz, CDCl₃, δ in ppm): 1.03 (t, J=7 Hz, 6H), 2.50 (q, J=7 Hz, 4H), 2.81 (s, 3H), 3.50 (s, 2H), 3.85 (mt, 2H), 4.34 (mt, 2H), 4.49 (s, 1H), 6.84 (tt, J=9 and 2.5 Hz, 1H), 6.99 (mt, 2H), from 7.20 to 7.40 (mt, 8H)].

EXAMPLE 101

The operation is carried out as described in Example 87, starting with 0.05 g of 1-{(R*)-[4-(chloromethyl)phenyl](4-

(chlorophenyl)methyl}-3-[(3,5-difluorophenyl)(methylsulfonyl)methylene]azetidine, form A isomer, 1.0 cm³ of dichloromethane, and 0.026 g of N-(hydroxyethyl)piperazine. The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 3 to 10 are combined and then concentrated to dryness under reduced pressure (2.7 kPa). 0.032 g of 1-{{(R*)-(4-chlorophenyl){4-[4-(hydroxyethyl)piperazin-1-ylmethyl]phenyl}methyl}}-3-[(3,5-difluorophenyl)(methylsulfonyl)methylene]azetidine, form A isomer, is obtained in the form of a white foam [¹H NMR spectrum (300 MHz, CDCl₃, δ in ppm): from 2.40 to 2.60 (mt, 8H), 2.54 (t, J=5.5 Hz, 2H), 2.80 (s, 3H), 3.44 (s, 2H), 3.60 (t, J=5.5 Hz, 2H), 3.84 (mt, 2H), 4.33 (mt, 2H), 4.50 (s, 1H), 6.84 (tt, J=9 and 2.5 Hz, 1H), 6.98 (mt, 2H), from 7.20 to 7.40 (mt, 8H)].

EXAMPLE 102

The operation is carried out as described in Example 87 but by stirring the reaction mixture for 4 days at 20° C., starting with 0.05 g of 1-{(R*)-[4-(chloromethyl)phenyl](4-chlorophenyl)methyl}-3-[(3,5-difluorophenyl)(methylsulfonyl)methylene]azetidine, form A isomer, 1.0 cm³ of dichloromethane, and 0.023 g of 2(RS),6(RS)-dimethylpiperidine. The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 2 to 9 are combined and then concentrated to dryness under reduced pressure (2.7 kPa). 0.024 g of 1-{(R*)-(4-chlorophenyl)[4-(2(RS), 6(RS)dimethyl(piperidin-1-ylmethyl)phenyl]methyl}-3-[(3,5-difluorophenyl)(methylsulfonyl)methylene]azetidine, form A isomer, is obtained in the form of a white foam [¹H NMR spectrum (400 MHz, CDCl₃ with addition of a few drops of CD₃COOD-d4, at a temperature of 353K, δ in ppm): from 1.20 to 1.45 (mt, 2H), 1.60(d, J=7 Hz, 6H), from 1.80 to 2.10 (mt, 4H), 2.80 (s, 3H), 3.17 (mt, 2H), 3.90 (mt, 2H), 4.34 (broad d, J=16 Hz, 1H), 4.40 (mt, 2H), 4.43 (broad d, J=16 Hz, 1H), 4.62 (s, 1H), 6.82 (tt, J=9 and 2.5 Hz, 1H), 6.98 (mt, 2H), from 7.20 to 7.50 (mt, 8H)].

EXAMPLE 103

The operation is carried out as described in Example 87, but by stirring the reaction mixture for 4 days at 20° C., starting with 0.05 g of 1-{(R*)-[4-(chloromethyl)phenyl](4-chlorophenyl)methyl}-3-[(3,5-difluorophenyl)(methylsulfonyl)methylene]azetidine, form A isomer, 1.0 cm³ of dichloromethane, and 0.024 g of piperazin-2-one. The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 3 to 8 are combined and then concentrated to dryness under reduced pressure (2.7 kPa). 0.022 g of 1-{(R*)-(4-chlorophenyl)[4-(piperazin-2-on-4-ylmethyl)phenyl]methyl}-3-[(3,5-difluorophenyl)(methylsulfonyl)methylene]azetidine, form A isomer, is obtained in the form of a white foam [¹H NMR spectrum (400 MHz, CDCl₃, δ in ppm) 2.62 (t, J=5.5 Hz, 2H), 2.80 (s, 3H), 3.11 (s, 2H), 3.34 (mt, 2H), 3.51 (s, 2H), 3.85 (mt, 2H), 4.34 (mt, 2H), 4.51 (s, 1H), 5.76 (unresolved complex, 1H), 6.84 (broad t, $J_{HF}$=9 Hz, 1H), 6.98 (mt, 2H) from 7.20 to 7.40 (mt, 8H)].

EXAMPLE 104

The operation is carried out as described in Example 87, starting with 0.05 g of 1-{(R*)-[4-(chloromethyl)phenyl](4-chlorophenyl)methyl}-3-[(3,5-difluorophenyl)(methylsulfonyl)methylene]azetidine, form A isomer, 1.0 cm³ of dichloromethane and 0.020 g of L-prolinol. The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 3 to 8 are combined and then concentrated to dryness under reduced pressure (2.7 kPa). 0.028 g of 1-{{(R*)-(4-chlorophenyl){4-[(2S)-(hydroxymethyl)pyrrolidin-1-ylmethyl]phenyl}methyl}}-3-[(3,5-difluorophenyl)(methylsulfonyl)methylene]azetidine, form A isomer, is obtained in the form of a white foam [¹H NMR spectrum (300 MHz, CDCl₃, δ in ppm): from 1.50 to 2.00 (mt, 4H), 2.24 (mt, 1H), 2.71 (mt, 1H), 2.80 (s, 3H), 2.93 (mt, 1H), 3.28 (d, J=13.5 Hz, 1H), 3.45 (mt, 1H), 3.65 (d, J=11 and 4 Hz, 1H), 3.84 (mt, 2H), 3.91 (d, J=13.5 Hz, 1H), 4.33 (mt, 2H), 4.50 (s, 1H), 6.83 (tt, J=8.5 and 2.5 Hz, 1H), 6.98 (mt, 2H), from 7.20 to 7.40 (mt, 8H)].

EXAMPLE 105

The operation is carried out as described in Example 87, starting with 0.05 g of 1-{(R*)-[4-(chloromethyl)phenyl](4-chlorophenyl)methyl}-3-[(3,5-difluorophenyl)(methylsulfonyl)methylene]azetidine, form A isomer, 1.0 cm³ of dichloromethane and 0.023 g of (2S)-(methoxymethyl)pyrrolidine. The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 2 to 6 are combined and then concentrated to dryness under reduced pressure (2.7 kPa). 0.037 g of 1-{{(R*)-(4-chlorophenyl){4-[(2S)-(methoxymethyl)pyrrolidin-1-ylmethyl]phenyl}methyl}}-3-[(3,5-difluorophenyl)(methylsulfonyl)methylene]azetidine, form A isomer, is obtained in the form of a white foam [¹H NMR spectrum (300 MHz, CDCl₃, δ in ppm): 1.66 (mt, 2H), 1.90 (mt, 1H), 2.16 (mt, 1H), 2.68 (mt, 1H), 2.80 (s, 3H), 2.89 (mt, 1H), from 3.25 to 3.45 (mt, 4H), 3.31 (s, 3H), 3.84 (mt, 2H), 4.04 (d, J=13.5 Hz, 1H), 4.33 (mt, 2H), 4.50 (s, 1H), 6.84 (tt, J=8.5 and 2.5 Hz, 1H), 6.98 (mt, 2H) from 7.20 to 7.40 (mt, 8H)].

EXAMPLE 106

The operation is carried out as described in Example 87, starting with 0.05 g of 1-{(R*)-[4-(chloromethyl)phenyl](4-chlorophenyl)methyl}-3-[(3,5-difluorophenyl)(methylsulfonyl)methylene]azetidine, form A isomer, 1.0 cm³ of dichloromethane and 0.020 g of 2(RS),5(RS)-dimethylpyrrolidine. The crude product is chromatographed on a silica gel column (particle size 0.06–0.200 mm, diameter 8 mm, height 8 cm), eluting with 80 cm³ of dichloromethane and then with a dichloromethane and methanol mixture (95/5 by volume), collecting 2.5 cm³ fractions immediately after using this eluent mixture. Fractions 3 to 6 are combined and then concentrated to dryness under reduced pressure (2.7 kPa). 0.024 g of 1-{(R*)-(4-chlorophenyl)[4-(2(RS),5(RS)-dimethylpyrrolidin-1-ylmethyl)phenyl]methyl}-3-[(3,5-difluorophenyl) (methylsulfonyl)methylene]azetidine, mixture of isomers, form A, is obtained in the form of a white foam [$^1$H NMR spectrum (400 MHz, CDCl$_3$ with addition of a few drops of CD$_3$COOD-d4, δ in ppm): 1.68 (d, J=7 Hz, 6H), from 2.00 to 2.15 (mt, 4H), 2.82 (s, 3H), 3.22 (mt, 2H), 3.92 (mt, 2H), 4.30 (s, 2H), 4.33 (mt, 1H), 4.45 (d, J=16.5 and 3 Hz, 1H), 4.63 (s, 1H), 6.84 (tt, J=8.5 and 2.5 Hz, 1H), 7.00 (mt, 2H), from 7.20 to 7.55 (mt, 8H)].

EXAMPLE 107

The operation is carried out as described in Example 87, starting with 0.05 g of 1-{(R*)-[4-(chloromethyl)phenyl]-4-(chlorophenyl)methyl}-3-[(3,5-difluorophenyl) (methylsulfonyl)methylene]azetidine, form A isomer, 1.0 cm$^3$ of dichloromethane and 0.023 g of L-prolinamide. The crude product is chromatographed on a silica gel column (particle size 0.06–0.200 mm, diameter 8 mm, height 8 cm), eluting with 80 cm$^3$ of dichloromethane and then with a dichloromethane and methanol mixture (95/5 by volume), collecting 2.5 cm$^3$ fractions immediately after using this eluent mixture. Fractions 2 to 5 are combined and then concentrated to dryness under reduced pressure (2.7 kPa). 0.028 g of 1-{(R)-(4-chlorophenyl)[4-((2S)-carbamoylpyrrolidin-1-ylmethyl)phenyl]methyl}-3-[(3,5-difluorophenyl)(methylsulfonyl)methylene]azetidine, form A isomer, is obtained in the form of a white foam [$^1$H NMR spectrum (400 MHz, CDCl$_3$, δ in ppm): from 1.65 to 1.85 (mt, 2H), 1.92 (mt, 1H), from 2.15 to 2.35 (mt, 2H), 2.80 (s, 3H), 3.00 (mt, 1H), 3.16 (dd, J=10 and 5.5 Hz, 1H), 3.41 (d, J=13.5 Hz, 1H), 3.86 (mt, 2H), 3.89 (d, J=13.5 Hz, 1H), 4.33 (mt, 2H), 4.51 (s, 1H), 5.23 (unresolved complex, 1H), 6.84 (tt, J=9 and 2.5 Hz, 1H), 6.98 (mt, 2H), 7.17 (unresolved complex, 1H), from 7.20 to 7.40 (mt, 8H)].

EXAMPLE 108

The operation is carried out as described in Example 87, but by stirring the reaction mixture for 4 days at 20° C., starting with 0.05 g of 1-{(R*)-[4-(chloromethyl)phenyl](4-(chlorophenyl)methyl}-3-[(3,5-difluorophenyl) (methylsulfonyl)methylene]azetidine, form A isomer, 1.0 cm$^3$ of dichloromethane and 0.021 g of diethanolamine. The crude product is chromatographed on a silica gel column (particle size 0.06–0.200 mm, diameter 8 mm, height 8 cm), eluting with 80 cm$^3$ of dichloromethane and then with a dichloromethane and methanol mixture (95/5 by volume), collecting 2.5 cm$^3$ fractions immediately after using this eluent mixture. Fractions 2 to 9 are combined and then concentrated to dryness under reduced pressure (2.7 kPa). 0.004 g of 1-{(R*)-(4-chlorophenyl)[4-(dihydroxyethylaminomethyl)phenyl]methyl}-3-[(3,5-difluorophenyl)(methylsulfonyl)methylene]azetidine, form A isomer, is obtained in the form of a white foam [$^1$H NMR spectrum (300 MHz, CDCl$_3$, δ in ppm): 2.69 (t, J=5.5 Hz, 4H), 2.80 (s, 3H), 3.61 (t, J=5.5 Hz, 4H), 3.65 (s, 2H), 3.84 (mt, 2H), 4.33 (mt, 2H), 4.50 (s, 1H), 6.83 (tt, J=9 and 2.5 Hz, 1H), 6.98 (mt, 2H), from 7.20 to 7.40 (mt, 8H)].

EXAMPLE 109

0.055 g of imidazole is added to solution of 0.24 g of 1-{(R*)-[4-(chloromethyl)phenyl](4-chlorophenyl) methyl}-3-[(3,5-difluorophenyl)(methylsulfonyl) methylene]azetidine, form A isomer, in 5 cm$^3$ of dichloromethane. After heating for 3 hours under reflux, the mixture is supplemented with 5 mg of sodium iodide. After stirring for 20 hours under reflux, the reaction mixture is cooled to 20° C. and then chromatographed on a silica gel column (particle size 0.06–0.200 mm, diameter 1.0 cm, height 20 cm), eluting with 120 cm$^3$ of dichloromethane without fractionating, and then with a dichloromethane and methanol mixture (98/2 and then 96/4 by volume), collecting 4 cm$^3$ fractions. Fractions 12 to 14 are combined and then concentrated to dryness under reduced pressure (2.7 kPa). 0.039 g of 1-{(R*)-(4-chlorophenyl)[4-(imidazol-1-ylmethyl)phenyl]methyl}-3-[(3,5-difluorophenyl) (methylsulfonyl)methylene]azetidine, form A isomer, is obtained in the form of a white foam.

EXAMPLE 110

The operation is carried out as described in Example 87, starting with 0.50 g of 1-{(R*)-[4-(chloromethyl)phenyl](4-(chlorophenyl)methyl}-3-[(3,5-difluorophenyl) (methylsulfonyl)methylene]azetidine, form B isomer, 5 mg of sodium iodide, 15 cm$^3$ of dichloromethane and 0.0190 g of pyrrolidine. The crude product is chromatographed on a silica gel column (particle size 0.06–0.200 mm, diameter 1.5 cm, height 20 cm), at an argon pressure of 0.1 bar, eluting with dichloromethane and then with a dichloromethane and methanol mixture (95/5 by volume) and collecting 25 cm$^3$ fractions. Fractions 20 to 40 are combined and then concentrated to dryness under reduced pressure (2.7 kPa). 0.028 g of 1-{(R*)-(4-chlorophenyl)[4-(pyrrolidin-1-ylmethyl) phenyl]methyl}-3-[(3,5-difluorophenyl)(methylsulfonyl) methylene]azetidine, form B isomer, is obtained in the form of a white foam. [a]$^{20}$365 nm=+26.8°+/−0.8 (c=0.5%, dichloromethane)[$^1$H NMR spectrum (300 MHz, CDCl$_3$, δ in ppm): 1.78 (mt, 4H), 2.50 (mt, 4H), 2.80 (s, 3H), 3.57 (s, 2H), 3.84 (mt, 2H), 4.34 (mt, 2H), 4.50 (s, 1H), 6.84 (tt, J=9 and 2.5 Hz, 1H), 6.98 (mt, 2H), from 7.20 to 7.40 (mt, 8H)].

1-{(R*)-[4-(chloromethyl)phenyl](4-(chlorophenyl) methyl}-3-[(3,5-difluorophenyl)(methylsulfonyl) methylene]azetidine, form B isomer, may be prepared by carrying out the operation as described in Example 87, starting with 7.3 g of the mixture of the 2 diastereoisomers (B forms) 1-{(R*)-[4-(chloromethyl)phenyl](4-chlorophenyl)methyl}-3-[(R)-(3,5-difluorophenyl) (methylsulfonyl)methylene]azetidin-3-ol and 1-{(R*) -[4-(chloromethyl)phenyl](4-chlorophenyl)methyl}-3-[(S)-(3, 5-difluorophenyl)(methylsulfonyl)methyl]azetidin-3-ol, 8.2 g of 4-dimethylaminopyridine, 150 cm$^3$ of dichloromethane and 3.2 cm$^3$ of methanesulfonyl chloride. The crude product is chromatographed on a silica gel column (particle size 0.04–0.06 mm, diameter 3 cm, height 30 cm), at an argon pressure of 0.2 bar, eluting with dichloromethane and collecting 100 cm$^3$ fractions. Fractions 15 to 30 are combined and then concentrated to dryness under reduced pressure (2.7 kPa). 2.50 g of 1-{(R*)-[4-(chloromethyl)phenyl]-(4-chlorophenyl)methyl}-3-{(3,5-difluorophenyl) (methylsulfonyl)methylene]azetidine, form B isomer, are obtained in the form of a white foam.

The mixture of the 2 diastereoisomers 1-{(R*)-[4-(chloromethyl)phenyl](4-chlorophenyl)methyl}-3-[(R)-(3, 5-difluorophenyl)(methylsulfonyl)methyl)]azetidin-3-ol and 1-{(R*)-[4-(chloromethyl)phenyl](4-chlorophenyl) methyl}-3-[(S)-(3,5-difluorophenyl)(methylsulfonyl) methyl)]azetidin-3-ol, may be prepared by carrying out the operation as described in Example 87, starting with 11.0 g of a mixture of the 2 diastereoisomers 1-{(R*)-[4-chlorophenyl][4-(hydroxymethyl)phenyl)methyl}-3-[(R)-(3,5-difluorophenyl)(methylsulfonyl)methyl)]azetidin-3-ol and 1-{(R)-[4-(chlorophenyl](4-(hydroxymethyl)phenyl) methyl}-3-[(S)-(3,5-difluorophenyl)(methylsulfonyl) methyl)]azetidin-3-ol, 250 cm³ of dichloromethane and 3.1 cm³ of thionyl chloride. The crude product is chromatographed on a silica gel column (particle size 0.04–0.06 mm, diameter 3 cm, height 30 cm), at an argon pressure of 0.2 bar, eluting with a cyclohexane and ethyl acetate mixture (70/30 by volume) and collecting 50 cm³ fractions. Fractions 9 to 25 are combined and then concentrated to dryness under reduced pressure (2.7 kPa). 7.3 g of the mixture of the 2 diastereoisomers (B forms) 1-{(R*)-[4-(chloromethyl) phenyl](4-chlorophenyl)methyl}-3-[(R)-(3,5-difluorophenyl)(methylsulfonyl)methyl)]azetidin-3-ol and 1-{(R*)-[4-(chloromethyl)phenyl](4-chlorophenyl) methyl}-3-[(S)-(3,5-difluorophenyl)(methylsulfonyl) methyl)]azetidin-3-ol are obtained in the form of a white foam.

The mixture of the 2 diastereoisomers (B forms) 1-{(R*)-(4-chlorophenyl)[4-(hydroxymethyl)phenyl]methyl}-3-[(R)-(3,5-difluorophenyl)(methylsulfonyl)methyl)]azetidin-3-ol and 1-{(R*)-(4-chlorophenyl)[4-(hydroxymethyl) phenyl]methyl}-3-[(R)-(3,5-difluorophenyl) (methylsulfonyl)methyl)]azetidin-3-ol may be prepared by carrying out the operation as described in Example 87, starting with 18.0 g of the mixture of the 2 diastereoisomers (B form) 3-acetoxy-1-{(R*)-(4-chlorophenyl)[4-(methoxycarbonyl)phenyl]methyl}-3-[(R)-(3,5-difluorophenyl)(methylsulfonyl)methyl]azetidine and 3-acetoxy-1-{(R*)-(4-chlorophenyl)[4-(methyloxycarbonyl)phenyl]methyl}-3-[(S)-(3,5-difluorophenyl)(methylsulfonyl)methyl]azetidine, 150 cm³ of anhydrous toluene and 100 cm³ of a 20% solution of diisobutylaluminum hydride in toluene. The crude product is chromatographed on a silica gel column (particle size 0.06–0.200 mm, diameter 3 cm, height 30 cm), at an argon pressure of 0.1 bar, eluting with a cyclohexane and ethyl acetate mixture (50/50 by volume) and collecting 50 cm³ fractions. Fractions 15 to 30 are combined and then concentrated to dryness under reduced pressure (2.7 kPa). 11.0 g of the mixture of the 2 diastereoisomers (B forms) 1-{(R*)-(4-chlorophenyl)[4-(hydroxymethyl)phenyl]methyl}-3-[(R)-(3,5-difluorophenyl)(methylsulfonyl)methyl] azetidin-3-ol and 1-{(R*)-(4-chlorophenyl)[4-(hydroxymethyl)phenyl]methyl}-3-[(S)-(3,5-difluorophenyl)(methylsulfonyl)methyl]azetidin-3-ol are obtained in the form of white foam.

The mixture of the 2 diastereoisomers (B forms) 3-acetoxy-1-{(R*)-(4-chlorophenyl)[4-(methoxycarbonyl) phenyl]methyl}-3-[(R)-(3,5-difluorophenyl) (methylsulfonyl)methyl)]azetidine and 3-acetoxy-1-{(R*)-(4-chlorophenyl)[4-(methoxycarbonyl)phenyl]methyl}-3-[(R)-(3,5-difluorophenyl)(methylsulfonyl)methyl)]azetidine may be prepared by carrying out the operation as described in Example 40, starting with 11.2 g of (3,5-difluorobenzyl) methylsulfone, 350 cm³ of tetrahydrofuran, 34 cm³ of a 1.6 N solution of n-butyllithium in hexane, 11.2 g of 1-{(R*)-(4-chlorophenyl)[4-(methoxycarbonyl)phenyl] methyl}azetidin-3-one, form B isomer, and 5.5 cm³ of acetyl chloride. The crude product is chromatographed on a silica gel column (particle size 0.06–0.200 mm, diameter 4 cm, height 40 cm), eluting with a cyclohexane and ethyl acetate mixture (70/30 by volume) and collecting 100 cm³ fractions. Fractions 10 to 30 are combined and then concentrated to dryness under reduced pressure (2.7 kPa). 21 g of a still impure cream-colored foam are obtained, which foam is chromatographed on a silica gel column (particle size 0.06–0.200 mm, diameter 4 cm, height 40 cm), eluting with dichloromethane and collecting 100 cm³ fractions. Fractions 11 to 30 are combined and then concentrated to dryness under reduced pressure (2.7 kPa). 20.0 g of the mixture of the 2 diastereoisomers (B forms) 3-acetoxy-{(R*)-(4-chlorophenyl)[4-(methoxycarbonyl)phenyl]methyl}-3-[(R)-(3,5-difluorophenyl)(methylsulfonyl)methyl)]azetidine and 3-acetoxy-{(R*)-(4-chlorophenyl)[4-(methoxycarbonyl) phenyl]methyl}-3-[(S)-(3,5-difluorophenyl) (methylsulfonyl)methyl)]azetidine are obtained in the form of a white foam.

1-{(R*)-(4-chlorophenyl)[4-(methoxycarbonyl)phenyl] methyl}azetidin-3-one, form B isomer, may be prepared by carrying out the operation as described in Example 40, starting with 8.7 cm³ of oxalyl chloride, 350 cm³ of dichloromethane, 14.2 cm³ of dimethyl sulfoxide, 29.0 g of 1-{(R*)-(4-chlorophenyl)[4-(methoxycarbonyl)phenyl] methyl}azetidin-3-ole, form B isomer, and 43 cm³ of triethylamine. The crude product is chromatographed on a silica gel column (particle size 0.06–0.200 mm, diameter 4 cm, height 40 cm), eluting with dichloromethane and collecting 250 cm³ fractions. Fractions 7 to 25 are combined and then concentrated to dryness under reduced pressure (2.7 kPa). 15.5 g of 1-{(R*)-(4-[chlorophenyl)[4-(methoxycarbonyl)phenyl]methyl}azetidin-3-one, form B isomer, are obtained in the form of an orange-colored oil.

1-{(R*)-(4-chlorophenyl)[4-(methoxycarbonyl)phenyl] methyl}azetidin-3-ol, form B isomer, may be prepared according to the procedure described by KATRITZKY A. R. et al., in J. Heterocycl. Chem., (1994), 271, starting with 25.5 g of methyl (−)-4-[1-(R*)-amino-1-(4-chlorophenyl) methyl]benzoate, 250 cm³ of ethanol, 7.9 g of sodium hydrogen carbonate, and 7.7 cm³ of epibromohydrin. 29 g of 1-{(R*)-(4-chlorophenyl)[4-(methoxycarbonyl)phenyl] methyl}azetidin-3-ol, form B isomer, are obtained in the form of a yellow oil.

Methyl (−)-4-[(R*)amino(4-chlorophenyl)methyl] benzoate, may be prepared by carrying out two successive recrystallizations of the white crystals (3.4 g) called "A crystals" of Example 87, from 68 cm³ of ethanol containing 5% water under reflux. The crystals obtained are filtered, drained and then dried under reduced pressure (2.7 kPa). 2.2 g of methyl (−)-4-[(R*)amino(4-chlorophenyl)methyl] benzoate D-(−)-tartrate are obtained in the form of white crystals which are dissolved in 50 cm³ of ethyl acetate. The solution obtained is supplemented with 50 cm³ of 1 N sodium hydroxide, stirred and then separated after settling out. The organic phase is washed with 50 cm³ of water and then dried over magnesium sulfate and concentrated to dryness under reduced pressure (2.7 kPa). 1.9 g of methyl (−)-4-[(R*)amino(4-chlorophenyl)methyl]benzoate are obtained in the form of a white solid [a]20° C., 365 nm=58.1°+/−1 (c=0.5%).

EXAMPLE 111

The operation is carried out as described in Example 110, but by stirring the reaction mixture for 48 hours at 20° C., starting with 0.05 g of 1-{(R*)-[4-(chloromethyl)phenyl](4-chlorophenyl)methyl}-3-[(3,5-difluorophenyl) (methylsulfonyl)methylene)]azetidine, form B isomer, 1.0 cm³ of dichloromethane and 0.030 cm³ of N-methylpiperazine. The crude product is chromatographed on a silica gel column (particle size 0.06–0.200 mm, diameter 8 mm, height 5 cm), eluting with 50 cm³ of dichloromethane and then with a dichloromethane and methanol mixture (95/5 by volume), collecting 3 cm³ fractions immediately after using this eluent mixture. Fractions 4 to 10 are combined and then concentrated to dryness under reduced pressure (2.7 kPa). 0.025 g of 1-{(R*)-(4-chlorophenyl)[4-(4-methylpiperazin-1-ylmethyl)phenyl]methyl}-3-[(3,5-difluorophenyl)(methylsulfonyl)methylene)]azetidine, form B isomer, is obtained in the form of a cream-colored foam [$^1$H NMR spectrum (300 MHz, CDCl$_3$, δ in ppm): 2.28 (s, 3H), 2.44 (unresolved complex, 8H), 2.80 (s, 3H), 3.45 (s, 2H), 3.85 (mt, 2H), 4.34 (mt, 2H), 4.50 (s, 1H), 6.84 (tt, J=9 and 2.5 Hz, 1H), 6.99 (mt, 2H), from 7.20 to 7.40 (mt, 8H)].

EXAMPLE 112

The operation is carried out as described in Example 110, but by stirring the reaction mixture for 48 hours at 20° C., starting with 0.05 g of 1-{(R*)-[4-(chloromethyl)phenyl](4-chlorophenyl)methyl}-3-[(3,5-difluorophenyl)(methylsulfonyl)methylene)]azetidine, form B isomer, 1.0 cm$^3$ of dichloromethane and 0.030 cm$^3$ of L-Prolinol. The crude product is chromatographed on a silica gel column (particle size 0.06–0.200 mm, diameter 8 mm, height 5 cm), eluting with 50 cm$^3$ of dichloromethane and then with a dichloromethane and methanol mixture (95/5 by volume), collecting 3 cm$^3$ fractions immediately after using this eluent mixture. Fractions 2 to 8 are combined and then concentrated to dryness under reduced pressure (2.7 kPa). 0.025 g of 1-{{(R*)-(4-chlorophenyl){4-[(2S)-(hydroxymethyl)pyrrolidin-1-ylmethyl]phenyl}methyl}}-3-[(3,5-difluorophenyl)(methylsulfonyl)methylene]azetidine, form B isomer, is obtained in the form of a cream-colored foam [$^1$H NMR spectrum (300 MHz, CDCl$_3$, δ in ppm): from 1.80 to 2.00 (mt, 4H), 2.24 (mt, 1H), 2.72 (mt, 1H), 2.80 (s, 3H), 2.94 (mt, 1H), 3.28 (d, J=13.5 Hz, 1H), 3.45 (mt, 1H), 3.65 (d, J=10.5 and 3.5 Hz, 1H), 3.85 (mt, 2H), 3.92 (d, J=13.5 Hz, 1H), 4.34 (mt, 2H), 4.50 (s, 1H), 6.84 (tt, J=8.5 and 2.5 Hz, 1H), 6.98 (mt, 2H), from 7.15 to 7.40 (mt, 8H)].

EXAMPLE 113

The operation is carried out as described in Example 110, but by stirring the reaction mixture for 48 hours at 20° C., starting with 0.05 g of 1-{(R*)[4-(chloromethyl)phenyl](4-chlorophenyl)methyl}-3-[(3,5-difluorophenyl)(methylsulfonyl)methylene)]azetidine, form B isomer, 1.0 cm$^3$ of dichloromethane and 0.030 cm$^3$ of D-Prolinol. The crude product is chromatographed on a silica gel column (particle size 0.06–0.200 mm, diameter 8 mm, height 5 cm), eluting with 50 cm$^3$ of dichloromethane and then with a dichloromethane and methanol mixture (95/5 by volume), collecting 3 cm$^3$ fractions immediately after using this eluent mixture. Fractions 2 to 9 are combined and then concentrated to dryness under reduced pressure (2.7 kPa). 0.029 g of 1-{{(R*)-(4-chlorophenyl){4-(2R)-(hydroxymethyl)pyrrolidin-1-ylmethyl]phenyl}methyl}}-3-[(3,5-difluorophenyl)(methylsulfonyl)methylene]azetidine, form B isomer, is obtained in the form of a cream-colored foam [$^1$H NMR spectrum (300 MHz, CDCl$_3$, δ in ppm): from 1.50 to 2.00 (mt, 4H), 2.24 (mt, 1H), 2.71 (mt, 1H), 2.81 (s, 3H), 2.93 (mt, 1H), 3.28 (d, J=13.5 Hz, 1H), 3.44 (split t, J=10.5 and 2.5 Hz, 1H), 3.66 (dd, J=10.5 and 3.5 Hz, 1H), 3.85 (mt, 2H), 3.92 (d, J=13.5 Hz, 1H), 4.33 (mt, 2H), 4.50 (s, 1H), 6.84 (tt, J=9 and 2.5 Hz, 1H), 6.98 (mt, 2H), from 7.15 to 7.40 (mt, 8H)].

EXAMPLE 114

The operation is carried out as described in Example 110, but by stirring the reaction mixture for 48 hours at 20° C., starting with 0.05 g of 1-{(R*)-[4-(chloromethyl)phenyl](4-chlorophenyl)methyl}-3-[(3,5-difluorophenyl)(methylsulfonyl)methylene]azetidine, form B isomer, 1.0 cm$^3$ of dichloromethane and 0.030 cm$^3$ of morpholine. The crude product is chromatographed on a silica gel column (particle size 0.06–0.200 mm, diameter 8 mm, height 5 cm), eluting with 50 cm$^3$ of dichloromethane and then with a dichloromethane and methanol mixture (95/5 by volume), collecting 3 cm$^3$ fractions immediately after using this eluent mixture. Fractions 2 to 9 are combined and then concentrated to dryness under reduced pressure (2.7 kPa). 0.047 g of 1-{(R*)-(4-chlorophenyl)[4-(morpholin-1-ylmethyl)phenyl]methyl}-3-[(3,5-difluorophenyl)(methylsulfonyl)methylene]azetidine, form B isomer, is obtained in the form of a white foam [$^1$H NMR spectrum (300 MHz, CDCl$_3$, δ in ppm): 2.40 (mt, 4H), 2.81 (s, 3H), 3.43 (s, 2H), 3.69 (mt, 4H), 3.84 (mt, 2H), 4.34 (mt, 2H), 4.50 (s, 1H), 6.84 (tt, J=8.5 and 2.5 Hz, 1H), 6.99 (mt, 2H), from 7.20 to 7.40 (mt, 8H)].

EXAMPLE 115

The operation is carried out as described in Example 110, but by stirring the reaction mixture for 48 hours at 20° C., starting with 0.05 g of 1-{(R*)-[4-(chloromethyl)phenyl](4-chlorophenyl)methyl}-3-[(3,5-difluorophenyl)(methylsulfonyl)methylene)]azetidine, form B isomer, 1.0 cm$^3$ of dichloromethane and 0.030 cm$^3$ of thiomorpholine. The crude product is chromatographed on a silica gel column (particle size 0.06–0.200 mm, diameter 8 mm, height 5 cm), eluting with 50 cm$^3$ of dichloromethane and then with a dichloromethane and methanol mixture (95/5 by volume), collecting 3 cm$^3$ fractions immediately after using this eluent mixture. Fractions 2 to 9 are combined and then concentrated to dryness under reduced pressure (2.7 kPa). 0.047 g of 1-{(R*)-(4-chlorophenyl)[4-(thiomorpholin-4-ylmethyl)phenyl]methyl}-3-[(3,5-difluorophenyl)(methylsulfonyl)methylene]azetidine, form B isomer, is obtained in the form of a white foam [$^1$H NMR spectrum (300 MHz, CDCl$_3$, δ in ppm): from 2.60 to 2.75 (mt, 8H), 2.81 (s, 3H), 3.44 (s, 2H), 3.85 (mt, 2H), 4.34 (mt, 2H), 4.50 (s, 1H), 6.84 (tt, J=8.5 and 2.5 Hz, 1H), 6.98 (mt, 2H), from 7.15 to 7.40 (mt, 8H)].

EXAMPLE 116

The operation is carried out as described in Example 110, but by stirring the reaction mixture for 48 hours at 20° C., starting with 0.200 g of 1-{(R*)-[4-(chloromethyl)phenyl](4-chlorophenyl)methyl}-3-[(3,5-difluorophenyl)(methylsulfonyl)methylene)]azetidine, form B isomer, 5.0 cm$^3$ of dichloromethane and 0.120 cm$^3$ of piperazin-2-one. The crude product is chromatographed on a silica gel column (particle size 0.06–0.200 mm, diameter 1.0 cm, height 10 cm), eluting with 50 cm$^3$ of dichloromethane and then with a dichloromethane and methanol mixture (95/5 by volume), collecting 5 cm$^3$ fractions immediately after using this eluent mixture. Fractions 3 to 13 are combined and then concentrated to dryness under reduced pressure (2.7 kPa). 0.090 g of 1-{(R*)-(4-chlorophenyl)[4-(piperazin-2-on-4-ylmethyl)phenyl]methyl}-3-[(3,5-difluorophenyl)(methylsulfonyl)methylene]azetidine, form B isomer, is obtained in the form of a white powder.

EXAMPLE 117

The operation is carried out as described in Example 110 starting with 0.200 g of 1-{(R*)-[4-(chloromethyl)phenyl](4-chlorophenyl)methyl}-3-[(3,5-difluorophenyl)(methylsulfonyl)methylene)]azetidine, form B isomer, 5.0 cm³ of dichloromethane and 0.120 of 3,3-dimethylpiperidine. The crude product is chromatographed on a silica gel column (particle size 0.06–0.200 mm, diameter 1.0 cm, height 10 cm), eluting with 50 cm³ of dichloromethane and then with a dichloromethane and methanol mixture (95/5 by volume), collecting 5 cm³ fractions immediately after using this eluent mixture. Fractions 4 to 11 are combined and then concentrated to dryness under reduced pressure (2.7 kPa). 0.120 g of 1-{(R*)-(4-chlorophenyl)[4-(3,3-dimethylpiperidinylmethyl)phenyl]methyl}-3-[(3,5-difluorophenyl)(methylsulfonyl)methylene]azetidine, form B isomer, is obtained in the form of a white powder.

EXAMPLE 118

The operation is carried out as described in Example 110, by stirring for 72 hours at 20° C., starting with 0.200 g of 1-{(R*)-[4-(chloromethyl)phenyl](4-chlorophenyl)methyl}-3-[(3,5-difluorophenyl)(methylsulfonyl)methylene)]azetidine, form B isomer, 5.0 cm³ of dichloromethane and 0.080 of imidazole. The reaction mixture is directly chromatographed on a silica gel column (particle size 0.06–0.200 mm, diameter 1.0 cm, height 10 cm), eluting with 100 cm³ of dichloromethane without fractionating, and then with a dichloromethane and methanol mixture (98/2 and then 96/4 by volume), collecting 5 cm³ fractions. Fractions 5 to 12 are combined and then concentrated to dryness under reduced pressure (2.7 kPa). 0.35 g of 1-{(R*)-(4-chlorophenyl)[4-(imidazol-1-ylmethyl)phenyl]methyl}-3-[(3,5-difluorophenyl)(methylsulfonyl)methylene]}azetidine, form B isomer, is obtained in the form of a white powder. $[a]^{20}D = -6.7°$ (c=0.5% dichloromethane).

EXAMPLE 119

2.47 g of potassium tert-butoxide are added to a suspension of 6.12 g of 1-[bis(4-chlorophenyl)methyl]azetidin-3-one and 5.15 g of methyl 5-(methylsulfonylmethyl)thiophene-2-carboxylate in 200 cm³ of tetrahydrofuran, under an argon atomosphere, cooled to –70° C. The mixture is stirred for 1 hour 30 min at a temperature close to –70° C., and then 1.7 cm³ of methanesulfonyl chloride in solution in 8 cm³ of ethyl ether is added. After stirring for 1 hour at a temperature close to –70° C., the mixture is allowed to return to room temperature and then 80 cm³ of distilled water are added. The mixture is concentrated in a rotary evaporator to one third of its initial volume, and is then extracted with 500 cm³ of dichloromethane. The organic phase is washed with three times 80 cm³ of distilled water, dried over magnesium sulfate and concentrated to dryness under reduced pressure (2.7 kPa). The residue obtained is chromatographed on a silica gel column (particle size 0.02–0.04 mm, diameter 7.5 cm, height 35 cm), eluting at a nitrogen pressure of 0.5 bar with a cyclohexane and ethyl acetate mixture (70/30 by volume) and collecting 40 cm³ fractions. Fractions 19 to 29 are combined and then concentrated to dryness under reduced pressure (2.7 kPa). 1.6 g of 1-[bis(4-chlorophenyl)methyl]-3-[(methylsulfonyl)(2-methoxycarbonylthien-5-yl)methylene]azetidine are obtained in the form of a cream-colored foam [¹H NMR spectrum (400 MHz, CDCl₃, δ in ppm): 2.91 (s, 3H), 3.88 (s, 3H), 4.08 (mt, 2H), 4.37 (mt, 2H), 4.53 (s, 1H), from 7.25 to 7.45 (mt, 9H), 7.71 (d, J=3.5 Hz, 1H)].

Fractions 34 to 48 are combined and then concentrated to dryness under reduced pressure (2.7 kPa). 2.6 g of (RS)-1-[bis(4-chlorophenyl)methyl]-3-hydroxy-3-[(methylsulfonyl)(2-methoxycarbonylthien-5-yl)methyl]azetidine are obtained in the form of cream-colored powder [¹H NMR spectrum (400 MHz, (CD₃)₂SO-d6, δ in ppm): 2.87 (s, 3H), 2.89 (d, J=8 Hz, 1H), 2.96 (d, J=8 Hz, 1H), 3.21 (d, J=8 Hz, 1H), 3.76 (d, J=8 Hz, 1H), 3.82 (s, 3H), 4.55 (s, 1H), 4.86 (s, 1H), 6.86 (s, 1H), from 7.35 to 7.45 (mt, 9H), 7.73 (d, J=4 Hz, 1H)].

Methyl 5-(methylsulfonylmethyl)thiophene-2-carboxylate may be prepared in the following manner: 6.94 g of sodium methanesulfinate are added, at room temperature, to a solution of 16 g of methyl 5-bromomethylthiophene-2-carboxylate in 150 cm³ of tetrahydrofuran. The suspension is stirred for 2 hours 30 min under reflux, and then after addition of 50 cm³ of ethanol is again stirred for 3 hours under reflux. The mixture is concentrated to dryness under reduced pressure (2.7 kPa) and the residue obtained is supplemented with 150 cm³ of distilled water and is then extracted with twice 300 cm³ of ethyl acetate. The organic phase is successively washed with 100 cm³ of distilled water and twice 50 cm³ of saturated aqueous sodium chloride solution and then dried over magnesium sulfate and concentrated to dryness under reduced pressure (2.7 kPa). 14 g of methyl 5-(methylsulfonylmethyl)thiophene-2-carboxylate are thus obtained in the form of a yellow solid melting around 133° C. [¹H NMR spectrum (400 MHz, (CD₃)₂SO-d6, at a temperature of 373 K, δ in ppm): 3.05 (s, 3H), 4.22 (mt, 2H), 4.40 (mt, 2H), 4.98 (broad s, 1H), 7.30 (d, J=3.5 Hz, 1H), 7.39 (d, J=8 Hz, 4H), 7.50 (d, J=8 Hz, 4H), 7.66 (d, J=3.5 Hz, 1H)].

Methyl 5-bromomethylthiophene-2-carboxylate may be prepared according to Curtin M. L., Davidsen S. K., Heyman H. R., Garland R. B., Sheppard G. S., J. Med. Chem., 1998, 41 (1), 74–95.

EXAMPLE 120

47 μl of N,N'-diisopropylcarbodiimide, 3.66 mg of 4-dimethylaminopyridine and 60 μl of isobutylamine are added to a solution of 163.5 mg of 1-[bis(4-chlorophenyl)methyl]-3-[(methylsulfonyl)(2-hydroxycarbonylthien-5-yl)methylene]azetidine hydrochloride in 3 cm³ of dichloromethane, at room temperature. The mixture is stirred for 18 hours at room temperature and then chromatographed on a silica gel column (particle size 0.04–0.06 mm), eluting with a dichloromethane and ethyl acetate mixture (90/10 by volume). 60 mg of 1-[bis(4-chlorophenyl)methyl]-3-[2-isobutylaminocarbonylthien-5-yl)(methylsulfonyl)methylene]azetidine are thus obtained in the form of a colorless lacquer [¹H NMR spectrum (400 MHz, CDCl₃, δ in ppm): 0.97 (d, J=7 Hz, 6H), 1.88 (mt, 1H), 2.90 (s, 3H), 3.25 (t, J=7 Hz, 2H), 4.08 (mt, 2H), 4.36 (mt, 2H), 4.52 (s, 1H), 4.56 (broad t, J=7 Hz, 1H), from 7.20 to 7.40 (mt, 10H)].

1-[bis(4-chlorophenyl)methyl]-3-[(methylsulfonyl)(2-hydroxycarbonylthien-5-yl)methylene]azetidine hydrochloride may be prepared in the following manner: 250 cm³ of concentrated hydrochloric acid are added to a solution of 14 g of 1-[bis(4-chlorophenyl)methyl]-3-[(methylsulfonyl)(2-methoxycarbonylthien-5-yl)methylene]azetidine in 250 cm³ of acetic acid, at room temperature. The mixture is stirred for 38 hours at a temperature of 50° C. and is then concentrated to dryness under reduced pressure (2.7 kPa). Three times, the residue is supplemented with 250 cm³ of toluene and concentrated to dryness under reduced pressure (2.7 kPa). After trituration of the residue in 400 cm³ of ethyl ether, 14.2 g of 1-[bis(4-chlorophenyl)methyl]-3-[(methylsulfonyl)(2-hydroxycarbonylthien-5-yl)methylene]azetidine hydrochloride are obtained in the form of a beige powder.

EXAMPLE 121

0.37 g of potassium tert-butoxide is added to a solution of 0.92 g of 1-[bis(4-chlorophenyl)methyl]azetidin-3-one and 0.75 g of [(3-methoxycarbonylphenyl)methyl]methylsulfone in 30 cm³ of tetrahydrofuran, under an argon atmosphere, cooled to −70° C., and the mixture is stirred for 2 hours at −70° C. 10 cm³ of a 0.1 N solution of hydrochloric acid are then added and the mixture is allowed to return to room temperature. After addition of 50 cm³ of ethyl acetate, the reaction mixture is separated after settling out, dried over magnesium sulfate, filtered and then concentrated to dryness under reduced pressure (2.7 pKa). The residue is chromatographed on a silica gel column (particle size 0.20–0.06 mm, diameter 3 cm, height 50 cm), eluting at a nitrogen pressure of 0.8 bar with a cyclohexane and ethyl acetate mixture (70/30 by volume) and collecting 120 cm³ fractions. Fractions 11 to 18 are combined and then concentrated to dryness under reduced pressure (2.7 kPA). The residue is crystallized from 10 cm³ of isopropyl ether and 30 cm³ of pentane. 0.30 g of 1-[bis(4-chlorophenyl)methyl]-3-[(3-methoxycarbonylphenyl)(methylsulfonyl)methyl-(RS)]azetidin-3-ol is thus obtained in the form of a white solid [$^1$H NMR spectrum (400 MHz, CDCl$_3$, δ in ppm): 2.73 (s, 3H), 3.05 (AB, J=9 Hz, 2H), 3.27 (d, J=9 Hz, 1H), 3.63 (s, 1H), 3.79 (d, J=9 Hz, 1H), 3.95 (s, 3H), 4.32 (s, 1H), 4.59 (s, 1H), from 7.15 to 7.35 (mt, 8H), 7.51 (t, J=8 Hz, 1H), 7.94 (broad d, J=8 Hz, 1H), 8.10 (broad d, J=8 Hz, 1H), 8.32 (broad s, 1H))].

EXAMPLE 122

By carrying out the operation according to the procedure of Example 1, starting with 0.66 g of methyl(pyridin-4-ylmethyl)sulfone and 1.18 g of 1-[bis(4-chlorophenyl)methyl]azetidin-3-one, 0.20 g of a white solid is obtained after purification on a silica gel column (particle size 0.20–0.06 mm, diameter 3 cm, height 50 cm), at a nitrogen pressure of 0.5 bar with a cyclohexane and ethyl acetate mixture (70/30 by volume) as eluent and collecting 120 cm³ fractions. The solid is taken up in 20 cm³ of diisopropyl ether. After filtration, draining and drying, 0.16 g of 1-[bis(4-chlorophenyl)methyl]-3-[(methylsulfonyl)(pyridin-4-yl)methyl-(RS)]-azetidin-3-ol is obtained [$^1$H NMR spectrum (400 MHz, CDCl$_3$, δ in ppm): 2.76 (s, 3H), 3.03 (AB, J=9 Hz, 2H), 3.27 (d, J=9 Hz, 1H), 3.53 (s, 1H), 3.83 (d, J=9 Hz, 1H), 4.32 (s, 1H), 4.51 (s, 1H), from 7.20 to 7.30 (mt, 8H), 7.63 (d, J=6 Hz, 2H), 8.68 (d, J=6 Hz, 2H)].

Methyl(pyridin-4-ylmethyl)sulfone may be prepared according to the reference JP43002711.

EXAMPLE 123

By carrying out the operation according to the procedure of Example 1, starting with 0.47 g of methyl(pyridin-3-ylmethyl)sulfone and 0.83 g of 1-[bis(4-chlorophenyl)methyl]azetidin-3-one, 0.50 g of a white solid is obtained after purification on a silica gel column (particle size 0.20–0.06 mm, diameter 3 cm, height 50 cm), at a nitrogen pressure of 0.5 bar with a cyclohexane and ethyl acetate mixture (70/30 by volume) as eluent and collecting 120 cm³ fractions. The solid is taken up in 30 cm³ of diisopropyl ether. After filtration, draining and drying, 0.40 g of 1-[bis(4-chlorophenyl)methyl]-3-[(methylsulfonyl)(pyridin-3-yl)methyl-(RS)]-azetidin-3-ol is obtained [$^1$H NMR spectrum (300 MHz, CDCl$_3$, δ in ppm): 2.77 (s, 3H), 3.03 (AB, J=9 Hz, 2H), 3.28 (d, J=9 Hz, 1H), 3.66 (s, 1H), 3.83 (d, J=9 Hz, 1H), 4.33 (s, 1H), 4.55 (s, 1H), from 7.20 to 7.30 (mt, 8H), 7.37 (dd, J=8 and 5 Hz, 1H), 8.16 (dt, J=8 and 2 Hz, 1H), 8.68 (dd, J=5 and 1.5 Hz, 1H), 8.83 (d, J=2 Hz, 1H)].

Methyl(pyridin-3-ylmethyl)sulfone may be prepared according to the reference JP43002711.

EXAMPLE 124

0.0388 cm³ of N-(3-aminopropyl)morpholine is added, at the same temperature, to a suspension of 150 mg of 3-({1-[bis(4-chlorophenyl)methyl]azetidin-3-ylidene}methanesulfonylmethyl)benzoic acid activated on TFP resin (165 μM) in 3 cm³ of dichloromethane, pre-stirred for 90 minutes at a temperature close to 20° C. The suspension is stirred at a temperature close to 20° C. for 22 hours and then filtered on sintered glass. The solid residue is rewashed with twice 1.5 cm³ of dichloromethane. The filtrates are combined and concentrated to dryness under reduced pressure (2.7 kPa) at a temperature close to 40° C. 60 mg of 3-({1-[bis(4-chlorophenyl)methyl]azetidin-3-ylidene}methanesulfonylmethyl)-N-(3-morpholin-4-ylpropyl)benzamide are thus obtained in the form of a pale yellow foam.

3-({1-[bis(4-chlorophenyl)methyl]azetidin-3-ylidene}methanesulfonylmethyl)-N-(3-morpholin-4-ylpropyl)benzamide may also be prepared in the following manner: 0.083 cm³ of N-(3-aminopropyl)morpholine, 110 mg of 1-(3-dimethylaminopropyl)-3-ethylcarbodiimide and 5 mg of 4-dimethylaminopyridine are successively added to a solution of 300 mg of 3-({1-[bis(4-chlorophenyl)methyl]azetidin-3-ylidene}methanesulfonylmethyl)benzoic acid in 10 cm³ of anhydrous dichloromethane (over calcium chloride) and 5 cm³ of dimethylformamide, under an inert atmosphere of nitrogen, at a temperature close to 20° C. The solution obtained is stirred at a temperature close to 20° C. for about 22 hours and then concentrated to dryness under reduced pressure (0.27 kPa) at a temperature close to 40° C. The solid residue is taken up in 25 cm³ of dichloromethane and washed with twice 20 cm³ of a saturated aqueous sodium bicarbonate solution. After separation after settling out, the organic phase is dried over magnesium sulfate, filtered and concentrated to dryness under reduced pressure (2.7 kPa) at a temperature close to 40° C. 400 mg of a yellow oil are thus obtained, which oil is purified by chromatography under nitrogen pressure (0.8 bar) on 60 cm³ of silica (0.040–0.063 mm) contained in a column 2.2 cm in diameter, eluting with a methanol/dichloromethane mixture (2-98 by volume). The fractions containing only the desired product are combined and concentrated to dryness under reduced pressure (0.27 kPa) at 40° C. for 2 hours. 130 mg of 3-({1-[bis(4-chlorophenyl)methyl]azetidin-3-ylidene}methanesulfonylmethyl)-N-(3-morpholin-4-ylpropyl)benzamide are thus obtained in the form of a white crystalline powder [$^1$H NMR spectrum (300 MHz, (CD$_3$)$_2$SO-d6, δ in ppm): 1.68 (mt, 2H), from 2.25 to 2.40 (mt, 6H), 2.97 (s, 3H), from 3.20 to 3.35 (mt, 2H), 3.57 (t, J=4.5 Hz, 4H), 3.81 (mt, 2H), 4.22 (mt, 2H), 4.79 (s, 1H), 7.36 (d, J=8.5 Hz, 4H), 7.46 (d, J=8.5 Hz, 4H), from 7.50 to 7.60 (mt, 2H), 7.83 (broad s, 1H), 7.86 (broad d, J=8 Hz, 1H), 8.53 (t, J=5.5 Hz, 1H)].

EXAMPLE 125

The operation is carried out under the conditions described in Example 124 starting with 150 mg of activated 3-({1-[bis(4-chlorophenyl)methyl]azetidin-3-ylidene}methanesulfonylmethyl)benzoic acid on TFP resin (165 μM) and 0.033 cm³ of N,N-dimethyl-1,3-propanediamine. 52 mg of 3-({1-[bis(4-chlorophenyl)methyl]azetidin-3-ylidene}methanesulfonylmethyl)-N-(3-dimethylaminopropyl)benzamide are thus obtained in the form of a white powder [$^1$H NMR spectrum (400 MHz, (CD$_3$)$_2$SO-d6, δ in ppm): 1.65 (mt, 2H), 2.18 (s, 6H), from 2.20 to 2.35 (mt, 2H), 2.98 (s, 3H), from 3.25 to 3.45 (mt, 2H), 3.82 (mt, 2H), 4.23 (mt, 2H), 4.80 (s, 1H), 7.36 (d, J=8.5 Hz, 4H), 7.46 (d, J=8.5 Hz, 4H), from 7.50 to 7.60 (mt, 2H), 7.83 (broad s, 1H), 7.86 (broad d, J=8 Hz, 1H), 8.57 (t, J=5.5 Hz, 1H)].

EXAMPLE 126

The operation is carried out under the conditions described in Example 124 starting with 150 mg of activated 3-({1-[bis(4-chlorophenyl)methyl]azetidin-3-ylidene}methanesulfonylmethyl)benzoic acid on TFP resin (165 μM) and 0.0333 cm$^3$ of 1-(aminoethyl)pyrrolidine. 39 mg of 3-({1-[bis(4-chlorophenyl)methyl]azetidin-3-ylidene}methanesulfonylmethyl)-N-(2-pyrrolidin-1-ylethyl)benzamide are thus obtained in the form of a pale yellow powder [$^1$H NMR spectrum (300 MHz, (CD$_3$)$_2$SO-d6 with addition of a few drops of CD$_3$COOD-d4, δ in ppm): from 1.80 to 2.00 (mt, 4H), 2.97 (s, 3H), 3.20 (mt, 6H), 3.57 (t, J=6.5 Hz, 2H), 3.80 (mt, 2H), 4.23 (mt, 2H), 4.77 (s, 1H), 7.35 (d, J=8.5 Hz, 4H), 7.45 (d, J=8.5 Hz, 4H), from 7.50 to 7.65 (mt, 2H), 7.87 (broad s, 1H), 7.90 (broad d, J=7.5 Hz, 1H)].

EXAMPLE 127

The operation is carried out under the conditions described in Example 124 starting with 150 mg of activated 3-({1-[bis(4-chlorophenyl)methyl]azetidin-3-ylidene}methanesulfonylmethyl)benzoic acid on TFP resin (165 μM) and 0.0333 cm$^3$ of 1-(dimethylamino)-2-propylamine. 49 mg of 3-({1-[bis(4-chlorophenyl)methyl]azetidin-3-ylidene}methanesulfonylmethyl)-N-(2-dimethylamino-1-methylethyl)benzamide are thus obtained in the form of a white powder [$^1$H NMR spectrum (400 MHz, (CD$_3$)$_2$SO-d6, δ in ppm): 1.13 (d, J=6.5 Hz, 3H), from 2.10 to 2.25 (mt, 1H), 2.15 (s, 6H), 2.38 (dd, J=13 and 8 Hz, 1H), 2.98 (s, 3H), 3.80 (mt, 2H), 4.14 (mt, 1H), 4.23 (mt, 2H), 4.79 (s, 1H), 7.36 (d, J=8 Hz, 4H), from 7.45 to 7.60 (mt, 2H), 7.46 (d, J=8 Hz, 4H), 7.83 (broad s, 1H), 7.87 (broad d, J=8 Hz, 1H), 8.16 (broad d, J=8 Hz, 1H)].

EXAMPLE 128

The operation is carried out under the conditions described in Example 124 starting with 150 mg of activated 3-({1-[bis(4-chlorophenyl)methyl]azetidin-3-ylidene}methanesulfonylmethyl)benzoic acid on TFP resin (165 μM) and 0.026 cm$^3$ of piperidine. 56 mg of 3-({1-[bis(4-chlorophenyl)methyl]azetidin-3-ylidene}methanesulfonylmethyl)-N-piperidin-1-ylbenzamide are thus obtained in the form of a white powder [$^1$H NMR spectrum (400 MHz, (CD$_3$)$_2$SO-d6, δ in ppm): from 1.45 to 1.70 (mt, 6H), from 2.90 to 3.05 (mt, 2H), 2.98 (s, 3H), 3.19 (unresolved complex, 1H), 3.57 (unresolved complex, 1H), 3.85 (mt, 2H), 4.23 (mt, 2H), 4.80 (s, 1H), from 7.30 to 7.55 (mt, 12H)].

EXAMPLE 129

The operation is carried out under the conditions described in Example 124 starting with 150 mg of activated 3-({1-[bis(4-chlorophenyl)methyl]azetidin-3-ylidene}methanesulfonylmethyl)benzoic acid on TFP resin (165 μM) and 0.0265 cm$^3$ of isobutylamine. 46 mg of 3-({1-[bis(4-chlorophenyl)methyl]azetidin-3-ylidene}methanesulfonylmethyl)-N-isobutylbenzamide are thus obtained in the form of a white powder [$^1$H NMR spectrum (400 MHz, (CD$_3$)$_2$SO-d6, δ in ppm): 0.89 (d, J=7 Hz, 6H), 1.85 (mt, 1H), 2.98 (s, 3H), 3.09 (t, J=6.5 Hz, 2H), 3.82 (mt, 2H), 4.23 (mt, 2H), 4.79 (s, 1H), 7.36 (d, J=8.5 Hz, 4H), 7.46 (d, J=8.5 Hz, 4H), from 7.50 to 7.60 (mt, 2H), 7.84 (broad s, 1H), 7.88 (broad d, J=8 Hz, 1H), 8.51 (t, J=6 Hz, 1H)].

EXAMPLE 130

The operation is carried out under the conditions described in Example 124 starting with 150 mg of activated 3-({1-[bis(4-chlorophenyl)methyl]azetidin-3-ylidene}methanesulfonylmethyl)benzoic acid on TFP resin (165 μM) and 0.0316 cm$^3$ of N-(3-aminopropyl)imidazole. 54 mg of 3-({1-[bis(4-chlorophenyl)methyl]azetidin-3-ylidene}methanesulfonylmethyl)-N-(3-imidazol-1-ylpropyl)benzamide are thus obtained in the form of a yellow foam [$^1$H NMR spectrum (400 MHz, (CD$_3$)$_2$SO-d6, δ in ppm): 1.97 (mt, 2H), 2.98 (s, 3H), 3.25 (mt, 2H), 3.81 (mt, 2H), 4.02 (t, J=7 Hz, 2H), 4.23 (mt, 2H), 4.79 (s, 1H), from 6.85 to 6.95 (mt, 2H), 7.36 (d, J=8.5 Hz, 4H), 7.46 (d, J=8.5 Hz, 4H), from 7.50 to 7.60 (mt, 2H), 7.84 (broad s, 1H), 7.88 (broad d, J=8 Hz, 1H), 8.56 (t, J=5.5 Hz, 1H)].

EXAMPLE 131

The operation is carried out under the conditions described in Example 124 starting with 150 mg of activated 3-({1-[bis(4-chlorophenyl)methyl]azetidin-3-ylidene}methanesulfonylmethyl)benzoic acid on TFP resin (165 μM) and 0.030 cm$^3$ of N,N-(dimethyl)ethylenediamine. 53 mg of 3-({1-[bis(4-chlorophenyl)methyl]azetidin-3-ylidene}methanesulfonylmethyl)-N-(2-dimethylaminoethyl)benzamide are thus obtained in the form of an ochre-colored foam [$^1$H NMR spectrum (400 MHz, (CD$_3$)$_2$SO-d6, δ in ppm): 2.18 (2s, 6H), from 2.35 to 2.45 (mt, 2H), 2.98 (s, 3H), from 3.25 to 3.50 (mt, 2H), 3.81 (mt, 2H), 4.23 (mt, 2H), 4.79 (s, 1H), 7.36 (d, J=8 Hz, 4H), 7.46 (d, J=8 Hz, 4H), from 7.45 to 7.60 (mt, 2H), 7.83 (broad s, 1H), 7.86 (broad d, J=8 Hz, 1H), 8.43 (t, J=6.5 Hz, 1H)].

EXAMPLE 132

The operation is carried out under the conditions described in Example 124 starting with 150 mg of activated 3-({1-[bis(4-chlorophenyl)methyl]azetidin-3-ylidene}methanesulfonylmethyl)benzoic acid on TFP resin (165 μM) and 0.0141 cm$^3$ of methylhydrazine. 42 mg of 3-({1-[bis(4-chlorophenyl)methyl]azetidin-3-ylidene}methanesulfonylmethyl)benzoic acid N'methylhydrazide are thus obtained in the form of a pale yellow foam [$^1$H NMR spectrum (400 MHz, (CD$_3$)$_2$SO-d6, δ in ppm): 2.96 (s, 3H), 3.18 (broad s, 3H), 3.83 (mt, 2H), 4.22 (mt, 2H), 4.80 (broad s, 2H), from 7.35 to 7.65 (mt, 12H)].

EXAMPLE 133

The operation is carried out under the conditions described in Example 124 starting with 150 mg of activated 3-({1-[bis(4-chlorophenyl)methyl]azetidin-3-ylidene}methanesulfonylmethyl)benzoic acid on TFP resin (165 μM) and 0.0345 cm$^3$ of N-(2-aminoethyl)morpholine. 62 mg of 3-({1-[bis(4-chlorophenyl)methyl]azetidin-3-ylidene}methanesulfonylmethyl)-N-(2-morpholin-4-ylethyl)benzamide are thus obtained in the form of an ochre-colored foam [$^1$H NMR spectrum (400 MHz, (CD$_3$)$_2$SO-d6, δ in ppm): from 2.30 to 2.45 (mt, 4H), 2.46 (t, J=7.5

Hz, 2H), 2.98 (s, 3H), 3.38 (mt, 2H), from 3.50 to 3.65 (mt, 4H), 3.82 (mt, 2H), 4.24 (mt, 2H), 4.79 (s, 1H), 7.36 (d, J=8.5 Hz, 4H), 7.46 (d, J=8.5 Hz, 4H), from 7.50 to 7.60 (mt, 2H), 7.83 (broad s, 1H), 7.85 (dd, J=8 and 2 Hz, 1H), 8.45 (t, J=6.5 Hz, 1H)].

EXAMPLE 134

The operation is carried out under the conditions described in Example 124 starting with 150 mg of activated 3-({1-[bis(4-chlorophenyl)methyl]azetidin-3-ylidene}methanesulfonylmethyl)benzoic acid on TFP resin (165 µM) and 0.0396 cm$^3$ of 2-(aminomethyl)-N-ethylpyrrolidine. 58 mg of 3-({1-[bis(4-chlorophenyl)methyl]azetidin-3-ylidene}methanesulfonylmethyl)-N-(1-ethylpyrrolidin-2-ylmethyl)benzamide are thus obtained in the form of an ochre-colored foam.

3-({1-[bis(4-chlorophenyl)methyl]azetidin-3-ylidene}methanesulfonylmethyl)-N-(1-ethylpyrrolidin-2-ylmethyl)benzamide may also be prepared under the conditions described in Example 126 starting with 700 mg of activated 3-({1-[bis(4-chlorophenyl)methyl]azetidin-3-ylidene}methanesulfonylmethyl)benzoic acid on TFP resin (770 µM), 0.324 cm$^3$ of triethylamine and 0.25 cm$^3$ of 2-(aminomethyl)-N-ethylpyrrolidine. 370 mg of a solid are thus obtained, which solid is purified by chromatography under nitrogen pressure (0.7 bar) on 100 cm$^3$ of silica (0.040–0.063 mm) contained in a column 2.5 cm in diameter, eluting with a methanol-dichloromethane mixture (15-85 by volume). The fractions containing only the desired product are combined and concentrated to dryness under reduced pressure (0.27 kPa) at 40° C. for 2 hours. 160 mg of 3-({1-[bis(4-chlorophenyl)methyl]azetidin-3-ylidene}methanesulfonylmethyl)-N-(1-ethylpyrrolidin-2-ylmethyl)benzamide are thus obtained in the form of a pale yellow powder [$^1$H NMR spectrum (400 MHz, (CD$_3$)$_2$SO-d6, δ in ppm): 1.04 (t, J=7 Hz, 3H), from 1.50 to 1.70 (mt, 3H), 1.78 (mt, 1H), 2.14 (mt, 1H), 2.28 (mt, 1H), 2.59 (mt, 1H), 2.83 (mt, 1H), 2.98 (s, 3H), from 3.00 to 3.15 (mt, 2H), from 3.30 to 3.45 (mt, 1H), 3.82 (mt, 2H), 4.23 (mt, 2H), 4.79 (s, 1H), 7.36 (d, J=8.5 Hz, 4H), 7.46 (d, J=8.5 Hz, 4H), from 7.50 to 7.60 (mt, 2H), 7.86 (broad s, 1H), 7.85 (broad d, J=8 Hz, 1H), 8.41 (t, J=6 Hz, 1H)].

EXAMPLE 135

The operation is carried out under the conditions described in Example 124 starting with 110 mg of activated 3-({1-[bis(4-chlorophenyl)methyl]azetidin-3-ylidene}methanesulfonylmethyl)benzoic acid on TFP resin (121 µM) and 0.023 cm$^3$ of neopentylamine. 69 mg of 3-({1-[bis(4-chlorophenyl)methyl]azetidin-3-ylidene}methanesulfonylmethyl)-N-(2,2-dimethylpropyl)benzamide are thus obtained in the form of a pale yellow powder [$^1$H NMR spectrum (400 MHz, (CD$_3$)$_2$SO-d6, δ in ppm): 0.90 (s, 9H), 2.98 (s, 3H), 3.11 (d, J=6.5 Hz, 2H), 3.82 (mt, 2H), 4.23 (mt, 2H), 4.79 (s, 1H), 7.36 (d, J=8 Hz, 4H), 7.46 (d, J=8 Hz, 4H), from 7.45 to 7.60 (mt, 2H), 7.83 (broad s, 1H), 7.86 (broad d, J=8 Hz, 1H), 8.37 (t, J=6.5 Hz, 1H)].

EXAMPLE 136

The operation is carried out under the conditions described in Example 124 starting with 110 mg of activated 3-({1-[bis(4-chlorophenyl)methyl]azetidin-3-ylidene}methanesulfonylmethyl)benzoic acid on TFP resin (121 µM) and 0.025 cm$^3$ of aminomethylcyclohexane. 44 mg of 3-({1-[bis(4-chlorophenyl)methyl]azetidin-3-ylidene}methanesulfonylmethyl)-N-cyclohexylmethylbenzamide are thus obtained in the form of a pale yellow powder whose characteristics are the following [$^1$H NMR spectrum (400 MHz, (CD$_3$)$_2$SO-d6, δ in ppm): 0.92 (mt, 2H), 1.17 (mt, 4H), from 1.45 to 1.80 (mt, 5H), 2.97 (s, 3H), 3.10 (d, J=6 Hz, 2H), 3.80 (mt, 2H), 4.23 (mt, 2H), 4.79 (s, 1H), 7.36 (d, J=8 Hz, 4H), 7.46 (d, J=8 Hz, 4H), from 7.45 to 7.60 (mt, 2H), 7.83 (broad s, 1H), 7.86 (broad d, J=8 Hz, 1H), 8.47 (t, J=6 Hz, 1H)].

EXAMPLE 137

The operation is carried out under the conditions described in Example 124 starting with 110 mg of activated 3-({1-[bis(4-chlorophenyl)methyl]azetidin-3-ylidene}methanesulfonylmethyl)benzoic acid on TFP resin (121 µM), 0.026 cm$^3$ of triethylamine and 21 mg of aminomethylcyclopropane hydrochloride. 68 mg of 3-({1-[bis(4-chlorophenyl)methyl]azetidin-3-ylidene}methanesulfonylmethyl)-N-cyclopropylmethylbenzamide are thus obtained in the form of a yellow foam [$^1$H NMR spectrum (400 MHz, (CD$_3$)$_2$SO-d6, δ in ppm): 0.24 (mt, 2H), 0.44 (mt, 2H), 1.03 (mt, 1H), 2.98 (s, 3H), 3.15 (t, J=6 Hz, 2H), 3.82 (mt, 2H), 4.23 (mt, 2H), 4.79 (s, 1H), 7.36 (d, J=8.5 Hz, 4H), 7.46 (d, J=8.5 Hz, 4H), from 7.50 to 7.60 (mt, 2H), 7.86 (broad s, 1H), 7.89 (broad d, J=8 Hz, 1H), 8.64 (t, J=6 Hz, 1H)].

EXAMPLE 138

The operation is carried out under the conditions described in Example 124 starting with 110 mg of activated 3-({1-[bis(4-chlorophenyl)methyl]azetidin-3-ylidene}methanesulfonylmethyl)benzoic acid on TFP resin (121 µM) and 0.023 cm$^3$ of 2-methylbutylamine. 49 mg of 3-({1-[bis(4-chlorophenyl)methyl]azetidin-3-ylidene}methanesulfonylmethyl)-N-(2-methylbutyl)benzamide are thus obtained [$^1$H NMR spectrum (400 MHz, (CD$_3$)$_2$SO-d6, δ in ppm): from 0.80 to 0.95 (mt, 6H), from 1.05 to 120 (mt, 1H), 1.41 (mt, 1H), 1.64 (mt, 1H), 2.98 (s, 3H), 3.06 (mt, 1H), 3.19 (mt, 1H), 3.81 (mt, 2H), 4.23 (mt, 2H), 4.79 (s, 1H), 7.36 (d, J=8 Hz, 4H), 7.46 (d, J=8 Hz, 4H), from 7.35 to 7.60 (mt, 2H), 7.84 (broad s, 1H), 7.87 (broad d, J=8 Hz, 1H), 8.49 (t, J=5.5 Hz, 1H)].

EXAMPLE 139

The operation is carried out under the conditions described in Example 124 starting with 110 mg of activated 3-({1-[bis(4-chlorophenyl)methyl]azetidin-3-ylidene}methanesulfonylmethyl)benzoic acid on TFP resin (121 µM) and 0.028 cm$^3$ of 2-methylphenethylamine. 42 mg of 3-({1-[bis(4-chlorophenyl)methyl]azetidin-3-ylidene}methanesulfonylmethyl)-N-(2-phenylpropyl)benzamide are thus obtained in the form of a yellow paste [$^1$H NMR spectrum (400 MHz, (CD$_3$)$_2$SO-d6, δ in ppm): 1.24 (d, J=7 Hz, 3H), 2.97 (s, 3H), 3.07 (mt, 1H), from 3.20 to 3.50 (mt, 2H), 3.80 (mt, 2H), 4.23 (mt, 2H), 4.80 (s, 1H), from 7.10 to 7.40 (mt, 5H), 7.38 (d, J=8 Hz, 4H), 7.47 (d, J=8 Hz, 4H), from 7.50 to 7.60 (mt, 2H), 7.77 (broad s, 1H), 7.79 (broad d, J=8 Hz, 1H), 8.55 (t, J=6 Hz, 1H)].

EXAMPLE 140

The operation is carried out under the conditions described in Example 124 starting with 110 mg of activated 3-({1-[bis(4-chlorophenyl)methyl]azetidin-3-ylidene}methanesulfonylmethyl)benzoic acid on TFP resin (121 µM) and 0.020 cm$^3$ of tetrahydrofurfurylmethylamine. 42 mg of 3-({1-[bis(4-chlorophenyl)methyl]azetidin-3- ylidene}methanesulfonylmethyl)-N-(tetrahydrofuran-2-ylmethyl)benzamide are thus obtained in the form of a yellow paste [$^1$H NMR spectrum (400 MHz, (CD$_3$)$_2$SO-d6, δ in ppm): 1.58 (mt, 1H), from 1.75 to 2.00 (mt, 3H), 2.98 (s, 3H), from 3.20 to 3.40 (mt, 2H), 3.63 (mt, 1H), 3.77 (mt, 1H), 3.82 (mt, 2H), 3.98 (mt, 1H), 4.23 (mt, 2H), 4.79 (s, 1H), 7.36 (d, J=8 Hz, 4H), 7.46 (d, J=8 Hz, 4H), from 7.50 to 7.60 (mt, 2H), 7.84 (broad s, 1H), 7.88 (broad d, J=8 Hz, 1H), 8.60 (t, J=6 Hz, 1H)].

EXAMPLE 141

The operation is carried out under the conditions described in Example 124 starting with 110 mg of activated 3-({1-[bis(4-chlorophenyl)methyl]azetidin-3-ylidene}methanesulfonylmethyl)benzoic acid on TFP resin (121 µM) and 39 mg of 2,2-diphenylethylamine. 39 mg of 3-({1-[bis(4-chlorophenyl)methyl]azetidin-3-ylidene}methanesulfonylmethyl)-N-(2,2-diphenylethyl)benzamide are thus obtained in the form of a yellow paste [$^1$H NMR spectrum (400 MHz, (CD$_3$)$_2$SO-d6, δ in ppm): 2.95 (s, 3H), 3.77 (mt, 2H), 3.90 (dd, J=8 and 6.5 Hz, 2H), 4.22 (mt, 2H), 4.42 (t, J=8 Hz, 1H), 4.79 (s, 1H), from 7.10 to 7.40 (mt, 10H), 7.38 (d, J=8.5 Hz, 4H), from 7.45 to 7.60 (mt, 2H), 7.48 (d, J=8.5 Hz, 4H), 7.70 (mt, 2H), 8.56 (t, J=6.5 Hz, 1H)].

EXAMPLE 142

The operation is carried out under the conditions described in Example 124 starting with 110 mg of activated 3-({1-[bis(4-chlorophenyl)methyl]azetidin-3-ylidene}methanesulfonylmethyl)benzoic acid on TFP resin (121 µM) and 19 mg of 2-ethylbutylamine. 47 mg of 3-({1-[bis(4-chlorophenyl)methyl]azetidin-3-ylidene}methanesulfonylmethyl)-N-(2-ethylbutyl)benzamide are thus obtained in the form of a pale yellow powder [$^1$H NMR spectrum (400 MHz, (CD$_3$)$_2$SO-d6, δ in ppm): 0.86 (t, J=7 Hz, 6H), from 1.20 to 1.40 (mt, 4H), 1.50 (mt, 1H), 2.98 (s, 3H), 3.19 (t, J=6 Hz, 2H), 3.82 (mt, 2H), 4.24 (mt, 2H), 4.79 (s, 1H), 7.36 (d, J=8.5 Hz, 4H), 7.46 (d, J=8.5 Hz, 4H), from 7.45 to 7.60 (mt, 2H), 7.83 (broad s, 1H), 7.86 (broad d, J=8 Hz, 1H), 8.42 (t, J=6 Hz, 1H)].

EXAMPLE 143

The operation is carried out under the conditions described in Example 124 starting with 110 mg of activated 3-({1-[bis(4-chlorophenyl)methyl]azetidin-3-ylidene}methanesulfonylmethyl)benzoic acid on TFP resin (121 µM), 0.026 cm$^3$ of triethylamine and 39 mg of 4-aminomethylcyclohexanecarboxylic acid methyl ester hydrochloride. 47 mg of 4-{[3-({1-[bis-(4-chlorophenyl)methyl]azetidin-3-ylidene}methanesulfonylmethyl)benzoylamino]methyl}cyclohexanecarboxylic acid methyl ester are thus obtained in the form of a pale yellow paste [$^1$H NMR spectrum (400 MHz, (CD$_3$)$_2$SO-d6, δ in ppm): from 0.90 to 1.05 (mt, 2H), from 1.20 to 1.40 (mt, 2H), 1.52 (mt, 1H), from 1.70 to 2.00 (mt, 4H), 2.27 (mt, 1H), 2.98 (s, 3H), 3.12 (t, J=6.5 Hz, 2H), 3.60 (s, 3H), 3.80 (mt, 2H), 4.23 (mt, 2H), 4.79 (s, 1H), 7.36 (d, J=8 Hz, 4H), 7.46 (d, J=8 Hz, 4H), from 7.45 to 7.60 (mt, 2H), 7.83 (broad s, 1H), 7.87 (broad d, J=8 Hz, 1H), 8.50 (t, J=6 Hz, 1H)].

Activated 3-({1-[bis(4-chlorophenyl)methyl]azetidin-3-ylidene}methanesulfonylmethyl)benzoic acid on TFP resin may be prepared under the following conditions: 1.18 g of 3-({1-[bis(4-chlorophenyl)methyl]azetidin-3-ylidene}methanesulfonylmethyl)benzoic acid is added, at the same temperature, to a suspension of 1.07 g of TFP resin (free phenol function, 1.1 mmol/g, that is to say 1.17 mM) in 15 cm$^3$ of anhydrous dimethylformamide, prestirred for 10 minutes at a temperature close to 20° C. After stirring for 10 minutes at a temperature close to 20° C., 14 mg of 4-dimethylaminopyridine are added and then after stirring for 10 minutes at the same temperature, 0.185 cm$^3$ of 1,3-diisopropylcarbodiimide. After stirring for 23 hours at a temperature close to 20° C., the suspension is filtered and the resin is washed with 45 cm$^3$ of dimethylformamide, 45 cm$^3$ of tetrahydrofuran, 45 cm$^3$ of dichloromethane, and then dried under vacuum to constant weight. 1.5 g of activated 3-({1-[bis(4-chlorophenyl)methyl]azetidin-3-ylidene}methanesulfonylmethyl)benzoic acid on TFP resin are thus obtained in the form of a pale yellow resin.

The TFP resin (structure below) may be prepared in the following manner:

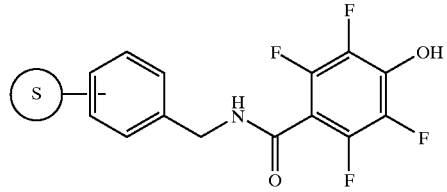

492 mg of diisopropylcarbodiimide, 819.3 mg of 2,3,5,6-tetrafluoro-4-hydroxybenzoic acid and 50 mg of 4-dimethylaminopyridine are successively added to a suspension of 2 g of commercially available aminomethyl polystyrene resin (0.39 mmol/g; 0.78 mmol) in 15 cm$^3$ of dimethylformamide, prestirred for 5 minutes at a temperature close to 20° C. After stirring for about 20 hours at a temperature close to 20° C., the suspension is filtered and the resin is rinsed with three times 20 cm$^3$ of dimethylformamide, three times 20 cm$^3$ of tetrahydrofuran and three times 20 cm$^3$ of dichloromethane. The resin obtained is dried under reduced pressure at a temperature close to 40° C. The resin obtained is then stirred, at a temperature close to 20° C., for about 20 hours, in suspension in a piperidine/dimethylformamide mixture (10/90 by volume). The suspension is filtered and the resin is rinsed with three times 20 cm$^3$ of dimethylformamide, three times 20 cm$^3$ of tetrahydrofuran and three times 20 cm$^3$ of dichloromethane. The resin obtained is dried under reduced pressure at a temperature close to 40° C. and is used as it is.

EXAMPLE 144

A solution of 76 mg of (2-{4-[3-({1-[bis-(4-chlorophenyl)methyl]azetidin-3-ylidene}methanesulfonylmethyl)phenyl]piperazin-1-yl}-2-oxoethyl)carbamic acid tert-butyl ester in 2.5 cm$^3$ of formic acid is stirred for 1 hour at a temperature close to 45° C. The reaction medium is concentrated to dryness under reduced pressure (5 kPa) at a temperature close to 30° C., taken up in 10 cm$^3$ of ethyl acetate and alkalinized with 10 cm$^3$ of a saturated aqueous sodium bicarbonate solution. After separating after settling out, the organic phase is washed with 10 cm$^3$ of water, dried over magnesium sulfate, filtered and concentrated to dryness under reduced pressure (1 kPa) at a temperature close to 40° C. 51 mg of 2-amino-1-{4-[3-({1-[bis-(4-chlorophenyl)methyl]azetidin-3-ylidene}methanesulfonylmethyl)phenyl]piperazin-1-yl}ethanone are thus obtained in the form of a beige lacquer [$^1$H NMR spectrum (300 MHz, CDCl$_3$, δ in ppm): from 1.95 to 2.25 (broad unresolved complex, 2H), 2.77 (s, 3H), from 3.10 to 3.30 (mt, 4H), from 3.50 to 3.60 (mt, 2H), 3.56 (broad s, 2H), from 3.75 to 3.90 (mt, 4H), 4.34 (mt, 2H), 4.50 (s, 1H), 6.84 (broad d, J=8 Hz, 1H), 6.91 (dd, J=8 and 2 Hz, 1H), 7.01 (mt, 1H), from 7.20 to 7.40 (mt, 9H)].

EXAMPLE 145

1.02 g of supported EDCI (5 mM), 44 mg of N-Boc-glycine and then 10 cm³ of dichloromethane are successively added, at a temperature close to 20° C., to 108.5 mg of 1-[3-({1-[bis-(4-chlorophenyl)methyl]azetidin-3-ylidene}methanesulfonylmethyl)phenyl]piperazine. After stirring for 20 hours at a temperature close to 20° C., the reaction mixture is filtered on sintered glass. The resin is rinsed with three times 5 cm³ of dichloromethane. The combined filtrates are washed with 20 cm³ of water, dried over magnesium sulfate, filtered on sintered glass and concentrated to dryness under reduced pressure (1 kPa) at a temperature close to 40° C. 143 mg of (2-{4-[3-({1-[bis-(4-chlorophenyl)methyl]azetidin-3-ylidene}methanesulfonylmethyl)phenyl]piperazin-1-yl}-2-oxoethyl)carbamic acid tert-butyl ester are thus obtained in the form of a cream-colored lacquer [¹H NMR spectrum (400 MHz, (CD₃)₂SO-d6, δ in ppm): 1.40 (s, 9H), 2.93 (s, 3H), from 3.05 to 3.20 (mt, 4H), 3.57 (mt, 4H), 3.80 (mt, 2H), 3.84 (d, J=6 Hz, 2H), 4.19 (mt, 2H), 4.78 (s, 1H), 6.79 (t, J=6 Hz, 1H), 6.82 (d, J=8 Hz, 1H), 6.93 (broad s, 1H), 6.99 (dd, J=8 and 2.5 Hz, 1H), 7.27 (t, J=8 Hz, 1H), 7.36 (d, J=8 Hz, 4H), 7.46 (d, J=8 Hz, 4H)].

The supported EDCI reagent is commercially available and may also be prepared according to the following reference: M. Desai, L. Stramiello, *Tetrahedron Letters*, 34, 48, 7685–7688 (1993).

EXAMPLE 146

A solution of 81 mg of (2-{4-[3-({1-[bis-(4-chlorophenyl)methyl]azetidin-3-ylidene}methanesulfonylmethyl)phenyl]piperazin-1-yl}-2-oxoethyl)-N-methylcarbamic acid tert-butyl ester in 2.5 cm³ of formic acid is stirred for 1 hour at a temperature close to 45° C. The reaction mixture is concentrated to dryness under reduced pressure (5 kPa) at a temperature close to 30° C., taken up in 10 cm³ of ethyl acetate and alkalinized with 10 cm³ of a saturated aqueous sodium bicarbonate solution. After separating after settling out, the organic phase is washed with 10 cm³ of water, dried over magnesium sulfate, filtered and concentrated to dryness under reduced pressure (1 kPa) at a temperature close to 40° C. 58 mg of 1-{4-[3-({1-[bis-(4-chlorophenyl)methyl]azetidin-3-ylidene}methanesulfonylmethyl)phenyl]piperazin-1-yl}-2-methylaminoethanone are thus obtained in the form of a beige lacquer [¹H NMR spectrum (300 MHz, CDCl₃), δ in ppm): from 1.95 to 2.15 (broad unresolved complex, 1H), 2.51 (broad s, 3H), 2.77 (s, 3H), from 3.10 to 3.30 (mt, 4H), 3.49 (broad s, 2H), 3.58 (mt, 2H), from 3.75 to 3.90 (mt, 4H), 4.33 (mt, 2H), 4.49 (s, 1H), 6.83 (broad d, J=8 Hz, 1H), 6.90 (dd, J=8 and 2 Hz, 1H), 7.00 (mt, 1H), from 7.20 to 7.40 (mt, 9H)].

EXAMPLE 147

1.02 g of supported EDCI (5 mM), 47.3 mg of N-Boc-sarcosine and then 10 cm³ of dichloromethane are successively added, at a temperature close to 20° C., to 108.5 mg of 1-[3-({1-[bis-(4-chlorophenyl)methyl]azetidin-3-ylidene}methanesulfonylmethyl)phenyl]piperazine. After stirring for 20 hours at a temperature close to 20° C., the reaction mixture is filtered on sintered glass. The resin is rinsed with three times 5 cm³ of dichloromethane. The combined filtrates are washed with 20 cm³ of water, dried over magnesium sulfate, filtered on sintered glass and concentrated to dryness under reduced pressure (1 kPa) at a temperature close to 40° C. 143 mg of (2-{4-[3-({1-[bis-(4-chlorophenyl)methyl]azetidin-3-ylidene}methanesulfonylmethyl)phenyl]piperazin-1-yl}-2-oxoethyl)-N-methylcarbamic acid tert-butyl ester are thus obtained in the form of a cream-colored lacquer [¹H NMR spectrum (400 MHz, (CD₃)₂SO-d6, δ in ppm). A mixture of rotamers is observed at room temperature; 1.31 and 1.41 (2s, 9H in total), 2.78 and 2.81 (2s, 3H in total), 2.93 (2s, 3H), from 3.10 to 3.25 (unresolved complex, 4H), from 3.45 to 3.65 (mt, 4H), 3.80 (mt, 2H), 4.06 and 4.09 (2s, 2H in total), 4.19 (mt, 2H), 4.78 (s, 1H), 6.83 (broad d, J=8 Hz, 1H), 6.93 (broad s, 1H), 7.00 (dd, J=8 and 2.5 Hz, 1H), 7.27 (t, J=8 Hz, 1H), 7.36 (d, J=8 Hz, 4H), 7.46 (d, J=8 Hz, 4H)].

EXAMPLE 148

2 cm³ of dichloromethane and then 11 mg of methyl isothiocyanate are successively added, at a temperature close to 20° C., to 54.25 mg of 1-[3-({1-[bis-(4-chlorophenyl)methyl]azetidin-3-ylidene}methanesulfonylmethyl)phenyl]piperazine. After stirring for 6 hours at a temperature close to 20° C., 0.05 cm³ of water is added to the reaction mixture. After stirring for 15 minutes at the same temperature, the reaction medium is dried over magnesium sulfate, filtered and concentrated to dryness under reduced pressure (1 kPa) at a temperature close to 40° C. 61 mg of 4-[3-({1-[bis-(4-chlorophenyl)methyl]azetidin-3-ylidene}methanesulfonylmethyl)phenyl]piperazine-1-carbothioic acid N-methylamide are thus obtained in the form of a beige lacquer [¹H NMR spectrum (400 MHz, CDCl₃), δ in ppm): 2.77 (s, 3H), 3.20 (d, J=5 Hz, 3H), 3.32 (t, J=5.5 Hz, 4H), 3.81 (mt, 2H), 4.00 (t, J=5.5 Hz, 4H), 4.33 (mt, 2H), 4.49 (s, 1H), 5.63 (broad q, J=5 Hz, 1H), 6.80 (d, J=8 Hz, 1H), 6.85 (dd, J=8 and 2.5 Hz, 1H), 6.94 (broad s, 1H), from 7.20 to 7.30 (mt, 5H), 7.32 (d, J=8 Hz, 4H)].

EXAMPLE 149

2 cm³ of dichloromethane and then 11.5 mg of methyl isocyanate are successively added, at a temperature close to 20° C., to 54.25 mg of 1-[3-({1-[bis-(4-chlorophenyl)methyl]azetidin-3-ylidene}methanesulfonylmethyl)phenyl]piperazine. After stirring for 4 hours at a temperature close to 20° C., 0.05 cm³ of water is added to the mixture. After stirring for 15 minutes at the same temperature, the reaction medium is dried over magnesium sulfate, filtered on paper and concentrated to dryness under reduced pressure (1 kPa) at a temperature close to 40° C. 66 mg of 4-[3-({1-[bis-(4-chlorophenyl)methyl]azetidin-3-ylidene}methanesulfonylmethyl)phenyl]piperazine-1-carboxylic acid N-methylamide are thus obtained in the form of a beige lacquer [¹H NMR spectrum (400 MHz, CDCl₃), δ in ppm): 2.75 (s, 3H), 2.85 (d, J=5 Hz, 3H), 3.19 (broad t, J=5.5 Hz, 4H), 3.52 (broad t, J=5.5 Hz, 4H), 3.80 (mt, 2H), 4.33 (mt, 2H), 4.45 (broad q, J=5 Hz, 1H), 4.49 (s, 1H), 6.81 (d, J=8 Hz, 1H), 6.89 (dd, J=8 and 2.5 Hz, 1H), 6.98 (broad s, 1H), from 7.20 to 7.30 (mt, 5H), 7.32 (d, J=8 Hz, 4H)].

EXAMPLE 150

2 cm³ of pyridine and then 10.4 mg of methyl chloroformate are successively added, at a temperature close to 20° C., to 54.25 mg of 1-[3-({1-[bis-(4-chlorophenyl)methyl]azetidin-3-ylidene}methanesulfonylmethyl)phenyl]piperazine. After stirring for 6 hours at a temperature close to 20° C., the reaction medium is concentrated to dryness under reduced pressure (5 kPa) at a temperature close to 30° C. The residue obtained is taken up in 5 cm$^3$ of ethyl acetate and 5 cm$^3$ of water. After separating after settling out, the organic phase is washed with 2 cm$^3$ of water, dried over magnesium sulfate, filtered and concentrated to dryness under reduced pressure (1 kPa) at a temperature close to 40° C. 62 mg of 4-[3-({1-[bis-(4-chlorophenyl)methyl]azetidin-3-ylidene}methanesulfonylmethyl)phenyl]piperazine-1-carboxylic acid methyl ester are thus obtained in the form of a beige lacquer [$^1$H NMR spectrum (400 MHz, CDCl$_3$), δ in ppm): 2.75 (s, 3H), 3.15 (broad t, J=5.5 Hz, 4H), 3.62 (mt, 4H), 3.74 (s, 3H), 3.80 (mt, 2H), 4.32 (mt, 2H), 4.49 (s, 1H), 6.81 (d, J=8 Hz, 1H), 6.90 (dd, J=8 and 2.5 Hz, 1H), 6.99 (broad s, 1H), from 7.20 to 7.40 (mt, 9H)].

EXAMPLE 151

32 mg of sodium acetoxyborohydride and then 22 mg of isobutyraldehyde are successively added, at a temperature close to 20° C., to a solution of 54.25 mg of 1-[3-({1-[bis-(4-chlorophenyl)methyl]azetidin-3-ylidene}methanesulfonylmethyl)phenyl]piperazine in 2 cm$^3$ of 1,2-dichloroethane. After stirring for 4 hours at a temperature close to 20° C., 3 cm$^3$ of dichloromethane and 2 cm$^3$ of a saturated aqueous sodium bicarbonate solution are added to the reaction medium. After separating after settling out, the organic [lacuna] is dried over magnesium sulfate, filtered and concentrated to dryness under reduced pressure (1 kPa) at a temperature close to 40° C. 63 mg of 1-[3-({1-[bis-(4-chlorophenyl)methyl]azetidin-3-ylidene}methanesulfonylmethyl)phenyl]-4-isobutylpiperazine are thus obtained in the form of a beige lacquer [$^1$H NMR spectrum (400 MHz, CDCl$_3$), δ in ppm): 0.92 (d, J=7 Hz, 6H), 1.82 (mt, 1H), 2.14 (d, J=8 Hz, 2H), 2.54 (t, J=5.5 Hz, 4H), 2.75 (s, 3H), 3.18 (t, J=5.5 Hz, 4H), 3.81 (mt, 2H), 4.32 (mt, 2H), 4.49 (s, 1H), 6.78 (d, J=8 Hz, 1H), 6.89 (dd, J=8 and 2.5 Hz, 1H), 6.97 (broad s, 1H), from 7.15 to 7.30 (mt, 5H), 7.32 (d, J=8 Hz, 4H)].

EXAMPLE 152

32 mg of sodium acetoxyborohydride and then 13 mg of acetaldehyde are successively added, at a temperature close to 20° C., to a solution of 54 mg of 1-[3-({1-[bis-(4-chlorophenyl)methyl]azetidin-3-ylidene}methanesulfonylmethyl)phenyl]piperazine in 2 cm$^3$ of 1,2-dichloroethane. After stirring for 21 hours at a temperature close to 20° C., 2 cm$^3$ of a saturated aqueous sodium bicarbonate solution are added to the reaction medium. After separating after settling out, the aqueous phase is reextracted with 2 cm$^3$ of dichloromethane. The pooled organic phases are dried over magnesium sulfate, filtered and concentrated to dryness under reduced pressure (1 kPa) at a temperature close to 20° C. 60 mg of a solid residue are thus obtained, which residue is taken up in 2 cm$^3$ of methanol and 0.5 cm$^3$ of dichloromethane. The solution obtained is deposited on a silica catridge (500 mg of SCX phase). The cartridge is washed with 5 cm$^3$ of methanol and then the expected product is eluted with 5 cm$^3$ of ammoniacal methanol (2 N) and then with an additional 5 cm$^3$ of methanol. The filtrate is concentrated to dryness under reduced pressure (1 kPa) at a temperature close to 30° C. 42 mg of 1-[3-({1-[bis-(4-chlorophenyl)methyl]azetidin-3-ylidene}methanesulfonylmethyl)phenyl]-4-ethylpiperazine are thus obtained in the form of a colorless lacquer [$^1$H NMR spectrum (300 MHz, CDCl$_3$) δ in ppm): 1.14 (t, J=7.5 Hz, 3H), 2.48 (q, J=7.5 Hz, 2H), 2.60 (broad t, J=5 Hz, 4H), 2.77 (s, 3H), 3.22 (broad t, J=5 Hz, 4H), 3.82 (mt, 2H), 4.33 (mt, 2H), 4.49 (s, 1H), 6.79 (broad d, J=8 Hz, 1H), 6.91 (dd, J=8 and 2 Hz, 1H), 6.98 (mt, 1H), from 7.20 to 7.40 (mt, 9H)].

EXAMPLE 153

2 cm$^3$ of pyridine and then 11.5 mg of acetic anhydride are successively added, at a temperature close to 20° C., to 54 mg of 1-[3-({1-[bis-(4-chlorophenyl)methyl]azetidin-3-ylidene}methanesulfonylmethyl)phenyl]piperazine. After stirring for 23 hours at a temperature close to 20° C., the reaction medium is concentrated to dryness under reduced pressure (1 kPa) at a temperature close to 30° C. The residue obtained is taken up in 5 cm$^3$ of ethyl acetate and 2 cm$^3$ of water. After separating after settling out, the organic phase is washed with 2 cm$^3$ of water, dried over magnesium sulfate, filtered and concentrated to dryness under reduced pressure (1 kPa) at a temperature close to 40° C. 52 mg of 4-acetyl 1-[3-({1-[bis-(4-chlorophenyl)methyl]azetidin-3-ylidene}methanesulfonylmethyl)phenyl]piperazine are thus obtained in the form of a beige foam [$^1$H NMR spectrum (300 MHz, CDCl$_3$), δ in ppm): 2.16 (s, 3H), 2.77 (s, 3H), from 3.10 to 3.25 (mt, 4H), 3.63 (broad t, J=5.5 Hz, 2H), 3.78 (broad t, J=5.5 Hz, 2H), 3.82 (mt, 2H), 4.34 (mt, 2H), 4.50 (s, 1H), 6.84 (broad d, J=8 Hz, 1H), 6.92 (dd, J=8 and 2 Hz, 1H), 7.02 (mt, 1H), from 7.20 to 7.40 (mt, 9H)].

EXAMPLE 154

511 mg of supported EDCI (2.5 mM), 11.5 mg of N,N-dimethylglycine and then 5 cm$^3$ of dichloromethane are successively added, at a temperature close to 20° C., to 54 mg of 1-[3-({1-[bis-(4-chlorophenyl)methyl]azetidin-3-ylidene}methanesulfonylmethyl)phenyl]piperazine. After stirring for 24 hours at a temperature close to 20° C., 35 mg of N,N-dimethylglycine are added. After stirring for 96 hours at a temperature close to 20° C., the reaction mixture is filtered on sintered glass. The resin is rinsed with three times 2.5 cm$^3$ of dichloromethane. The combined filtrates are washed with 10 cm$^3$ of water, dried over magnesium sulfate, filtered and concentrated to dryness under reduced pressure (5 kPa) at a temperature close to 20° C. 53 mg of 1-{4-[3-({1-[bis-(4-chlorophenyl)methyl]azetidin-3-ylidene}methanesulfonylmethyl)phenyl]piperazin-1-yl}-2-dimethylaminoethanone are thus obtained in the form of a beige foam [$^1$H NMR spectrum (400 MHz, (CD$_3$)$_2$SO-d6, δ in ppm): 2.20 (s, 6H), 2.94 (s, 3H), 3.12 (s, 2H), 3.16 (mt, 4H), 3.58 (mt, 2H), 3.68 (mt, 2H), 3.80 (mt, 2H), 4.19 (mt, 2H), 4.78 (s, 1H), 6.81 (broad d, J=8 Hz, 1H), 6.93 (broad s, 1H), 6.99 (dd, J=8 and 2.5 Hz, 1H), 7.26 (t, J=8 Hz, 1H), 7.36 (d, J=8 Hz, 4H), 7.46 (d, J=8 Hz, 4H)].

EXAMPLE 155

A solution of 320 mg of 4-[3-({1-[bis-(4-chlorophenyl) methyl]azetidin-3-ylidene}methanesulfonylmethyl)phenyl] piperazine-1-carboxylic acid tert-butyl ester in 5 cm$^3$ of formic acid is stirred for 5 hours at a temperature close to 20° C., and then for 1 hour at a temperature close to 45° C. The reaction medium is concentrated to dryness under reduced pressure (5 kPa) at a temperature close to 30° C., taken up in 20 cm$^3$ of ethyl acetate and alkalinized with 10 cm$^3$ of a saturated aqueous sodium bicarbonate solution. After separating after settling out, the organic phase is washed with three times 10 cm$^3$ of water, dried over magnesium sulfate, filtered and concentrated to dryness under reduced pressure (1 kPa) at a temperature close to 40° C. The residue obtained is purified by depositing, in solution in a minimum of dichloromethane, on silica gel deposited on a plate [(gel 0.5 mm thick, 5 plates of 20 ⊕ 20 cm, eluent: dichloromethane-methanol (80-20 by volume)]. The zone corresponding to the adsorbed desired product, located with UV rays, is scraped and the silica recovered is washed on sintered glass with a dichloromethanemethanol mixture (75-25 by volume). The filtrates are combined and concentrated to dryness under reduced pressure (1 kPa) at a temperature close to 30° C. 180 mg of 1-[3-({1-[bis-(4-chlorophenyl)methyl]azetidin-3-ylidene}methanesulfonylmethyl)phenyl]piperazine are thus obtained in the form of a white powder [$^1$H NMR spectrum (300 MHz, CDCl$_3$, δ in ppm): 2.77 (s, 3H), 3.05 (mt, 4H), 3.16 (mt, 4H), 3.81 (mt, 2H), 4.33 (mt, 2H), 4.49 (s, 1H), 6.79 (broad d, J=8 Hz, 1H), 6.90 (dd, J=8 and 2.5 Hz, 1H), 6.98 (mt, 1H), from 7.20 to 7.40 (mt, 9H)].

4-[3-({1-[bis-(4-chlorophenyl)methyl]azetidin-3-ylidene}methanesulfonylmethyl)phenyl]piperazine-1-carboxylic acid tert-butyl ester may be prepared in the following manner: on carrying out the operation according to the procedure of Example 4 starting with 1.32 g of 4-[3-({1-[bis-(4-chlorophenyl)methyl]-3-hydroxyazetidin-3-yl}methanesulfonylmethyl)phenyl]piperazine1-1-carboxylic acid tert-butyl ester, 0.232 cm$^3$ of methanesulfonyl chloride and 0.733 g of 4-dimethylaminopyridine, the residue obtained is purified by chromatography on a silica gel column (particle size 0.063–0.200 mm, diameter 2 cm, height 25 cm) at atmospheric pressure with a dichloromethane-methanol mixture (99.5-0.5 by volume) as eluent and collecting 15 cm$^3$ fractions. The fractions containing the desired product are combined and concentrated to dryness under reduced pressure (5 kPa) at a temperature close to 30° C. 0.86 g of 4-[3-({1-[bis-(4-chlorophenyl)methyl]azetidin-3-ylidene}methanesulfonylmethyl)phenyl]piperazine-1-carboxylic acid tert-butyl ester is thus obtained in the form of a white foam [$^1$H NMR spectrum (400 MHz, CDCl$_3$, δ in ppm): 1.50 (s, 9H), 2.77 (s, 3H), 3.14 (t, J=5 Hz, 4H), 3.57 (t, J=5 Hz, 4H), 3.81 (mt, 2H), 4.34 (mt, 2H) 4.49 (s, 1H), 6.81 (d, J=8 Hz, 1H), 6.90 (dd, J=8 and 2.5 Hz, 1H), 6.99 (broad s, 1H), from 7.20 to 7.30 (mt, 5H), 7.32 (d, J=8 Hz, 4H)].

4-[3-({1-[bis-(4-chlorophenyl)methyl]-3-hydroxyazetidin-3-yl}methanesulfonylmethyl)phenyl]piperazine-1-carboxylic acid tert-butyl ester may be prepared in the following manner: on carrying out the operation according to the procedure of Example 1 starting with 0.886 g of 4-(3-methanesulfonylmethylphenyl)piperazine-1-carboxylic acid tert-butyl ester, 0.765 g of 1-[bis-(4-chlorophenyl)methyl]azetidin-3-one and 1.72 cm$^3$ of a 1.6 M solution of n-butyllithium in hexane, 1.37 g of 4-[3-({1-[bis-(4-chlorophenyl)methyl]-3-hydroxyazetidin-3-yl}methanesulfonylmethyl)phenyl]piperazine-1-carboxylic acid tert-butyl ester are obtained in the form of a beige powder.

4-(3-Methanesulfonylmethylphenyl)piperazine-1-carboxylic acid tert-butyl ester may be prepared in the following manner: on carrying out the operation according to the procedure of Example 10 starting with 1.55 g of 4-(3-chloromethylphenyl)piperazine-1-carboxylic acid tert-butyl ester and 0.766 g of sodium methanesulfinate, 0.9 g of 4-(3-methanesulfonylmethylphenyl)piperazine-1-carboxylic acid tert-butyl ester is obtained in the form of a beige powder.

4-(3-Chloromethylphenyl)piperazine-1-carboxylic acid tert-butyl ester may be prepared in the following manner: by reacting 16.4 g of 4-(3-hydroxymethylphenyl)piperazine-1-carboxylic acid tert-butyl ester in 150 cm$^3$ of dichloromethane, at a temperature close to 20° C., with 29 cm$^3$ of diisopropylethylamine and 8.7 cm$^3$ of methanesulfonyl chloride, 15 g of 4-(3-chloromethylphenyl)piperazine-1-carboxylic acid tert-butyl ester are obtained in the form of a beige powder after purification on a chromatographic column (silica 0.063–0.200 mm, diameter 6 cm, height 45 cm, 100 cm$^3$ fractions), eluting with dichloromethane.

4-(3-Hydroxymethylphenyl)piperazine-1-carboxylic acid tert-butyl ester may be prepared in the following manner: by reacting 15.8 g of tert-butyl esters of 4-(3-butoxycarbonylphenyl)piperazine-1-carboxylic and 4-(3-n-butyloxycarbonylphenyl)piperazine-1-carboxylic acids in solution in 500 cm$^3$ of anhydrous THF, at a temperature close to –10° C., with 102 cm$^3$ of diisobutylaluminum hydride in solution in toluene (20% by weight), 12.8 g of 4-(3-hydroxymethylphenyl)piperazine-1-carboxylic acid tert-butyl ester are obtained in the form of a beige oil.

The mixture of tert-butyl esters of 4-(3-ethoxycarbonylphenyl)piperazine-1-carboxylic and 4-(3-n-butyloxycarbonylphenyl)piperazine-1-carboxylic acids may be prepared according to the method described in patent WO 9726250.

EXAMPLE 156

On carrying out the operation according to Example 38 (method 2) starting with 0.3 g of 3-acetoxy-1-[bis(4-methoxycarbonylphenyl)methyl]-3-[(3,5-difluorophenyl)(methylsulfonyl)methyl(RS)]azetidine and 105 mg of lithium hydroxide monohydrate in 10 cm$^3$ of acetonitrile, at a temperature close to 70° C., 0.24 g of 1-[bis(4-methoxycarbonylphenyl)methyl]-3-[(3,5-difluorophenyl)(methylsulfonyl)methylene]azetidine is obtained in the form of an orange-colored foam [$^1$H NMR spectrum (300 MHz, CDCl$_3$, δ in ppm): 2.81 (s, 3H), from 3.85 to 3.95 (mt, 2H), 3.89 (s, 6H), 4.37 (mt, 2H), 4.67 (s, 1H), 6.84 (tt, J=9 and 2.5 Hz, 1H), 6.99 (mt, 2H), 7.50 (d, J=8 Hz, 4H), 7.97 (d, J=8 Hz, 4H)].

EXAMPLE 157

On carrying out the operation according to the procedure of Example 40 starting with 4.45 g of (3,5-difluorobenzyl)methylsulfone, 6.36 g of 1-[bis(4-methoxycarbonylphenyl)methyl]azetidin-3-one, 2.18 cm$^3$ of acetyl chloride and 17 cm$^3$ of a 1.6 M solution of n-butyllithium in hexane, 10.8 g of 3-acetoxy-1-[bis(4-methoxycarbonylphenyl)methyl]-3-[(3,5-difluorophenyl)(methylsulfonyl)methyl(RS)]azetidine are obtained in the form of a pale yellow foam [$^1$H NMR spectrum (400 MHz, (CD$_3$)$_2$SO-d6, δ in ppm): 2.03 (s, 3H), 2.96 (s, 3H), from 3.25 to 3.40 (mt, 2H), 3.52 (broad d, J=8 Hz, 1H), from 3.75 to 3.90 (mt, 1H), 3.82 (s, 3H), 3.83 (s, 3H), 4.72 (s, 1H), 5.36 (s, 1H), 7.27 (d, J=8 Hz, 2H), from 7.35 to 7.45 (mt, 2H), 7.43 (d, J=8 Hz, 2H), 7.54 (tt, J=9.5 and 2.5 Hz, 1H), 7.81 (d, J=8 Hz, 2H), 7.88 (d, J=8 Hz, 2H)].

1-[bis(4-methoxycarbonylphenyl)methyl]azetidin-3-one may be prepared in the same manner as 1-{(R)-(4-chlorophenyl)[4-(methoxycarbonyl)phenyl]methyl}azetidin-3-one (Example 110) from 1-[bis(4-methoxycarbonylphenyl)methyl]azetidin-3-ol.

1-[bis(4-methoxycarbonylphenyl)methyl]azetidin-3-ol, may be prepared in the same manner as 1-{(R*)-(4-chlorophenyl)[4-(methoxycarbonyl)phenyl]methyl}azetidin-3-ol (Example 110) from bis(4-methoxycarbonylphenyl)methylamine.

Bis(4-methoxycarbonylphenyl)methylamine may be prepared in the same manner as methyl 4-[(RS)-amino-(4-chlorophenyl)methyl]benzoate (Example 87) from 4,4'-dimethoxycarbonylbenzophenone.

EXAMPLE 158

On carrying out the operation according to the procedure of Example 110 starting with 40 mg of (RS)-1-{[4-(chloromethyl)phenyl](4-chlorophenyl)methyl}-3-[(3,5-difluorophenyl)(methylsulfonyl)methyl)methylsulfonylmethylene]azetidine, 0.25 cm³ of dichloromethane and 0.0196 cm³ of morpholine, 35.8 mg of (RS)-4-[4-((4-chlorophenyl){3-[(3,5-difluorophenyl)methanesulfonylmethylene]azetidin-1-yl}methyl)benzyl]morpholine are obtained in the form of a white foam [¹H NMR spectrum (400 MHz, CDCl₃, δ in ppm): 2.41 (mt, 4H), 2.80 (s, 3H), 3.42 (s, 2H), 3.69 (t, J=4.5 Hz, 4H), 3.84 (mt, 2H), 4.33 (mt, 2H), 4.50 (s, 1H), 6.83 (tt, J=9 and 2.5 Hz, 1H), 6.98 (mt, 2H), from 7.20 to 7.40 (mt, 8H)].

(RS)-1-{[4-(chloromethyl)phenyl](4-chlorophenyl)methyl}-3-[(3,5-difluorophenyl)(methylsulfonyl)methyl)methylsulfonylmethylene]azetidine may be prepared in the following manner: on carrying out the operation according to Example 87 starting with 415 mg of (RS)-1-{(4-(chlorophenyl)[4-(hydroxymethyl)phenyl]methyl}-3-[(3,5-difluorophenyl)(methylsulfonyl)methylene]azetidine, 5 cm³ of dichloromethane, 0.19 cm³ of methanesulfonyl chloride and 0.53 cm³ of diisopropylethylamine, 421.2 mg of (RS)-1-{[4-(chloromethyl)phenyl](4-chlorophenyl)methyl}-3-[(3,5-difluorophenyl)(methylsulfonyl)methyl)methylsulfonylmethylene]azetidine are obtained in the form of a cream-colored foam.

EXAMPLE 159

25 mg of potassium carbonate and then 0.016 cm³ of morpholine are successively added, at a temperature close to 20° C., under an inert atmosphere of argon, to a solution of 33 mg of 1-benzhydryl-3-{[3-(4-bromobutoxy)phenyl]methanesulfonylmethylene}azetidine in 2 cm³ of anhydrous acetonitrile. After stirring for 17 hours at a temperature close to 20° C., the reaction medium is diluted with 10 cm³ of ethyl acetate and 4 cm³ of water. The separated organic phase is washed with 4 cm³ of a saturated aqueous sodium chloride solution, dried over magnesium sulfate, filtered on sintered glass and then concentrated to dryness under reduced pressure (1 kPa) at a temperature close to 40° C. The residue obtained is purified by depositing, in solution in a minimum of dichloromethane, on chromatography on silica gel deposited on a plate [(gel 0.5 mm thick, 2 plates of 20 ⌀ 20 cm, eluent: dichloromethane-methanol (92.5-7.5 by volume)]. The zone corresponding to the desired product adsorbed, located with UV rays, is scraped and the silica recovered is washed on sintered glass with a dichloromethane-methanol mixture (80-20 by volume). The filtrates are combined and concentrated to dryness under reduced pressure (1 kPa) at a temperature close to 40° C. 25.2 mg of 4-(4-{3-[(1-benzhydrylazetidin-3-ylidene)methanesulfonylmethyl]phenoxy}butyl)morpholine are obtained in the form of a pale yellow foam [¹H NMR spectrum (400 MHz, CDCl₃, δ in ppm): 1.66 (mt, 2H), 1.81 (mt, 2H), 2.40 (t, J=7.5 Hz, 2H), 2.46 (mt, 4H), 2.77 (s, 3H), 3.72 (t, J=5 Hz, 4H), 3.84 (mt, 2H), 3.96 (t, J=6.5 Hz, 2H), 4.36 (mt, 2H), 4.53 (s, 1H), 6.87 (dd, J=8 and 2 Hz, 1H), 6.93 (d, J=8 Hz, 1H), 6.96 (d, J=2 Hz, 1H), from 7.10 to 7.35 (mt, 7H), 7.42 (d, J=8 Hz, 4H)].

1-Benzhydryl-3-{[3-(4-bromobutoxy)phenyl]methanesulfonylmethylene}azetidine may be prepared in the following manner: 0.586 cm³ of 1,4-dibromobutane and 255 mg of potassium carbonate are successively added at a temperature close to 20° C., under an inert atmosphere of argon, to a solution of 500 mg of 1-benzhydryl-3-[(3-hydroxyphenyl)(methylsulfonyl)methylene]azetidine in 10 cm³ of methylethyl ketone. The reaction mixture is heated at the reflux temperature of the solvent, under an inert atomosphere of argon, for 7 hours and then left at a temperature close to 20° C. for about 4 days. The reaction mixture is filtered on sintered glass covered with celite. The solid residue is rinsed with ethyl acetate and then the filtrate is concentrated to dryness under reduced pressure (10 kPa) at a temperature close to 40° C. The brown oil obtained is purified by chromatography at atmospheric pressure on 40 g of silica (0.063–0.200 mm) contained in a column 3 cm in diameter, eluting with a methanol-dichloromethane mixture (0.5-99.5 by volume). The fractions (10 cm³) containing only the desired product are combined and concentrated to dryness under reduced pressure (0.27 kPa) at 40° C. for 2 hours, 408.4 mg of 1-benzhydryl-3-{[3-(4-bromobutoxy)phenyl]methanesulfonylmethylene}azetidine are thus obtained in the form of a brown foam.

EXAMPLE 160

0.110 cm³ of morpholine and then 35 mg of potassium carbonate are successively added, at a temperature close to 20° C., to a solution of 45 mg of 1-benzhydryl-3-{[3-(4-bromopropyloxy)phenyl]methanesulfonylmethylene}azetidine in 3.5 cm³ of anhydrous acetonitrile. After stirring for 20 hours at a temperature close to 20° C., the reaction medium is diluted with 40 cm³ of ethyl acetate and 10 cm³ of water. The separated organic phase is washed with 10 cm³ of water, and then twice 10 cm³ of a saturated aqueous sodium chloride solution, dried over magnesium sulfate, filtered on sintered glass and then concentrated to dryness under reduced pressure (9 kPa) at a temperature close to 40° C. The yellow lacquer obtained is purified by depositing, in solution in a minimum of dichloromethane, on chromatography on silica gel deposited on a plate [(gel 0.5 mm thick, 2 plates of 20 ⌀ 20 cm, eluent: dichloromethane-methanol (97.5-2.5 by volume)]. The zone corresponding to the desired product adsorbed, located with UV rays, is scraped and the silica recovered is washed on sintered glass with a dichloromethane-methanol mixture (85-15 by volume). The filtrates are combined and concentrated to dryness under reduced pressure (1 kPa) at a temperature close to 40° C. 33 mg of 4-(4-{3-[(1-benzhydrylazetidin-3-ylidene)methanesulfonylmethyl]phenoxy}propyl)morpholine are thus obtained in the form of a white foam [¹H NMR spectrum (300 MHz, (CD₃)₂SO-d6, δ in ppm): 1.87 (mt, 2H), 2.37 (mt, 4H), 2.42 (t, J=7.5 Hz, 2H), 2.94 (s, 3H), 3.58 (mt, 4H), 3.80 (mt, 2H), 4.02 (t, J=7 Hz, 2H), 4.20 (mt, 2H), 4.74 (s, 1H), 6.97 (mt, 3H), 7.22 (t, J=7.5 Hz, 2H), from 7.25 to 7.40 (mt, 1H), 7.32 (t, J=7.5 Hz, 4H), 7.48 (d, J=7.5 Hz, 4H)].

1-Benzhydryl-3-{[3-(4-bromopropyloxy)phenyl]methanesulfonylmethylene}azetidine may be prepared in the following manner: 0.5 cm³ of 1,3-dibromopropane and 255 mg of potassium carbonate are successively added at a temperature close to 20° C., under an inert atmosphere of argon, to a solution of 500 mg of 1-benzhydryl-3-[(3-hydroxyphenyl)(methylsulfonyl)methylene]azetidine in 10 cm³ of methyl ethyl ketone. The reaction mixture is heated at the reflux temperature of the solvent, under an inert atmosphere of argon, for 7 hours, and then left at a temperature close to 20° C. for about 4 days. The reaction mixture is filtered on sintered glass covered with celite. The solid residue is rinsed with ethyl acetate and then the filtrate is concentrated to dryness under reduced pressure (10 kPa) at a temperature close to 40° C. The brown oil obtained is purified by chromatography at atmospheric pressure on 40 g of silica (0.063–0.200 mm) contained in a column 3 cm in diameter, eluting with a methanol-dichloromethane mixture (0.5-99.5 by volume). The fractions (10 cm$^3$) containing only the desired product are combined and concentrated to dryness under reduced pressure (0.27 kPa) at 40° C. for 2 hours. 511.1 mg of benzhydryl-3-{[3-(4-bromopropyloxy)phenyl]methanesulfonylmethylene}azetidine are thus obtained in the form of a brown foam.

The medicaments according to the invention consists of a compound of formula (I) or an isomer or a salt of such a compound, in the pure state or in the form of a composition in which it is combined with any other pharmaceutically compatible product which may be inert or physiologically active. The medicaments according to the invention may be used orally, parenterally, rectally or topically.

As solid compositions for oral administration, tablets, pills, powders (gelatine capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

Sterile compositions for parenteral administration may be preferably solutions which are aqueous or nonaqueous, suspensions or emulsions. As solvent or vehicle, there may be used water, propylene glycol, polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. Sterilization may be carried out in several ways, for example by aseptisizing filtration, by incorporating sterilizing agents into the composition, by irradiation or by heating. They may also be prepared in the form of sterile solid compositions which may be dissolved at the time of use in sterile water or any other injectable sterile medium.

Compositions for rectal administration are suppositories or rectal capsules which contain, in addition to the active product, excipients such as cocoa butter, semisynthetic glycerides or polyethylene glycols.

Compositions for topical administration may be, for example, creams, lotions, collyria, collutoria, nasal drops or aerosols.

In human therapy, the compounds according to the invention are particularly useful for the treatment and/or prevention of psychoses including schizophrenia, anxiety disorders, depression, epilepsy, neurodegeneration, cerebellar and spinocerebellar disorders, cognitive disorders, cranial trauma, panic attacks, peripheral neuropathies, glaucomas, migraine, Parkinson's disease, Alzheimer's disease, Huntington's chorea, Raynaud's syndrome, tremor, obsessive-compulsive disorder, senile dementia, thymic disorders, Tourette's syndrome, tardive dyskinesia, bipolar disorders, cancers, movement disorders induced by medicaments, dystonia, endotoxemic shocks, hemorrhagic shocks, hypotension, insomnia, immunological diseases, multiple sclerosis, vomiting, asthma, appetite disorders (bulimia, anorexia), obesity, memory disorders, intestinal transit disorders, in weaning from chronic treatments and alcohol or drug abuse (opiods, barbiturates, cannabis, cocaine, amphetamine, phencyclide, hallucinogens, benzodiazepines for example), as analgesics or potentiators of the analgesic activity of the narcotic and normarcotic drugs as antibacterial, antiviral and antiparasitic agents.

The doses depend on the desired effect, the duration of the treatment and the route of administration used; they are generally between 5 mg and 1000 mg per day orally for an adult with unit doses ranging from 1 mg to 250 mg of active substance.

In general, the doctor will determine the appropriate dosage depending on the age, weight and any other factors specific to the subject to be treated.

The following examples illustrate the compositions according to the invention:

EXAMPLE A

Gelatin capsules containing a dose of 50 mg of active product and having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing a dose of 50 mg of active product and having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerin, titanium oxide (72-3.5-24.5) qs 1 finished film-coated tablet containing 245 mg | |

EXAMPLE C

An injectable solution containing 10 mg of active product and having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| Ethanol, 95% | 0.4 ml |
| Sodium hydroxide | 24 mg |
| Propylene glycol | 1.6 ml |
| Water | qs 4 ml |

What is claimed:

1. A method of treating a condition selected from the group consisting of obesity and weaning from a drug of abuse, wherein the drug is said drug of abuse is cannabis, this method comprising administering to a patient in need of such treatment an effective amount to treat said condition of a compound of formula:

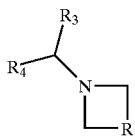
(I)

in which

R represents

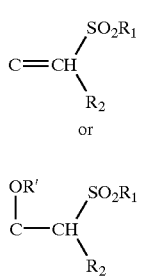

(A)

or (B)

$R_1$ represents a methyl or ethyl radical;

$R_2$ represents either an aromatic radical selected from phenyl, naphthyl and indenyl, these aromatic radicals being nonsubstituted or substituted with one or more substituents selected from halogen, alkyl, alkoxy, —CO-alk, hydroxyl, —COOR$_5$, formyl, trifluoromethyl, trifluoromethylsulfanyl, trifluoromethoxy, nitro, —NR$_6$R$_7$, —CO—NH—NR$_6$R$_7$, —N(alk)COOR$_8$, cyano, —CONHR$_9$, —CO—NR$_{16}$R$_{17}$, alkylsulfanyl, hydroxyalkyl, —O-alk-NR$_{12}$R$_{13}$ and alkylthioalkyl or a heteroaromatic radical selected from benzofuryl, benzothiazolyl, benzothienyl, benzoxazolyl, chromanyl, 2,3-dihydrobenzofuryl, 2,3-dihydrobenzothienyl, indolinyl, indolyl, isochromanyl, isoquinolyl, pyridyl, quinolyl, 1,2,3,4-tetrahydroisoquinolyl, 1,2,3,4-tetrahydroquinolyl, thiazolyl, and thienyl, these heteroaromatic radicals being nonsubstituted or substituted with a substituent selected from halogen, alkyl, alkoxy, —COOR$_5$, trifluoromethyl, trifluoromethylsulfanyl, trifluoromethoxy, nitro, —NR$_6$R$_7$, —CO—NH—NR$_6$R$_7$, cyano, —CONHR$_9$, alkylsulfanyl, hydroxyalkyl and alkylthioalkyl;

$R_3$ and $R_4$, which are identical or different, each represent either an aromatic radical selected from phenyl, naphthyl and indenyl, these aromatic radicals being nonsubstituted or substituted with one or more substituents selected from halogen, alkyl, alkoxy, formyl, hydroxyl, trifluoromethyl, trifluoromethoxy, —CO-alk, cyano, —COOR$_5$, —CONR$_{10}$R$_{11}$, —CO—NH—NR$_6$R$_7$, alkylsulfanyl, hydroxyalkyl, -alk-NR$_6$R$_7$ and alkylthioalkyl; or a heteroaromatic radical selected from benzofuryl, benzothiazolyl, benzothienyl, benzoxazolyl, chromanyl, 2,3-dihydrobenzofuryl, 2,3-dihydrobenzothienyl, furyl, isochromanyl, isoquinolyl, pyrrolyl, quinolyl, 1,2,3,4-tetrahydroisoquinolyl, thiazolyl and thienyl, these heteroaromatics being nonsubstituted or substituted with a substituent selected from halogen, alkyl, alkoxy, hydroxyl, trifluoromethyl, trifluoromethoxy, cyano, —COOR$_5$, —CO—NH— NR$_6$R$_7$, —CONR$_{10}$R$_{11}$, -alk-NR$_6$R$_7$, alkylsulfanyl, hydroxyalkyl and alkylthioalkyl;

$R_5$ is an alkyl or phenyl radical which is optionally substituted with one or more halogens;

$R_6$ and $R_7$, which are identical or different, represent a hydrogen, alkyl, —COOalk, cycloalkyl, alkylcycloalkyl, -alk-O-alk or hydroxyalkyl radical or, alternatively, $R_6$ and $R_7$ together with the nitrogen atom to which they are attached, form a 3- to 10-membered saturated or unsaturated mono- or bicyclic heterocycle optionally containing another heteroatom selected from oxygen, sulfur and nitrogen and being optionally substituted with one or more alkyl, —COalk, —COOalk, —CO—NHalk, —CS—NHalk, —CO-alk-NR$_{14}$R$_{15}$, oxo, hydroxyalkyl, -alk-O-alk or —CO—NH$_2$ radicals;

$R_8$ represents an alkyl radical;

$R_9$ represents a hydrogen or unsubstituted alkyl radical or an alkyl radical that is substituted with a dialkylamino, phenyl, cycloalkyl (optionally substituted with —COOalk) or a 3- to 10-membered saturated or unsaturated mono- or bicyclic heterocycle containing one or more heteroatoms selected from oxygen, sulfur and nitrogen and being optionally substituted with one or more alkyl radicals;

$R_{10}$ and $R_{11}$, which are identical or different, each represent a hydrogen atom or an alkyl radical or, alternatively, $R_{10}$ and $R_{11}$, together with the nitrogen atom to which they are attached, form a 3- to 10-membered saturated mono- or bicyclic heterocycle optionally containing another heteroatom selected from oxygen, sulfur and nitrogen and are optionally substituted with an alkyl radical;

$R_{12}$ and $R_{13}$, which are identical or different, represent a hydrogen, alkyl or cycloalkyl radical or, alternatively, $R_{12}$ and $R_{13}$, together with the nitrogen atom to which they are attached, form a 3- to 10-membered saturated mono- or bicyclic heterocycle optionally containing another heteroatom selected from oxygen, sulfur and nitrogen and being optionally substituted with an alkyl, —COalk, —COOalk, —CO—NHalk, —CS—NHalk or —CO-alk-NR$_{14}$R$_{15}$ radical, or a 3- to 10-membered saturated mono- or bicyclic heterocycle containing a heteroatom selected from oxygen, sulfur and nitrogen;

$R_{14}$ and $R_{15}$, which are identical or different, represent a hydrogen, alkyl or —COOalk radical;

$R_{16}$ and $R_{17}$, together with the nitrogen atom to which they are attached, form a 3- to 10-membered saturated mono- or bicyclic heterocycle optionally containing another heteroatom selected from oxygen, sulfur and nitrogen;

R' represents a hydrogen or —CO-alk radical;

alk represents an alkyl or alkylene radical, it being understood that the alkyl and alkylene radicals and portions and the alkoxy radicals and portions are in the form of a straight or branched chain and contain 1 to 6 carbon atoms, or an optical isomer thereof or a salt thereof with an inorganic or organic acid.

2. The method of claim 1 wherein, in the compound of formula (I) according to claim 1, when $R_6$ and $R_7$ together with the nitrogen atom to which they are attached, form a 3- to 10-membered saturated or unsaturated mono- or bicyclic heterocycle, the latter is an azetidinyl, pyrrolidinyl, piperazinyl, piperidyl, morpholinyl, imidazolyl, thiomorpholinyl or furyl ring, these rings being optionally substituted with an alkyl, hydroxyalkyl, -alk-O-alk, —CONH$_2$, —COalk, —COOalk, oxo, —CSNHalk, —CONHalk or —CO-alk-NR$_{14}$R$_{15}$ in which alk, R$_{14}$ and R$_{15}$ have the same meanings as in claim 1, or an optical isomer thereof or a salt thereof with an inorganic or organic acid.

3. The method of claim 1 wherein, in the compound of formula (I) according to claim 1, when R$_{10}$ and R$_{11}$, together with the nitrogen atom to which they are attached, form a 3- to 10-membered saturated mono- or bicyclic heterocycle, said heterocycle is an azetidinyl, pyrrolidinyl, piperazinyl, piperidyl, morpholinyl or thiomorpholinyl ring, these rings being optionally substituted with an alkyl.

4. The method of claim 1 wherein, in the compound of formula (I) according to claim 1, when R$_{12}$ and R$_{13}$, together with the nitrogen atom to which they are attached, form a 3- to 10-membered saturated mono- or bicyclic heterocycle, said heterocycle is selected from azetidinyl, pyrrolidinyl, piperazinyl, piperidyl, morpholinyl and thiomorpholinyl rings, these rings being optionally substituted with an alkyl, —COalk, —COOalk, —CO—NHalk, —CS—NHalk or —CO-alk-NR$_{14}$R$_{15}$ radical or a 3- to 10-membered saturated mono- or bicyclic heterocycle containing a heteroatom selected from oxygen, sulfur and nitrogen, alk, R$_{14}$ and R$_{15}$ having the same meanings as in claim 1, an optical isomer thereof, or a salt thereof with an inorganic or organic acid.

5. The method of claim 4 wherein said heterocycle is a thiomorpholinyl radical.

6. The method of claim 1 wherein, in the compound of formula (I) according to claim 1, when R$_{16}$ and R$_{17}$, together with the nitrogen atom to which they are attached, form a 3- to 10-membered saturated mono- or bicyclic heterocycle, said heterocycle is a piperidyl ring, or an optical isomer thereof or a salt thereof with an inorganic or organic acid.

7. The method of claim 1 wherein, in the compound of formula (I) according to claim 1, R$_9$ is an alkyl radical substituted with a 3- to 10-membered saturated or unsaturated mono- or bicyclic heterocycle selected from pyrrolidinyl, tetrahydrofuryl, morpholinyl and pyrrolyl rings, these rings being optionally substituted with one or more alkyl radicals, an optical isomer thereof or a salt thereof with an inorganic or organic acid.

8. The method of claim 1 wherein, in the compound of formula (I) according to claim 1, R represents structure (A) or (B);

R' represents a hydrogen atom or a —COalk radical;

R$_1$ represents a methyl or ethyl radical;

R$_2$ represents either an aromatic radical selected from phenyl and naphthyl, these aromatic radicals being nonsubstituted or substituted with one or more substituents selected from halogen, alkyl, alkoxy, hydroxyl, —COOR$_5$, trifluoromethyl, trifluoromethylsulfanyl, trifluoromethoxy, —NR$_6$R$_7$, —CO—NH—NR$_6$R$_7$, cyano, —CONHR$_9$, alkylsulfanyl, hydroxyalkyl, nitro, —CO—NR$_{16}$R$_{17}$, —O-alkNR$_{12}$R$_{13}$ and alkylthioalkyl, or a heteroaromatic radical selected from isoquinolyl, pyridyl, quinolyl, 1,2,3,4-tetrahydroisoquinolyl, 1,2,3,4-tetrahydroquinolyl and thienyl, these heteroaromatic radicals being unsubstituted or substituted with a halogen, alkyl, alkoxy, —COOR$_5$, trifluoromethyl, trifluoromethylsulfanyl, trifluoromethoxy, —NR$_6$R$_7$, —CO—NH—NR$_6$R$_7$, cyano, —CONHR$_9$, alkylsulfanyl, hydroxyalkyl, nitro or alkylthioalkyl substituent;

R$_3$ and R$_4$, which may be identical or different, represent either an aromatic radical selected from phenyl and naphthyl, these aromatic radicals being nonsubstituted or substituted with one or more substituents selected from halogen, alkyl, alkoxy, trifluoromethyl, trifluoromethoxy, —CONR$_{10}$R$_{11}$, -alk-NR$_6$R$_7$, hydroxyalkyl, formyl and —COOR$_5$, or a heteroaromatic radical selected from thiazolyl and thienyl rings, these heteroaromatic rings being nonsubstituted or substituted by a halogen, alkyl, alkoxy, —CONR$_{10}$R$_{11}$, -alk-NR$_6$R$_7$, hydroxyalkyl or —COOR$_5$;

R$_5$ is alkyl or phenyl which is optionally substituted with one or more halogens;

R$_6$ and R$_7$, which may be identical or different, represent a hydrogen, alkyl, —COOalk, cycloalkyl, alkylcycloalkyl, alk-O-alk or hydroxyalkyl radical or, alternatively, R$_6$ and R$_7$, together with the nitrogen atom to which they are attached, form a 3- to 10-membered saturated or unsaturated mono- or bicyclic heterocycle optionally containing another heteroatom selected from oxygen, sulfur and nitrogen and being optionally substituted with one or more alkyl, —COalk, —COOalk, —CO—NHalk, —CS—NHalk, —CO-alk-NR$_{14}$R$_{15}$, oxo, hydroxyalkyl, alk-O-alk or —CO—NH$_2$ radicals;

R$_9$ represents a hydrogen or unsubstituted alkyl radical or an alkyl radical substituted with dialkylamino, phenyl, cycloalkyl (optionally substituted with —COOalk) or a 3- to 10-membered saturated or unsaturated mono- or bicyclic heterocycle containing one or more heteroatoms selected from oxygen, sulfur and nitrogen and being optionally substituted with one or more alkyl radicals;

R$_{10}$ and R$_{11}$, which may be identical or different, represent a hydrogen or alkyl radical or, alternatively, R$_{10}$ and R$_{11}$, together with the nitrogen atom to which they are attached, form a 3- to 10-membered saturated mono- or bicyclic heterocycle optionally containing another heteroatom selected from oxygen, sulfur and nitrogen and being optionally substituted with an alkyl radical;

R$_{12}$ and R$_{13}$, which may be identical or different, represent a hydrogen, alkyl or cycloalkyl radical or, alternatively, R$_{12}$ and R$_{13}$, together with the nitrogen atom to which they are attached, form a 3- to 10-membered saturated mono- or bicyclic heterocycle optionally containing another heteroatom selected from oxygen, sulfur and nitrogen and being optionally substituted with an alkyl, —COalk, —COOalk, —CO—NHalk, —CS—NHalk or —CO-alk-NR$_{14}$R$_{15}$ radical, or a 3- to 10-membered saturated mono- or bicyclic heterocycle containing a heteroatom selected from oxygen, sulfur and nitrogen;

R$_{14}$ and R$_{15}$, which may be identical or different, represent a hydrogen, alkyl or —COOalk radical;

R$_{16}$ and R$_{17}$, together with the nitrogen atom to which they are attached, form a 3- to 10-membered saturated mono- or bicyclic heterocycle optionally containing another heteroatom selected from oxygen, sulfur and nitrogen;

alk represents an alkyl or alkylene radical, it being understood that the alkyl and alkylene radicals and portions and the alkoxy radicals and portions are in the form of a straight or branched chain and contain 1 to 6 carbon atoms, an optical isomer thereof or a salt thereof with an inorganic or organic acid.

9. The method of claim 1 wherein said compound is selected from: 1-[bis(4-chlorophenyl)methyl]-3-[(3,5- difluorophenyl)(methylsulfonyl)methylene]azetidine, 1-[bis (4-chlorophenyl)methyl]-3-[(3,5-difluorophenyl) (methylsulfonyl)methyl-(RS)]azetidin-3ol, 3-acetoxy-1-[bis-(4-chlorophenyl)methyl]-3-[(3,5-difluorophenyl) (methylulfonyl)methyl)methylsulfonylmethyl-(RS)] azetidine, their optical isomers and their salts with an inorganic or organic acid.

10. The method of claim 1 wherein, in the compound of formula (I) according to claim 1, R represents structure (A) or (B);

R' representing a hydrogen or —COalk radical;

$R_1$ represents a methyl or ethyl radical;

$R_2$ represents either (I) an aromatic selected from naphthyl, phenyl, phenyl substituted with one or more halogen, alkyl, alkoxy, hydroxyl, —$COOR_5$ (in which $R_5$ represents an alkyl or phenyl radical optionally substituted with several halogens) trifluoromethyl, trifluoromethylsulfanyl, trifluoromethoxy, —$NR_6R_7$ (in which $R_6$ and $R_7$, which may be identical or different, represent a hydrogen, alkyl or —COOalk radical or, alternatively, $R_6$ and $R_7$, together with the nitrogen atom to which they are attached, form a heterocycle selected from pyrrolidinyl, piperidyl, piperazinyl and piperazinyl substituted with one or more alkyl, —COalk, —COOalk, —CO—NHalk, —CS—NHalk or —CO-alk-$NR_{14}R_{15}$ radicals (in which $R_{14}$ and $R_{15}$, which may be identical or different, represent a hydrogen or alkyl radical, —CO—NH—$NR_6R_7$ (in which $R_6$ and $R_7$, which may be identical or different, represent a hydrogen or alkyl radical or, alternatively, $R_6$ and $R_7$, together with the nitrogen atom to which they are attached, form a heterocycle selected from piperidyl, pyrrolyl, piperazinyl and piperazyl substituted with one or more alkyl radicals), cyano, —$CONHR_9$ (in which $R_9$ represents a hydrogen or unsubstituted alkyl radical or an alkyl radical substituted with dialkylamino, phenyl or cycloalkyl (optionally substituted with —COOalk)) or (II) a heterocycle selected from pyrrolidinyl (optionally substituted with alkyl), tetrahydrofuryl or morpholinyl), alkylsulfanyl, hydroxyalkyl, nitro, —CO—$NR_{16}R_{17}$, (in which $R_{16}$ and $R_{17}$, together with the nitrogen atom to which they are attached, form a piperidyl ring), —O-alk$NR_{12}R_{13}$ (in which $R_{12}$ and $R_{13}$, together with the nitrogen atom to which they are attached, form a morpholino ring) and alkylthioalkyl, or (III) a heteroaromatic selected from isoquinolyl, pyridyl, quinolyl, 1,2,3,4-tetrahydroisoquinolyl, 1,2,3,4-tetrahydroquinolyl, thienyl, and thienyl substituted with a —$COOR_5$ (in which $R_5$ represents an alkyl radical) or —$CONHR_9$, (in which $R_9$ represents an alkyl radical);

$R_3$ and $R_4$, which may be identical or different, represent either (IV) an aromatic selected from phenyl and phenyl substituted with one or more substituents selected from halogen, alkyl, alkoxy, trifluoromethyl, trifluoromethoxy, hydroxyalkyl, formyl, —$COOR_5$ (in which $R_5$ is an alkyl radical), —$CONR_{10}R_{11}$ (in which $R_{10}$ and $R_{11}$, which may be identical or different, represent a hydrogen or alkyl radical), -alk-$NR_6R_7$ (in which $R_6$ and $R_7$, which may be identical or different, represent a hydrogen, alkyl, cycloalkyl, -alk-O-alk or hydroxyalkyl radical or, alternatively, $R_6$ and $R_7$, together with the nitrogen atom to which they are attached, form a heterocycle selected from piperidyl (optionally substituted with alkyl or oxo), pyrrolidinyl (optionally substituted with alkyl, hydroxyalkyl, -alk-O-alk or —CO—$NH_2$), thiomorpholinyl, morpholinyl, pyrrolyl, piperazinyl optionally substituted with oxo, alkyl, hydroxyalkyl, and —$COOR_5$ (in which $R_5$ is an alkyl radical), or (V) a heteroaromatic selected from thiazolyl and thienyl;

alk represents an alkyl or alkylene radical, it being understood that the alkyl and alkylene radicals and portions and the alkoxy radicals and portions are in the form of a straight or branched chain and contain 1 to 6 carbon atoms, an optical isomer thereof or a salt thereof with an inorganic or organic acid.

11. The method of claim 1 wherein said compound is selected from:

1-benzhydryl-3-[(methylsulfonyl)(phenyl)methylene] azetidine, 1-benzhydryl-3-[(3-methylphenyl)(methylsulfonyl) methylene]azetidine, 1-benzhydryl-3-[(3-chlorophenyl)(methylsulfonyl) methylene]azetidine, 1-benzhydryl-3-[(3,5-dichlorophenyl)(methylsulfonyl) methylene]azetidine, 1-benzhydryl-3-[(2,5-dichlorophenyl)(methylsulfonyl) methylene]azetidine, 1-benzhydryl-3-[(2,3-dichlorophenyl)(methylsulfonyl) methylene]azetidine, 1-benzhydryl-3-[(3-fluorophenyl)(methylsulfonyl) methylene]azetidine, 1-benzhydryl-3-[(3,5-difluorophenyl)(methylsulfonyl) methylene]azetidine, 1-benzhydryl-3-[(3-bromophenyl)(methylsulfonyl) methylene]azetidine, 1-benzhydryl-3-[(3-iodophenyl)(methylsulfonyl) methylene]azetidine, 1-benzhydryl-3-[(methylsulfonyl)(3-trifluoromethoxyphenyl)methylene]azetidine, 1-benzhydryl-3-[(3-methylsulfonyl)(3-trifluoromethylphenyl)methylene]azetidine, 1-benzhydryl-3-{[3,5-bis(trifluoromethyl)phenyl] (methylsulfonyl)methylene}azetidine, 1-benzhydryl-3-[(3,5-dibromophenyl)(methylsulfonyl) methylene]azetidine, 1-benzhydryl-3-[(3-methoxycarbonylphenyl) (methylsulfonyl)methylene]azetidine, 1-benzhydryl-3-[(3-cyanophenyl)(methylsulfonyl) methylene]azetidine, 1-benzhydryl-3-[(3-carbamoylphenyl)(methylsulfonyl) methylene]azetidine, 1-benzhydryl-3-[(methylsulfonyl)(naphth-1-yl) (methylsulfonyl)methylene]azetidine, 1-[bis(4-chlorophenyl)methyl]-3-[(3,5-difluorophenyl) (methylsulfonyl)methylene]azetidine, 1-[bis(4-methoxyphenyl)methyl]-3-[(3,5-difluorophenyl) (methylsulfonyl)methylene]azetidine, 1-[bis(4-methylphenyl)methyl]-3-[(3,5-difluorophenyl) (methylsulfonyl)methylene]azetidine, (RS)-3-[(3,5-difluorophenyl)(methylsulfonyl)methylene]-1-[(4-methoxyphenyl)(phenyl)methyl]azetidine, (R)-3-[(3,5-difluorophenyl)(methylsulfonyl)methylene]-1-[(4-methoxyphenyl)(phenyl)methyl]azetidine, (S)-3-[(3,5-difluorophenyl)(methylsulfonyl)methylene]-1-[(4-methoxyphenyl)(phenyl)methyl]azetidine, 1-[bis(4-trifluoromethoxyphenyl)methyl]-3-[(3,5-difluorophenyl)(methylsulfonyl)methylene]azetidine, and 1-[bis(4-trifluoromethylphenyl)methyl]-3-[(3,5-difluorophenyl)(methylsulfonyl)methylene]azetidine.

12. The method of claims 1, wherein said compound is selected from:

1-[bis(4-chlorophenyl)methyl]-3-{[3,5-bis-(trifluoromethyl)phenyl]methylsulfonylmethylene]azetidine, (RS)-1-[(4-chlorophenyl)(2,4-dichlorophenyl)methyl]-3-[(3,5-difluorophenyl)(methylsulfonyl)methylene]azetidine, (R)-1-[(4-chlorophenyl)(2,4-dichlorophenyl)methyl]-3-[(3,5-difluorophenyl)(methylsulfonyl)methylene]azetidine, (S)-1-[(4-chlorophenyl)(2,4-dichlorophenyl)methyl]-3-[(3,5-difluorophenyl)(methylsulfonyl)methylene]azetidine, (RS)-1-{(4-chlorophenyl)[4-(hydroxymethyl)phenyl]methyl}-3-[(3,5-difluorophenyl)(methylsulfonyl)methylene]azetidine, (R)-1-{(4-chlorophenyl)[4-(hydroxymethyl)phenyl]methyl}-3-[(3,5-difluorophenyl)(methylsulfonyl)methylene]azetidine, (S)-1-{(4-chlorophenyl)[4-(hydroxymethyl)phenyl]methyl}-3-[(3,5-difluorophenyl)(methylsulfonyl)methylene]azetidine, (RS)-1-{(4-chlorophenyl)[4-(pyrrolidylmethyl)phenyl]methyl}-3-[(3,5-difluorophenyl)(methylsulfonyl)methylene]azetidine, (R)-1-{(4-chlorophenyl)[4-(pyrrolidylmethyl)phenyl]methyl}-3-[(3,5-difluorophenyl)(methylsulfonyl)methylene]azetidine, (S)-1-{(4-chlorophenyl)[4-(pyrrolidylmethyl)phenyl]methyl}-3-[(3,5-difluorophenyl)(methylsulfonyl)methylene]azetidine, 1-{(RS)-(4-chlorophenyl)[4-(3,3-dimethylpiperidin-1-ylmethyl)phenyl]methyl}-3-[(3,5-difluorophenyl)(methylsulfonyl)methylene]azetidine, 1-{(R)-(4-chlorophenyl)[4-(3,3-dimethylpiperidin-1-ylmethyl)phenyl]methyl}-3-[(3,5-difluorophenyl)(methylsulfonyl)methylene]azetidine, 1-{(S)-(4-chlorophenyl)[4-(3,3-dimethylpiperidin-1-ylmethyl)phenyl]methyl}-3-[(3,5-difluorophenyl)(methylsulfonyl)methylene]azetidine, 1-{(RS)-(4-chlorophenyl)[4-(thiomorpholin-4-ylmethyl)phenyl]methyl}-3-[(3,5-difluorophenyl)(methylsulfonyl)methylene]azetidine, 1-{(R)-(4-chlorophenyl)[4-(thiomorpholin-4-ylmethyl)phenyl]methyl}-3-[(3,5-difluorophenyl)(methylsulfonyl)methylene]azetidine, 1-{(S)-(4-chlorophenyl)[4-(thiomorpholin-4-ylmethyl)phenyl]methyl}-3-[(3,5-difluorophenyl)(methylsulfonyl)methylene]azetidine, 1-{(RS)-(4-chlorophenyl)[4-(N-ethyl-N-cyclohexylaminomethyl)phenyl]methyl}-3-[(3,5-difluorophenyl)(methylsulfonyl)methylene]azetidine, 1-{(R)-(4-chlorophenyl)[4-(N-ethyl-N-cyclohexylaminomethyl)phenyl]methyl}-3-[(3,5-difluorophenyl)(methylsulfonyl)methylene]azetidine, 1-{(S)-(4-chlorophenyl)[4-(N-ethyl-N-cyclohexylaminomethyl)phenyl]methyl}-3-[(3,5-difluorophenyl)(methylsulfonyl)methylene]azetidine, and 1-{{(RS)-(4-chlorophenyl){4-[(4-ethoxycarbonylpiperazinyl)methyl]phenyl}methyl}}-3-[(3,5-difluorophenyl)(methylsulfonyl)methylene]azetidine, their optical isomers and their salts with an inorganic or organic acid.

13. The method of claim 1, wherein said compound is selected from:

1-{{(R)-(4-chlorophenyl){4-[(4-ethoxycarbonylpiperazinyl)methyl]phenyl}methyl}}-3-[(3,5-difluorophenyl)(methylsulfonyl)methylene]azetidine, 1-{{(S)-(4-chlorophenyl){4-[(4-ethoxycarbonylpiperazinyl)methyl]phenyl}methyl}}-3-[(3,5-difluorophenyl)(methylsulfonyl)methylene]azetidine, 1-{(RS)-(4-chlorophenyl)[4-(N-cyclopropyl-N-propylaminomethyl)phenyl]methyl}-3-[(3,5-difluorophenyl)(methylsulfonyl)methylene]azetidine, 1-{(R)-(4-chlorophenyl)[4-(N-cyclopropyl-N-propylaminomethyl)phenyl]methyl}-3-[(3,5-difluorophenyl)(methylsulfonyl)methylene]azetidine, 1-{(S)-(4-chlorophenyl)[4-(N-cyclopropyl-N-propylaminomethyl)phenyl]methyl}-3-[(3,5-difluorophenyl)(methylsulfonyl)methylene]azetidine, 1-{(RS)-(4-chlorophenyl)[4-(diisopropylaminomethyl)phenyl]methyl}-3-[(3,5-difluorophenyl)(methylsulfonyl)methylene]azetidine, 1-{(R)-(4-chlorophenyl)[4-(diisopropylaminomethyl)phenyl]methyl}-3-[(3,5-difluorophenyl)(methylsulfonyl)methylene]azetidine, 1-{(S)-(4-chlorophenyl)[4-(diisopropylaminomethyl)phenyl]methyl}-3-[(3,5-difluorophenyl)(methylsulfonyl)methylene]azetidine, 1-{{(RS)-(4-chlorophenyl){4-[bis-(2-methoxyethyl)aminomethyl]phenyl}methyl}}-3-[(3,5-difluorophenyl)(methylsulfonyl)methylene]azetidine, 1-{{(R)-(4-chlorophenyl){4-[bis-(2-methoxyethyl)aminomethyl]phenyl}methyl}}-3-[(3,5-difluorophenyl)(methylsulfonyl)methylene]azetidine, 1-{{(S)-(4-chlorophenyl){4-[bis-(2-methoxyethyl)aminomethyl]phenyl}methyl}}-3-[(3,5-difluorophenyl)(methylsulfonyl)methylene]azetidine, 1-{(RS)-(4-chlorophenyl)[4-(di-n-propylaminomethyl)phenyl]methyl}-3-[(3,5-difluorophenyl)(methylsulfonyl)methylene]azetidine, 1-{(R)-(4-chlorophenyl)[4-(di-n-propylaminomethyl)phenyl]methyl}-3-[(3,5-difluorophenyl)(methylsulfonyl)methylene]azetidine, 1-{(S)-(4-chlorophenyl)[4-(di-n-propylaminomethyl)phenyl]methyl}-3-[(3,5-difluorophenyl)(methylsulfonyl)methylene]azetidine, 1-{(RS)-(4-chlorophenyl)[4-(piperidin-1-ylmethyl)phenyl]methyl}-3-[(3,5-difluorophenyl)(methylsulfonyl)methylene]azetidine, 1-{(R)-(4-chlorophenyl)[4-(piperidin-1-ylmethyl)phenyl]methyl}-3-[(3,5-difluorophenyl)(methylsulfonyl)methylene]azetidine, 1-{(S)-(4-chlorophenyl)[4-(piperidin-1-ylmethyl)phenyl]methyl}-3-[(3,5-difluorophenyl)(methylsulfonyl)methylene]azetidine, and 1-{(RS)-(4-chlorophenyl)[4-(4-methylpiperazin-1-ylmethyl)phenyl]methyl}-3-[(3,5-difluorophenyl)(methylsulfonyl)methylene]azetidine, their optical isomers and their salts with an inorganic or organic acid.

14. The method of claim 1, wherein said compound is selected from:

1-{(R)-(4-chlorophenyl)[4-(4-methylpiperazin-1-yl-methyl)phenyl]methyl}-3-[(3,5-difluorophenyl)(methylsulfonyl)methylene]azetidine, 1-{(S)-(4-chlorophenyl)[4-(4-methylpiperazin-1-yl-methyl)phenyl]methyl}-3-[(3,5-difluorophenyl)(methylsulfonyl)methylene]azetidine, 1-{(RS)-(4-chlorophenyl)[4-(morpholin-4-yl-methyl)phenyl]methyl}-3-[(3,5-difluorophenyl)(methylsulfonyl)methylene]azetidine, 1-{(R)-(4-chlorophenyl)[4-(morpholin-4-yl-methyl)phenyl]methyl}-3-[(3,5-difluorophenyl)(methylsulfonyl)methylene]azetidine, 1-{(S)-(4-chlorophenyl)[4-(morpholin-4-yl-methyl)phenyl]methyl}-3-[(3,5-difluorophenyl)(methylsulfonyl)methylene]azetidine, 1-{(RS)-(4-chlorophenyl)[4-(diethylaminomethyl)phenyl]methyl}-3-[(3,5-difluorophenyl)(methylsulfonyl)methylene]azetidine, 1-{(R)-(4-chlorophenyl)[4-(diethylaminomethyl)phenyl]methyl}-3-[(3,5-difluorophenyl)(methylsulfonyl)methylene]azetidine,
1-{(S)-(4-chlorophenyl)[4-(diethylaminomethyl)phenyl]methyl}-3-[(3,5-difluorophenyl)(methylsulfonyl)methylene]azetidine,
1-{(RS)-(4-chlorophenyl)[4-(piperazin-2-on-4-yl-methyl)phenyl]methyl}-3-[3,5-difluorophenyl)(methylsulfonyl)methylene]azetidine,
1-{(R)-(4-chlorophenyl)[4-(piperazin-2-on-4-yl-methyl)phenyl]methyl}-3-[3,5-difluorophenyl)(methylsulfonyl)methylene]azetidine,
1-{(S)-(4-chlorophenyl)[4-(piperazin-2-on-4-yl-methyl)phenyl]methyl}-3-[(3,5-difluorophenyl)(methylsulfonyl)methylene]azetidine,
1-{(RS)-(4-chlorophenyl)[4-(imidazol-1-yl-methyl)phenyl]methyl}-3-[(3,5-difluorophenyl)(methylsulfonyl)methylene]azetidine,
1-{(R)-(4-chlorophenyl)[4-(imidazol-1-yl-methyl)phenyl]methyl}-3-[(3,5-difluorophenyl)(methylsulfonyl)methylene]azetidine,
1-{(S)-(4-chlorophenyl)[4-(imidazol-1-yl-methyl)phenyl]methyl}-3-[(3,5-difluorophenyl)(methylsulfonyl)methylene]azetidine,
(RS)-1-{(4-chlorophenyl)[4-(N,N-dimethylcarbamoyl)phenyl]methyl}-3-[(3,5-difluorophenyl)(methylsulfonyl)methylene]azetidine,
(R)-1-{(4-chlorophenyl)[4-(N,N-dimethylcarbamoyl)phenyl]methyl}-3-[(3,5-difluorophenyl)(methylsulfonyl)methylene]azetidine,
(S)-1-{(4-chlorophenyl)[4-(N,N-dimethylcarbamoyl)phenyl]methyl}-3-[(3,5-difluorophenyl)(methylsulfonyl)methylene]azetidine,
(RS)-1-{(4-chlorophenyl)[4-(N-ethylcarbamoyl)phenyl]methyl}-3-[(3,5-difluorophenyl)(methylsulfonyl)methylene]azetidine,
(R)-1-{(4-chlorophenyl)[4-(N-ethylcarbamoyl)phenyl]methyl}-3-[(3,5-difluorophenyl)(methylsulfonyl)methylene]azetidine,
(S)-1-{(4-chlorophenyl)[4-(N-ethylcarbamoyl)phenyl]methyl}-3-[(3,5-difluorophenyl)(methylsulfonyl)methylene]azetidine,
(RS)-1-[(4-carbamoylphenyl)(4-chlorophenyl)methyl]-3-[(3,5-difluorophenyl)(methylsulfonyl)methylene]azetidine,
(R)-1-[(4-carbamoylphenyl)(4-chlorophenyl)methyl]-3-[(3,5-difluorophenyl)(methylsulfonyl)methylene]azetidine, and
(S)-1-[(4-carbamoylphenyl)(4-chlorophenyl)methyl]-3-[(3,5-difluorophenyl)(methylsulfonyl)methylene]azetidine, their optical isomers and their salts with an inorganic or organic acid.

15. The method of claim 1, wherein said compound is selected from:
1-[bis(4-chlorophenyl)methyl]-3-[(3,5-dichlorophenyl)(methylsulfonyl)methylene]azetidine,
1-benzhydryl-3-[(3-methylsulfanylphenyl)(methylsulfonyl)methylene]azetidine,
1-benzhydryl-3-[(3-methylsulfanylmethyl)phenyl)](methylsulfonyl)methylene]azetidine,
1-[bis(4-chlorophenyl)methyl]-3-[(3-cyanophenyl)(methylsulfonyl)methylene]azetidine,
1-[bis(4-chlorophenyl)methyl]-3-[(3-carbamoylphenyl)(methylsulfonyl)methylene]azetidine,
1-[bis(4-chlorophenyl)methyl]-3-[(3-methoxyphenyl)(methylsulfonyl)methylene]azetidine,
1-[bis(4-chlorophenyl)methyl]-3-[(3-hydroxyphenyl)(methylsulfonyl)methylene]azetidine,
1-[bis(4-chlorophenyl)methyl]-3-[(methylsulfonyl)-(3-pyrrolidinylphenyl)methylene]azetidine,
1-[bis(4-chlorophenyl)methyl]-3-[(3-hydroxymethyl-phenyl)(methylsulfonyl)methylene]azetidine,
1-[bis(4-chlorophenyl)methyl]3-{(methylsulfonyl)[3-(N-piperidylcarbamoyl)phenyl]methylene}azetidine,
1-[bis(4-chlorophenyl)methyl]-3-[(methylsulfonyl)-(3-trifluoromethylsulfanylphenyl)(methylsulfonyl)-methylene]azetidine,
1-[bis(4-fluorophenyl)methyl]-3-[(3,5-difluorophenyl)(methylsulfonyl)methylene]azetidine,
1-[bis(2-fluorophenyl)methyl]-3-[3,5-difluorophenyl)(methylsulfonyl)methylene]azetidine,
1-[bis(3-fluorophenyl)methyl]-3-[(3,5-difluorophenyl)(methylsulfonyl)methylene]azetidine,
(RS)-1-[(4-chlorophenyl)(thiazol-2-yl)methyl]-3-[(methylsulfonyl)(phenyl)methylene]azetidine,
(R)-1-[(4-chlorophenyl)(thiazol-2-yl)methyl]-3-[(methylsulfonyl)(phenyl)methylene]azetidine,
(S)-1-[(4-chlorophenyl)(thiazol-2-yl)methyl]-3-[(methylsulfonyl)(phenyl)methylene]azetidine,
(RS)-1-[(4-chlorophenyl)(thien-2-yl)methyl]-3-[(3,5-difluorophenyl)(methylsulfonyl)methylene]azetidin
(R)-1-[(4-chlorophenyl)(thien-2-yl)methyl]-3-[(3,5-difluorophenyl)(methylsulfonyl)methylene]azetidine,
(S)-1-[(4-chlorophenyl)(thien-2-yl)methyl]-3-[(3,5-difluorophenyl)(methylsulfonyl)methylene]azetidine,
1-benzhydryl-3-[(ethylsulfonyl)(phenyl)methylene]azetidine,
1-[bis(4-chlorophenyl)methyl]-3-{{3-[N-(4-methylpiperazinyl)carbamoyl]phenyl}(methylsulfonyl)methylene}azetidine,
1-[bis(4-chlorophenyl)methyl]-3-{[3-(2,2-dimethylcarbohydrazido)phenyl](methylsulfonyl)methylene)azetidine,
1-[bis(thien-2-yl)methyl]-3-[3,5-difluorophenyl)(methylsulfonyl)methylene]azetidine,
1-[bis(p-tolyl)methyl]-3-[(methylsulfonyl)(phenyl)methylene]azetidine,
1-[(4-chlorophenyl)(4-hydroxymethylphenyl)methyl]-3-[(3,5-difluorophenyl)(methylsulfonyl)methylene]azetidine,
1-[bis(4-chlorophenyl)methyl]-3-[(3-methylaminophenyl)(methylsulfonyl)methylene]azetidine,
(RS)-1-[(4-chlorophenyl)(thiazol-2-yl)methyl]-3-[(3,5-difluorophenyl)(methylsulfonyl)methylene]azetidine,
(R)-1-[(4-chlorophenyl)(thiazol-2-yl)methyl]-3-[(3,5-difluorophenyl)(methylsulfonyl)methylene]azetidine,
(S)-1-[(4-chlorophenyl)(thiazol-2-yl)methyl]-3-[(3,5-difluorophenyl)(methylsulfonyl)methylene]azetidine,
1-[bis(4-chlorophenyl)methyl]-3-[(methylsulfonyl)(2-methoxycarbonylthien-5-yl)methylene]azetidine, and
(RS)-1-[bis(4-chlorophenyl)methyl]-3-hydroxy-3-[(methylsulfonyl)(2-methoxycarbonylthien-5-yl)methyl]azetidine, their optical isomers and their salts with an inorganic or organic acid.

16. The method of claim 1, wherein said compound is selected from:
1-[bis(4-chlorophenyl)methyl]-3-[(2-isobutylaminocarbonylthien-5-yl)(methylsulfonyl)methylene]azetidine,
1-[bis(4-chlorophenyl)methyl]-3-[(3-methoxycarbonylphenyl)(methylsulfonyl)methyl-(RS)azetidin-3-ol,
1-[bis(4-chlorophenyl)methyl]-3-[(methylsulfonyl)(pyridin-4-yl)methyl-(RS)azetidin-3-ol,
1-[bis(4-chlorophenyl)methyl]-3-[(methylsulfonyl)(pyridin-3-yl)methyl-(RS)azetidin-3-ol, 3-({1-[bis(4-chlorophenyl)methyl]azetidin-3-ylidene}-methanesulfonylmethyl)-N-(3-morpholin-4-yl-propyl)benzamide,
3-({1-[bis(4-chlorophenyl)methyl]azetidin-3-ylidene}-methanesulfonylmethyl)-N-(3-dimethylaminopropyl)benzamide,
3-({1-[bis(4-chlorophenyl)methyl]azetidin-3-ylidene}-methanesulfonylmethyl)-N-(2-pyrrolidin-1-ylethyl)benzamide,
3-({1-[bis(4-chlorophenyl)methyl]azetidin-3-ylidene}-methanesulfonylmethyl)-N-(2-dimethylamino-1-methylethyl)benzamide,
3-({1-[bis(4-chlorophenyl)methyl]azetidin-3-ylidene}-methanesulfonylmethyl)-N-piperidin-1-ylbenzamide,
3-({1-[bis(4-chlorophenyl)methyl]azetidin-3-ylidene}-methanesulfonylmethyl)-N-isobutylbenzamide,
3-({1-[bis(4-chlorophenyl)methyl]azetidin-3-ylidene}-methanesulfonylmethyl)-N-(3-imidazol-1-ylpropyl)benzamide,
3-({1-[bis(4-chlorophenyl)methyl]azetidin-3-ylidene}-methanesulfonylmethyl)-N-(2-dimethylaminoethyl)benzamide,
3-({1-[bis-(4-chlorophenyl)methyl]azetidin-3-ylidene}methanesulfonylmethyl)benzoic acid N'-methylhydrazide,
3-({1-[bis-(4-chlorophenyl)methyl]azetidin-3-ylidene}-methanesulfonylmethyl)-N-(2-morpholin-4-ylethyl)benzamide,
3-({1-[bis-(4-chlorophenyl)methyl]azetidin-3-ylidene}-methanesulfonylmethyl)-N-(1-ethylpyrrolidin-2-ylmethyl)benzamide,
3-({1-[bis-(4-chlorophenyl)methyl]azetidin-3-ylidene}-methanesulfonylmethyl)-N-(2,2-dimethylpropyl)benzamide,
3-({1-[bis-(4-chlorophenyl)methyl]azetidin-3-ylidene}-methanesulfonylmethyl)-N-cyclohexylmethylbenzamide, and
3-({1-[bis-(4-chlorophenyl)methyl]azetidin-3-ylidene}-methanesulfonylmethyl)-N-cyclopropylmethylbenzamide, their optical isomers and their salts with an inorganic or organic acid.

17. The method of claim 1, wherein said compound is selected from:
3-({1-[bis-(4-chlorophenyl)methyl]azetidin-3-ylidene}-methanesulfonylmethyl)-N-(2-methylbutyl)benzamide,
3-({1-[bis-(4-chlorophenyl)methyl]azetidin-3-ylidene}-methanesulfonylmethyl)-N-(2-phenylpropyl)benzamide,
3-({1-[bis-(4-chlorophenyl)methyl]azetidin-3-ylidene}-methanesulfonylmethyl)-N-(tetrahydrofuran-2-ylmethyl)benzamide,
3-({1-[bis-(4-chlorophenyl)methyl]azetidin-3-ylidene}-methanesulfonylmethyl)-N-(2,2-diphenylethyl)benzamide,
3-({1-[bis-(4-chlorophenyl)methyl]azetidin-3-ylidene}-methanesulfonylmethyl)-N-(2-ethylbutyl)benzamide,
4-{[3-({1-[bis-(4-chlorophenyl)methyl]azetidin-3-ylidene}methanesulfonylmethyl)benzoylamino]methyl}cyclohexanecarboxylic acid methyl ester,
2-amino-1-{4-[3-({1-[bis-(4-chlorophenyl)methyl]azetidin-3-ylidene}methanesulfonylmethyl)phenyl]piperazin-1-yl}ethanone,
(2-{4-[3-({1-[bis(4-chlorophenyl)methyl]azetidin-3-ylidene}methanesulfonylmethyl)phenyl]piperazin-1-yl}-2-oxoethyl)carbamic acid tert-butyl ester,
1-{4-[3-({1-[bis(4-chlorophenyl)methyl]azetidin-3-ylidene}methanesulfonylmethyl)phenyl]piperazin-1-yl}-2-methylaminoethanone,
(2-{4-[3-({1-[bis(4-chlorophenyl)methyl]azetidin-3-ylidene}methanesulfonylmethyl)phenyl]piperazin-1-yl}-2-oxoethyl)-N-methylcarbamic acid tert-butyl ester,
4-[3-({1-[bis(4-chlorophenyl)methyl]azetidin-3-ylidene}methanesulfonylmethyl)phenyl]piperazine-1-carbothioic acid N-methylamide,
4-[3-({1-[bis(4-chlorophenyl)methyl]azetidin-3-ylidene}methanesulfonylmethyl)phenyl]piperazine-1-carboxylic acid N-methylamide,
4-[3-({1-[bis(4-chlorophenyl)methyl]azetidin-3-ylidene}methanesulfonylmethyl)phenyl]piperazine-1-carboxylic acid methyl ester,
1-[3-({1-[bis(4-chlorophenyl)methyl]azetidin-3-ylidene}methanesulfonylmethyl)phenyl]-4-isobutylpiperazine,
1-[3-({1-[bis(4-chlorophenyl)methyl]azetidin-3-ylidene}methanesulfonylmethyl)phenyl]-4-ethylpiperazine,
4-acetyl 1-[3-({1-[bis(4-chlorophenyl)methyl]azetidin-3-ylidene}methanesulfonylmethyl)phenyl]piperazine,
1-{4-[3-({1-[bis(4-chlorophenyl)methyl]azetidin-3-ylidene}methanesulfonylmethyl)phenyl]piperazin-1-yl}-2-dimethylaminoethanone,
1-[3-({1-[bis(4-chlorophenyl)methyl]azetidin-3-ylidene}methanesulfonylmethyl)phenyl]piperazine,
4-[3-({1-[bis(4-chlorophenyl)methyl]azetidin-3-ylidene}methanesulfonylmethyl)phenyl]piperazine-1-carboxylic acid tert-butyl ester,
1-[bis(4-methoxycarbonylphenyl)methyl]-3-[(3,5-difluorophenyl)(methylsulfonyl)methylene]azetidine,
3-acetoxy-1-[bis(4-methoxycarbonylphenyl)methyl]-3-[(3,5-difluorophenyl)(methylsulfonyl)methyl-(RS)azetidine,
(RS)-4-[4-((4-chlorophenyl){3-[(3,5-difluorophenyl)methanesulfonylmethylene]azetidin-1-yl}methyl)benzyl]morpholine, and
4-(4-{3-[(1-benzhydrylazetidin-3-ylidene)methanesulfonylmethyl]phenoxy}butyl)morpholine,
4-(4-{3-[(1-benzhydrylazetidin-3-ylidene)methanesulfonylmethyl]phenoxy}propyl)morpholine, their optical isomers and their salts with an inorganic or organic acid.

18. The method of claim 1 wherein said condition is obesity.

19. The method of claim 1, wherein said drug of abuse is cannabis.

20. The method of claim 1, wherein said treatment is weaning from a drug of abuse and said drug of abuse is cannabis.

* * * * *